United States Patent
Chen

(10) Patent No.: US 11,254,680 B2
(45) Date of Patent: Feb. 22, 2022

(54) CYCLIC IMINOPYRIMIDINE DERIVATIVES AS KINASE INHIBITORS

(71) Applicant: ABM Therapeutics Corporation, San Diego, CA (US)

(72) Inventor: Chen Chen, San Diego, CA (US)

(73) Assignee: ABM Therapeutics Corporation, San Diego, CA (US)

(*) Notice: Subject to any disclaimer, the term of this patent is extended or adjusted under 35 U.S.C. 154(b) by 0 days.

(21) Appl. No.: 16/648,908

(22) PCT Filed: Sep. 20, 2018

(86) PCT No.: PCT/US2018/052047
§ 371 (c)(1),
(2) Date: Mar. 19, 2020

(87) PCT Pub. No.: WO2019/060611
PCT Pub. Date: Mar. 28, 2019

(65) Prior Publication Data
US 2020/0247813 A1    Aug. 6, 2020

Related U.S. Application Data

(60) Provisional application No. 62/561,142, filed on Sep. 20, 2017.

(51) Int. Cl.
*C07D 487/06* (2006.01)
*A61K 31/517* (2006.01)
*C07D 487/04* (2006.01)
*A61P 35/04* (2006.01)
*C07D 471/14* (2006.01)
*A61K 45/06* (2006.01)

(52) U.S. Cl.
CPC ............ *C07D 487/04* (2013.01); *A61P 35/04* (2018.01); *C07D 471/14* (2013.01); *A61K 45/06* (2013.01)

(58) Field of Classification Search
CPC .. C07D 487/14; C07D 487/06; A61K 31/517; A61P 35/00; A61P 25/28
USPC ................... 544/250, 251; 514/257
See application file for complete search history.

(56) References Cited

FOREIGN PATENT DOCUMENTS

| EP | 2 813 491 | 12/2014 |
|---|---|---|
| RU | 2 469 036 | 7/2011 |
| RU | 2 635 354 | 3/2016 |
| WO | WO-2008/079903 | 7/2008 |
| WO | WO-2008/150799 | 12/2008 |
| WO | WO-2009/012283 | 1/2009 |
| WO | WO-2012/118492 | 9/2012 |

OTHER PUBLICATIONS

Corbett T. H., et al., "Tumor Induction Relationships in Development of Transplantable Cancers of the Colon in Mice for Chemotherapy Assays, with a Note on Carcinogen Structure", Cancer Res., 35, 2434-2439 (1975).
Corbett T. H., et al., "A Mouse Colon-tumor Model for Experimental Therapy", Cancer Chemother. Rep. (Part 2), 5, 169-186 (1975).
Geran, R. I., et al. "Protocols for Screening Chemical Agents and Natural Products Against Animal Tumors and Other Biological Systems", Third Edition, Cancer Chemother. Rep., 3, 1-104 (1972).
International Search Report and Written Opinion for PCT/US2018/052047, dated Jan. 23, 2019, 13 pages.
Wenglowsky et al., "Highly potent and selective 3-N-methylquinazoline-4(3H)-one based inhibitors of B-Raf(V600E) kinase," Bioorg Med Chem Lett. (2014) 24(8):1923-1927.
Mass et al., "A somatic mutation in erythro-myeloid progenitors causes neurodegenerative disease," Nature (2017): 549:389-393.
Packer et al., "Identification of direct transcriptional targets of $^{V600E}$BRAF/MEK signalling in melanoma," Pigment Cell Melanoma Res. (2009) 22:785-798.
Yang, "RG7204 (PLX4032), a Selective BRAF$^{V600E}$ Inhibitor, Displays Potent Antitumor Activity in Preclinical Melanoma Models," Cancer Res. (2010) 70(13):5518-5527.
Office Action and Search Report (including translation) for RU 2020113707, dated Dec. 23, 2021, 15 pages.

*Primary Examiner* — Charanjit Aulakh
(74) *Attorney, Agent, or Firm* — Morrison & Foerster LLP

(57) ABSTRACT

Provided are cyclic iminopyridimdine compounds and their bicyclic derivatives, pharmaceutical compositions comprising such compounds, and methods of using such compounds or compositions, such as methods of treating a proliferation disorder, such as a cancer or a tumor, or in some embodiments disease or disorders related to the dysregulation of kinase such as, but not limited to B-Raf V600E kinase.

31 Claims, No Drawings

CYCLIC IMINOPYRIMIDINE DERIVATIVES AS KINASE INHIBITORS

CROSS-REFERENCE PARAGRAPH

This application is a National Stage application under 35 U.S.C. § 371 of International Application No. PCT/US2018/052047 filed on Sep. 20, 2018, which claims priority to U.S. Provisional Application No. 62/561,142, filed Sep. 20, 2017, the contents of which are incorporated by reference in their entirety.

FIELD

Provided herein are cyclic iminopyrimidine derivatives, pharmaceutical compositions comprising such compounds, and methods of using such compounds or compositions, such as methods of treating a proliferation disorder, a cancer or a tumor, or in some embodiments disease or disorders related to the dysregulation of kinase such as, but not limited to B-Raf V600E kinase.

BACKGROUND

The present disclosure relates to the treatment of abnormal cell growth in mammals especially humans, such as cancer and, more specifically brain cancer, with novel cyclic iminopyrimidines and their bicyclic compounds described therein, and their isotopic derivatives as well as pharmaceutical compositions containing such compounds. In addition, the present disclosure relates to the methods of preparing such compounds.

A kinase is an enzyme that catalyzes the transfer of phosphate groups from high-energy, phosphate-donating molecules to specific substrates. This process is known as phosphorylation, where the substrate gains a phosphate group and the high-energy ATP molecule donates a phosphate group. This transesterification produces a phosphorylated substrate and ADP.

Kinases are classified into broad groups by the substrate they act upon: protein kinases, lipid kinases, carbohydrate kinases. Kinases can be found in a variety of species, from bacteria to mold to worms to mammals. More than five hundred different kinases have been identified in humans.

MAP kinases (MAPKs) are a family of serine/threonine kinases that respond to a variety of extracellular growth signals. For example, growth hormone, epidermal growth factor, platelet-derived growth factor, and insulin are all considered mitogenic stimuli that can engage the MAPK pathway. Activation of this pathway at the level of the receptor initiates a signaling cascade whereby the Ras GTPase exchanges GDP for GTP. Next, Ras activates Raf kinase (also known as MAPKKK), which activates MEK (MAPKK). MEK activates MAPK (also known as ERK), which can go on to regulate transcription and translation. Whereas RAF and MAPK are both serine/threonine kinases, MAPKK is a tyrosine/threonine kinase.

The carcinogenic potential of the MAPK pathway makes it clinically significant. It is implicated in cell processes that can lead to uncontrolled growth and subsequent tumor formation. Mutations within this pathway alter its regulatory effects on cell differentiation, proliferation, survival, and apoptosis, all of which are implicated in various forms of cancer.

It is known that such kinases are frequently aberrantly expressed in common human cancers such as melanoma, colorectal cancer, thyroid cancer, glioma, breast cancer and lung cancer. It has also been shown that B-Raf, which possesses kinase activity, is mutated and/or overactive in many human cancers such as brain, lung, melanoma, colorectal cancer, ovarian cancer and papillary thyroid cancer.

Inhibition of the kinase is a useful method for disrupting the growth of mammalian cancer cells, therefore, for treating certain forms of cancer. Various compounds, such as pyrrolopyridine and thiazole derivatives, have been shown to possess kinase inhibitory properties. Many patent publications refer to certain bicyclic derivatives, in particular quinazolinone derivatives.

Several compounds with diversified chemical structures have been developed into B-Raf V600E mutant inhibitors, and two of them (Vemurafenib and Dabrafenib) are very effective in clinical applications. For example, Vemurafenib and Dabrafenib are marketed drugs treating various cancers by targeting B-Raf V600E mutation. Others compounds such as Encorafenib, which also inhibits B-Raf V600E mutant kinase, are in clinical development.

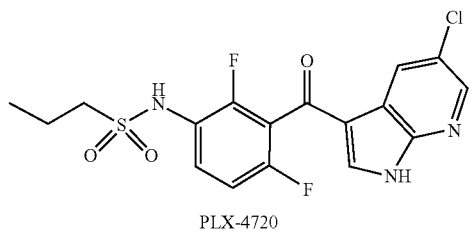

PLX-4720

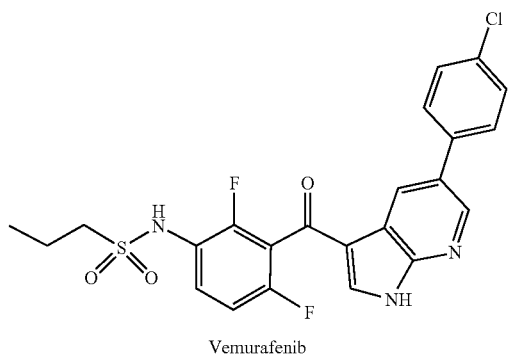

Vemurafenib

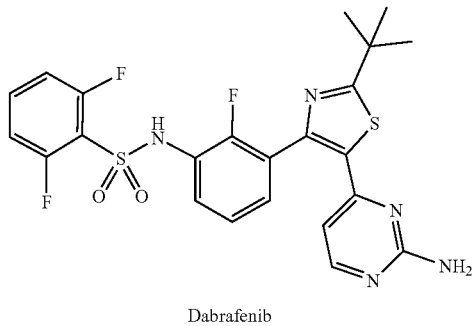

Dabrafenib

3
-continued

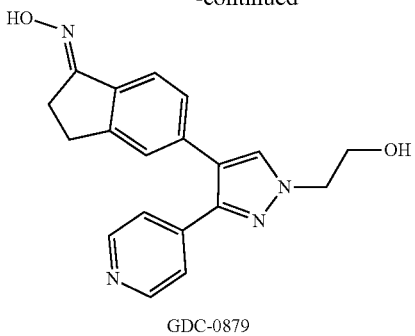

GDC-0879

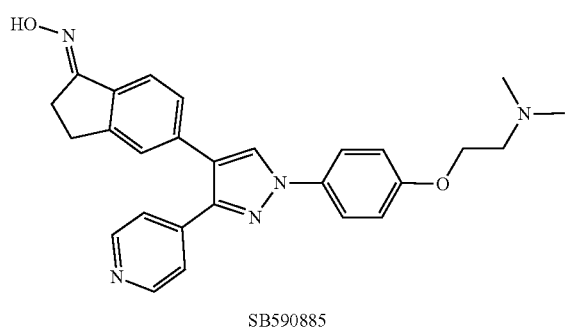

SB590885

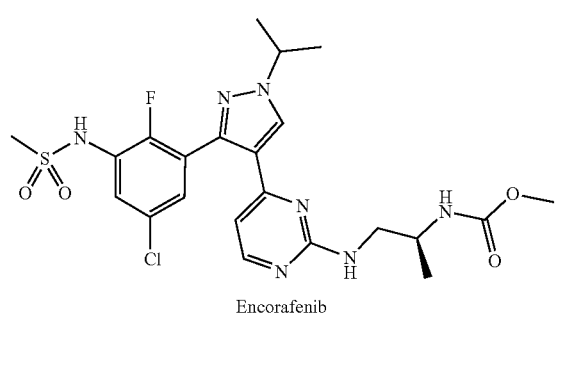

Encorafenib

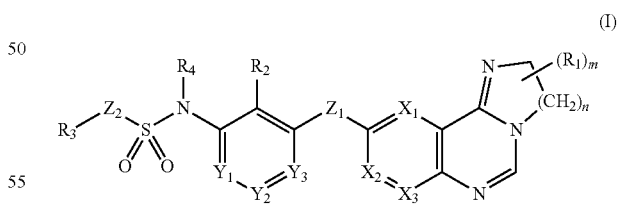

AZ628

4
-continued

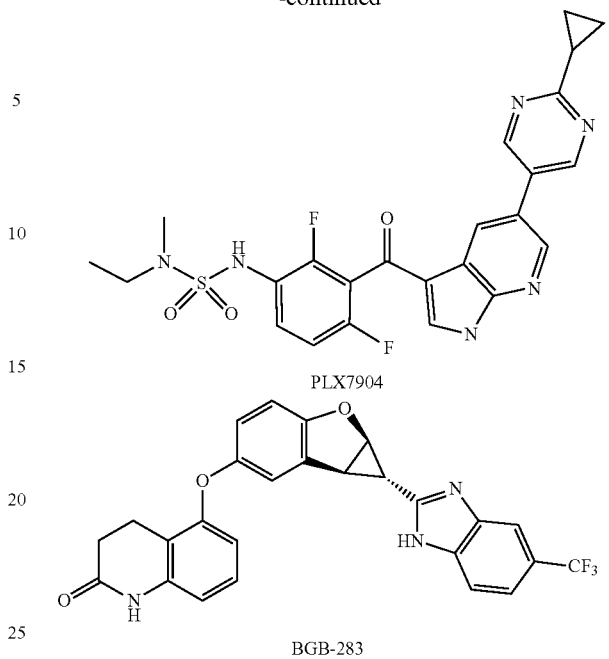

However, due to their structural characteristics, many kinase inhibitors are substrates of active transporters such as P-glycoproteins (P-gp) or breast cancer resistance protein (BCRP), and have very low tendency to penetrate into cell membrane, as well as into brain. Therefore, they are not suitable to be used for the treatment of tumors or cancers in the brain, which is protected by the blood-brain barrier (BBB).

Thus, the compounds of the present disclosure, which are selective inhibitors of certain kinases, are useful in the treatment of abnormal cell growth, in particular cancers in mammals. In addition, these compounds have good penetration of cell membrane, therefore, are useful for treating tumors or cancers, including brain tumors, in humans.

SUMMARY

In one aspect, provided is a compound of Formula (I):

(I)

or a pharmaceutically acceptable salt, solvate or isotopic derivative thereof, wherein:
$X_1$, $X_2$, and $X_3$ are each independently N or $CR^a$;
$Y_1$, $Y_2$, and $Y_3$ are each independently N or $CR^b$;
$Z_1$ is O, S, $NR^c$ or $CR^dR^e$;
$Z_2$ is a bond or $NR^f$;
m is 0, 1, 2 or 3;
n is 1, 2 or 3;
$R_1$, $R_2$, $R_3$, $R^a$, $R^b$, $R^d$, and $R^e$ are each independently selected from the group consisting of hydrogen, halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$, —NR$^g$C(O)OR$^h$, substituted or unsubstituted cycloalkyl, substituted or unsubstituted cycloalkenyl, substituted or unsubstituted aryl, substituted or unsubstituted heteroaryl, and substituted or unsubstituted heterocycloalkyl;

R$_4$ is hydrogen or C$_1$-C$_6$ alkyl; and

R$^c$, R$^f$, R$^g$, R$^h$, and R$^i$ are each independently H, C$_1$-C$_6$ alkyl, or C$_1$-C$_6$ haloalkyl.

Provided in other aspects are compounds of Formula (I-1),

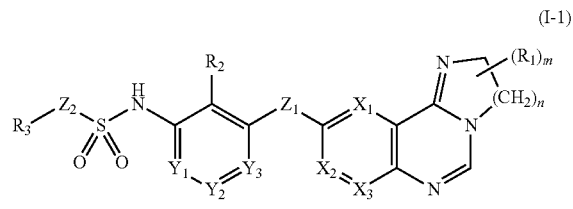
(I-1)

wherein

X$_1$, X$_2$, and X$_3$ are each independently N or CR$^a$;

Y$_1$, Y$_2$, and Y$_3$ are each independently N or CR$^b$;

Z$_1$ is O, S, NR$^c$ or CR$^d$R$^e$;

Z$_2$ is a bond or NR$^f$;

m is 0, 1, 2 or 3;

n is 1, 2 or 3;

R$_1$, R$_2$, R$_3$, R$^a$, R$^b$, R$^d$, and R$^e$ are each independently selected from the group consisting of hydrogen, halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, —OR$^g$, —SR$^g$, —S(O)$_{2R}$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$, —NR$^g$C(O)OR$^h$, substituted or unsubstituted cycloalkyl, substituted or unsubstituted cycloalkenyl, substituted or unsubstituted aryl, substituted or unsubstituted heteroaryl, and substituted or unsubstituted heterocycloalkyl; and R$^c$, R$^f$, R$^g$, R$^h$, and R$^i$ are each independently H or C$_1$-C$_6$ alkyl.

Provided in other aspects are compounds of Formula (I-2a), (I-2b), and (I-2c):

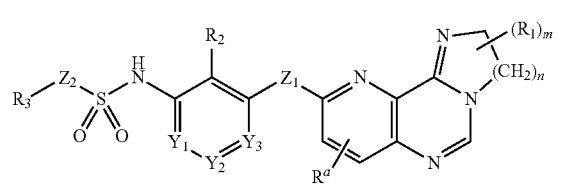
(I-2a)

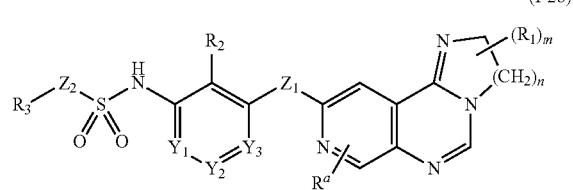
(I-2b)

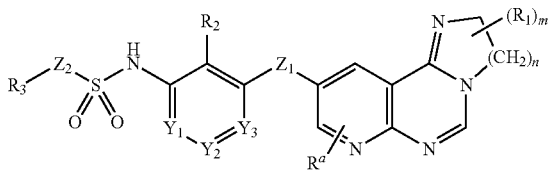
(I-2c)

or a pharmaceutically acceptable salt, solvate or isotopic derivative thereof, wherein Y$_1$, Y$_2$, Y$_3$, Z$_1$, Z$_2$, R$_1$, R$_2$, R$_3$, m, n, and R$^a$ are as defined for Formula (I).

Provided in other aspects are compounds of Formula (I-2d), (I-2e), or (I-2f):

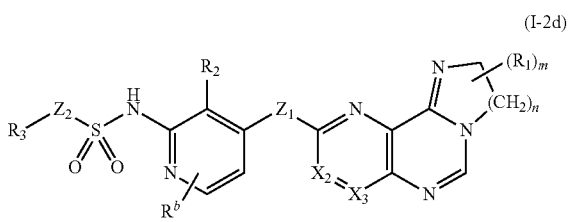
(I-2d)

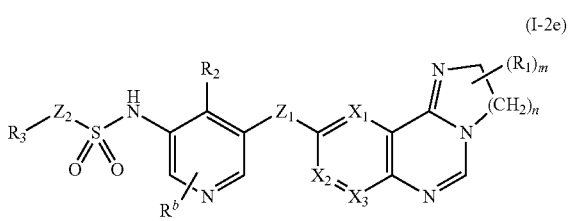
(I-2e)

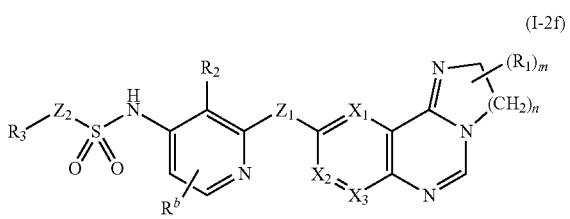
(I-2f)

or a pharmaceutically acceptable salt, solvate or isotopic derivative thereof, wherein X$_1$, X$_2$, X$_3$, Z$_1$, Z$_2$, R$_1$, R$_2$, R$_3$, m, n, and R$^b$ are as defined for Formula (I).

Provided in other aspects are compounds of Formula (I-3a) or (I-3b):

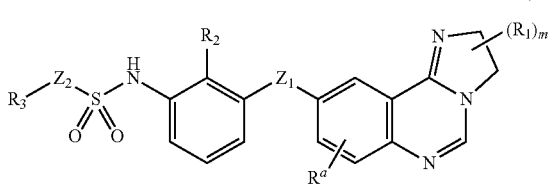
(I-3a)

-continued (I-3b)

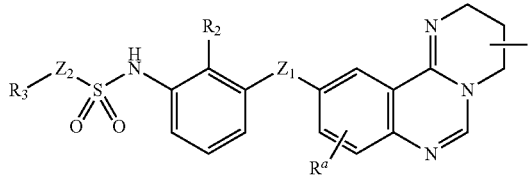

(I-5b)

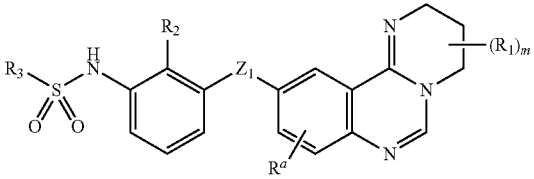

or a pharmaceutically acceptable salt, solvate or isotopic derivative thereof, wherein $Z_1$, $Z_2$, $R_1$, $R_2$, $R_3$, m, and $R^a$ are as defined for Formula (I).

Provided in other aspects are compounds of Formula (I-4a), (I-4b), or (I-4c):

(I-4a)

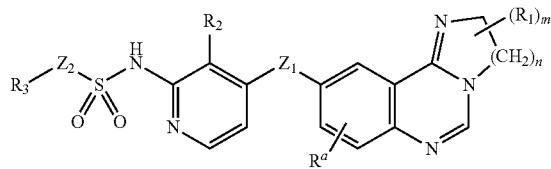

(I-4b)

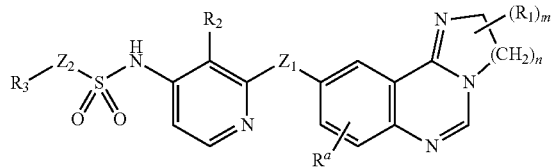

(I-4c)

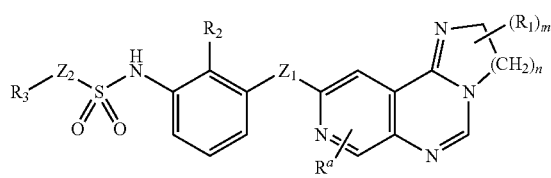

or a pharmaceutically acceptable salt, solvate or isotopic derivative thereof, wherein $Z_1$, $Z_2$, $R_1$, $R_2$, $R_3$, m, n, and $R^a$ are as defined for Formula (I).

Provided in other aspects are compounds of Formula (I-5a) or (I-5b):

(I-5a)

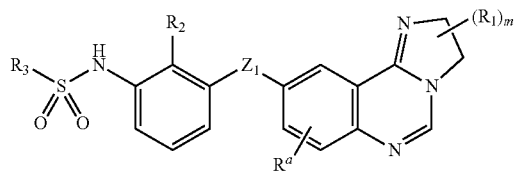

or a pharmaceutically acceptable salt, solvate or isotopic derivative thereof, wherein $Z_1$, $R_1$, $R_2$, $R_3$, m, and $R^a$ are as defined for Formula (I).

In some embodiments of any of the formulae provided herein, such as Formula (I), (I-1), (I-2a), (I-2b), (I-2c), (I-2d), (I-2e), (I-2f), (I-3a), (I-3b), (I-4a), (I-4b), (I-4c), (I-5a), or (I-5b), or a pharmaceutically acceptable salt, solvate or isotopic derivative thereof, $Z_1$ is O. In some embodiments of any of the formulae provided herein, or a pharmaceutically acceptable salt, solvate or isotopic derivative thereof, $Z_2$ is a bond.

In some embodiments of any of the formulae provided herein, or a pharmaceutically acceptable salt, solvate or isotopic derivative thereof, m is 0. In some embodiments, m is 1. In other embodiments, m is 2. In some embodiments of any of the formulae provided herein, or a pharmaceutically acceptable salt, solvate or isotopic derivative thereof, n is 1. In some embodiments, n is 2.

In some embodiments of any of the formulae provided herein, or a pharmaceutically acceptable salt, solvate or isotopic derivative thereof, each $R_1$ is independently hydrogen, —OH, —$C_1$-$C_6$ alkyl, $C_1$-$C_6$ alkoxy, or $C_1$-$C_6$ dialkylamino, wherein the $C_1$-$C_6$ alkyl is optionally substituted with halogen. Examples of $C_1$-$C_6$ dialkylamino (i.e., —$NR^xR^y$, wherein $R^x$ and $R^y$ are each independently —$C_1$-$C_6$ alkyl) include, but are not limited to —$N(CH_3)_2$, —$N(CH_2CH_3)_2$, —$N(CH_3)CH_2CH_3$, and —$N(CH(CH_3)_2)_2$. In some embodiments, each $R_1$ is independently $C_1$-$C_6$ alkyl substituted with halogen, —CN, —$NO_2$, —OH, oxo, and —$NR^{1a}R^{1b}$, wherein $R^{1a}$ and $R^{1b}$ are each independently H or $C_1$-$C_6$ alkyl. In some embodiments, $R_1$ is hydrogen. In some embodiments of any of the formulae provided herein, or a pharmaceutically acceptable salt, solvate or isotopic derivative thereof, $R_2$ is hydrogen, cyano, nitro, halogen, $MeSO_2$, $C_1$-$C_6$ alkyl, $C_1$-$C_6$ alkoxy, or —$NR^hR^i$, wherein the $C_1$-$C_6$ alkyl is optionally substituted with one or more halogen, and $R^h$ and $R^i$ are each independently $C_1$-$C_6$ alkyl. In some embodiments, $R_2$ is CN. In some embodiments, $R_2$ is Cl. In some embodiments, $R_2$ is $CF_3$.

In some embodiments of any of the formulae provided herein, or a pharmaceutically acceptable salt, solvate or isotopic derivative thereof, $R_3$ is $C_1$-$C_6$ alkyl, or aryl or heteroaryl, wherein the aryl or heteroaryl is optionally substituted with one or more groups selected from halogen and $C_1$-$C_6$ alkyl. In some embodiments, $R_3$ is 2-fluorophenyl. In some embodiments, $R_3$ is pyrrolidinyl. In certain embodiments, $R_3$ is 3-fluoropyrrolidinyl. In some embodiments, $R_3$ is propyl. In some embodiments, $R_3$ is thiophenyl. In some embodiments, $R_3$ is $C_1$-$C_6$ alkyl substituted with one or more groups selected from halogen, —CN, —$NO_2$, —OH, oxo, and —$NR^{3a}R^{3b}$, wherein $R^{3a}$ and $R^{3b}$ are each independently H or $C_1$-$C_6$ alkyl. In particular embodiments, $R_3$ is 3-fluoropropyl or 3-hydroxypropyl. In some embodiments, $R_3$ is —$NR^hR^i$, and $R^h$ and $R^i$ are each independently H or $C_1$-$C_6$ alkyl, or $C_1$-$C_6$ haloalkyl. In certain embodiments, $R_3$ is —N(CH$_3$)CH$_2$CH$_3$, —N(CH$_3$)CH$_2$CH$_2$F, or —N(CH$_3$)CH$_3$.

In some embodiments of any of the formulae provided herein, or a pharmaceutically acceptable salt, solvate or isotopic derivative thereof, $R^a$ is H. In some embodiments, $R^a$ is F. In some embodiments of any of the formulae provided herein, or a pharmaceutically acceptable salt, solvate or isotopic derivative thereof, $R^b$ is H. In some embodiments, $R^b$ is F.

Provided in some embodiments are compounds of Table 1, or a pharmaceutically acceptable salt, solvate or isotopic derivative thereof. Also provided are compounds of Table 2, or a pharmaceutically acceptable salt, solvate or isotopic derivative thereof.

In some aspects, provided are pharmaceutical compositions containing a compound of any of the formulae described herein, or a pharmaceutically acceptable salt, solvate or isotopic derivative thereof, and a pharmaceutically acceptable diluent or carrier.

In some aspects, provided are combinations containing at least one compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt, solvate or isotopic derivative thereof, and a second prophylactic or therapeutic agent.

In some aspects, provided are compounds of Formula (I), such as compounds of Formula (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt, solvate or isotopic derivative thereof, for use in treating and/or preventing a proliferation disorder, such as a cancer, or a tumor in a subject. In some embodiments, the proliferation disorder or cancer is selected from the group consisting of malignant or benign tumors of the liver, kidney, bladder, breast, gastric, ovarian, colorectal, prostate, pancreatic, lung, vulval, thyroid, hepatic carcinomas, sarcomas, glioblastomas, head and neck, melanoma, and other hyperplastic conditions such as benign hyperplasia of the skin and benign hyperplasia of the prostate.

Provided in some aspects are methods of treating and/or preventing a proliferation disorder, such as a cancer, or a tumor in a subject, wherein the method includes administering to the subject an effective amount of a compound of any of the formulae presented herein, or a pharmaceutically acceptable salt, solvate or isotopic derivative thereof, or a pharmaceutical composition containing a compound of any of the formulae disclosed herein, or a combination containing any of the formulae disclosed herein. In some embodiments, the proliferation disorder or cancer is selected from the group consisting of malignant or benign tumors of the liver, kidney, bladder, breast, gastric, ovarian, colorectal, prostate, pancreatic, lung, vulval, thyroid, hepatic carcinomas, sarcomas, glioblastomas, head and neck, melanoma, and other hyperplastic conditions such as benign hyperplasia of the skin and benign hyperplasia of the prostate.

In some aspects, the present disclosure provides use of at least one compound of any of the formulae described herein, or a pharmaceutically acceptable salt, solvate or isotopic derivative thereof, for the manufacture of a medicament.

In some aspects, the present disclosure provides a method for producing an anti-proliferative effect in a subject having a proliferation disorder, a cancer, or a tumor which is sensitive to inhibition of B-Raf V600E kinase, including administering to the subject an effective amount of a compound of any of the formulae presented herein, or a pharmaceutically acceptable salt, solvate or isotopic derivative thereof, or a pharmaceutical composition containing a compound of any of the formulae disclosed herein, or a combination containing any of the formulae disclosed herein.

In some aspects, provided are compounds of Formula (I), such as compounds of Formula (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt, solvate or isotopic derivative thereof, for use in the treatment of a neurodegenerative disease. In some embodiments, the neurodegenerative disease is selected from the group consisting of Amyotrophic lateral sclerosis, Parkinson's disease, Alzheimer's disease, and Huntington's disease.

In some aspects, the present disclosure provides a method for treating a neurodegenerative disease in a subject. In some embodiments, the method includes administering to the subject an effective amount of a compound of any of the formulae presented herein, or a pharmaceutically acceptable salt, solvate or isotopic derivative thereof, or a pharmaceutical composition containing a compound of any of the formulae disclosed herein, or a combination containing any of the formulae disclosed herein. In some embodiments, the neurodegenerative disease is selected from the group consist of Amyotrophic lateral sclerosis, Parkinson's disease, Alzheimer's disease, and Huntington's disease.

In yet another aspect, provided are methods for inhibiting an activity of a B-Raf V600E kinase in a cell, including contacting the cell with an effective amount of a compound of any of the formulae presented herein, or a pharmaceutically acceptable salt, solvate or isotopic derivative thereof, or a pharmaceutical composition containing a compound of any of the formulae disclosed herein, or a combination containing any of the formulae disclosed herein, wherein the contacting is in vitro, ex vivo, or in vivo.

DETAILED DESCRIPTION

Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

As used herein, reference to "about" a value or parameter herein includes (and describes) embodiments that are directed to that value or parameter per se. For example, description referring to "about X" includes description of "X".

Unless clearly indicated otherwise, "an individual" or "a subject" as used herein intends a mammal, including but not limited to a human, bovine, primate, equine, canine, feline, porcine, and ovine animals. Thus, the compositions and methods provided herein have use in both human medicine and in the veterinary context, including use in agricultural animals and domestic pets. The individual may be a human who has been diagnosed with or is suspected of having a condition described herein, such as cancer. The individual may be a human who exhibits one or more symptoms associated with a condition described herein, such as cancer. The individual may be a human who has a mutated or abnormal gene associated with a condition described herein, such as cancer. The individual may be a human who is genetically or otherwise predisposed to or at risk of developing a condition described herein, such as cancer.

As used herein, "treatment" or "treating" is an approach for obtaining beneficial or desired results including clinical results. For purposes of the compositions and methods provided herein, beneficial or desired clinical results include, but are not limited to, one or more of the following: decreasing one or more symptoms resulting from the condition, diminishing the extent of the condition, stabilizing the condition (e.g., preventing or delaying the worsening of the condition), preventing or delaying the spread (e.g., metastasis) of the condition, delaying or slowing the progression of the condition, ameliorating a disease state, providing a remission (whether partial or total) of a disease, decreasing the dose of one or more other medications required to treat the condition, enhancing the effect of another medication used to treat the condition, increasing the quality of life of an individual having the condition, and/or prolonging survival. A method of treating cancer encompasses a reduction of the pathological consequence of cancer. The methods described herein contemplate any one or more of these aspects of treatment.

As used herein, an "at risk" individual is an individual who is at risk of developing a disease or condition described herein, such as cancer. An individual "at risk" may or may not have detectable disease, and may or may not have displayed detectable disease prior to the treatment methods described herein. "At risk" denotes that an individual has one or more so-called risk factors, which are measurable parameters that correlate with development of a disease or condition described herein, such as cancer. An individual having one or more of these risk factors has a higher probability of developing the disease or condition than an individual without these risk factor(s).

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound provided herein alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound provided herein which in combination with its parameters of efficacy and toxicity, should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds. In various embodiments, an effective amount of the composition or therapy may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of a disease or condition described herein, such as cancer.

As is understood in the art, an "effective amount" may be in one or more doses, i.e., a single dose or multiple doses may be required to achieve the desired treatment endpoint. An effective amount may be considered in the context of administering one or more therapeutic agents, and a compound, or pharmaceutically acceptable salt thereof, may be considered to be given in an effective amount if, in conjunction with one or more other agents, a desirable or beneficial result may be or is achieved.

A "therapeutically effective amount" refers to an amount of a compound or salt thereof sufficient to produce a desired therapeutic outcome (e.g., reducing the severity or duration of, stabilizing the severity of, or eliminating one or more symptoms of a disease or condition described herein, such as cancer). For therapeutic use, beneficial or desired results include, e.g., decreasing one or more symptoms resulting from the disease (biochemical, histologic and/or behavioral), including its complications and intermediate pathological phenotypes presenting during development of the disease or condition, increasing the quality of life of those suffering from the disease or condition, decreasing the dose of other medications required to treat the disease or condition, enhancing effect of another medication, delaying the progression of the disease or condition, and/or prolonging survival of patients.

It is understood that an effective amount of a compound or pharmaceutically acceptable salt thereof, including a prophylactically effective amount, may be given to an individual in the adjuvant setting, which refers to a clinical setting in which an individual has had a history of cancer, and generally (but not necessarily) has been responsive to therapy, which includes, but is not limited to, surgery (e.g., surgical resection), radiotherapy, and chemotherapy. However, because of their history of cancer, these individuals are considered at risk of developing cancer. Treatment or administration in the "adjuvant setting" refers to a subsequent mode of treatment.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound provided herein in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound provided herein as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear or branched univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl") or 1 to 6 carbon atoms (a "$C_1$-$C_6$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl and iso-propyl. This term is exemplified by groups such as methyl, t-butyl, n-heptyl, octyl, and the like.

"Cycloalkyl" refers to and includes cyclic univalent hydrocarbon structures. Cycloalkyl can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl, and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —CH=CH—CH=$CH_2$.

"Cyclolkenyl" refers to an unsaturated hydrocarbon group within a cycloalkyl having at least one site of olefinic unsaturation (i.e., having at least one moiety of the formula C=C). Cycloalkenyl can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl, and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like.

The term "alkoxy" refers to an —O-alkyl group, where the O is the point of attachment to the rest of the molecule, and alkyl is as defined above.

"Haloalkyl" refers to an alkyl group with one or more halo substituents, such as one, two, or three halo substituents. Examples of haloalkyl groups include —$CF_3$, —$(CH_2)F$, —$CHF_2$, $CH_2Br$, —$CH_2CF_3$, —$CH_2CHF_2$, and —$CH_2CH_2F$.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

The term "halogen" represents chlorine, fluorine, bromine, or iodine. The term "halo" represents chloro, fluoro, bromo, or iodo.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

Any formula given herein is intended to represent compounds having structures depicted by the structural formula as well as certain variations or forms. In particular, compounds of any formula given herein, such compound of Formula (I), (I-1), (I-2a), (I-2b), (I-2c), (I-2d), (I-2e), (I-2f), (I-3a), (I-3b), (I-4a), (I-4b), (I-4c), (I-5a), or (I-5b), may have asymmetric centers and therefore exist in different enantiomeric forms. These steromeric mixtures can be separated into their individual stereomers on the basis of their physical chemical or optical differences by methods known to those skilled in the art, for example, by chromatography or fractional crystallization. All such isomers, including diastereomers and enantiomers are considered as part of the invention. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds described herein include isotopes of hydrogen, carbon, nitrogen, oxygen, phosphorous, fluorine, chlorine, and iodine, such as $^{2}H$, $^{3}H$, C, $^{13}C$, $^{14}C$, $^{15}N$, $^{18}O$, $^{17}O$, $^{31}P$, $^{32}P$, $^{5}S$, $^{18}F$, $^{36}Cl$, and $^{125}I$, respectively. Substitution with heavier isotopes such as deuterium (i.e., $^{2}H$) may afford certain therapeutic advantages resulting from greater metabolic stability, for example increased in vivo half-life or reduced dosage requirements. Isotopically labeled compounds described herein and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Exemplary Compounds

Formula I

Compounds and salts thereof (such as pharmaceutically acceptable salts) are detailed herein, including in the Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

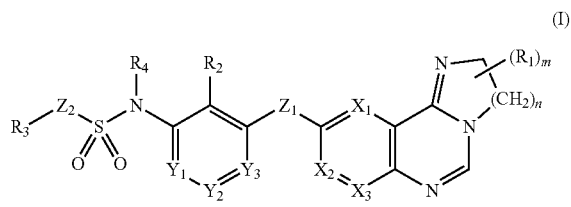

(I)

or a pharmaceutically acceptable salt, solvate or isotopic derivative thereof, wherein:
$X_1$, $X_2$, and $X_3$ are each independently N or $CR^a$;
$Y_1$, $Y_2$, and $Y_3$ are each independently N or $CR^b$;
$Z_1$ is O, S, $NR^c$ or $CR^dR^e$;
$Z_2$ is a bond or $NR^f$;
m is 0, 1, 2 or 3;
n is 1, 2 or 3;
$R_1$, $R_2$, $R_3$, $R^a$, $R^b$, $R^d$, and $R^e$ are each independently selected from the group consisting of hydrogen, halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, —$OR^g$, —$SR^g$, —$S(O)_2R^g$, —$NR^hR^i$, —$C(O)R^g$, —$OC(O)R^g$, —$C(O)OR^g$, —$C(O)NR^hR^i$, —$OC(O)NR^hR^i$, —$NR^gC(O)R^h$, —$NR^gC(O)OR^h$, substituted or unsubstituted cycloalkyl, substituted or unsubstituted cycloalkenyl, substituted or unsubstituted aryl, substituted or unsubstituted heteroaryl, and substituted or unsubstituted heterocycloalkyl;
$R_4$ is hydrogen or $C_1$-$C_6$ alkyl; and
$R^c$, $R^f$, $R^g$, $R^h$, and $R^i$ are each independently H, $C_1$-$C_6$ alkyl, or $C_1$-$C_6$ haloalkyl.

In some embodiments, the compound of Formula (I) is a compound of Formula (I-1),

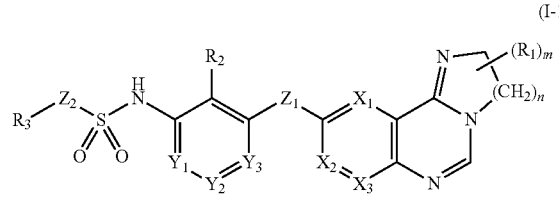
(I-1)

wherein
$X_1$, $X_2$, and $X_3$ are each independently N or $CR^a$;
$Y_1$, $Y_2$, and $Y_3$ are each independently N or $CR^b$;
$Z_1$ is O, S, $NR^c$ or $CR^dR^e$;
$Z_2$ is a bond or $NR^f$;
m is 0, 1, 2 or 3;
n is 1, 2 or 3;
$R_1$, $R_2$, $R_3$, $R^a$, $R^b$, $R^d$, and $R^e$ are each independently selected from the group consisting of hydrogen, halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, —$OR^g$, —$SR^g$, —$S(O)_2R^g$, —$NR^hR^i$, —$C(O)R^g$, —$OC(O)R^g$, —$C(O)OR^g$, —$C(O)NR^hR^i$, —$OC(O)NR^hR^i$, —$NR^gC(O)R^h$, —$NR^gC(O)OR^h$, substituted or unsubstituted cycloalkyl, substituted or unsubstituted cycloalkenyl, substituted or unsubstituted aryl, substituted or unsubstituted heteroaryl, and substituted or unsubstituted heterocycloalkyl; and
$R^c$, $R^f$, $R^g$, $R^h$, and $R^i$ are each independently H or $C_1$-$C_6$ alkyl.

In some aspects, provided are compounds of Formula (I-2a), (I-2b), and (I-2c):

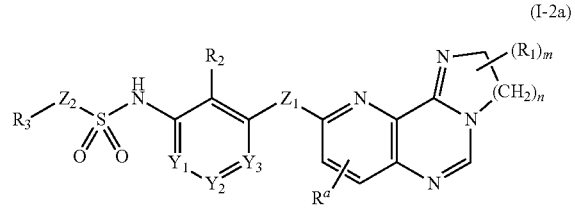
(I-2a)

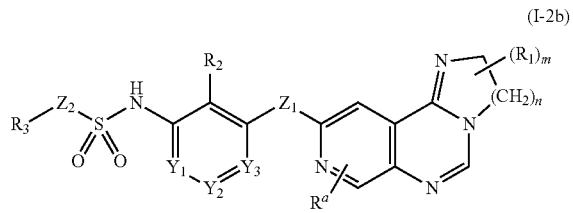
(I-2b)

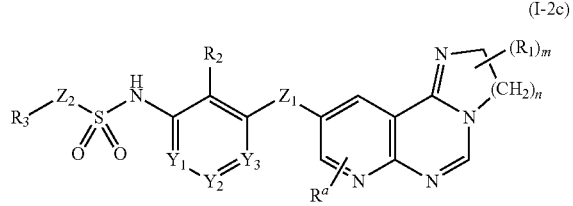
(I-2c)

wherein $Y_1$, $Y_2$, $Y_3$, $Z_1$, $Z_2$, $R_1$, $R_2$, $R_3$, m, n, and $R^a$ are as defined for Formula (I).

In some aspects, provided are compounds of Formula (I-2d), (I-2e), and (I-2f):

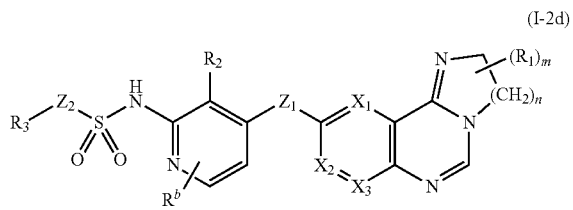
(I-2d)

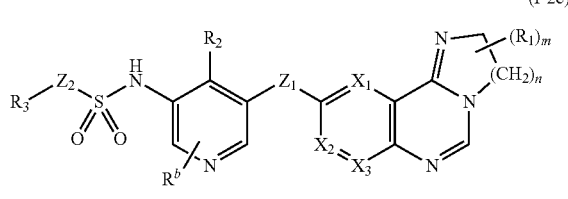
(I-2e)

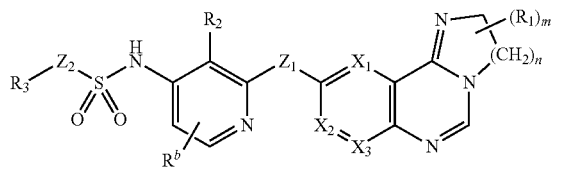
(I-2f)

wherein $X_1$, $X_2$, $X_3$, $Z_1$, $Z_2$, $R_1$, $R_2$, $R_3$, m, n, and $R^b$ are as defined for Formula (I).

In some aspects, provided are compounds of Formula (I-3a) and (I-3b):

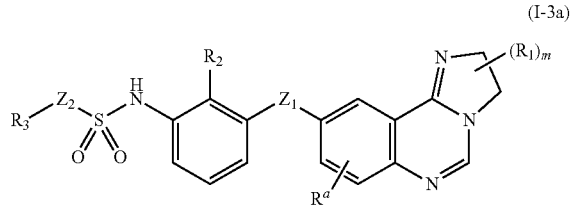
(I-3a)

-continued (I-3b)

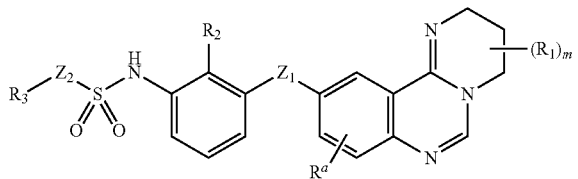

wherein $Z_1$, $Z_2$, $R_1$, $R_2$, $R_3$, m, and $R^a$ are as defined for Formula (I).

In some aspects, provided are compounds of Formula (I-4a), (I-4b), and (I-4c):

(I-4a)

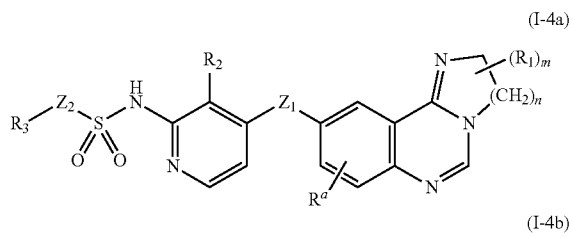

(I-4b)

(I-4c)

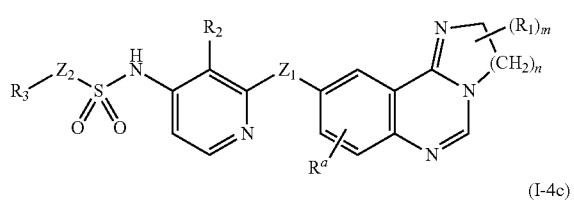

wherein $Z_1$, $Z_2$, $R_1$, $R_2$, $R_3$, m, n, and $R^a$ are as defined for Formula (I).

In other aspects, provided are compounds of Formula (I-5a) and (I-5b):

(I-5a)

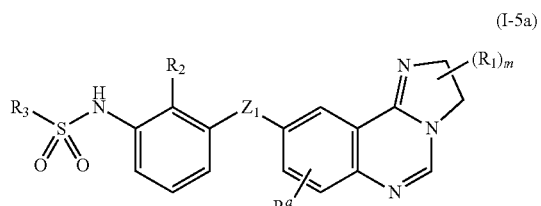

(I-5b)

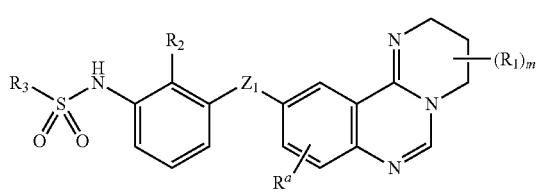

wherein $Z_1$, $R_1$, $R_2$, $R_3$, m, n, and $R^a$ are as defined for Formula (I).

In some embodiments of Formula (I) or any variation thereof, $X_1$, $X_2$, and $X_3$ are each independently N or $CR^a$, wherein at least one of $X_1$, $X_2$, and $X_3$ is N. In some embodiments, $X_1$, $X_2$, and $X_3$ are each $CR^a$. In some embodiments, one of $X_1$, $X_2$, and $X_3$ is N. In some embodiments, $X_1$ is N, $X_2$ is $CR^a$, and $X_3$ is $CR^a$. In some embodiments, $X_1$ is $CR^a$, $X_2$ is N, and $X_3$ is $CR^a$. In some embodiments, $X_1$ is $CR^a$, $X_2$ is $CR^a$, and $X_3$ is N. In some embodiments, two of $X_1$, $X_2$, and $X_3$ are N. In some embodiments, $X_1$ and $X_2$ are each N, and $X_3$ is $CR^a$. In some embodiments, $X_1$ and $X_3$ are each N, and $X_2$ is $CR^a$. In some embodiments, $X_2$ and $X_3$ are each N, and $X_1$ is $CR^a$. In some embodiments, $X_1$, $X_2$, and $X_3$ are each N. In any of the foregoing embodiments, each $R^a$ is selected from the group consisting of hydrogen, halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$, —NR$^g$C(O)OR$^h$, substituted or unsubstituted cycloalkyl, substituted or unsubstituted cycloalkenyl, substituted or unsubstituted aryl, substituted or unsubstituted heteroaryl, and substituted or unsubstituted heterocycloalkyl. In some embodiments, each $R^a$ is selected from the group consisting of hydrogen, halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$ and —NR$^g$C(O)OR$^h$, wherein each R$^g$, R$^h$, and R$^i$ are each independently H or $C_1$-$C_6$ alkyl. In some embodiments, each $R^a$ is selected from the group consisting of hydrogen, halogen, —CN, —NO$_2$, substituted or unsubstituted $C_1$-$C_6$ alkyl, $C_1$-$C_6$ alkoxyl, and —NR$^h$R$^i$, wherein R$^h$ and R$^i$ are each $C_1$-$C_6$ alkyl. In some embodiments, each $R^a$ is selected from the group consisting of hydrogen, halogen, —CN and —NO$_2$. In some embodiments, $R^a$ is H. In some embodiments, $R^a$ is halogen. In some embodiments, $R^a$ is fluoro. In some embodiments, $X_1$, $X_2$, and $X_3$ are each CH.

In some embodiments of Formula (I) or any variation thereof, $Y_1$, $Y_2$, and $Y_3$ are each independently N or $CR^b$, wherein at least one of $Y_1$, $Y_2$, and $Y_3$ is N. In some embodiments, $Y_1$, $Y_2$, and $Y_3$ are each $CR^b$. In some embodiments, one of $Y_1$, $Y_2$, and $Y_3$ is N. In some embodiments, $Y_1$ is N, $Y_2$ is $CR^b$, and $Y_3$ is $CR^b$. In some embodiments, $Y_1$ is $CR^b$, $Y_2$ is N, and $Y_3$ is $CR^b$. In some embodiments, $Y_1$ is $CR^b$, $Y_2$ is $CR^b$, and $Y_3$ is N. In some embodiments, two of $Y_1$, $Y_2$, and $Y_3$ are N. In some embodiments, $Y_1$ and $Y_2$ are each N, and $Y_3$ is $CR^b$. In some embodiments, $Y_1$ and $Y_3$ are each N, and $Y_2$ is $CR^b$. In some embodiments, $Y_2$ and $Y_3$ are each N, and $Y_1$ is $CR^b$. In some embodiments, $Y_1$, $Y_2$, and $Y_3$ are each N. In any of the foregoing embodiments, each $R^b$ is selected from the group consisting of hydrogen, halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$, —NR$^g$C(O)OR$^h$, substituted or unsubstituted cycloalkyl, substituted or unsubstituted cycloalkenyl, substituted or unsubstituted aryl, substituted or unsubstituted heteroaryl, and substituted or unsubstituted heterocycloalkyl. In some embodiments, each $R^b$ is selected from the group consisting of hydrogen, halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$ and —NR$^g$C(O)OR$^h$, wherein each R$^g$, R$^h$, and R$^i$ are each independently H or C$_1$-C$_6$ alkyl. In some embodiments, each R$^b$ is selected from the group consisting of hydrogen, halogen, —CN, —NO$_2$, substituted or unsubstituted C$_1$-C$_6$ alkyl, C$_1$-C$_6$ alkoxyl, and —NR$^h$R$^i$, wherein R$^h$ and R$^i$ are each C$_1$-C$_6$ alkyl. In some embodiments, each R$^b$ is selected from the group consisting of hydrogen, halogen, —CN and —NO$_2$. In some embodiments, R$^b$ is H. In some embodiments, R$^b$ is halogen. In some embodiments, R$^b$ is fluoro. In some embodiments, R$^b$ is chloro. In some embodiments, R$^b$ is C$_1$-C$_6$ alkyl, substituted with halogen. In some embodiments, R$^b$ is C$_1$-C$_6$ alkyl, substituted with —CF$_3$. In some embodiments, R$^b$ is —CN. In some embodiments, R$^b$ is —NO$_2$. In some embodiments, R$^b$ is —NH$_2$. In some embodiments, Y$_1$, Y$_2$, and Y$_3$ are each CH.

In some embodiments of Formula (I) or any variation thereof, X$_1$, X$_2$, and X$_3$ are each CR$^a$, and Y$_1$, Y$_2$, and Y$_3$ are each CR$^b$. In some embodiments of Formula (I) or any variation thereof, each R$^a$ and R$^b$ are independently selected from the group consisting of hydrogen, halogen, —CN, —NH$_2$ and —NO$_2$. In some embodiments, each R$^a$ is selected from the group consisting of hydrogen, halogen, —CN and —NO$_2$. In some embodiments, each R$^a$ is H or halogen. In some embodiments, each R$^a$ is H. In some embodiments, one of X$_1$, X$_2$, and X$_3$ is CR$^a$, wherein R$^a$ is selected from halogen, —CN, —NH$_2$ and —NO$_2$; and the other two of X$_1$, X$_2$, and X$_3$ are each independently N or CH. In some embodiments, two of X$_1$, X$_2$, and X$_3$ are CR$^a$, wherein each R$^a$ is independently selected from halogen, —CN, —NH$_2$ and —NO$_2$; and the remaining one of X$_1$, X$_2$, and X$_3$ is N or CH. In other embodiments, three of X$_1$, X$_2$, and X$_3$ are CR$^a$, and each R$^a$ is independently selected from halogen, —CN, —NH$_2$ and —NO$_2$. In some embodiments, one or more R$^a$ is halogen. In some embodiments, R$^a$ is F. In some embodiments, one of Y$_1$, Y$_2$, and Y$_3$ is CR$^b$, wherein R$^b$ is selected from halogen, —CN, —NH$_2$ and —NO$_2$; and the other two of Y$_1$, Y$_2$, and Y$_3$ are each independently N or CH. In some embodiments, two of Y$_1$, Y$_2$, and Y$_3$ are CR$^b$, wherein each R$^b$ is independently selected from halogen, —CN, —NH$_2$ and —NO$_2$, and the remaining one of X$_1$, X$_2$, and X$_3$ is N or CH. In other embodiments, three of Y$_1$, Y$_2$, and Y$_3$ are CR$^b$, wherein each R$^b$ is independently selected from halogen, —CN, —NH$_2$ and —NO$_2$. In some embodiments, each R$^b$ is selected from the group consisting of hydrogen, halogen, —CN, —NH$_2$ and —NO$_2$. In some embodiments, each R$^b$ is H or halogen. In some embodiments, each R$^b$ is H. In some embodiments, one or more R$^b$ is halogen. In some embodiments, R$^b$ is F. In some embodiments, R$^b$ is NH$_2$. In some embodiments R$^a$ and R$^b$ are both H.

In some embodiments of Formula (I) or any variation thereof, Z$_1$ is O. In some embodiments, Z$_1$ is S. In some embodiments, Z$_1$ is NR$^c$ or CR$^d$R$^e$. In some embodiments, Z$_2$ is a bond. In some embodiments, Z$_2$ is NR$^f$, wherein R$^f$ is H or C$_1$-C$_6$ alkyl. In some embodiments, Z$_1$ is O and Z$_2$ is NR$^f$. In some embodiments, Z$_1$ is O and Z$_2$ is NH. In some embodiments, Z$_1$ is O and Z$_2$ is N(CH$_3$).

In some embodiments of Formula (I) or any variation thereof, each R$_1$ is independently selected from the group consisting of hydrogen, halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$ and —NR$^g$C(O)OR$^h$, wherein each R$^g$, R$^h$, and R$^i$ are each independently H or C$_1$-C$_6$ alkyl. In some embodiments, each R$_1$ is independently selected from the group consisting of hydrogen, C$_1$-C$_6$ alkyl, —OR$^g$, and —NR$^h$R$^i$, wherein the C$_1$-C$_6$ alkyl is optionally substituted with one or more halogen, and R$^g$, R$^h$ and R$^i$ are each independently H or C$_1$-C$_6$ alkyl. In some embodiments of Formula (I) or any variation thereof, m is 0. In some embodiments, m is 1. In some embodiments, m is 2. In some embodiments, m is 3. It is understood that when m is 0, there are no substituents on the ring bearing —(R$_1$)$_m$ other than hydrogen. In some embodiments, R$_1$ is hydrogen. In some embodiments, R$_1$ is unsubstituted C$_1$-C$_6$ alkyl. In other embodiments, R$_1$ is C$_1$-C$_6$ alkyl substituted with halogen, —CN, —NO$_2$, —OH, oxo, and —NR$^{1a}$R$^{1b}$, wherein R$^{1a}$ and R$^{1b}$ are each independently H or C$_1$-C$_6$ alkyl. In some embodiments, R$_1$ is C$_1$-C$_6$ alkyl substituted with —NR$^{1a}$R$^{1b}$, wherein R$^{1a}$ and R$^{1b}$ are each independently H or C$_1$-C$_6$ alkyl. In some embodiments, m is 1 and each R$_1$ is independently selected from the group consisting of halogen, —CN, —NO$_2$, substituted or unsubstituted C$_1$-C$_6$ alkyl, substituted or unsubstituted C$_2$-C$_6$ alkenyl, and substituted or unsubstituted C$_2$-C$_6$ alkynyl. In some embodiments, m is 1 and R$_1$ is methyl substituted with —N(CH$_3$)$_2$. In some embodiments, m is 1 or 2; and R$_1$ is C$_1$-C$_6$ alkyl, unsubstituted or substituted with —NR$^{1a}$R$^{1b}$, wherein R$^{1a}$ and R$^{1b}$ are each independently H or C$_1$-C$_6$ alkyl. In some embodiments, m is 2 and each R$_1$ is independently selected from the group consisting of halogen, —CN, —NO$_2$, substituted or unsubstituted C$_1$-C$_6$ alkyl, substituted or unsubstituted C$_2$-C$_6$ alkenyl, and substituted or unsubstituted C$_2$-C$_6$ alkynyl. In some embodiments, m is 2 and each R$_1$ is independently C$_1$-C$_6$ alkyl. In certain embodiments, m is 2 and each R$_1$ is methyl.

In some embodiments of Formula (I) or any variation thereof, R$_2$ is selected from the group consisting of hydrogen, halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$ and —NR$^g$C(O)OR$^h$, wherein each R$^g$, R$^h$, and R$^i$ are each independently H or C$_1$-C$_6$ alkyl. In some embodiments, R$_2$ is selected from the group consisting of hydrogen, cyano, nitro, halogen, MeSO$_2$, C$_1$-C$_6$ alkyl, C$_1$-C$_6$ alkoxy, and C$_1$-C$_6$ dialkylamino group, wherein the C$_1$-C$_6$ alkyl is optionally substituted with one or more halogen. Examples of C$_1$-C$_6$ dialkylamino (i.e., —NR$^x$R$^y$, wherein R$^x$ and R$^y$ are each independently —C$_1$-C$_6$ alkyl) include, but are not limited to —N(CH$_3$)$_2$, —N(CH$_2$CH$_3$)$_2$, —N(CH$_3$)CH$_2$CH$_3$, and —N(CH(CH$_3$)$_2$)$_2$. In some embodiments, R$_2$ is hydrogen. In some embodiments, R$_2$ is —CN. In some embodiments, R$_2$ is —NO$_2$. In some embodiments, R$_2$ is halogen. In some embodiments, R$_2$ is Cl. In some embodiments, R$_2$ is F. In some embodiments, R$_2$ is C$_1$-C$_6$ alkyl, optionally substituted with one or more halogen. In some embodiments, R$_2$ is —CF$_3$.

In some embodiments of Formula (I) or any variation thereof, R$_3$ is selected from the group consisting of hydrogen, halogen, —CN, —NO$_2$, substituted or unsubstituted C$_1$-C$_6$ alkyl, substituted or unsubstituted C$_2$-C$_6$ alkenyl, substituted or unsubstituted C$_2$-C$_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$ and —NR$^g$C(O)OR$^h$, wherein each R$^g$, R$^h$, and R$^i$ are each independently H or C$_1$-C$_6$ alkyl. In some embodiments, R$_3$ is C$_1$-C$_6$ alkyl, or aryl or heteroaryl, wherein the aryl or heteroaryl is optionally substituted with one or more groups selected from halogen and $C_1$-$C_6$ alkyl. In some embodiments, $R_3$ is $C_1$-$C_6$ alkyl. In some embodiments, $R_3$ is $C_1$-$C_6$ alkyl substituted with one or more groups selected from halogen, —CN, —NO$_2$, —OH, oxo, and —NR$^{3a}$R$^{3b}$, wherein R$^{3a}$ and R$^{3b}$ are each independently H or $C_1$-$C_6$ alkyl. In some embodiments, $R_3$ is methyl, ethyl, propyl, isopropyl, butyl, isobutyl, secbutyl or tertbutyl, substituted with halogen or —OH. In some embodiments, $R_3$ is methyl. In some embodiments, $R_3$ is ethyl. In some embodiments, $R_3$ is propyl. In some embodiments, $R_3$ is n-propyl or isopropyl. In some embodiments, $R_3$ is n-propyl or isopropyl substituted with halo or —OH. In s embodiments, $R_3$ is 3-fluoropropyl or 3-hydroxypropyl. In some embodiments, $R_3$ is —NR$^h$R$^i$, wherein R$^h$ and R$^i$ are each independently H or $C_1$-$C_6$ alkyl, or $C_1$-$C_6$ haloalkyl. In some embodiments, $R_3$ is —N(CH$_3$)CH$_2$CH$_3$. In some embodiments, $R_3$ is —N(CH$_3$)CH$_2$CH$_2$F. In other embodiments, $R_3$ is —N(CH$_3$)CH$_3$. In some embodiments, $R_3$ is aryl or heteroaryl, each optionally substituted with one or more groups selected from halogen and $C_1$-$C_6$ alkyl. In some embodiments, $R_3$ is phenyl. In some embodiments, $R_3$ is phenyl, substituted with one or more groups selected from halogen and $C_1$-$C_6$ alkyl. In some embodiments, $R_3$ is 2-fluorophenyl. In some embodiments, $R_3$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl, each optionally substituted with one or more groups selected from halogen and $C_1$-$C_6$ alkyl. In some embodiments, $R_3$ is unsubstituted pyrrolidinyl. In other embodiments, $R_3$ is pyrrolidinyl, substituted with one or more groups selected from halogen and $C_1$-$C_6$ alkyl. In some embodiments, $R_3$ is 3-fluoropyrrolidinyl. In certain embodiments, $R_3$ is (R)-3-fluoropyrrolidinyl. In some embodiments, $R_3$ is thiophenyl.

In some embodiments of Formula (I) or any variation thereof, $R_4$ is hydrogen. In other embodiments, $R_4$ is $C_1$-$C_6$ alkyl, which includes, but is not limited to, methyl, ethyl, n-propyl, isopropyl, n-butyl, isobutyl, secbutyl, or tertbutyl. In certain embodiments, $R_4$ is methyl.

In some embodiments, n is 1. In some embodiments, n is 2. In some embodiments, n is 3.

Any of the embodiments detailed herein with respect to Formula (I), where applicable, apply equally to Formula (I-1), (I-2a), (I-2b), (I-2c), (I-2d), (I-2e), (I-2f), (I-3a), (I-3b), (I-4a), (I-4b), (I-4c), (I-5a), and (I-5b). It is also understood that the descriptions of any variable of Formula (I), (I-1), (I-2a), (I-2b), (I-2c), (I-2d), (I-2e), (I-2f), (I-3a), (I-3b), (I-4a), (I-4b), (I-4c), (I-5a), or (I-5b) may, where applicable, be combined with one or more descriptions of any other variable, the same as if each and every combination of variables were specifically and individually listed. For example, every description of $R_2$ may be combined with every description of $R_1$, $R_3$, $Z_1$, $Z_2$, $Y_1$, $Y_2$, $Y_3$, $X_1$, $X_2$, $X_3$, m, and n the same as if each and every combination were specifically and individually listed. Likewise, every description of $R_3$ may be combined with every description of $R_1$, $R_2$, $Z_1$, $Z_2$, $Y_1$, $Y_2$, $Y_3$, $X_1$, $X_2$, $X_3$, m, and n the same as if each and every description were specifically and individually listed.

In one variation, compounds of the formulae provided herein contain one or more of the following structural features: (i) $Z_1$ is selected from the group consisting of O, NH, and N(CH$_3$); (ii) $Z_2$ is selected from the group consisting of a bond, N(CH$_3$), and N(CH$_2$CH$_3$); (iii) m is 0, m is 1 and $R_1$ is —CH$_2$N(CH$_3$)$_2$, or m is 2 and each $R_1$ is —CH$_3$; (iv) $R_2$ is selected from the group consisting of hydrogen, —CN, —NO$_2$, —NH$_2$, —F, —Cl, and CF$_3$; (v) $R_3$ is selected from the group consisting of n-propyl, isopropyl, 2-fluorophenyl, thiophenyl, 3-fluoropropyl, 3-hydroxypropyl, pyrrolidinyl, 3-fluoropyrrolidinyl, —N(CH$_3$)CH$_2$CH$_3$, —N(CH$_3$)CH$_2$CH$_2$F, and —N(CH$_3$)CH$_3$; (vi) n is 1 or 2; and (vii) $R_4$ is hydrogen or —CH$_3$.

In some embodiments, provided herein are compounds of Formula (I), (I-1), (I-2a), (I-2b), (I-2c), (I-2d), (I-2e), (I-2f), (I-3a), (I-3b), (I-4a), (I-4b), (I-4c), (I-5a), and (I-5b), or pharmaceutically acceptable salts thereof.

In some embodiments, provided herein are compounds and salts thereof described in Table 1, and uses thereof.

TABLE 1

| Compound No. | Structure | Chemical Name |
|---|---|---|
| 1 | 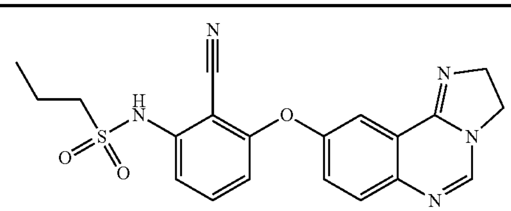 | N-(2-Cyano-3-((2,3-dihydroimidazo[1,2-c]quinazolin-9-yl)oxy)phenyl)propane-1-sulfonamide |
| 2 | 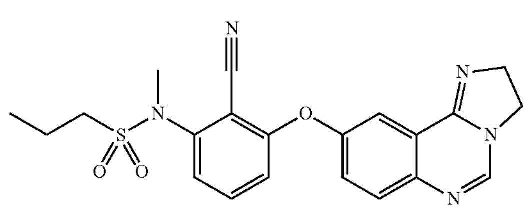 [SMILES: CCCS(=O)(=O)N(C)c1cccc(Oc2ccc3c(c2)C2=NCCN2C=N3)c1C#N] | N-(2-Cyano-3-((2,3-dihydroimidazo[1,2-c]quinazolin-9-yl)oxy)phenyl)-N-methylpropane-1-sulfonamide |

TABLE 1-continued

| Compound No. | Structure | Chemical Name |
|---|---|---|
| 3 | 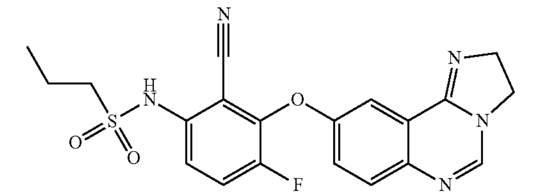 [SMILES: CCCS(=O)(=O)Nc1ccc(F)c(Oc2ccc3c(c2)C2=NCCN2C=N3)c1C#N] | N-(2-Cyano-3-((2,3-dihydroimidazo[1,2-c]quinazolin-9-yl)oxy)-4-fluorophenyl)propane-1-sulfonamide |
| 4 | 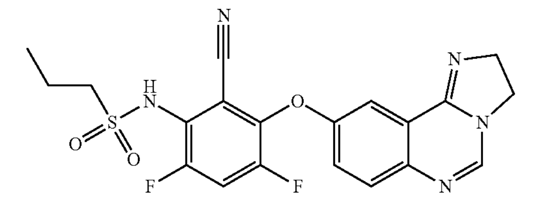 [SMILES: CCCS(=O)(=O)Nc1c(F)cc(F)c(Oc2ccc3c(c2)C2=NCCN2C=N3)c1C#N] | N-(2-Cyano-3-((2,3-dihydroimidazo[1,2-c]quinazolin-9-yl)oxy)-4,6-difluorophenyl)propane-1-sulfonamide |
| 5 | 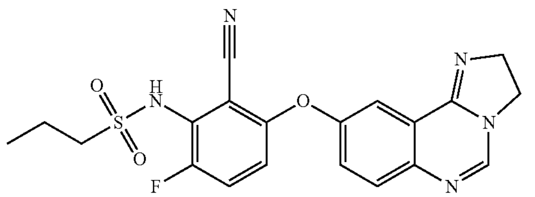 [SMILES: CCCS(=O)(=O)Nc1c(F)ccc(Oc2ccc3c(c2)C2=NCCN2C=N3)c1C#N] | N-(2-Cyano-3-((2,3-dihydroimidazo[1,2-c]quinazolin-9-yl)oxy)-6-fluorophenyl)propane-1-sulfonamide |
| 6 | 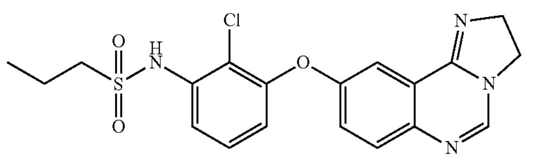 | N-(2-Chloro-3-((2,3-dihydroimidazo[1,2-c]quinazolin-9-yl)oxy)phenyl)propane-1-sulfonamide |
| 7 | 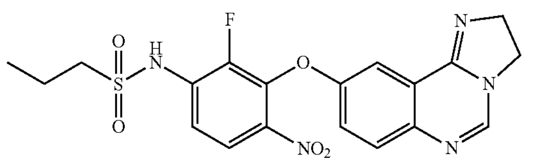 | N-(3-((2,3-Dihydroimidazo[1,2-c]quinazolin-9-yl)oxy)-2-fluoro-4-nitrophenyl)propane-1-sulfonamide |
| 8 | 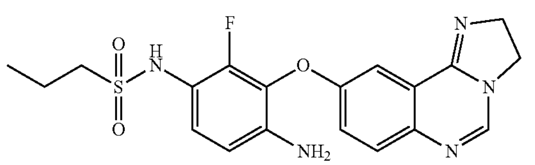 [SMILES: CCCS(=O)(=O)Nc1ccc([N+](=O)[O-])c(Oc2ccc3c(c2)C2=NCCN2C=N3)c1F] | N-(4-Amino-3-((2,3-dihydroimidazo[1,2-c]quinazolin-9-yl)oxy)-2-fluorophenyl)propane-1-sulfonamide |
| 9 | 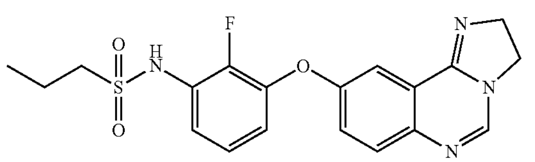 [SMILES: CCCS(=O)(=O)Nc1cccc(Oc2ccc3c(c2)C2=NCCN2C=N3)c1F] | N-(3-((2,3-Dihydroimidazo[1,2-c]quinazolin-9-yl)oxy)-2-fluorophenyl)propane-1-sulfonamide |
| 10 | 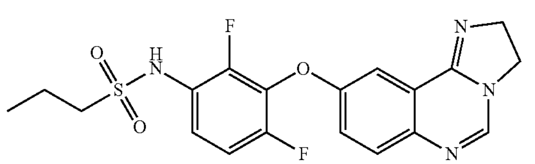 [SMILES: CCCS(=O)(=O)Nc1ccc(F)c(Oc2ccc3c(c2)C2=NCCN2C=N3)c1F] | N-(3-((2,3-Dihydroimidazo[1,2-c]quinazolin-9-yl)oxy)-2,4-difluorophenyl)propane-1-sulfonamide |
| 11 | 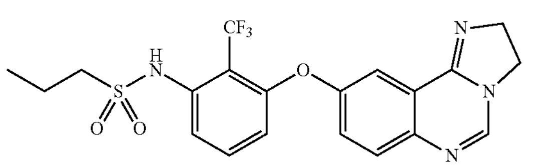 [SMILES: CCCS(=O)(=O)Nc1cccc(Oc2ccc3c(c2)C2=NCCN2C=N3)c1C(F)(F)F] | N-(3-((2,3-Dihydroimidazo[1,2-c]quinazolin-9-yl)oxy)-2-(trifluoromethyl)phenyl)propane-1-sulfonamide |

TABLE 1-continued

| Compound No. | Structure | Chemical Name |
|---|---|---|
| 12 | 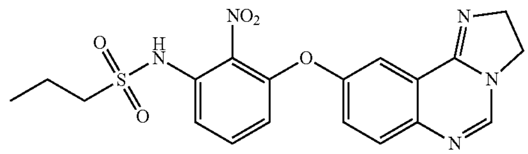 [SMILES: CCCS(=O)(=O)Nc1cccc(Oc2ccc3c(c2)C2=NCCN2C=N3)c1[N+](=O)[O-]] | N-(3-((2,3-Dihydroimidazo[1,2-c]quinazolin-9-yl)oxy)-2-nitrophenyl)propane-1-sulfonamide |
| 13 | 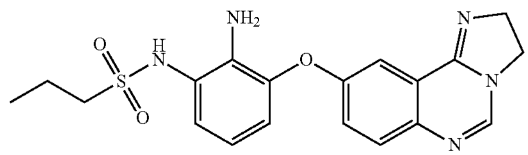 [SMILES: CCCS(=O)(=O)Nc1cccc(Oc2ccc3c(c2)C2=NCCN2C=N3)c1N] | N-(2-Amino-3-((2,3-dihydroimidazo[1,2-c]quinazolin-9-yl)oxy)phenyl)propane-1-sulfonamide |
| 14 | 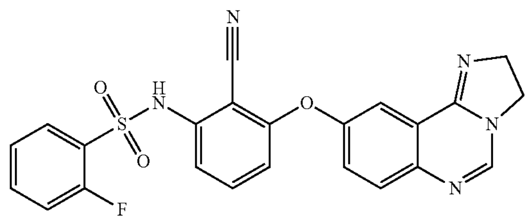 [SMILES: N#Cc1c(NS(=O)(=O)c2ccccc2F)cccc1Oc1ccc2c(c1)C1=NCCN1C=N2] | N-(2-Cyano-3-((2,3-dihydroimidazo[1,2-c]quinazolin-9-yl)oxy)phenyl)-2-fluorobenzenesulfonamide |
| 15 | 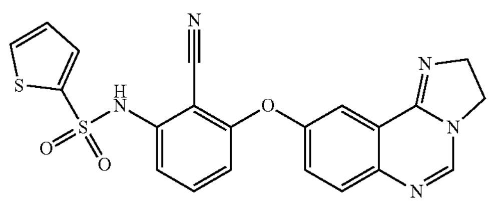 [SMILES: N#Cc1c(NS(=O)(=O)c2cccs2)cccc1Oc1ccc2c(c1)C1=NCCN1C=N2] | N-(2-Cyano-3-((2,3-dihydroimidazo[1,2-c]quinazolin-9-yl)oxy)phenyl)thiophene-2-sulfonamide |
| 16 | 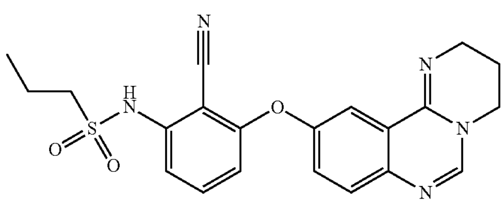 [SMILES: CCCS(=O)(=O)Nc1cccc(Oc2ccc3c(c2)C2=NCCCN2C=N3)c1C#N] | N-(2-cyano-3-((3,4-dihydro-2H-pyrimido[1,2-c]quinazolin-10-yl)oxy)phenyl)propane-1-sulfonamide |
| 17 | 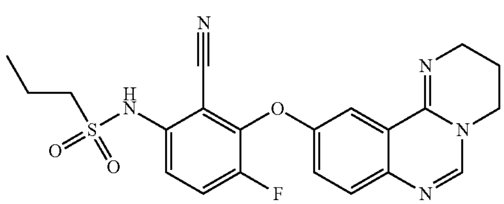 [SMILES: CCCS(=O)(=O)Nc1ccc(F)c(Oc2ccc3c(c2)C2=NCCCN2C=N3)c1C#N] | N-(2-cyano-3-((3,4-dihydro-2H-pyrimido[1,2-c]quinazolin-10-yl)oxy)-4-fluorophenyl)propane-1-sulfonamide |
| 18 | 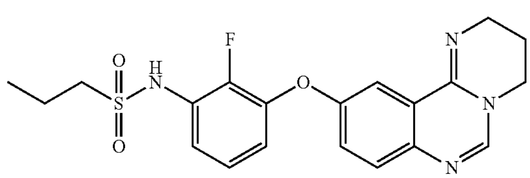 [SMILES: CCCS(=O)(=O)Nc1cccc(Oc2ccc3c(c2)C2=NCCCN2C=N3)c1F] | N-(3-((3,4-Dihydro-2H-pyrimido[1,2-c]quinazolin-10-yl)oxy)-2-fluorophenyl)propane-1-sulfonamide |
| 19 | 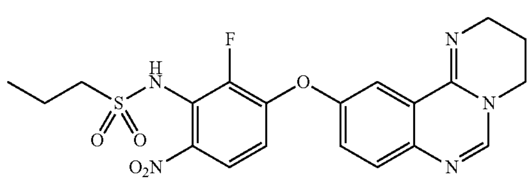 [SMILES: CCCS(=O)(=O)Nc1c([N+](=O)[O-])ccc(Oc2ccc3c(c2)C2=NCCCN2C=N3)c1F] | N-(3-((3,4-Dihydro-2H-pyrimido[1,2-c]quinazolin-10-yl)oxy)-2-fluoro-6-nitrophenyl)propane-1-sulfonamide |

TABLE 1-continued

| Compound No. | Structure | Chemical Name |
|---|---|---|
| 20 | 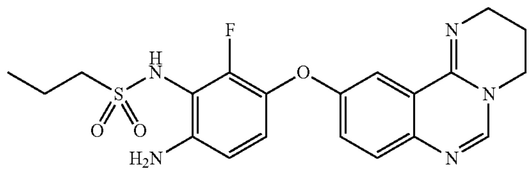 [SMILES: CCCS(=O)(=O)Nc1c(N)ccc(Oc2ccc3c(c2)C2=NCCCN2C=N3)c1F] | N-(6-Amino-3-((3,4-dihydro-2H-pyrimido[1,2-c]quinazolin-10-yl)oxy)-2-fluorophenyl)propane-1-sulfonamide |
| 21 | 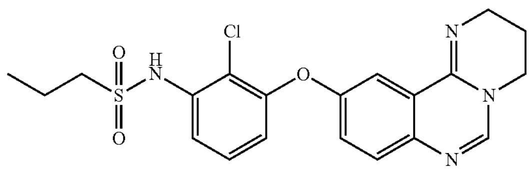 [SMILES: CCCS(=O)(=O)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)propane-1-sulfonamide |
| 22 | 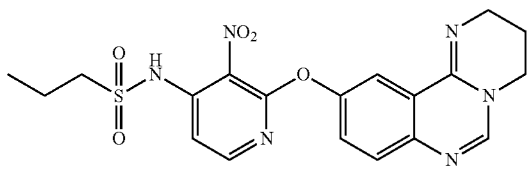 [SMILES: CCCS(=O)(=O)Nc1ccnc(Oc2ccc3c(c2)C2=NCCCN2C=N3)c1[N+](=O)[O-]] | N-(2-((3,4-Dihydro-2H-pyrimido[1,2-c]quinazolin-10-yl)oxy)-3-nitropyridin-4-yl)propane-1-sulfonamide |
| 23 | 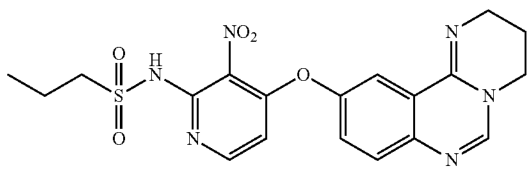 [SMILES: CCCS(=O)(=O)Nc1nccc(Oc2ccc3c(c2)C2=NCCCN2C=N3)c1[N+](=O)[O-]] | N-(4-((3,4-Dihydro-2H-pyrimido[1,2-c]quinazolin-10-yl)oxy)-3-nitropyridin-2-yl)propane-1-sulfonamide |
| 24 | 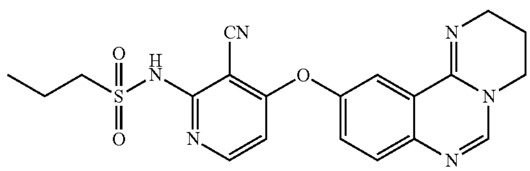 [SMILES: CCCS(=O)(=O)Nc1nccc(Oc2ccc3c(c2)C2=NCCCN2C=N3)c1C#N] | N-(3-Cyano-4-((3,4-dihydro-2H-pyrimido[1,2-c]quinazolin-10-yl)oxy)pyridin-2-yl)propane-1-sulfonamide |
| 25 | 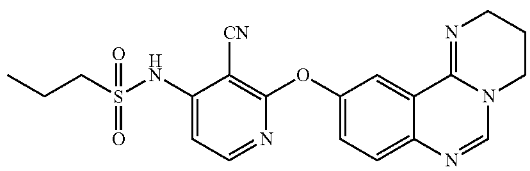 [SMILES: CCCS(=O)(=O)Nc1ccnc(Oc2ccc3c(c2)C2=NCCCN2C=N3)c1C#N] | N-(3-Cyano-2-((3,4-dihydro-2H-pyrimido[1,2-c]quinazolin-10-yl)oxy)pyridin-4-yl)propane-1-sulfonamide |
| 26 | 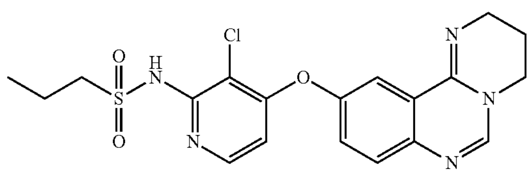 [SMILES: CCCS(=O)(=O)Nc1nccc(Oc2ccc3c(c2)C2=NCCCN2C=N3)c1Cl] | N-(3-Chloro-4-((3,4-dihydro-2H-pyrimido[1,2-c]quinazolin-10-yl)oxy)pyridin-2-yl)propane-1-sulfonamide |
| 27 | 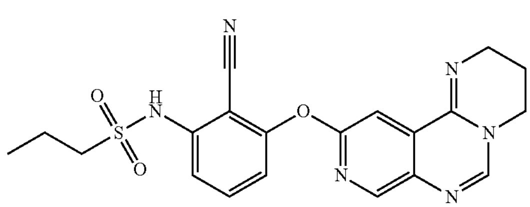 [SMILES: CCCS(=O)(=O)Nc1cccc(Oc2cc3c(cn2)N=CN2CCCN=C32)c1C#N] | N-(2-Cyano-3-((3,4-dihydro-2H-pyrido[4,3-e]pyrimido[1,2-c]pyrimidin-10-yl)oxy)phenyl)propane-1-sulfonamide |

TABLE 1-continued

| Compound No. | Structure | Chemical Name |
|---|---|---|
| 28 | 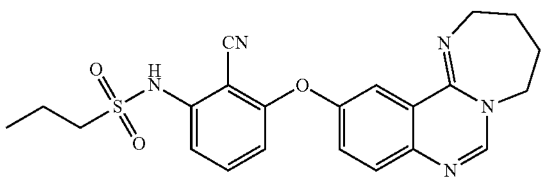 [SMILES: CCCS(=O)(=O)Nc1cccc(Oc2ccc3c(c2)C2=NCCCCN2C=N3)c1C#N] | N-(2-Cyano-3-((2,3,4,5-tetrahydro-[1,3]diazepino[1,2-c]quinazolin-11-yl)oxy)phenyl)propane-1-sulfonamide |
| 37 | 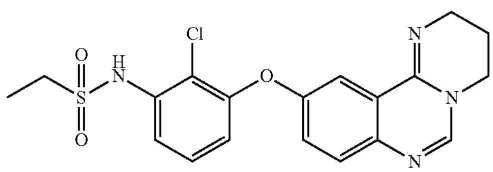 [SMILES: CCS(=O)(=O)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)ethanesulfonamide |
| 38 | 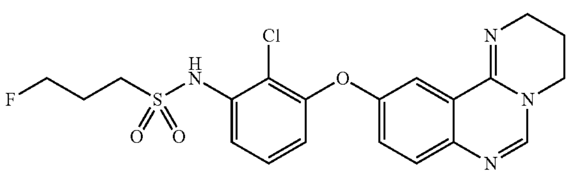 [SMILES: O=S(=O)(CCCF)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)-3-fluoropropane-1-sulfonamide |
| 39 | 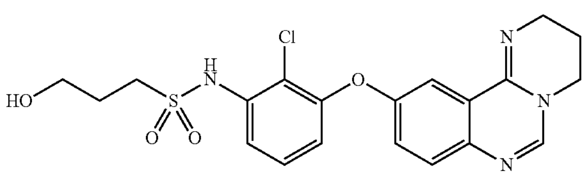 [SMILES: O=S(=O)(CCCO)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)-3-hydroxypropane-1-sulfonamide |
| 40 | 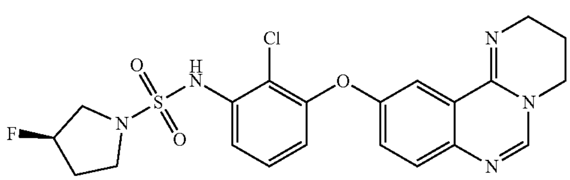 [SMILES: O=S(=O)(Nc1cccc(Oc2ccc3c(c2)C2=NCCCN2C=N3)c1Cl)N1CC[C@@H](F)C1] | (R)-N-(2-Chloro-3-((3,4-dihydro-2H-pyrimido[1,2-c]quinazolin-10-yl)oxy)phenyl)-3-fluoropyrrolidine-1-sulfonamide |
| 41 | 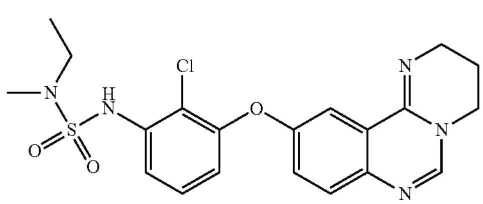 [SMILES: CCN(C)S(=O)(=O)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)-N-ethyl-N-methylamino-1-sulfonamide |
| 42 | 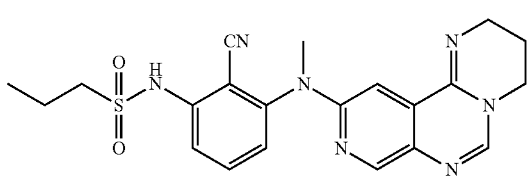 [SMILES: CCCS(=O)(=O)Nc1cccc(N(C)c2cc3c(cn2)N=CN2CCCN=C32)c1C#N] | N-(2-Cyano-3-((3,4-dihydro-2H-pyrido[4,3-c]pyrimido[1,2-c]pyrimidin-10-yl)(methyl)amino)phenyl)propane-1-sulfonamide |
| 43 | 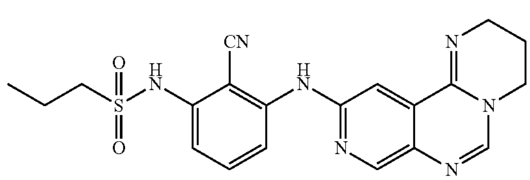 [SMILES: CCCS(=O)(=O)Nc1cccc(Nc2cc3c(cn2)N=CN2CCCN=C32)c1C#N] | N-(2-Cyano-3-((3,4-dihydro-2H-pyrido[4,3-c]pyrimido[1,2-c]pyrimidin-10-yl)amino)phenyl)propane-1-sulfonamide |

TABLE 1-continued

| Compound No. | Structure | Chemical Name |
|---|---|---|
| 44 | 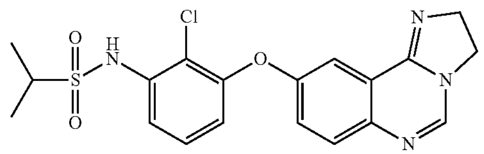 [SMILES: CC(C)S(=O)(=O)Nc1cccc(Oc2ccc3c(c2)C2=NCCN2C=N3)c1Cl] | N-(2-Chloro-3-((2,3-dihydroimidazo[1,2-c]quinazolin-9-yl)oxy)phenyl)propane-2-sulfonamide |
| 45 | 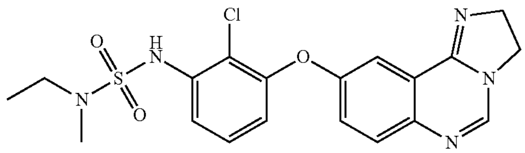 [SMILES: CCN(C)S(=O)(=O)Nc1cccc(Oc2ccc3c(c2)C2=NCCN2C=N3)c1Cl] | N-(2-Chloro-3-((2,3-dihydroimidazo[1,2-c]quinazolin-9-yl)oxy)phenyl)-N-ethyl-N-methylamino-1-sulfonamide |
| 46 | 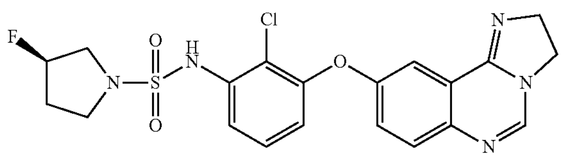 [SMILES: O=S(=O)(Nc1cccc(Oc2ccc3c(c2)C2=NCCN2C=N3)c1Cl)N1CC[C@@H](F)C1] | (R)-N-(2-Chloro-3-((2,3-dihydroimidazo[1,2-c]quinazolin-9-yl)oxy)phenyl)-3-fluoropyrrolidine-1-sulfonamide |
| 47 | 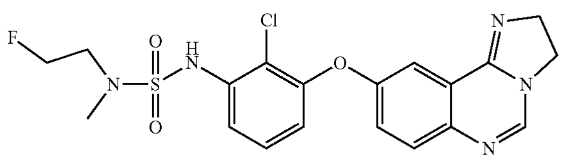 [SMILES: CN(CCF)S(=O)(=O)Nc1cccc(Oc2ccc3c(c2)C2=NCCN2C=N3)c1Cl] | N-(2-Chloro-3-((2,3-dihydroimidazo[1,2-c]quinazolin-9-yl)oxy)phenyl)-(2-fluoroethyl)(methyl)amino-1-sulfonamide |
| 48 | 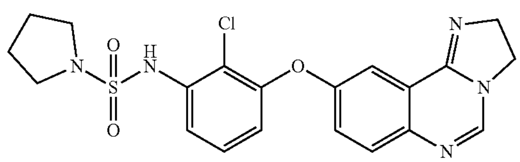 [SMILES: O=S(=O)(Nc1cccc(Oc2ccc3c(c2)C2=NCCN2C=N3)c1Cl)N1CCCC1] | N-(2-Chloro-3-((2,3-dihydroimidazo[1,2-c]quinazolin-9-yl)oxy)phenyl)pyrrolidine-1-sulfonamide |
| 49 | 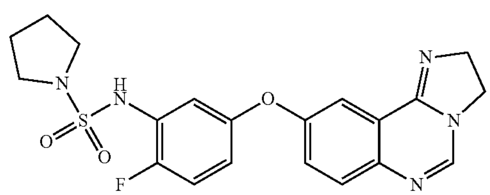 [SMILES: O=S(=O)(Nc1cc(Oc2ccc3c(c2)C2=NCCN2C=N3)ccc1F)N1CCCC1] | N-(5-((2,3-Dihydroimidazo[1,2-c]quinazolin-9-yl)oxy)-2-fluorophenyl)pyrrolidine-1-sulfonamide |
| 50 | 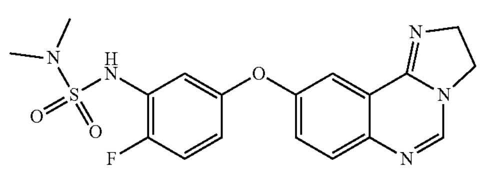 [SMILES: CN(C)S(=O)(=O)Nc1cc(Oc2ccc3c(c2)C2=NCCN2C=N3)ccc1F] | N-(5-((2,3-Dihydroimidazo[1,2-c]quinazolin-9-yl)oxy)-2-fluorophenyl)-N,N-dimethylamino-1-sulfonamide |
| 51 | 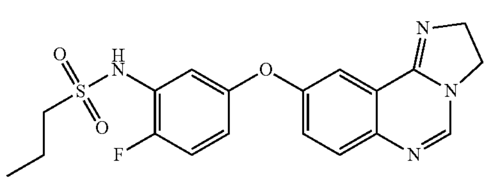 [SMILES: CCCS(=O)(=O)Nc1cc(Oc2ccc3c(c2)C2=NCCN2C=N3)ccc1F] | N-(5-((2,3-Dihydroimidazo[1,2-c]quinazolin-9-yl)oxy)-2-fluorophenyl)propane-1-sulfonamide |
| 52 | 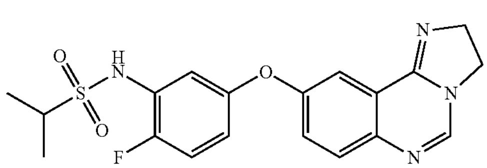 [SMILES: CC(C)S(=O)(=O)Nc1cc(Oc2ccc3c(c2)C2=NCCN2C=N3)ccc1F] | N-(5-((2,3-Dihydroimidazo[1,2-c]quinazolin-9-yl)oxy)-2-fluorophenyl)propane-2-sulfonamide |

TABLE 1-continued

| Compound No. | Structure | Chemical Name |
|---|---|---|
| 53 | 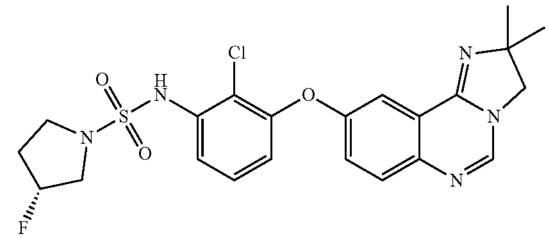 [SMILES: CC1(C)CN2C=Nc3ccc(Oc4cccc(NS(=O)(=O)N5CC[C@@H](F)C5)c4Cl)cc3C2=N1] | (R)-N-(2-Chloro-3-((2,2-dimethyl-2,3-dihydroimidazo[1,2-c]quinazolin-9-yl)oxy)phenyl)-3-fluoropyrrolidine-1-sulfonamide |
| 54 | 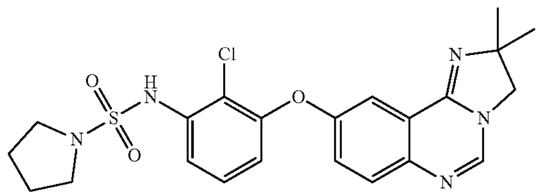 [SMILES: CC1(C)CN2C=Nc3ccc(Oc4cccc(NS(=O)(=O)N5CCCC5)c4Cl)cc3C2=N1] | N-(2-Chloro-3-((2,2-dimethyl-2,3-dihydroimidazo[1,2-c]quinazolin-9-yl)oxy)phenyl)pyrrolidine-1-sulfonamide |
| 55 | 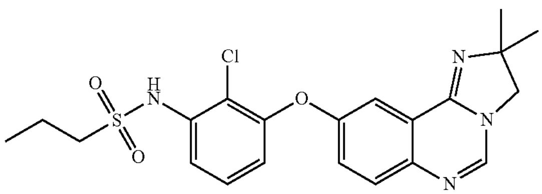 [SMILES: CCCS(=O)(=O)Nc1cccc(Oc2ccc3c(c2)C2=NC(C)(C)CN2C=N3)c1Cl] | N-(2-Chloro-3-((2,2-dimethyl-2,3-dihydroimidazo[1,2-c]quinazolin-9-yl)oxy)phenyl)propane-1-sulfonamide |
| 56 | 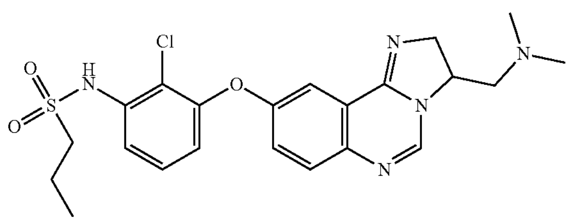 [SMILES: CCCS(=O)(=O)Nc1cccc(Oc2ccc3c(c2)C2=NCC(CN(C)C)N2C=N3)c1Cl] | N-(2-Chloro-3-((3-((dimethylamino)methyl)-2,3-dihydroimidazo[1,2-c]quinazolin-9-yl)oxy)phenyl)propane-1-sulfonamide |

In some embodiments, provided herein are compounds and salts thereof described in Table 2, and uses thereof.

TABLE 2

| Compound No. | Structure | Chemical Name |
|---|---|---|
| 1 | 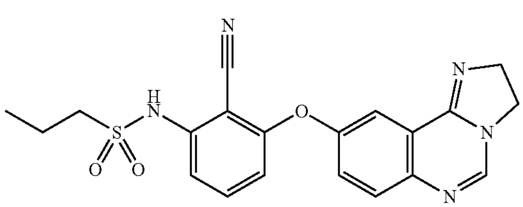 [SMILES: CCCS(=O)(=O)Nc1cccc(Oc2ccc3c(c2)C2=NCCN2C=N3)c1C#N] | N-(2-Cyano-3-((2,3-dihydroimidazo[1,2-c]quinazolin-9-yl)oxy)phenyl)propane-1-sulfonamide |
| 16 | 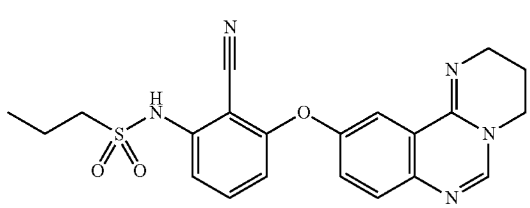 [SMILES: CCCS(=O)(=O)Nc1cccc(Oc2ccc3c(c2)C2=NCCCN2C=N3)c1C#N] | N-(2-cyano-3-((3,4-dihydro-2H-pyrimido[1,2-c]quinazolin-10-yl)oxy)phenyl)propane-1-sulfonamide |

TABLE 2-continued

| Compound No. | Structure | Chemical Name |
|---|---|---|
| 12 | 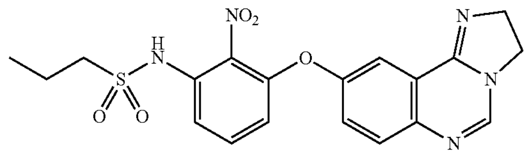 [SMILES: CCCS(=O)(=O)Nc1cccc(Oc2ccc3c(c2)C2=NCCN2C=N3)c1[N+](=O)[O-]] | N-(3-((2,3-Dihydroimidazo[1,2-c]quinazolin-9-yl)oxy)-2-nitrophenyl)propane-1-sulfonamide |
| 29 | 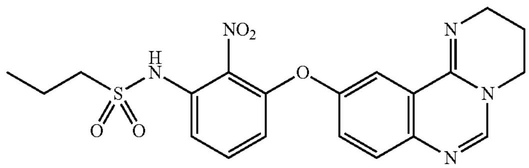 [SMILES: CCCS(=O)(=O)Nc1cccc(Oc2ccc3c(c2)C2=NCCCN2C=N3)c1[N+](=O)[O-]] | N-(3-((3,4-dihydro-2H-pyrimido[1,2-c]quinazolin-10-yl)oxy)-2-nitrophenyl)propane-1-sulfonamide |
| 9 | 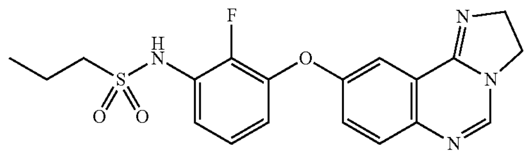 [SMILES: CCCS(=O)(=O)Nc1cccc(Oc2ccc3c(c2)C2=NCCN2C=N3)c1F] | N-(3-((2,3-Dihydroimidazo[1,2-c]quinazolin-9-yl)oxy)-2-fluorophenyl)propane-1-sulfonamide |
| 18 | 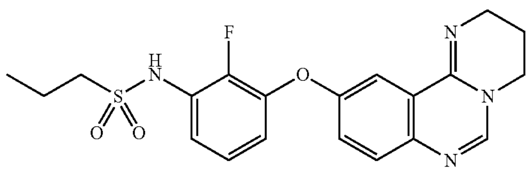 [SMILES: CCCS(=O)(=O)Nc1cccc(Oc2ccc3c(c2)C2=NCCCN2C=N3)c1F] | N-(3-((3,4-Dihydro-2H-pyrimido[1,2-c]quinazolin-10-yl)oxy)-2-fluorophenyl)propane-1-sulfonamide |
| 6 | 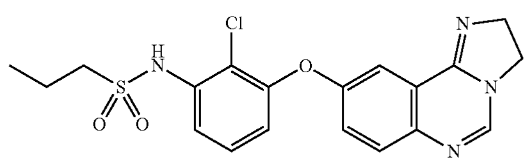 | N-(2-Chloro-3-((2,3-dihydroimidazo[1,2-c]quinazolin-9-yl)oxy)phenyl)propane-1-sulfonamide |
| 21 | 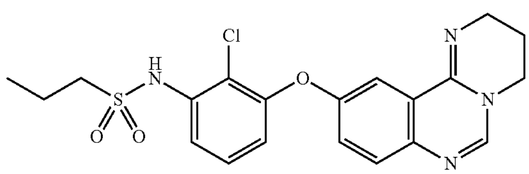 [SMILES: CCCS(=O)(=O)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)propane-1-sulfonamide |
| 11 | 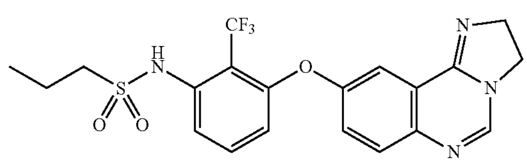 [SMILES: CCCS(=O)(=O)Nc1cccc(Oc2ccc3c(c2)C2=NCCN2C=N3)c1C(F)(F)F] | N-(3-((2,3-Dihydroimidazo[1,2-c]quinazolin-9-yl)oxy)-2-(trifluoromethyl)phenyl)propane-1-sulfonamide |
| 30 | 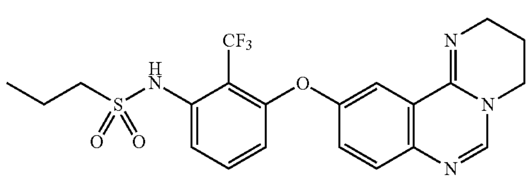 [SMILES: CCCS(=O)(=O)Nc1cccc(Oc2ccc3c(c2)C2=NCCCN2C=N3)c1C(F)(F)F] | N-(3-((3,4-dihydro-2H-pyrimido[1,2-c]quinazolin-10-yl)oxy)-2-(trifluoromethyl)phenyl)propane-1-sulfonamide |
| 31 | 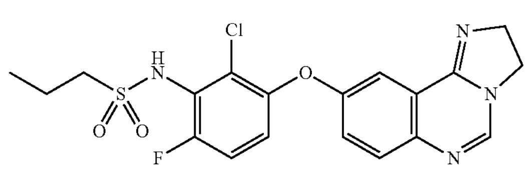 | N-(2-chloro-3-((2,3-dihydroimidazo[1,2-c]quinazolin-9-yl)oxy)-6-fluorophenyl)propane-1-sulfonamide |

TABLE 2-continued

| Compound No. | Structure | Chemical Name |
|---|---|---|
| 32 | 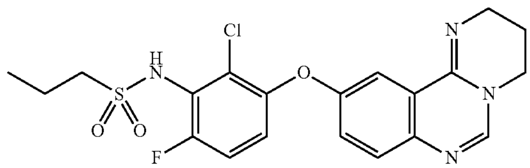 [SMILES: CCCS(=O)(=O)Nc1c(F)ccc(Oc2ccc3c(c2)C2=NCCCN2C=N3)c1Cl] | N-(2-chloro-3-((3,4-dihydro-2H-pyrimido[1,2-c]quinazolin-10-yl)oxy)-6-fluorophenyl)propane-1-sulfonamide |
| 33 | 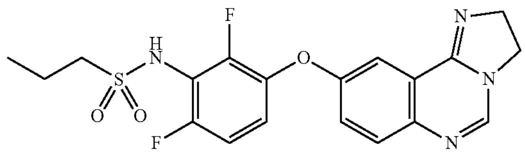 [SMILES: CCCS(=O)(=O)Nc1c(F)ccc(Oc2ccc3c(c2)C2=NCCN2C=N3)c1F] | N-(3-((2,3-dihydroimidazo[1,2-c]quinazolin-9-yl)oxy)-2,6-difluorophenyl)propane-1-sulfonamide |
| 34 | 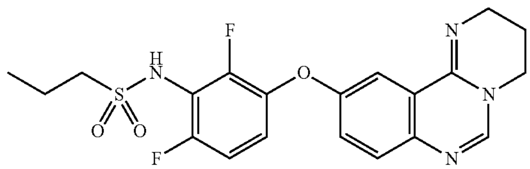 [SMILES: CCCS(=O)(=O)Nc1c(F)ccc(Oc2ccc3c(c2)C2=NCCCN2C=N3)c1F] | N-(3-((3,4-dihydro-2H-pyrimido[1,2-c]quinazolin-10-yl)oxy)-2,6-difluorophenyl)propane-1-sulfonamide |
| 10 | 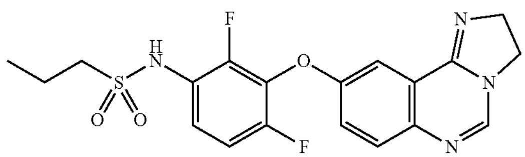 [SMILES: CCCS(=O)(=O)Nc1ccc(F)c(Oc2ccc3c(c2)C2=NCCN2C=N3)c1F] | N-(3-((2,3-Dihydroimidazo[1,2-c]quinazolin-9-yl)oxy)-2,4-difluorophenyl)propane-1-sulfonamide |
| 35 | 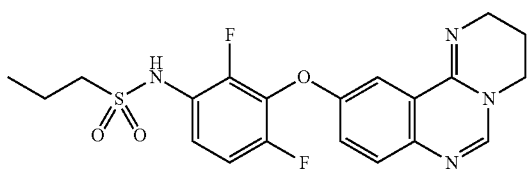 [SMILES: CCCS(=O)(=O)Nc1ccc(F)c(Oc2ccc3c(c2)C2=NCCCN2C=N3)c1F] | N-(3-((3,4-dihydro-2H-pyrimido[1,2-c]quinazolin-10-yl)oxy)-2,4-difluorophenyl)propane-1-sulfonamide |
| 36 | 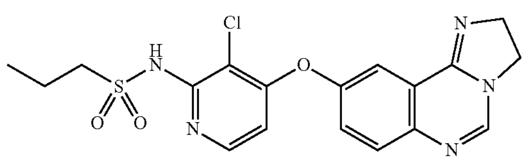 [SMILES: CCCS(=O)(=O)Nc1nccc(Oc2ccc3c(c2)C2=NCCN2C=N3)c1Cl] | N-(3-chloro-4-((2,3-dihydroimidazo[1,2-c]quinazolin-9-yl)oxy)pyridin-2-yl)propane-1-sulfonamide |
| 26 | 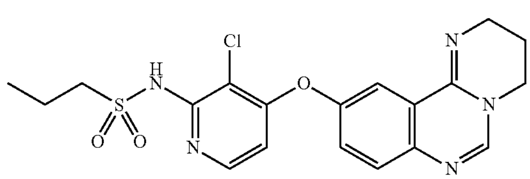 [SMILES: CCCS(=O)(=O)Nc1nccc(Oc2ccc3c(c2)C2=NCCCN2C=N3)c1Cl] | N-(3-Chloro-4-((3,4-dihydro-2H-pyrimido[1,2-c]quinazolin-10-yl)oxy)pyridin-2-yl)propane-1-sulfonamide |
| 40 | 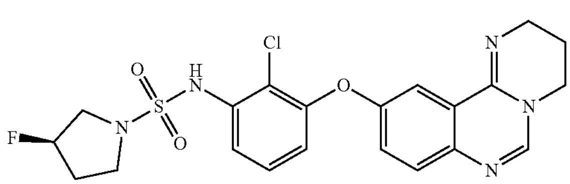 [SMILES: O=S(=O)(Nc1cccc(Oc2ccc3c(c2)C2=NCCCN2C=N3)c1Cl)N1CC[C@@H](F)C1] | (R)-N-(2-Chloro-3-((3,4-dihydro-2H-pyrimido[1,2-c]quinazolin-10-yl)oxy)phenyl)-3-fluoropyrrolidine-1-sulfonamide |
| 46 | 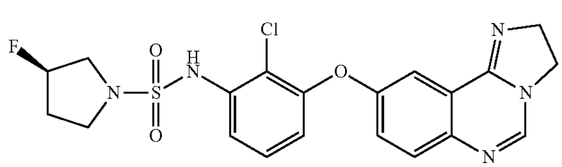 [SMILES: O=S(=O)(Nc1cccc(Oc2ccc3c(c2)C2=NCCN2C=N3)c1Cl)N1CC[C@@H](F)C1] | (R)-N-(2-Chloro-3-((2,3-dihydroimidazo[1,2-c]quinazolin-9-yl)oxy)phenyl)-3-fluoropyrrolidine-1-sulfonamide |

TABLE 2-continued

| Compound No. | Structure | Chemical Name |
|---|---|---|
| 48 | 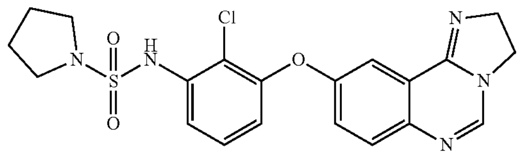 [SMILES: O=S(=O)(Nc1cccc(Oc2ccc3c(c2)C2=NCCN2C=N3)c1Cl)N1CCCC1] | N-(2-Chloro-3-((2,3-dihydroimidazo[1,2-c]quinazolin yl)oxy)phenyl)pyrrolidine-1-sulfonamide |

Any formula or compound given herein, such as Formula (I), (I-1), (I-2a), (I-2b), (I-2c), (I-2d), (I-2e), (I-2f), (I-3a), (I-3b), (I-4a), (I-4b), (I-4c), (I-5a), or (I-5b), or compounds of Tables 1 or 2, is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 or Table 2 is depicted with a particular stereochemical configuration, also provided herein is any alternative stereochemical configuration of the compound, as well as a mixture of stereoisomers of the compound in any ratio. For example, where a compound of Table 1 or Table 2 has a stereocenter that is in an "S" stereochemical configuration, also provided herein is enantiomer of the compound wherein that stereocenter is in an "R" stereochemical configuration. Likewise, when a compound of Table 1 or Table 2 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 or Table 2 has two or more stereocenters, also provided are any enantiomer or diastereomer of the compound. Furthermore, certain structures may exist as geometric isomers (i.e., cis and trans isomers), as tautomers, or as atropisomers. Additionally, any compound of Table 1 or Table 2 is intended to represent a racemate, one or more enantiomeric forms, one or more diastereomeric forms, one or more atropisomeric forms, and mixtures thereof in any ratio. Furthermore, certain structures may exist as geometric isomers (i.e., cis and trans isomers), as tautomers, or as atropisomers. Additionally, any formula given herein, such as Formula (I), (I-1), (I-2a), (I-2b), (I-2c), (I-2d), (I-2e), (1-2f), (I-3a), (I-3b), (I-4a), (I-4b), (I-4c), (I-5a), or (I-5b) is intended to refer to hydrates, solvates, and amorphous forms of such compounds, and mixtures thereof, even if such forms are not listed explicitly. In some embodiments, the solvent is water and the solvates are hydrates.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $X_1$, $X_2$, $X_3$, $Y_1$, $Y_2$, $Y_3$, $Z_1$, $Z_2$, $R_1$, $R_2$, $R_3$, $R_4$, m, and n provided herein can be combined with every other variation or embodiment of $X_1$, $X_2$, $X_3$, $Y_1$, $Y_2$, $Y_3$, $Z_1$, $Z_2$, $R_1$, $R_2$, $R_3$, $R_4$, m, and n, as if each combination had been individually and specifically described.

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, the present disclosure provides for a pharmaceutical composition comprising a compound described above admixed with at least one pharmaceutically acceptable carrier or excipient. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds that are substantially pure.

Also provided are packaged pharmaceutical compositions, comprising a pharmaceutical composition as described herein and instructions for using the composition to treat a patient suffering from a disease or condition described herein.

Pharmaceutical Formulations

The present disclosure also provides a composition, e.g., a pharmaceutical composition, containing one or more of the compounds described herein, formulated together with a pharmaceutically acceptable carrier. Pharmaceutical compositions of the invention also can be administered in combination therapy, i.e., combined with other agents. For example, the combination therapy can include a compound as described herein combined with at least one other active agent.

Pharmaceutically acceptable carriers may include any and all carriers, excipients, stabilizers, solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the compound described herein, may be coated in a material to protect the compound from the action of acids and other natural conditions that may inactivate the compound.

Acceptable carriers, excipients, or stabilizers are nontoxic to recipients at standard dosages and concentrations to be administered, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ or polyethylene glycol (PEG).

The pharmaceutical compositions of the invention may include one or more pharmaceutically acceptable salts. A pharmaceutically acceptable salt retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Any suitable formulation of the compounds described herein can be prepared. See generally, Remington's Pharmaceutical Sciences, (2000) Hoover, J. E. editor, 20 th edition, Lippincott Williams and Wilkins Publishing Company, Easton, Pa., pages 780-857. A formulation is selected to be suitable for an appropriate route of administration. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, $\alpha$-ketoglutarate, and $\alpha$-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The compounds having formula I-III as described herein are generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. In one embodiment, the present invention provides formulations prepared by mixing a compound having formula I-III with a pharmaceutically acceptable carrier. In one aspect, the formulation may be prepared using a method comprising: a) dissolving a described compound in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

Drug Combinations

The methods of the embodiments comprise administering an effective amount of at least one exemplary compound of the present disclosure; optionally the compound may be administered in combination with one or more additional therapeutic agents. In some embodiments, the additional therapeutic agent is known to be useful for treating a proliferation disorder, such as a cancer, o a tumor in a subject. In some embodiments, the additional therapeutic agent is known to be useful for treating a neurodegenerative disorder.

The additional active ingredients may be administered in a separate pharmaceutical composition from at least one exemplary compound of the present disclosure or may be included with at least one exemplary compound of the present disclosure in a single pharmaceutical composition. The additional active ingredients may be administered simultaneously with, prior to, or after administration of at least one exemplary compound of the present disclosure.

Dosages and Dosage Forms

For the prevention or treatment of disease, the appropriate dosage of compounds described herein will depend on the type of disease to be treated, the severity and course of the disease, whether the compound is administered for preventive or therapeutic purposes, mode of delivery, previous therapy, and the subject's clinical history. The compounds described herein are suitably administered to a subject at one time or over a series of treatments. Depending on the type and severity of the disease, a typical daily dosage might range from about 0.0001 mg/kg to 100 mg/kg or more, depending on the factors mentioned above. For repeated administrations over several days or longer, depending on the condition, the treatment is sustained until a desired suppression of disease symptoms occurs.

For example dosages can be 0.3 mg/kg body weight, 1 mg/kg body weight, 3 mg/kg body weight, 5 mg/kg body weight or 10 mg/kg body weight or within the range of 1-10 mg/kg. Treatment regimens may comprise administration once per week, once every two weeks, once every three weeks, once every four weeks, once per month, once every 3 months or once every three to 6 months. In other embodiments, sustained release formulations are administered, which would result in less frequent administration compared to non-sustained release formulations.

The amount of active ingredient which can be combined with a carrier material to produce a single dosage form will generally be that amount of the composition which produces a therapeutic effect, without being toxic to the subject. Generally, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Administration

A composition described herein can be administered via one or more routes of administration using one or more of a variety of methods known in the art. As will be appreciated by the skilled artisan, the route and/or mode of administration will vary depending upon the desired results. Routes of administration for the compounds and compositions described herein include oral, sublingual, buccal, intranasal, topical, rectal, intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Methods of Treatment

The compounds and pharmaceutical compositions herein may be used for any suitable purpose. For example, the present compounds can be used in therapy and/or testing.

The compounds and pharmaceutical compositions herein may be used to treat and/or prevent a proliferation disorder, such as a cancer, or a tumor in an individual. In some embodiments, provided are methods of treating or preventing a proliferation disorder, such as a cancer, or a tumor in an individual, comprising administering to the individual in need thereof a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof. In some embodiments, provided are methods of treating or preventing a proliferation disorder, such as a cancer, or a tumor in a subject in need thereof comprising administering to the subject a therapeutically effective amount of at least one chemical entity as described herein.

In some embodiments, the compounds of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or compounds of Tables 1 or 2, or a pharmaceutically acceptable salt thereof, are inhibitors of the MAPK family of oncogenic protein tyrosine kinases such as B-Raf, particularly B-Raf V600E mutant, and thus are all adapted to therapeutic use as antiproliferative agents (e.g., anticancer) in mammals, particularly in humans. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, melanoma, and other hyperplastic conditions such as benign hyperplasia of the skin (eg., psoriasis) and benign hyperplasia of the prostate (eg., BPH). In addition, it is expected that a compound of the present invention may possess activity against brain metastases originated from these disorders.

In some embodiments, compounds of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or compounds of Tables 1 or 2, or a pharmaceutically acceptable salt thereof, may also be useful in the treatment of additional disorders in which aberrant expression ligand/receptor interactions or activation or signaling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signaling of tyrosine kinases are involved.

Also provided herein is the use of a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof in the manufacture of a medicament for treatment of a proliferation disorder, such as a cancer, or a tumor in a subject.

In some embodiments, the proliferation disorder or cancer is selected from the group consisting of malignant or benign tumors of the liver, kidney, bladder, breast, gastric, ovarian, colorectal, prostate, pancreatic, lung, vulval, thyroid, hepatic carcinomas, sarcomas, glioblastomas, head and neck, melanoma, and other hyperplastic conditions such as benign hyperplasia of the skin (eg., psoriasis) and benign hyperplasia of the prostate (eg., BPH). In some embodiments, the compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, may possess activity against brain metastases originated from these disorders.

Also provided are methods for inhibiting an activity of a B-Raf V600E kinase, which method comprises administering to an individual in need thereof a therapeutically effective amount of at least one chemical entity as described herein. In some embodiments, provided are methods of inhibiting B-Raf V600E kinase in a cell, comprising contacting the cell with at least one chemical entity as described herein, such as a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof. Additionally provided herein is the use of at least one chemical entity as described herein, such as a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof in the manufacture of a medicament for inhibiting an activity of a B-Raf V600E kinase of an individual.

Also provided are methods for treating and/or preventing a proliferation disorder, such as a cancer, or a tumor in a subject which method comprises administering to an individual in need thereof a therapeutically effective amount of at least one chemical entity as described herein such as a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof. Additionally provided herein is the use of at least one chemical entity as described herein, such as a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof in the manufacture of a medicament for treating and/or preventing a proliferation disorder, a cancer, or a tumor in a subject.

In one embodiment, the disease or condition to be treated or prevented is abnormal cell proliferation such as cancer. The term "cancer" refers to pre-cancerous conditions, non-malignant, low-grade, high-grade, and malignant cancer. Cancer of any tissue type is contemplated for treatment or prevention by the compounds disclosed herein. Exemplary types of cancer include carcinoma, lymphoma, blastoma, sarcoma, leukemia, and lymphoid malignancies. More specifically, in certain embodiments the cancer is squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Provided herein is a method of treating cancer in an individual in need thereof by administering to the individual a therapeutically effective amount of a compound or composition described herein. Also provided herein is the use of a compound or composition described herein in the manufacture of a medicament for treatment of cancer in an individual in need thereof. Also provided herein is the use of a compound or composition described herein for treatment of cancer in an individual in need thereof. Also provided herein is a compound or composition described herein for use in treatment of cancer in an individual in need thereof.

In another embodiment, the disease or condition to be treated or prevented is neurodegenerative disease. Exemplary types of neurodegenerative disease include, but are not limited to, Amyotrophic lateral sclerosis, Parkinson's disease, Alzheimer's disease, and Huntington's disease that occurs as a result of neurodegenerative processes.

In some embodiments, provided are methods of treating or preventing a neurodegenerative disease, such as Amyotrophic lateral sclerosis, Parkinson's disease, Alzheimer's disease, and Huntington's disease, comprising administering to the individual in need thereof a compound of Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or a compound of Tables 1 or 2, or a pharmaceutically acceptable salt thereof. In some embodiments, provided are methods of treating or preventing a neurodegenerative disease, such as Amyotrophic lateral sclerosis, Parkinson's disease, Alzheimer's disease, and Huntington's disease, comprising administering to the subject a therapeutically effective amount of at least one chemical entity as described herein.

Provided herein is a method of treating a neurodegenerative disease in an individual in need thereof by administering to the individual a therapeutically effective amount of a compound or composition described herein. Also provided herein is the use of a compound or composition described herein in the manufacture of a medicament for treatment of a neurodegenerative disease in an individual in need thereof. Also provided herein is the use of a compound or composition described herein for treatment of a neurodegenerative disease in an individual in need thereof. Also provided herein is a compound or composition described herein for use in treatment of neurodegenerative disease in an individual in need thereof.

In one aspect, provided herein are kits containing a compound or composition described herein and instructions for use. In some embodiments, the kits may contain instructions for use in the treatment of cancer in an individual in need thereof. In other embodiments, the kits may contain instructions for use in the treatment of a neurodegenerative disease in an individual in need thereof. A kit may additionally contain any materials or equipment that may be used in the administration of the compound or composition, such as vials, syringes, or IV bags. A kit may also contain sterile packaging.

General Synthetic Methods

Compounds of Formula (I) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (I-1), (I-2a), (I-2b), (I-2c), (I-2d), (I-2e), (I-2f), (I-3a), (I-3b), (I-4a), (I-4b), (I-4c), (I-5a), (I-5b), or any variation thereof. Other compounds described herein may be prepared by similar methods.

General synthetic methods which may be referred to for preparing the compounds of the present invention such as B1 are provided in Claudi F. et al, J. Org. Chem. 1974, 39, p. 3508. Certain starting materials may be prepared according to methods familiar to those skilled in the art and certain synthetic modifications may be done according to methods familiar to those skilled in the art. A standard procedure for preparing 2-alkyl-1-iminoquinazoline is provided in Bartra Sanmarti, M. et al., WO2011/076813.

In some embodiments, the compound of Formula (I) is synthesized via the reaction of phenol or aniline A1 with quinazolinimine B1 as shown in Scheme A.

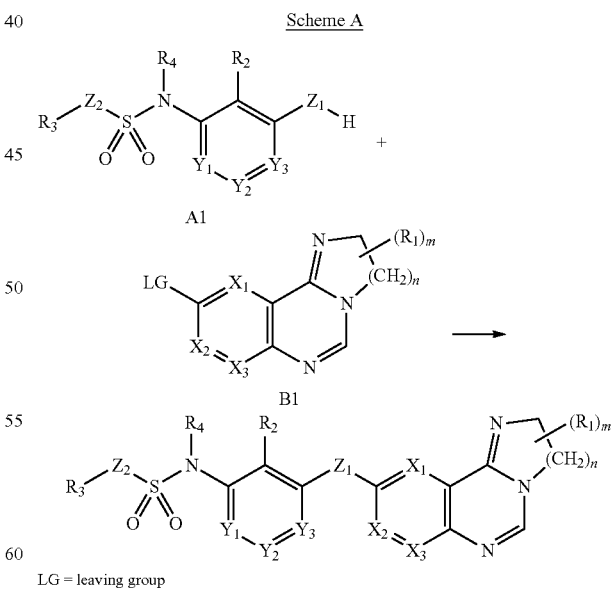

LG = leaving group wherein $X_1$, $X_2$, $X_3$, $Y_1$, $Y_2$, $Y_3$, $Z_1$, $Z_2$, $R_1$, $R_2$, $R_3$, $R_4$, m, and n are as defined for Formula (I), or any variation thereof detailed herein, and LG is a leaving group. Particular examples are provided in the Example section below.

In some embodiments, the compound of Formula (I) is synthesized via the reaction of phenyl or heteroaryl compound A2 with quinazolinimine B2 as shown in Scheme B.

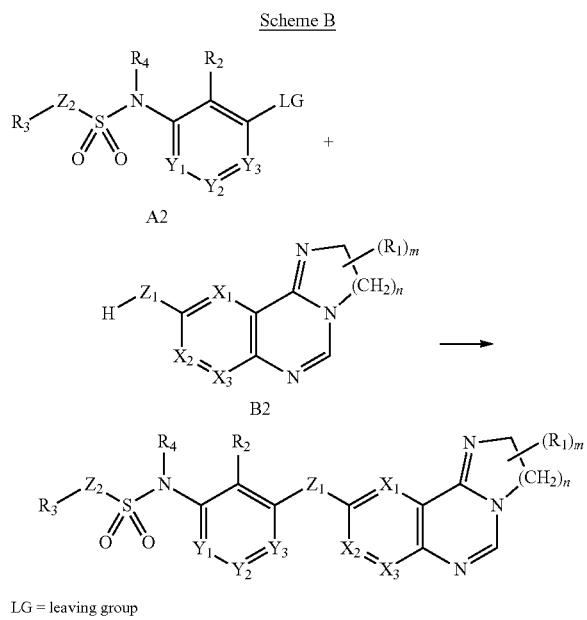

Scheme B

A2

B2

LG = leaving group wherein $X_1$, $X_2$, $X_3$, $Y_1$, $Y_2$, $Y_3$, $Z_1$, $Z_2$, $R_1$, $R_2$, $R_3$, $R_4$, m, and n are as defined for Formula (I), or any variation thereof detailed herein, and LG is a leaving group. Particular examples are provided in the Example section below.

Starting materials, the synthesis of which is not specifically described above, are either commercially available or can be prepared using methods well known to those of skill in the art.

In some embodiments, compounds of the formula A1 are be prepared according to the synthesis outlined in Scheme C.

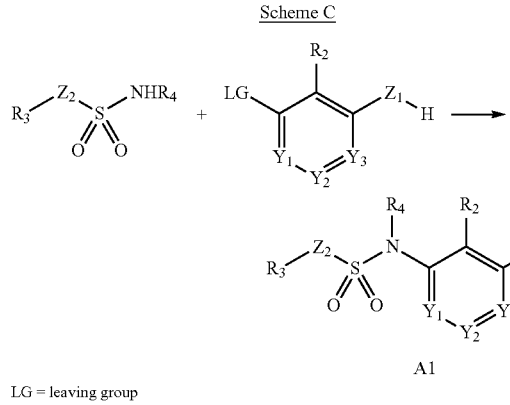

Scheme C

A1

LG = leaving group wherein $Y_1$, $Y_2$, $Y_3$, $Z_1$, $Z_2$, $R_2$, $R_3$, and $R_4$ are as defined for Formula (I), or any variation thereof detailed herein, and LG is a leaving group.

In some embodiments, compounds of the formula B1 are prepared according to the synthesis outlined in Scheme D.

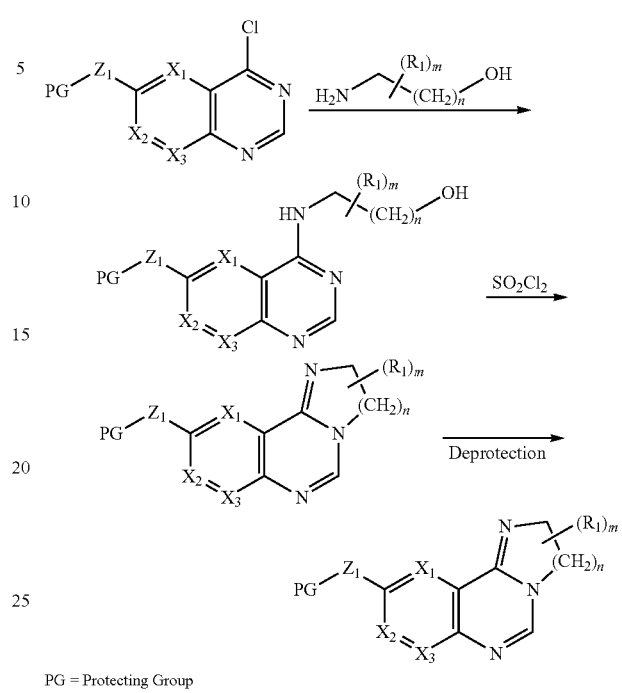

Scheme D

PG = Protecting Group wherein $X_1$, $X_2$, $X_3$, $Z_1$, $R_1$, m, and n are as defined for Formula (I), or any variation thereof detailed herein, and PG is a protecting group.

In some embodiments, compounds of Formula (I) are prepared according to the synthesis outlined in Scheme E.

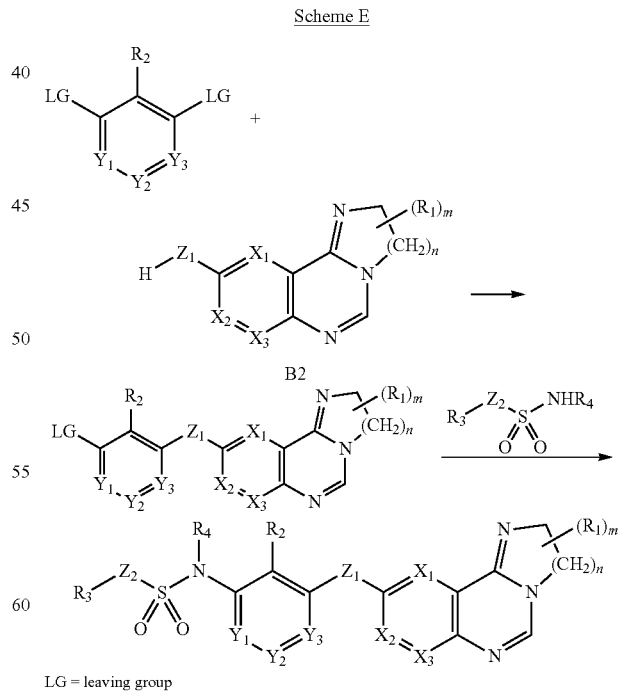

Scheme E

B2

LG = leaving group wherein $X_1$, $X_2$, $X_3$, $Y_1$, $Y_2$, $Y_3$, $Z_1$, $Z_2$, $R_1$, $R_2$, $R_3$, $R_4$, m, and n are as defined for Formula (I), or any variation thereof detailed herein, and LG is a leaving group. Particular examples are provided in the Example section below.

EXAMPLES

The following examples are offered to illustrate but not to limit the compositions, uses, and methods provided herein. One of skill in the art will recognize that the following synthetic reactions and schemes may be modified by choice of suitable starting materials and reagents in order to access other compounds of Formula (I), (I-1), (I-2a), (I-2b), (I-2c), (I-2d), (I-2e), (I-2f), (I-3a), (I-3b), (I-4a), (I-4b), (I-4c), (I-5a), or (I-5b), or a salt thereof. The compounds are prepared using the general methods described above.

The following chemical abbreviations are used throughout the Examples: ACN (acetonitrile), DCM (dichloromethane), DIEA (N, N-Diisopropylethylamine), DMF (dimethylformamide), DMAP (4-dimethylaminopyridine), DMSO (dimethyl sulfoxide), Et$_3$N (triethylamine), EtOAc (ethyl acetate), $^1$H NMR (proton nuclear magnetic resonance), HPLC (high-performance liquid chromatography), i-PrOH (isopropyl alcohol), LCMS (Liquid chromatography-mass spectrometry), MeI (methyl iodide), MeOH (methanol), NMP (N-Methyl-2-pyrrolidone), PE (petroleum ether), SEMCl (2-(trimethylsilyl)ethoxymethylchloride), THF (tetrahydrofuran), and TFA (trifluoroacetic acid).

Example 1: Preparation of N-(2-Cyano-3-((2,3-dihydroimidazo[1,2-c]quinazolin-9-yl)oxy)phenyl) propane-1-sulfonamide (Compound 1)

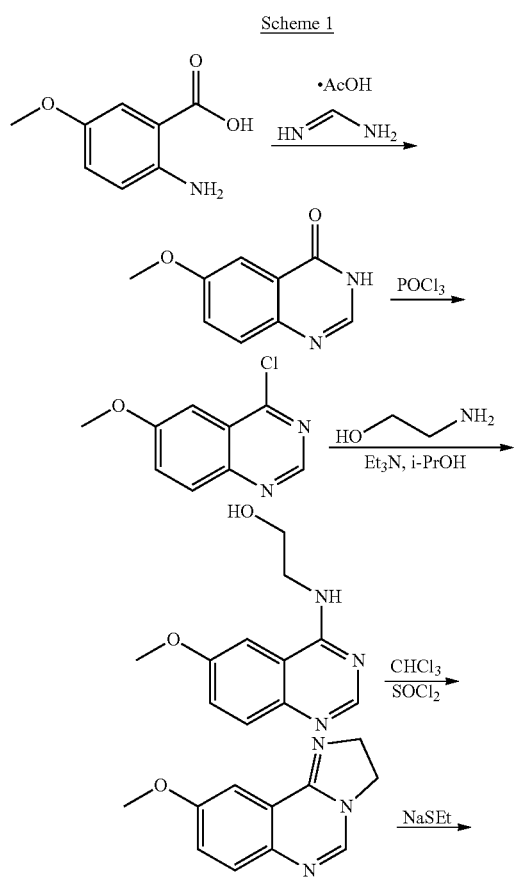

Scheme 1

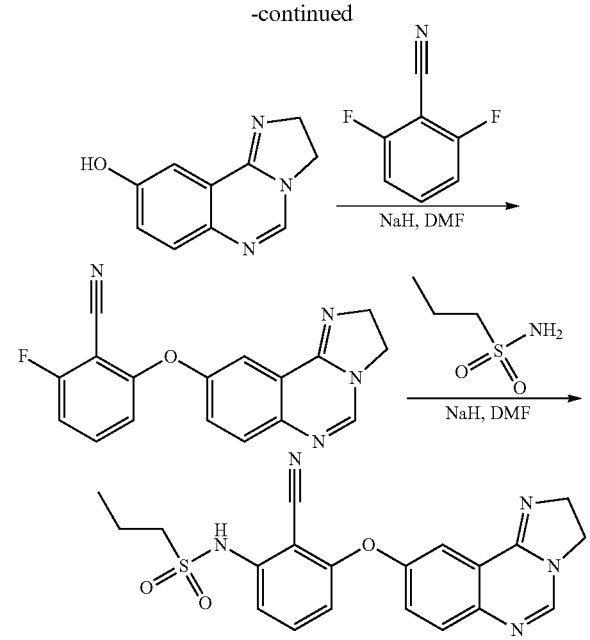

Step 1: Synthesis of 6-Methoxyquinazolin-4(3H)-one

A mixture of 2-amino-5-methoxybenzoic acid (10.0 g, 59.9 mmol), formamidine acetate (12.3 g, 119 mmol) in 80 mL of 2-methoxyethanol was heated at 125° C. for 18 hours. After being cooled to room temperature, the precipitate was collected by filtration, washed twice with 2-methoxyethanol and dried in the vacuum to provide 6-methoxyquinazolin-4 (3H)-one (9.1 g, 87% yield).

Step 2: Synthesis of 4-Chloro-6-methoxyquinazoline

A solution of 6-methoxyquinazolin-4(3H)-one (3.0 g, 17.0 mmol) in POCl$_3$ (30 mL) was stirred at 120° C. overnight. Then the mixture was cooled to room temperature and evaporated. The residue was purified by silica column chromatography (PE/EtOAc from 10:1 to 5:1, v/v) to afford 4-chloro-6-methoxyquinazoline (3.0 g, 91% yield).

Step 3: Synthesis of 2-((6-Methoxyquinazolin-4-yl)amino)ethan-1-ol

To a solution of 4-chloro-6-methoxyquinazoline (2.5 g, 12.9 mmol) in i-PrOH (30 mL) were added 2-aminoethanol (5.0 mL) and Et$_3$N (5.0 mL). The mixture was stirred at 80° C. for 20 min, then cooled and concentrated in vacuo. The residue was purified by silica column chromatography (DCM/MeOH from 50:1 to 20:1, v/v) to afford 2-((6-methoxyquinazolin-4-yl)amino)ethan-1-ol (2.0 g, 71% yield).

Step 4: Synthesis of 9-Methoxy-2,3-dihydroimidazo [1,2-c]quinazoline

To a mixture of 2-((6-methoxyquinazolin-4-yl)amino) ethan-1-ol (2.0 g, 9.13 mmol) in CHCl$_3$ (30 mL) was added SOCl$_2$ (10.0 mL) which was degassed with N$_2$ and stirred at 70° C. overnight. The resulting mixture was cooled to room temperature and concentrated in vacuo. The residue was dissolved in aq. NaHCO₃ (50.0 mL) and extracted with DCM (200 mL×3). The combined organic layer was dried over Na₂SO₄, filtered and concentrated in vacuo to provide 9-methoxy-2,3-dihydroimidazo[1,2-c]quinazoline (1.5 g, 82% yield) as a tan solid.

Step 5: Synthesis of 2,3-Dihydroimidazo[1,2-c]quinazolin-9-ol

To a solution of 9-methoxy-2,3-dihydroimidazo[1,2-c] quinazoline (200 mg, 1.0 mmol) in DMF (10.0 mL) was added NaSEt (200 mg, 2.0 mmol). The reaction mixture was degassed with N₂ and stirred at 130° C. overnight, then cooled down to room temperature. The resulting mixture was evaporated and the residue was purified by silica column chromatography (DCM/MeOH from 50:1 to 20:1, v/v) to afford 2,3-dihydroimidazo[1,2-c]quinazolin-9-ol (150 mg, 80% yield).

Step 6: Synthesis of 2-((2,3-Dihydroimidazo[1,2-c]quinazolin-9-yl)oxy)-6-fluorobenzonitrile NaH (60% in mineral oil, 30 mg, 0.73 mmol) was slowly added to a solution of 2,3-dihydroimidazo[1,2-c]quinazolin-9-ol (105 mg, 0.56 mmol) in DMF (10.0 mL) at 0° C. The reaction mixture was degassed with N₂ and stirred at room temperature for 15 min. Then 2,6-difluorobenzonitrile (78 mg, 0.56 mmol) was added and the mixture was stirred at 80° C. for 1 h. The resulting mixture was evaporated and the residue was purified by silica column chromatography (DCM/MeOH from 100:1 to 30:1, v/v) to afford 2-((2,3-dihydroimidazo[1,2-c]quinazolin-9-yl)oxy)-6-fluorobenzonitrile (120 mg, 70% yield).

Step 7: Synthesis of N-(2-Cyano-3-((2,3-dihydroimidazo[1,2-c]quinazolin-9-yl)oxy)phenyl)propane-1-sulfonamide NaH (60% in mineral oil, 17.0 mg, 0.43 mmol) was slowly added to a solution of propane-1-sulfonamide (48.0 mg, 0.39 mmol) in DMF (15.0 mL) at 0° C. The reaction mixture was degassed with N₂ and stirred at room temperature for 30 min. Then 2-((2,3-dihydroimidazo[1,2-c]quinazolin-9-yl)oxy)-6-fluorobenzonitrile (100 mg, 0.33 mmol) was added and the mixture was stirred at 100° C. overnight under N₂. The resulting mixture was evaporated and the residue was purified by flash column (ACN/H₂O) to afford N-(2-Cyano-3-((2,3-dihydroimidazo[1,2-c]quinazolin-9-yl)oxy)phenyl)propane-1-sulfonamide (20 mg, 15% yield) as a white solid. ¹H NMR (400 MHz, DMSO-d₆): δ 8.73 (s, 1H), 8.06-7.96 (m, 3H), 7.75 (t, J=8.0 Hz, 1H), 7.40 (d, J=8.0 Hz, 1H), 7.08 (d, J=8.4 Hz, 1H), 4.74-4.69 (m, 2H), 4.19-4.15 (m, 2H), 3.25 (t, J=7.2 Hz, 2H), 1.85-1.79 (m, 2H), 1.02 (t, J=7.2 Hz, 3H). LCMS (M+H⁺) m/z: 410.7.

Example 2: Preparation of N-(2-Cyano-3-((2,3-dihydroimidazo[1,2-c]quinazolin-9-yl)oxy)phenyl)-N-methylpropane-1-sulfonamide (Compound 2)

Scheme 2

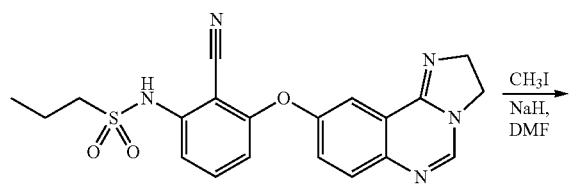

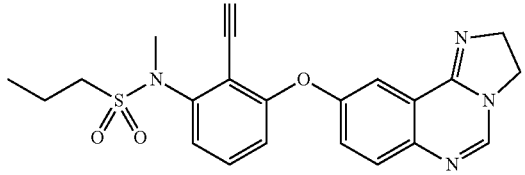

Synthesis of N-(2-Cyano-3-((2,3-dihydroimidazo[1,2-c]quinazolin-9-yl)oxy)phenyl)-N-methylpropane-1-sulfonamide NaH (60% in mineral oil, 16.0 mg, 0.39 mmol) was slowly added to a solution of N-(2-cyano-3-((2,3-dihydroimidazo[1,2-c]quinazolin-9-yl)oxy)phenyl)propane-1-sulfonamide (80 mg, 0.20 mmol) in DMF (10.0 mL) at 0° C. The reaction mixture was degassed with N₂ and stirred at room temperature for 60 min. Then iodomethane (43 mg, 0.30 mmol) was added and the mixture was stirred at room temperature overnight under N₂. The resulting mixture was evaporated and the residue was purified by flash column (ACN/H₂O) to afford N-(2-cyano-3-((2,3-dihydroimidazo[1,2-c]quinazolin-9-yl)oxy)phenyl)-N-methylpropane-1-sulfonamide (30 mg, 35% yield) as a white solid. 1H NMR (400 MHz, DMSO-d₆): δ 7.98 (s, 1H), 7.72 (t, J=8.4 Hz, 1H), 7.54-7.44 (m, 4H), 7.07 (d, J=8.4 Hz, 1H), 4.12 (t, J=9.6 Hz, 2H), 3.92 (t, J=9.6 Hz, 2H), 3.34-3.30 (m, 2H), 3.29 (s, 3H), 1.81-1.75 (m, 2H), 1.02 (t, J=7.2 Hz, 3H). LCMS (M+H⁺) m/z: 424.2 [M+1].

Example 3: Preparation of N-(2-Cyano-3-((2,3-dihydroimidazo[1,2-c]quinazolin-9-yl)oxy)-4-fluorophenyl)propane-1-sulfonamide (Compound 3)

Scheme 3

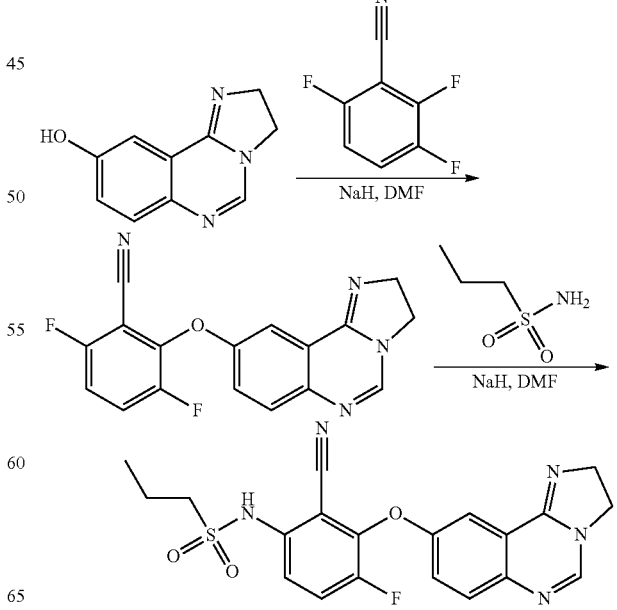

Step 1: Synthesis of 2-((2,3-Dihydroimidazo[1,2-c]quinazolin-9-yl)oxy)-3,6-difluorobenzonitrile NaH (60% in mineral oil, 111 mg, 2.78 mmol) was slowly added to a solution of 2,3-dihydroimidazo[1,2-c]quinazolin-9-ol (400 mg, 2.14 mmol) in DMF (20 mL) at 0° C. The reaction mixture was degassed with $N_2$ and stirred at rt for 60 min. Then 2,3,6-trifluorobenzonitrile (37.0 mg, 2.35 mmol) was added and the mixture was stirred at 80° C. for 1 hour. The resulting mixture was evaporated and the residue was purified by column chromatography on silica gel (DCM/MeOH from 100:1 to 30:1, v/v) to afford 2-((2,3-dihydroimidazo[1,2-c]quinazolin-9-yl)oxy)-3,6-difluorobenzonitrile (200 mg, 29% yield).

Step 2: Synthesis of N-(2-Cyano-3-((2,3-dihydroimidazo[1,2-c]quinazolin-9-yl)oxy)-4-fluorophenyl)propane-1-sulfonamide NaH (60% in mineral oil, 32 mg, 0.81 mmol) was slowly added to a solution of propane-1-sulfonamide (84 mg, 0.68 mmol) in DMF (20 mL) at 0° C. The reaction mixture was degassed with $N_2$ and stirred at rt for 60 min. Then 2-((2,3-dihydroimidazo[1,2-c]quinazolin-9-yl)oxy)-3,6-difluorobenzonitrile (200 mg, 0.62 mmol) was added and the mixture was stirred at 100° C. overnight under $N_2$. The resulting mixture was evaporated and the residue was purified by flash column (ACN/$H_2O$) to afford N-(2-cyano-3-((2,3-dihydroimidazo[1,2-c]quinazolin-9-yl)oxy)-4-fluorophenyl)propane-1-sulfonamide (30 mg, 10% yield) as a white solid. 1H NMR (400 MHz, $CD_3OD$): δ 7.91 (s, 1H), 7.50 (d, J=8.8 Hz, 1H), 7.43-7.34 (m, 3H), 7.25 (t, J=9.6 Hz, 1H), 4.19 (t, J=9.6 Hz, 2H), 4.00 (t, J=9.6 Hz, 2H), 2.98-2.94 (m, 2H), 1.88-1.83 (m, 2H), 1.02 (t, J=7.2 Hz, 3H). LCMS (M+H$^+$) m/z: 428.7.

Example 4: Preparation of N-(2-Cyano-3-((2,3-dihydroimidazo[1,2-c]quinazolin-9-yl)oxy)-4,6-difluorophenyl)propane-1-sulfonamide (Compound 4)

Scheme 4

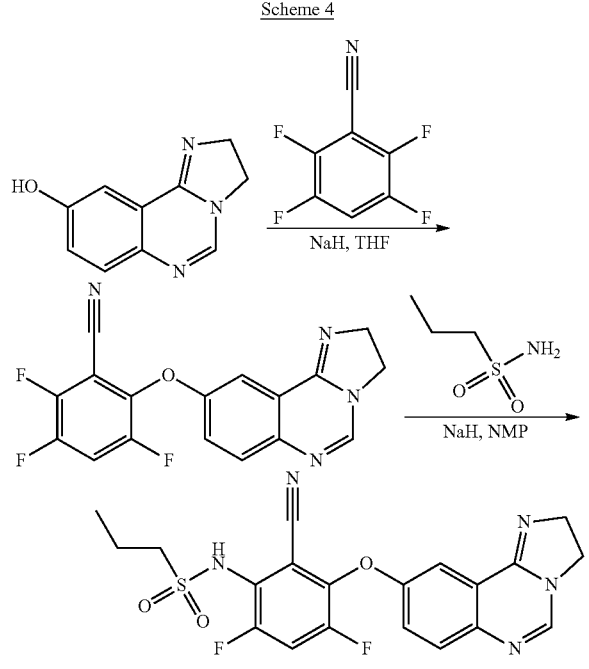

Step 1: Synthesis of 2-((2,3-Dihydroimidazo[1,2-c]quinazolin-9-yl)oxy)-3,5,6-trifluorobenzonitrile NaH (60% in mineral oil, 128 mg, 3.2 mmol) was slowly added to a solution of 2,3-dihydroimidazo[1,2-c]quinazolin-9-ol (300 mg, 1.6 mmol) in THF (10 mL) at 0° C. The reaction mixture was degassed with $N_2$ and stirred at 0° C. for 30 min. Then 2,3,5,6-tetrafluorobenzonitrile (308 mg, 1.8 mmol) was added and the mixture was stirred at room temperature for 18 hours. The reaction mixture was quenched by MeOH (5 mL) at 0° C. The resulting mixture was evaporated and the residue was purified on silica gel column flash chromatography (DCM/MeOH from 60:1 to 10:1, v/v) to afford 2-((2,3-dihydroimidazo[1,2-c]quinazolin-9-yl)oxy)-3,5,6-trifluorobenzonitrile (200 mg, 36% yield) as a yellow solid.

Step 2: Synthesis of N-(2-Cyano-3-((2,3-dihydroimidazo[1,2-c]quinazolin-9-yl)oxy)-4,6-difluorophenyl)propane-1-sulfonamide NaH (60% in mineral oil, 48 mg, 1.2 mmol) was slowly added to a solution of propane-1-sulfonamide (86 mg, 0.7 mmol) in NMP (10 mL) at 0° C. The reaction mixture was degassed with $N_2$ and stirred at 0° C. for 30 min. Then 2-((2,3-dihydroimidazo[1,2-c]quinazolin-9-yl)oxy)-3,5,6-trifluorobenzonitrile (200 mg, 0.6 mmol) was added and the mixture was stirred at 80° C. overnight under $N_2$. Then cooled down to room temperature. The resulting mixture was evaporated and the residue was purified on silica gel column flash chromatography (DCM/MeOH from 60:1 to 10:1, v/v) to afford the crude product which was purified by Perp-TLC (DCM/MeOH=10:1, v/v) to afford N-(2-cyano-3-((2,3-dihydroimidazo[1,2-c]quinazolin-9-yl)oxy)-4,6-difluorophenyl)propane-1-sulfonamide (16 mg, 6% yield) as a yellow solid. 1H NMR (400 MHz, $CD_3OD$): δ 8.11 (s, 1H), 7.71-7.66 (m, 2H), 7.56 (dd, J=8.8, 2.8 Hz, 1H), 7.48 (d, J=2.4 Hz, 1H), 4.37 (t, J=10.0 Hz, 2H), 4.08 (t, J=10.0 Hz, 2H), 3.19 (t, J=7.6 Hz, 2H), 1.97-1.91 (m, 2H), 1.07 (t, J=7.6 Hz, 3H). LCMS (M+H$^+$) m/z: 446.2.

Example 5: Preparation of N-(2-Cyano-3-((2,3-dihydroimidazo[1,2-c]quinazolin-9-yl)oxy)-6-fluorophenyl)propane-1-sulfonamide (Compound 5)

Scheme 5

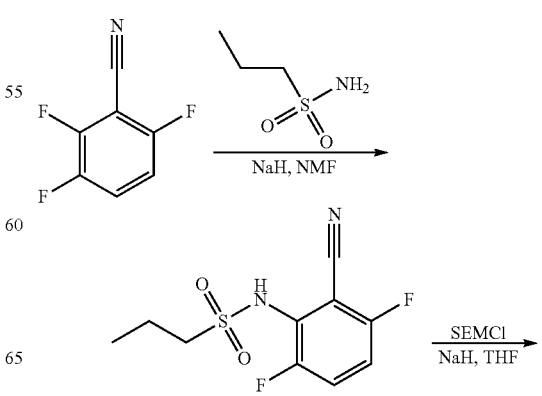

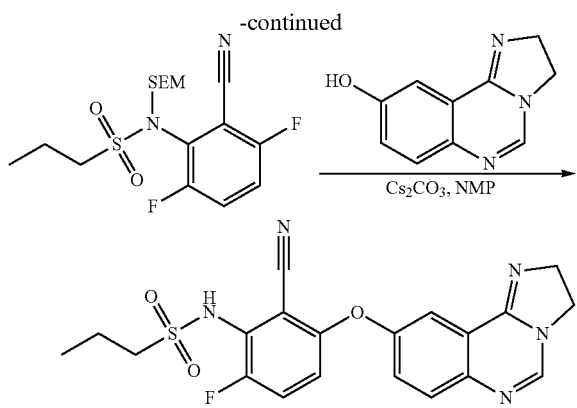

Step 1: Synthesis of N-(2-Cyano-3,6-difluorophenyl)propane-1-sulfonamide

NaH (60% in mineral oil, 320 mg, 8.0 mmol) was slowly added to a solution of propane-1-sulfonamide (590 mg, 4.8 mmol) in DMF (10 mL) at 0° C. The reaction mixture was degassed with N₂ and stirred at 0° C. for 30 min. Then 2,3,6-trifluorobenzonitrile (628 mg, 4.0 mmol) was added and the mixture was stirred at room temperature for 18 hours. The reaction mixture was quenched by H₂O (5 mL) at 0° C. The resulting mixture was evaporated and the residue was purified on silica gel column flash chromatography (PE/EtOAc from 10:1 to 4:1, v/v) to afford N-(2-cyano-3,6-difluorophenyl)propane-1-sulfonamide (920 mg, 88% yield) as a white solid.

Step 2: Synthesis of N-(2-Cyano-3,6-difluorophenyl)-N-((2-(trimethylsilyl)ethoxy)methyl)propane-1-sulfonamide NaH (60% in mineral oil, 212 mg, 5.3 mmol) was slowly added to a solution of N-(2-cyano-3,6-difluorophenyl)propane-1-sulfonamide (920 mg, 3.5 mmol) in THF (40 mL) at 0° C. The reaction mixture was degassed with N₂ and stirred at 0° C. for 30 min. Then (2-(chloromethoxy)ethyl)trimethylsilane (709 mg, 4.3 mmol) was added and the mixture was stirred at room temperature overnight under N₂. The reaction mixture was quenched by MeOH (5 mL) at 0° C. The resulting mixture was evaporated and the residue was purified on silica gel column flash chromatography (PE/EtOAc from 10:1 to 4:1, v/v) to afford N-(2-cyano-3,6-difluorophenyl)-N-((2-(trimethylsilyl)ethoxy)methyl)propane-1-sulfonamide (800 mg, 58% yield) as yellow oil.

Step 3: Synthesis of N-(2-Cyano-3-((2,3-dihydroimidazo[1,2-c]quinazolin-9-yl)oxy)-6-fluorophenyl)propane-1-sulfonamide A 50 mL round bottomed flask was charged with N-(2-cyano-3,6-difluorophenyl)-N-((2-(trimethylsilyl)ethoxy)methyl)propane-1-sulfonamide (580 mg, 1.5 mmol), 2,3-dihydroimidazo[1,2-c]quinazolin-9-ol (277 mg, 1.5 mmol), Cs₂CO₃ (724 mg, 2.2 mmol) and 20 mL of NMP. The resulting solution was heated at 100° C. for 18 hours. After being cooled to room temperature, the resulting mixture was evaporated and the residue was purified on silica gel column flash chromatography (DCM/MeOH from 40:1 to 10:1, v/v) to afford N-(2-cyano-3-((2,3-dihydroimidazo[1,2-c]quinazolin-9-yl)oxy)-6-fluorophenyl)propane-1-sulfonamide (80 mg, 13% yield) as a white solid. 1H NMR (400 MHz, DMSO-d₆): δ 10.48 (br, 1H), 8.13 (s, 1H), 7.63-7.52 (m, 3H), 7.45 (d, J=2.4 Hz, 1H), 6.99-6.96 (m, 1H), 4.24 (t, J=10.0 Hz, 2H), 3.96 (t, J=10.0 Hz, 2H), 3.12 (t, J=7.6 Hz, 2H), 1.85-1.79 (m, 2H), 1.00 (t, J=7.2 Hz, 3H). LCMS (M+H⁺) m/z: 428.2.

Example 6: Preparation of N-(2-Chloro-3-((2,3-dihydroimidazo[1,2-c]quinazolin-9-yl)oxy)phenyl)propane-1-sulfonamide (Compound 6)

Scheme 6

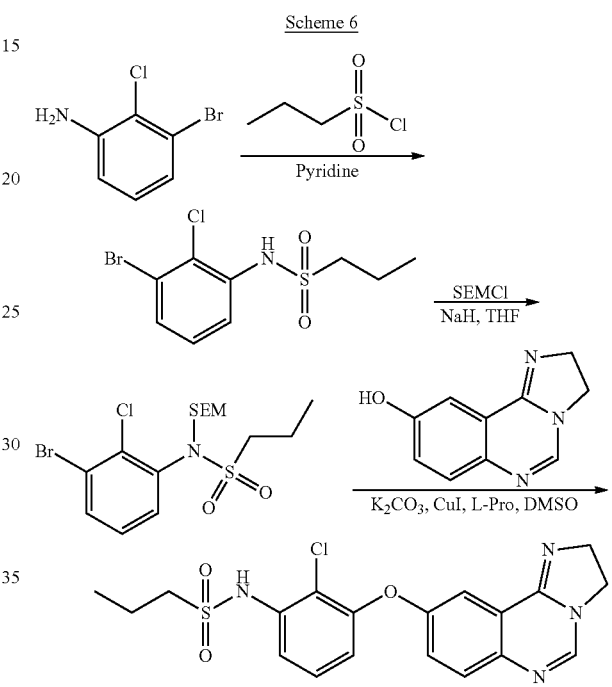

Step 1: Synthesis of N-(3-Bromo-2-chlorophenyl)propane-1-sulfonamide

To a solution of 3-bromo-2-chloroaniline (3.0 g, 12.7 mmol) in pyridine (30 mL) was added propane-1-sulfonyl chloride (5.4 g, 38.1 mmol), the reaction was stirred at room temperature overnight under N₂, after the reaction was completed, the solvent was removed. The residue was purified on silica gel column chromatography (PE/EtOAc=10/1) to afford N-(3-bromo-2-chlorophenyl)propane-1-sulfonamide (700 mg, 18% yield) as yellow oil.

Step 2: Synthesis of N-(3-Bromo-2-chlorophenyl)-N-((2-(trimethylsilyl)ethoxy)methyl)propane-1-sulfonamide To a solution of N-(3-bromo-2-chlorophenyl)propane-1-sulfonamide (700 mg, 2.2 mmol) in THF (30 mL) was added NaH (60% in mineral oil, 176 mg, 4.4 mmol) in portions at 0° C. The mixture was stirred for 1 hour at 0° C., and then SEMCl (730 mg, 4.4 mmol) was added dropwise at 0° C. The resulting mixture was stirred at room temperature for 3 hours. After the reaction completed, it was quenched by water (5 mL) at 0° C. The solvent was removed. The residue was purified on silica gel column chromatography (PE/EtOAc=10/1) to afford N-(3-bromo-2-chlorophenyl)-N-((2-

(trimethylsilyl)ethoxy)methyl)propane-1-sulfonamide (700 mg, 72% yield) as yellow oil.

Step 3: Synthesis of N-(2-Chloro-3-((2,3-dihydroimidazo[1,2-c]quinazolin-9-yl)oxy)phenyl)propane-1-sulfonamide A mixture of N-(3-bromo-2-chlorophenyl)-N-((2-(trimethylsilyl)ethoxy)methyl)propane-1-sulfonamide (700 mg, 1.58 mmol), 2,3-dihydroimidazo[1,2-c]quinazolin-9-ol (319 mg, 1.70 mmol), $K_2CO_3$ (650 mg, 4.74 mmol), CuI (120 mg, 0.63 mmol) and L-Pro (60 mg, 0.63 mmol) in DMSO (20 mL) was stirred at 150° C. for 16 hours under $N_2$, after the reaction was completed, the mixture was filtered and concentrated. The residue was purified by prep-HPLC to afford N-(2-chloro-3-((2,3-dihydroimidazo[1,2-c]quinazolin-9-yl)oxy)phenyl)propane-1-sulfonamide (5 mg, 1% yield) as a white solid. 1H NMR (400 MHz, $CD_3OD$): δ 8.03 (s, 1H), 7.58 (d, J=8.4 Hz, 1H), 7.51 (d, J=7.6 Hz, 1H), 7.43-7.33 (m, 3H), 7.02 (d, J=7.2 Hz, 1H), 4.29 (t, J=10.0 Hz, 2H), 4.04 (t, J=10.0 Hz, 2H), 3.15 (t, J=7.6 Hz, 2H), 1.88-1.82 (m, 2H), 1.03 (t, J=7.6 Hz, 3H). LCMS (M+H$^+$) m/z: 419.1.

Example 7: Preparation of N-(3-((2,3-Dihydroimidazo[1,2-c]quinazolin-9-yl)oxy)-2-fluoro-4-nitrophenyl)propane-1-sulfonamide (Compound 7)

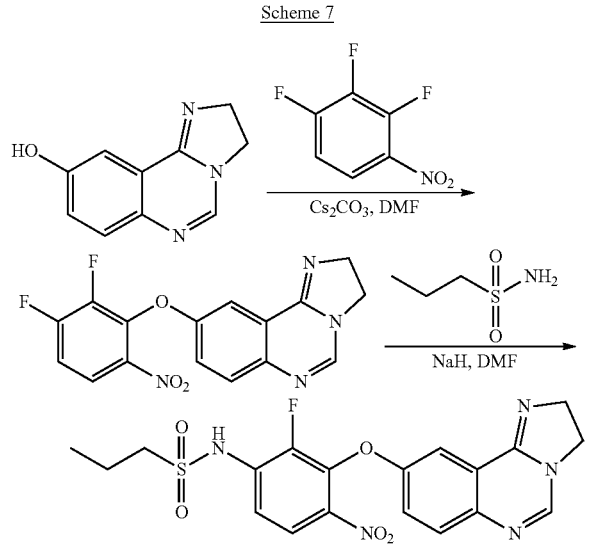

Scheme 7

Step 1: Synthesis of 9-(2,3-Difluoro-6-nitrophenoxy)-2,3-dihydroimidazo[1,2-c]quinazoline A mixture of 2,3-dihydroimidazo[1,2-c]quinazolin-9-ol (300 mg, 1.6 mmol), 1,2,3-trifluoro-4-nitrobenzene (852 mg, 4.8 mmol) and $Cs_2CO_3$ (783.6 mg, 2.4 mmol) in DMF (15 mL) was stirred at room temperature overnight. The reaction mixture was evaporated, the residue was purified by silica gel column chromatography (DCM/MeOH/$NH_3H_2O$ from 100:1:1 to 10:1:0.1, v/v/v) to afford 9-(2,3-difluoro-6-nitrophenoxy)-2,3-dihydroimidazo[1,2-c]quinazoline (410 mg, 74% yield) as a yellow solid.

Step 2: Synthesis of N-(3-((2,3-Dihydroimidazo[1,2-c]quinazolin-9-yl)oxy)-2-fluoro-4-nitrophenyl)propane-1-sulfonamide To a solution of propane-1-sulfonamide (161 mg, 1.31 mmol) in DMF (10 mL) was added NaH (60% in mineral oil, 119 mg, 2.98 mmol) at 0° C. The reaction mixture was stirred at 0° C. for 30 minutes, then a solution of 9-(2,3-difluoro-6-nitrophenoxy)-2,3-dihydroimidazo[1,2-c]quinazoline (410 mg, 1.19 mmol) in DMF (2 mL) was added to the stirred mixture dropwise. The reaction mixture was stirred at room temperature overnight. To the mixture was added water (10 mL), the solvent was evaporate, the residue was purified by prep-HPLC to afford N-(3-((2,3-dihydroimidazo[1,2-c]quinazolin-9-yl)oxy)-2-fluoro-4-nitrophenyl)propane-1-sulfonamide (221 mg, 38% yield) as a yellow solid. 1H NMR (400 MHz, DMSO-$d_6$): δ 11.19 (br s, 1H), 8.46 (s, 1H), 7.93 (d, J=9.6 Hz, 1H), 7.85 (d, J=9.2 Hz, 1H), 7.78 (dd, J=9.2, 2.0 Hz, 1H), 7.50 (s, 1H), 7.38 (t, J=8.8 Hz, 1H), 4.51 (t, J=10.0 Hz, 2H), 4.05 (t, J=10.0 Hz, 2H), 2.93 (t, J=7.6 Hz, 2H), 1.73-1.68 (m, 2H), 0.95 (t, J=7.6 Hz, 3H). LCMS (M+H$^+$) m/z: 448.1.

Example 8: Preparation of N-(4-Amino-3-((2,3-dihydroimidazo[1,2-c]quinazolin-9-yl)oxy)-2-fluorophenyl)propane-1-sulfonamide (Compound 8)

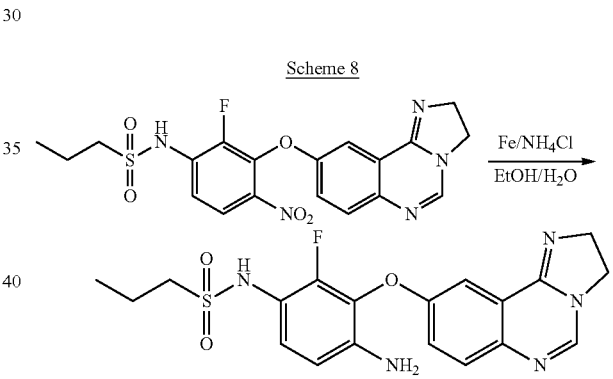

Scheme 8

Synthesis of N-(4-Amino-3-((2,3-dihydroimidazo[1,2-c]quinazolin-9-yl)oxy)-2-fluorophenyl)propane-1-sulfonamide A mixture of N-(3-((2,3-dihydroimidazo[1,2-c]quinazolin-9-yl)oxy)-2-fluoro-4-nitrophenyl)propane-1-sulfonamide (160 mg, 0.35 mmol), Fe (100 mg, 1.78 mmol) and $NH_4Cl$ (144 mg, 2.68 mmol) in EtOH/$H_2O$ (10 mL/1 mL) was stirred at 95° C. for 2 hours. The reaction mixture was evaporated, the residue was purified by column chromatography on silica gel (DCM/MeOH/$NH_3H_2O$ from 100:1:1 to 10:1:0.1, v/v/v) to afford N-(4-amino-3-((2,3-dihydroimidazo[1,2-c]quinazolin-9-yl)oxy)-2-fluorophenyl)propane-1-sulfonamide (100 mg, 68% yield) as a white solid. 1H NMR (400 MHz, DMSO-$d_6$): δ 11.46 (br, 1H), 9.15 (s, 1H), 8.65 (s, 1H), 7.97 (d, J=9.2 Hz, 1H), 7.79 (dd, J=9.2, 2.4 Hz, 1H), 7.64 (s, 1H), 7.05 (t, J=8.8 Hz, 1H), 6.66 (d, J=8.4 Hz, 1H), 4.68 (t, J=10.0 Hz, 2H), 4.12 (t, J=10.0 Hz, 2H), 2.97 (t, J=7.6 Hz, 2H), 1.73-1.67 (m, 2H), 0.92 (t, J=7.6 Hz, 3H). LCMS (M+H$^+$) m/z: 418.2.

Example 9: Preparation of N-(3-((2,3-Dihydroimidazo[1,2-c]quinazolin-9-yl)oxy)-2-fluorophenyl)propane-1-sulfonamide (Compound 9)

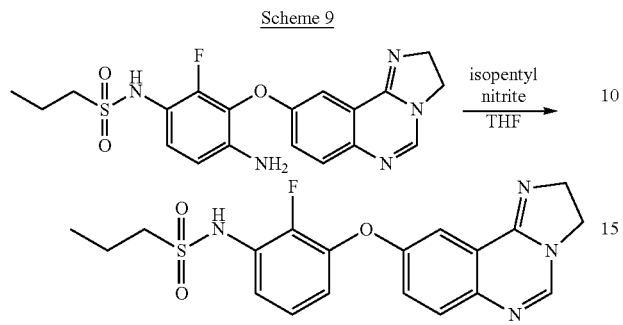

Scheme 9

Synthesis of N-(3-((2,3-Dihydroimidazo[1,2-c]quinazolin-9-yl)oxy)-2-fluorophenyl)propane-1-sulfonamide A mixture of N-(4-amino-3-((2,3-dihydroimidazo[1,2-c]quinazolin-9-yl)oxy)-2-fluorophenyl)propane-1-sulfonamide (70 mg, 0.16 mmol) and isopentyl nitrite (196 mg, 1.67 mmol) in THF (10 mL) was stirred at 75° C. for 2 hours. After the reaction was completed, the solvent was evaporated, the residue was purified by prep-HPLC to afford N-(3-((2,3-dihydroimidazo[1,2-c]quinazolin-9-yl)oxy)-2-fluorophenyl)propane-1-sulfonamide (TFA salt, 20.1 mg, 23% yield) as a brown solid. 1H NMR (400 MHz, DMSO-$d_6$): δ 11.62 (br, 1H), 9.92 (s, 1H), 8.67 (s, 1H), 7.98 (d, J=9.2 Hz, 1H), 7.86 (dd, J=9.2, 2.4 Hz, 1H), 7.78 (s, 1H), 7.40-7.38 (m, 1H), 7.30 (t, J=8.8 Hz, 1H), 7.22-7.19 (m, 1H), 4.68 (t, J=10.0 Hz, 2H), 4.13 (t, J=10.0 Hz, 2H), 3.15 (t, J=8.0 Hz, 2H), 1.76-1.71 (m, 2H), 0.96 (t, J=7.6 Hz, 3H). LCMS (M+H$^+$) m/z: 403.2.

Example 10: Preparation of N-(3-((2,3-Dihydroimidazo[1,2-c]quinazolin-9-yl)oxy)-2,4-difluorophenyl)propane-1-sulfonamide (Compound 10)

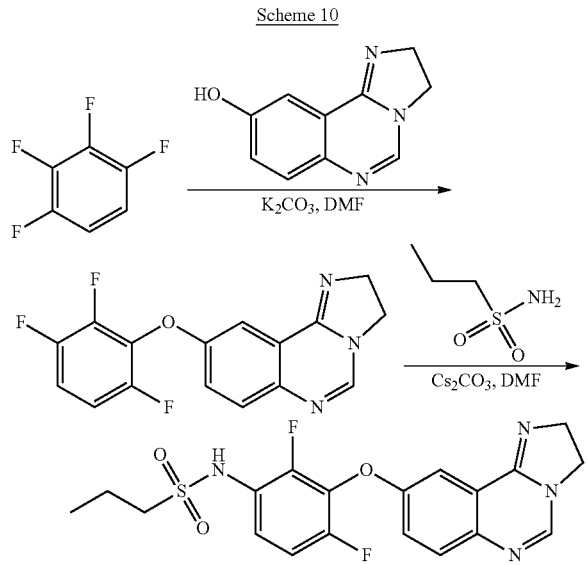

Scheme 10

Step 1: Synthesis of 9-(2,3,6-Trifluorophenoxy)-2,3-dihydroimidazo[1,2-c]quinazoline To a solution of 1,2,3,4-tetrafluorobenzene (300 mg, 2.0 mmol) and 2,3-dihydroimidazo[1,2-c]quinazolin-9-ol (374 mg, 2.0 mmol) in DMF (10 mL) was added K$_2$CO$_3$ (552 mg, 4.0 mmol). The mixture was stirred at 120° C. for 18 hours. After being cooled to room temperature, the resulting mixture was evaporated and the residue was purified by flash column chromatography on silica gel (DCM/MeOH from 60:1 to 10:1, v/v) to afford 9-(2,3,6-trifluorophenoxy)-2,3-dihydroimidazo[1,2-c]quinazoline (477 mg, 75% yield) as a brown solid.

Step 2: Synthesis of N-(3-((2,3-Dihydroimidazo[1,2-c]quinazolin-9-yl)oxy)-2,4-difluorophenyl)propane-1-sulfonamide A 50 mL round bottomed flask was charged with 9-(2,3,6-trifluorophenoxy)-2,3-dihydroimidazo[1,2-c]quinazoline (427 mg, 1.35 mmol), propane-1-sulfonamide (332 mg, 2.70 mmol), Cs$_2$CO$_3$ (880 mg, 2.70 mmol) and 10 mL of DMF. The resulting solution was heated at 120° C. for 18 hours. After being cooled to room temperature, the resulting mixture was evaporated and the residue was purified by flash column chromatography on silica gel (DCM/MeOH from 40:1 to 10:1, v/v) to afford N-(3-((2,3-dihydroimidazo[1,2-c]quinazolin-9-yl)oxy)-2,4-difluorophenyl)propane-1-sulfonamide (28.1 mg, 5% yield) as a white solid. 1H NMR (400 MHz, DMSO-$d_6$): δ 9.61 (br, 1H), 7.99 (s, 1H), 7.52-7.45 (m, 2H), 7.38-7.35 (m, 2H), 7.18 (s, 1H), 4.14 (t, J=9.6 Hz, 2H), 3.91 (t, J=9.6 Hz, 2H), 3.07 (t, J=7.6 Hz, 2H), 1.73-1.67 (m, 2H), 0.89 (t, J=7.6 Hz, 3H). LCMS m/z: 421.1 [M+1]$^+$

Example 11: Preparation of N-(3-((2,3-Dihydroimidazo[1,2-c]quinazolin-9-yl)oxy)-2-(trifluoromethyl)phenyl)propane-1-sulfonamide (Compound 11)

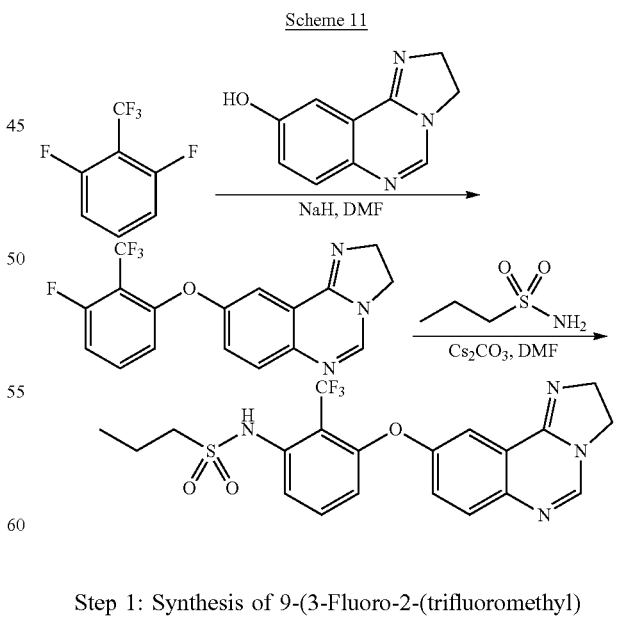

Scheme 11

Step 1: Synthesis of 9-(3-Fluoro-2-(trifluoromethyl)phenoxy)-2,3-dihydroimidazo[1,2-c]quinazoline To a solution of 1,3-difluoro-2-(trifluoromethyl)benzene (182 mg, 1.0 mmol) in DMF (5 mL) was added NaH (60% in mineral oil, 48 mg, 1.2 mmol) at room temperature, the mixture was stirred at room temperature for 30 min, then 2,3-dihydroimidazo[1,2-c]quinazolin-9-ol (187 mg, 1.0 mmol) was added, the reaction was stirred at room temperature overnight. After the reaction was completed, water was added to quenched the reaction, the solvent was removed, the residue was purified on silica gel column chromatography (DCM/MeOH=30/1+5% c $NH_3 \cdot H_2O$) to afford 9-(3-fluoro-2-(trifluoromethyl)phenoxy)-2,3-dihydroimidazo[1,2-c]quinazoline (130 mg, 37% yield) as a white solid.

Step 2: Synthesis of N-(3-((2,3-Dihydroimidazo[1,2-c]quinazolin-9-yl)oxy)-2-(trifluoromethyl)phenyl)propane-1-sulfonamide A mixture of 9-(3-fluoro-2-(trifluoromethyl)phenoxy)-2,3-dihydroimidazo[1,2-c]quinazoline (130 mg, 0.37 mmol), propane-1-sulfonamide (136 mg, 1.11 mmol), and $Cs_2CO_3$ (241 mg, 0.74 mmol) in DMF (5 mL) was stirred at 120° C. for 16 hours under $N_2$, after the reaction was completed, the solvent was removed. The residue was purified by Prep-HPLC to afford N-(3-((2,3-dihydroimidazo[1,2-c]quinazolin-9-yl)oxy)-2-(trifluoromethyl)phenyl)propane-1-sulfonamide (TFA salt, 26 mg, 12% yield) as a yellow solid. 1H NMR (400 MHz, DMSO-$d_6$): δ 11.54 (br, 1H), 9.70 (s, 1H), 8.69 (s, 1H), 8.00 (d, J=8.8 Hz, 1H), 7.87-7.84 (m, 2H), 7.73 (t, J=8.0 Hz, 1H), 7.40 (d, J=8.0 Hz, 1H), 7.19 (d, J=8.0 Hz, 1H), 4.70 (t, J=10.0 Hz, 2H), 4.15 (t, J=10.0 Hz, 2H), 3.18 (t, J=7.6 Hz, 2H), 1.82-1.76 (m, 2H), 1.02 (t, J=7.6 Hz, 3H). LCMS (M+H$^+$) m/z: 453.1.

Example 12: Preparation of N-(3-((2,3-Dihydroimidazo[1,2-c]quinazolin-9-yl)oxy)-2-nitrophenyl)propane-1-sulfonamide (Compound 12)

Scheme 12

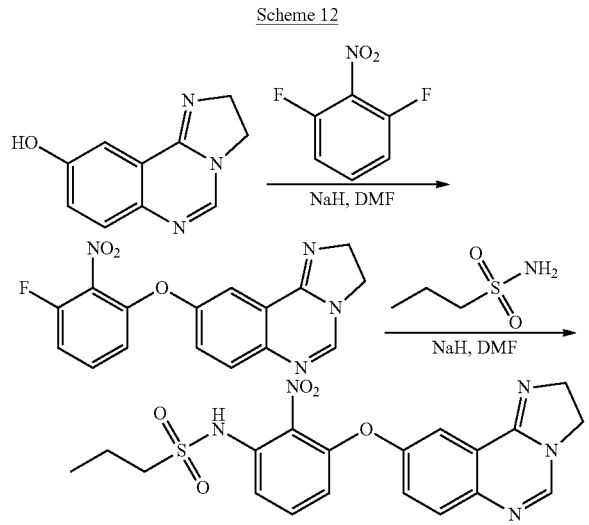

Step 1: Synthesis of 9-(3-Fluoro-2-nitrophenoxy)-2,3-dihydroimidazo[1,2-c]quinazoline A solution of 2,3-dihydroimidazo[1,2-c]quinazolin-9-ol (500 mg, 2.67 mmol) in DMF (20 mL) was cooled to 0° C., and then NaH (60% in mineral oil, 138 mg, 3.47 mmol) was added to the mixture. After addition, the reaction mixture was stirred at 0° C. for 30 min. 1,3-Difluoro-2-nitrobenzene (510 mg, 3.2 mmol) was added, and then stirred at room temperature for 3 hours. The resulting mixture was evaporated and the residue was purified by flash column (ACN/$H_2O$) to afford 9-(3-fluoro-2-nitrophenoxy)-2,3-dihydroimidazo[1,2-c]quinazoline (600 mg, 69% yield) as a yellow solid.

Step 2: Synthesis of N-(3-((2,3-Dihydroimidazo[1,2-c]quinazolin-9-yl)oxy)-2-nitrophenyl)propane-1-sulfonamide NaH (60% in mineral oil, 80 mg, 1.99 mmol) was slowly added to a solution of propane-1-sulfonamide (226 mg, 1.84 mmol) in DMF (20.0 mL) at 0° C. The reaction mixture was degassed with $N_2$ and stirred at room temperature for 60 min. Then 9-(3-fluoro-2-nitrophenoxy)-2,3-dihydroimidazo[1,2-c]quinazoline (500 mg, 1.53 mmol) was added and the mixture was stirred at 80° C. overnight under $N_2$. The resulting mixture was evaporated and the residue was purified by flash column (ACN/$H_2O$) to afford N-(3-((2,3-dihydroimidazo[1,2-c]quinazolin-9-yl)oxy)-2-nitrophenyl)propane-1-sulfonamide (240 mg, 37% yield) as a yellow solid. 1H NMR (400 MHz, DMSO-$d_6$): δ 8.24 (s, 1H), 7.67 (d, J=8.8 Hz, 1H), 7.57-7.51 (m, 2H), 7.39-7.32 (m, 2H), 6.68 (d, J=7.2 Hz, 1H), 4.34 (t, J=10.0 Hz, 2H), 4.00 (t, J=10.0 Hz, 2H), 2.96 (t, J=7.6 Hz, 2H), 1.72-1.66 (m, 2H), 0.96 (t, J=7.6 Hz, 3H). LCMS (M+H$^+$) m/z: 430.1.

Example 13: Preparation of N-(2-Amino-3-((2,3-dihydroimidazo[1,2-c]quinazolin-9-yl)oxy)phenyl)propane-1-sulfonamide (Compound 13)

Scheme 13

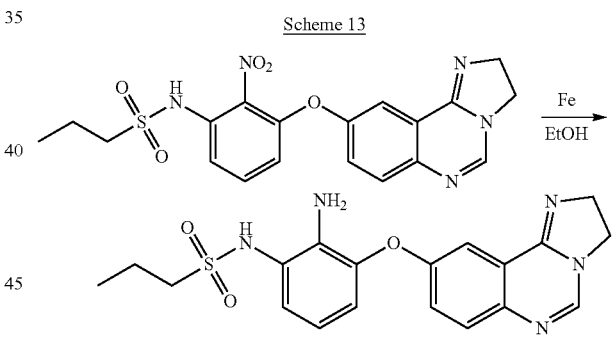

Synthesis of N-(2-Amino-3-((2,3-dihydroimidazo[1,2-c]quinazolin-9-yl)oxy)phenyl)propane-1-sulfonamide A mixture of N-(3-((2,3-dihydroimidazo[1,2-c]quinazolin-9-yl)oxy)-2-nitrophenyl)propane-1-sulfonamide (200 mg, 0.47 mmol), Fe (130 mg, 2.33 mmol), and $NH_4Cl$ (15 mg, 0.28 mmol) in EtOH/$H_2O$ (20 mL/3 mL) was stirred at 60° C. for 2 hours under $N_2$, after the reaction was completed, the solvent was removed. The residue was purified by column chromatography on silica gel (DCM/MeOH=25/1+5% c $NH_3 \cdot H_2O$) to afford N-(2-amino-3-((2,3-dihydroimidazo[1,2-c]quinazolin-9-yl)oxy)phenyl)propane-1-sulfonamide (60 mg, 32% yield) as a yellow solid. 1H NMR (400 MHz, DMSO-$d_6$): δ 8.94 (br s, 1H), 7.89 (s, 1H), 7.43 (d, J=8.8 Hz, 1H), 7.29 (dd, J=8.8, 2.8 Hz, 1H), 7.09 (d, J=2.8 Hz, 1H), 7.05 (d, J=7.6 Hz, 1H), 6.83 (d, J=7.6 Hz, 1H), 6.62 (t, J=7.6 Hz, 1H), 5.00 (br s, 2H), 4.07 (t, J=10.0 Hz, 2H), 3.86 (t, J=10.0 Hz, 2H), 3.02 (t, J=7.6 Hz, 2H), 1.77-1.68 (m, 2H), 0.95 (t, J=7.6 Hz, 3H). LCMS (M+H⁺) m/z: 400.1.

Example 14: Preparation of N-(2-Cyano-3-((2,3-dihydroimidazo[1,2-c]quinazolin-9-yl)oxy)phenyl)-2-fluorobenzenesulfonamide (Compound 14)

Scheme 14

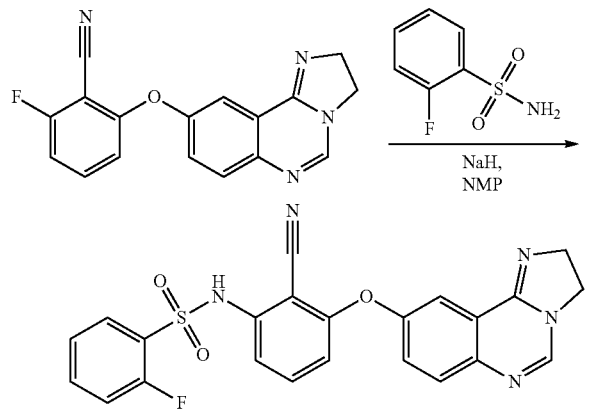

Synthesis of N-(2-Cyano-3-((2,3-dihydroimidazo[1,2-c]quinazolin-9-yl)oxy)phenyl)-2-fluorobenzenesulfonamide NaH (60% in mineral oil, 25 mg, 0.64 mmol) was slowly added to a solution of 2-fluorobenzenesulfonamide (103 mg, 0.58 mmol) in NMP (10.0 mL) at 0° C. The reaction mixture was degassed with N₂ and stirred at room temperature for 60 min. Then 2-((2,3-dihydroimidazo[1,2-c]quinazolin-9-yl)oxy)-6-fluorobenzonitrile (150 mg, 0.49 mmol) was added and the mixture was stirred at 80° C. overnight under N₂. The resulting mixture was evaporated and the residue was purified by flash column (ACN/H₂O) to afford N-(2-cyano-3-((2,3-dihydroimidazo[1,2-c]quinazolin-9-yl)oxy)phenyl)-2-fluorobenzenesulfonamide (90 mg, 40% yield) as a white solid. 1H NMR (400 MHz, DMSO-d₆): δ 7.92 (s, 1H), 7.82-7.76 (m, 1H), 7.69-7.64 (m, 1H), 7.45-7.30 (m, 3H), 7.25-7.17 (m, 3H), 7.07 (t, J=8.4 Hz, 1H), 6.95 (d, J=8.8 Hz, 1H), 6.08 (d, J=7.6 Hz, 1H), 4.09 (t, J=9.6 Hz, 2H), 3.90 (t, J=9.6 Hz, 2H). LCMS (M+H⁺) m/z: 462.2.

Example 15: Preparation of N-(2-Cyano-3-((2,3-dihydroimidazo[1,2-c]quinazolin-9-yl)oxy)phenyl)thiophene-2-sulfonamide (Compound 15)

Scheme 15

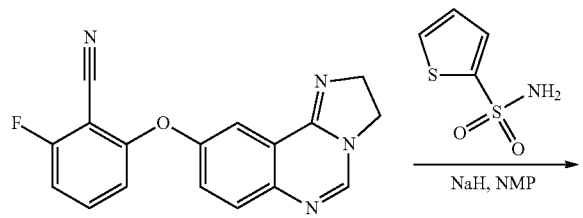

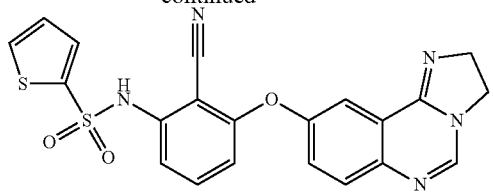

Synthesis of N-(2-Cyano-3-((2,3-dihydroimidazo[1,2-c]quinazolin-9-yl)oxy)phenyl)thiophene-2-sulfonamide NaH (60% in mineral oil, 33.0 mg, 0.85 mmol) was slowly added to a solution of thiophene-2-sulfonamide (130 mg, 0.78 mmol) in NMP (10.0 mL) at 0° C. The reaction mixture was degassed with N₂ and stirred at room temperature for 60 min. Then 2-((2,3-dihydroimidazo[1,2-c]quinazolin-9-yl)oxy)-6-fluorobenzonitrile (200 mg, 0.65 mmol) was added and the mixture was stirred at 80° C. overnight under N₂. The resulting mixture was evaporated and the residue was purified by flash column (ACN/H₂O) to afford N-(2-cyano-3-((2,3-dihydroimidazo[1,2-c]quinazolin-9-yl)oxy)phenyl)thiophene-2-sulfonamide (100 mg, 34% yield) as a white solid. 1H NMR (400 MHz, DMSO-d₆): δ 7.92 (s, 1H), 7.54 (d, J=3.6 Hz, 1H), 7.44 (d, J=8.8 Hz, 1H), 7.33-7.30 (m, 2H), 7.24 (d, J=2.8 Hz, 1H), 7.14-7.06 (m, 2H), 6.96 (dd, J=4.8, 3.6 Hz, 1H), 6.10 (d, J=7.6 Hz, 1H), 4.09 (t, J=9.6 Hz, 2H), 3.90 (t, J=9.6 Hz, 2H). LCMS (M+H⁺) m/z: 450.1.

Example 16: Preparation of N-(2-cyano-3-((3,4-dihydro-2H-pyrimido[1,2-c]quinazolin-10-yl)oxy)phenyl)propane-1-sulfonamide (Compound 16)

Scheme 16

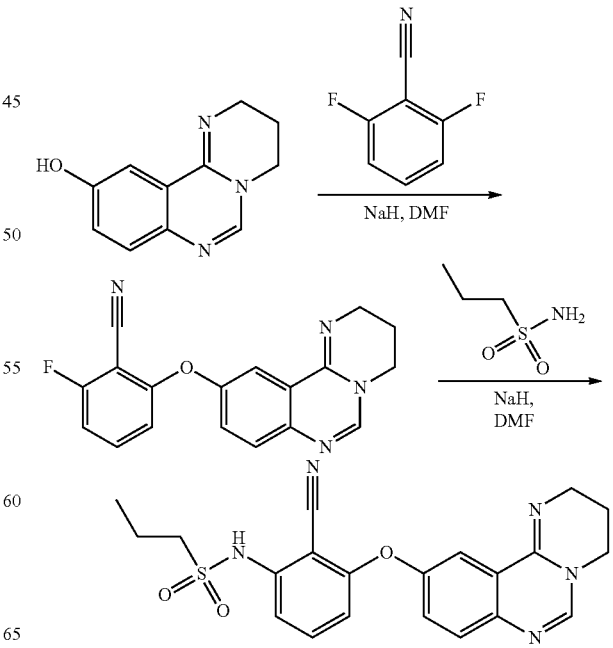

Step 1: Synthesis of 2-((3,4-dihydro-2H-pyrimido[1,2-c]quinazolin-10-yl)oxy)-6-fluorobenzonitrile NaH (60% in mineral oil, 150 mg, 3.72 mmol) was slowly added to a solution of 3,4-dihydro-2H-pyrimido[1,2-c]quinazolin-10-ol (500 mg, 2.48 mmol) in DMF (20.0 mL) at 0° C. The reaction mixture was degassed with $N_2$ and stirred at room temperature for 60 min. Then 2,6-difluorobenzonitrile (344.0 mg, 2.48 mmol) was added and the mixture was stirred at 80° C. for 1 hour. The resulting mixture was evaporated and the residue was purified by column chromatography on silica gel (DCM/MeOH from 100:1 to 30:1, v/v) to afford 2-((3,4-dihydro-2H-pyrimido[1,2-c]quinazolin-10-yl)oxy)-6-fluorobenzonitrile (200 mg, 25% yield).

Step 2: Synthesis of N-(2-cyano-3-((3,4-dihydro-2H-pyrimido[1,2-c]quinazolin-10-yl)oxy)phenyl)propane-1-sulfonamide NaH (60% in mineral oil, 50 mg, 0.84 mmol) was slowly added to a solution of propane-1-sulfonamide (70 mg, 0.56 mmol) in DMF (20.0 mL) at 0° C. The reaction mixture was degassed with $N_2$ and stirred at room temperature for 60 min. Then 2-((3,4-dihydro-2H-pyrimido[1,2-c]quinazolin-10-yl)oxy)-6-fluorobenzonitrile (180 mg, 0.56 mmol) was added and the mixture was stirred at 100° C. overnight under $N_2$. The resulting mixture was evaporated and the residue was purified by flash column (ACN/$H_2O$) to afford N-(2-cyano-3-((3,4-dihydro-2H-pyrimido[1,2-c]quinazolin-10-yl)oxy)phenyl)propane-1-sulfonamide (50 mg, 21% yield) as a white solid. 1H NMR (400 MHz, DMSO-$d_6$): δ 8.21 (s, 1H), 7.88 (d, J=2.4 Hz, 1H), 7.78 (d, J=8.8 Hz, 1H), 7.65 (dd, J=8.8, 2.4 Hz, 1H), 7.28 (t, J=8.4 Hz, 1H), 7.18 (d, J=8.4 Hz, 1H), 6.26 (d, J=8.0 Hz, 1H), 4.17 (t, J=5.2 Hz, 2H), 3.56 (t, J=5.2 Hz, 2H), 2.86 (t, J=7.6 Hz, 2H), 2.10-2.06 (m, 2H), 1.75-1.69 (m, 2H), 0.96 (t, J=7.6 Hz, 3H). LCMS (M+H$^+$) m/z: 424.2.

Example 17: Preparation of N-(2-cyano-3-((3,4-dihydro-2H-pyrimido[1,2-c]quinazolin-10-yl)oxy)-4-fluorophenyl)propane-1-sulfonamide (Compound 17)

Scheme 17

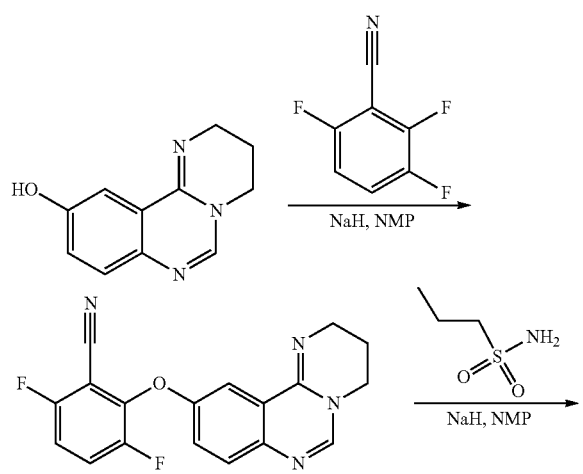

-continued

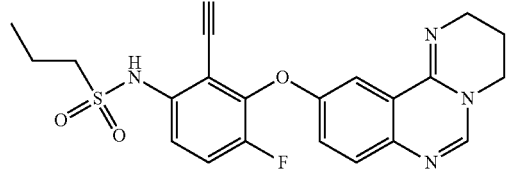

Step 1: Synthesis of 2-((3,4-Dihydro-2H-pyrimido[1,2-c]quinazolin-10-yl)oxy)-3,6-difluorobenzonitrile To a solution of 3,4-dihydro-2H-pyrimido[1,2-c]quinazolin-10-ol (200 mg, 1.0 mmol) in NMP (10 mL) was added NaH (60% in mineral oil, 60 mg, 1.5 mmol) in portions at 0° C. The mixture was stirred for 1 hour at 0° C., and then 2,3,6-trifluorobenzonitrile (188 mg, 1.2 mmol) was added and the mixture was stirred at 0° C. overnight. The resulting mixture was evaporated and the residue was purified by column chromatography on silica gel (DCM/MeOH from 100:1 to 30:1, v/v) to afford 2-((3,4-dihydro-2H-pyrimido[1,2-c]quinazolin-10-yl)oxy)-3,6-difluorobenzonitrile (100 mg, 30% yield) as yellow oil.

Step 2: Synthesis of N-(2-cyano-3-((3,4-dihydro-2H-pyrimido[1,2-c]quinazolin-10-yl)oxy)-4-fluorophenyl)propane-1-sulfonamide NaH (60% in mineral oil, 48 mg, 1.2 mmol) was slowly added to a solution of propane-1-sulfonamide (100 mg, 0.80 mmol) in NMP (20.0 mL) at 0° C. The reaction mixture was degassed with $N_2$ and stirred at room temperature for 60 min. Then 2-((3,4-dihydro-2H-pyrimido[1,2-c]quinazolin-10-yl)oxy)-3,6-difluorobenzonitrile (188 mg, 0.56 mmol) was added and the mixture was stirred at 80° C. overnight under $N_2$. The resulting mixture was evaporated and the residue was purified by flash column (ACN/$H_2O$) to afford N-(2-cyano-3-((3,4-dihydro-2H-pyrimido[1,2-c]quinazolin-10-yl)oxy)-4-fluorophenyl)propane-1-sulfonamide (40 mg, 16% yield) as a white solid. 1H NMR (400 MHz, DMSO-$d_6$): δ 10.65 (br s, 1H), 8.27 (s, 1H), 7.83-7.78 (m, 2H), 7.71 (d, J=8.8 Hz, 1H), 7.38 (t, J=9.6 Hz, 1H), 7.28 (dd, J=9.6, 4.4 Hz, 1H), 4.18 (t, J=5.6 Hz, 2H), 3.56 (t, J=5.6 Hz, 2H), 2.82 (t, J=7.6 Hz, 2H), 2.12-2.08 (m, 2H), 1.73-1.67 (m, 2H), 0.95 (t, J=7.6 Hz, 3H). LCMS (M+H$^+$) m/z: 442.4.

Example 18: Synthesis of N-(3-((3,4-Dihydro-2H-pyrimido[1,2-c]quinazolin-10-yl)oxy)-2-fluorophenyl)propane-1-sulfonamide (Compound 18)

Scheme 18

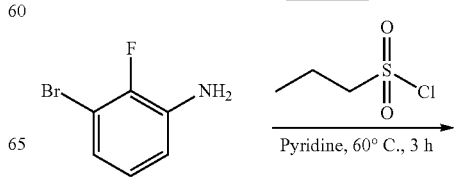

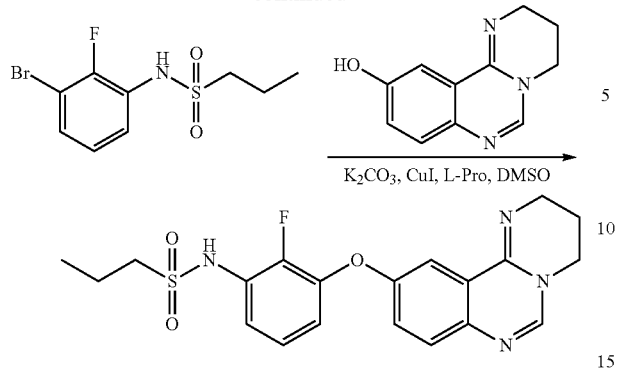

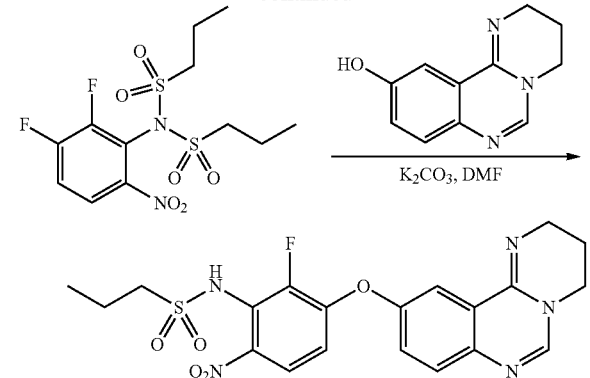

Step 1: Synthesis of N-(3-Bromo-2-fluorophenyl)propane-1-sulfonamide

To a solution of 3-bromo-2-fluoroaniline (0.5 g, 2.63 mmol) in Pyridine (20 mL) was added propane-1-sulfonyl chloride (3.75 g, 26.3 mmol) at rt, the reaction was stirred at 60° C. for 3 h under $N_2$, after the reaction was completed, the solvent was removed. The residue was purified on silica gel column chromatography (PE/EtOAc=10/1) to afford N-(3-bromo-2-fluorophenyl)propane-1-sulfonamide (364 mg, 47% yield) as a yellow solid (the product has no MS).

Step 2: Synthesis of N-(3-((3,4-Dihydro-2H-pyrimido[1,2-c]quinazolin-10-yl)oxy)-2-fluorophenyl)propane-1-sulfonamide A mixture of N-(3-bromo-2-fluorophenyl)propane-1-sulfonamide (95 mg, 0.32 mmol), 3,4-dihydro-2H-pyrimido[1,2-c]quinazolin-10-ol (129 mg, 0.64 mmol), $K_2CO_3$ (132 mg, 0.96 mmol), CuI (61 mg, 0.32 mmol) and L-Pro (30 mg, 0.32 mmol) in DMSO (5 mL) was stirred at 150° C. for 16 h under $N_2$, after the reaction was completed, the mixture was filtered and concentrated. The residue was purified by Prep-HPLC to afford N-(3-((3,4-Dihydro-2H-pyrimido[1,2-c]quinazolin-10-yl)oxy)-2-fluorophenyl)propane-1-sulfonamide (TFA salt, 17 mg, 10% yield) as a white solid. $^1$H NMR (400 MHz, $CD_3OD$): δ 8.30 (s, 1H), 7.93 (d, J=8.8 Hz, 1H), 7.79 (s, 1H), 7.74 (d, J=8.8 Hz, 1H), 7.46 (t, J=7.6 Hz, 1H), 7.25 (t, J=8.0 Hz, 1H), 7.09 (t, J=7.6 Hz, 1H), 4.37 (m, 2H), 3.69 (t, J=4.8 Hz, 2H), 3.15 (t, J=7.2 Hz, 2H), 2.30 (m, 2H), 1.88-1.82 (m, 2H), 1.04 (t, J=7.2 Hz, 3H). LCMS (M+H$^+$) m/z: 417.3.

Example 19: Preparation of N-(3-((3,4-Dihydro-2H-pyrimido[1,2-c]quinazolin-10-yl)oxy)-2-fluoro-6-nitrophenyl)propane-1-sulfonamide (Compound 19)

Step 1: Synthesis of N-(2,3-Difluoro-6-nitrophenyl)-N-(propylsulfonyl)propane-1-sulfonamide To a solution of 2,3-difluoro-6-nitroaniline (870 mg, 5.0 mmol) in THF (10 mL) was added NaH (60% in mineral oil, 900 mg, 22.5 mmol) at room temperature, the mixture was stirred at room temperature for 30 min, then propane-1-sulfonyl chloride (3.56 g, 25 mmol) was added, the reaction was stirred at room temperature overnight. After the reaction was completed, water was added to quenched the reaction, the mixture was extracted with EtOAc, the organic layer was dried over $Na_2SO_4$ and concentrated, the residue was purified by column chromatography on silica gel (PE/EtOAc=4/1) to afford N-(2,3-difluoro-6-nitrophenyl)-N-(propylsulfonyl)propane-1-sulfonamide (1.9 g, 98% yield) as a yellow solid.

Step 2: Synthesis of N-(3-((3,4-Dihydro-2H-pyrimido[1,2-c]quinazolin-10-yl)oxy)-2-fluoro-6-nitrophenyl)propane-1-sulfonamide A mixture of N-(2,3-difluoro-6-nitrophenyl)-N-(propylsulfonyl)propane-1-sulfonamide (1.22 g, 3.16 mmol), 3,4-dihydro-2H-pyrimido[1,2-c]quinazolin-10-ol (635 mg, 3.16 mmol), and $K_2CO_3$ (872 mg, 6.32 mmol) in DMF (20 mL) was stirred at 120° C. for 16 hours under $N_2$, after the reaction was completed, the solvent was removed. The residue was purified by column chromatography on silica gel (DCM/MeOH=30/1) to afford N-(3-((3,4-dihydro-2H-pyrimido[1,2-c]quinazolin-10-yl)oxy)-2-fluoro-6-nitrophenyl)propane-1-sulfonamide (390 mg, 27% yield) as a yellow solid. 1H NMR (400 MHz, DMSO-$d_6$): δ 10.36 (br, 1H), 8.05 (s, 1H), 7.78 (d, J=2.0 Hz, 1H), 7.71-7.61 (m, 3H), 6.88 (t, J=8.0 Hz, 1H), 4.08 (t, J=4.8 Hz, 2H), 3.53 (t, J=5.2 Hz, 2H), 2.92 (t, J=7.6 Hz, 2H), 2.03-2.00 (m, 2H), 1.75-1.65 (m, 2H), 0.93 (t, J=7.6 Hz, 3H). LCMS (M+H+) m/z: 462.1.

Example 20: Preparation of N-(6-Amino-3-((3,4-dihydro-2H-pyrimido[1,2-c]quinazolin-10-yl)oxy)-2-fluorophenyl)propane-1-sulfonamide (Compound 20)

Scheme 19

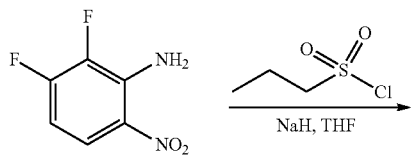

Scheme 20

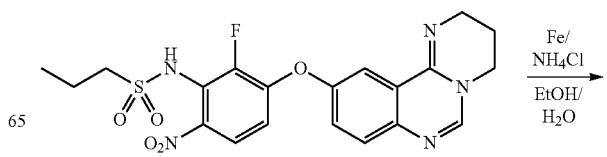

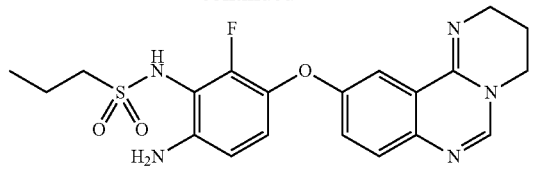

Synthesis of N-(6-Amino-3-((3,4-dihydro-2H-pyrimido[1,2-c]quinazolin-10-yl)oxy)-2-fluorophenyl)propane-1-sulfonamide A mixture of N-(3-((3,4-dihydro-2H-pyrimido[1,2-c]quinazolin-10-yl)oxy)-2-fluoro-6-nitrophenyl)propane-1-sulfonamide (330 mg, 0.72 mmol), Fe (200 mg, 3.58 mmol), and NH$_4$Cl (287 mg, 5.37 mmol) in EtOH/H$_2$O (30 mL/3 mL) was stirred at 90° C. for 1 hour under N$_2$, after the reaction was completed, the solvent was removed. The residue was purified by column chromatography on silica gel (DCM/MeOH=25/1+5% c NH$_3$.H$_2$O) to afford N-(6-amino-3-((3,4-dihydro-2H-pyrimido[1,2-c]quinazolin-10-yl)oxy)-2-fluorophenyl)propane-1-sulfonamide (280 mg, 90% yield) as a white solid. 1H NMR (400 MHz, DMSO-d$_6$): δ 9.00 (br s, 1H), 7.56 (s, 1H), 7.35 (d, J=8.8 Hz, 1H), 7.28 (d, J=2.4 Hz, 1H), 7.23 (dd, J=8.8, 2.8 Hz, 1H), 7.00 (t, J=8.8 Hz, 1H), 6.60 (d, J=8.8 Hz, 1H), 5.33 (br s, 2H), 3.84 (t, J=5.2 Hz, 2H), 3.42 (t, J=5.2 Hz, 2H), 3.06 (t, J=7.6 Hz, 2H), 1.84-1.79 (m, 2H), 1.77-1.69 (m, 2H), 0.93 (t, J=7.2 Hz, 3H). LCMS (M+H$^+$) m/z: 432.1.

Example 21: Preparation of N-(2-Chloro-3-((3,4-dihydro-2H-pyrimido[1,2-c]quinazolin-10-yl)oxy)phenyl)propane-1-sulfonamide (Compound 21)

Scheme 21

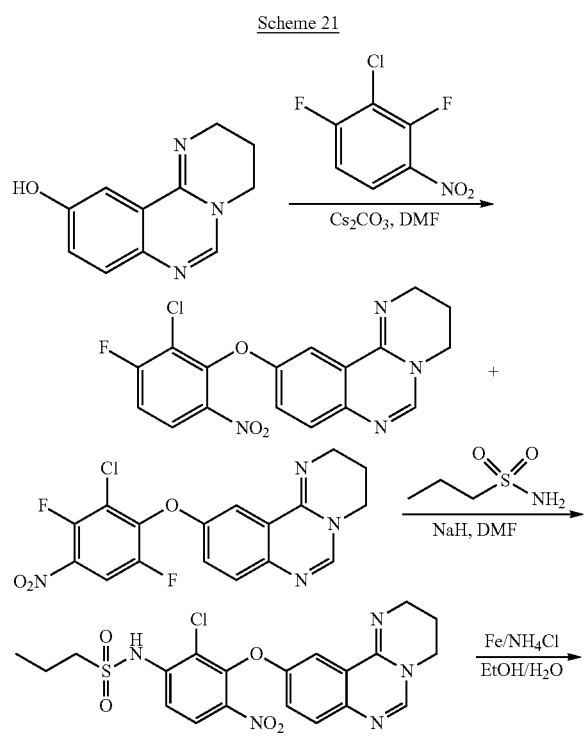

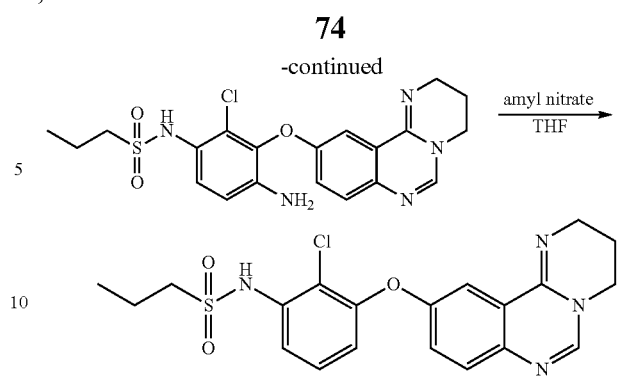

Step 1: Synthesis of 10-(2-Chloro-3-fluoro-6-nitrophenoxy)-3,4-dihydro-2H-pyrimido[1,2-c]quinazoline and 10-(2-Chloro-3-fluoro-4-nitrophenoxy)-3,4-dihydro-2H-pyrimido[1,2-c]quinazoline To a solution of 3,4-dihydro-2H-pyrimido[1,2-c]quinazolin-10-ol (30 g, 146 mmol) and 2-chloro-1,3-difluoro-4-nitrobenzene (56 g, 292 mmol) in DMF (300 mL) was added Cs$_2$CO$_3$ (95 g, 292 mmol). The reaction mixture was degassed with N$_2$ and stirred at room temperature for 2 hours. The resulting mixture was evaporated and the residue was purified by column chromatography on silica gel (DCM/MeOH from 100:1 to 30:1, v/v) to afford a mixture of 10-(2-chloro-3-fluoro-6-nitrophenoxy)-3,4-dihydro-2H-pyrimido[1,2-c]quinazoline and 10-(2-chloro-3-fluoro-4-nitrophenoxy)-3,4-dihydro-2H-pyrimido[1,2-c]quinazoline (43 g, 80% yield) as a yellow solid.

Step 2: Synthesis of N-(2-Chloro-3-((3,4-dihydro-2H-pyrimido[1,2-c]quinazolin-10-yl)oxy)-4-nitrophenyl)propane-1-sulfonamide NaH (60% in mineral oil, 8.0 g, 200 mmol) was slowly added to a solution of propane-1-sulfonamide (19 g, 152 mmol) in DMF (200 mL) at 0° C. The reaction mixture was degassed with N$_2$ and stirred at room temperature for 60 minutes. Then a mixture of 10-(2-chloro-3-fluoro-6-nitrophenoxy)-3,4-dihydro-2H-pyrimido[1,2-c]quinazoline and 10-(2-chloro-3-fluoro-4-nitrophenoxy)-3,4-dihydro-2H-pyrimido[1,2-c]quinazoline (38 g, 101 mmol) was added and the mixture was stirred at room temperature overnight under N$_2$. The resulting mixture was evaporated and the residue was purified by column chromatography on silica gel (DCM/MeOH from 100:1 to 50:1, v/v) to afford N-(2-chloro-3-((3,4-dihydro-2H-pyrimido[1,2-c]quinazolin-10-yl)oxy)-4-nitrophenyl)propane-1-sulfonamide (18 g, 37% yield) as a yellow solid.

Step 3: Synthesis of N-(4-Amino-2-chloro-3-((3,4-dihydro-2H-pyrimido[1,2-c]quinazolin-10-yl)oxy)phenyl)propane-1-sulfonamide A mixture of N-(2-chloro-3-((3,4-dihydro-2H-pyrimido[1,2-c]quinazolin-10-yl)oxy)-4-nitrophenyl)propane-1-sulfonamide (18 g, 37.7 mmol), Fe (21 g, 377 mmol), and NH$_4$Cl (1.2 g, 22.6 mmol) in EtOH/H$_2$O (200 mL/40 mL) was stirred at 80° C. for 2 hours under N$_2$, after the reaction was completed, the solvent was removed. The residue was purified by column chromatography on silica gel (DCM/MeOH=25/1+5% c NH$_3$.H$_2$O) to afford N-(4-amino-2- chloro-3-((3,4-dihydro-2H-pyrimido[1,2-c]quinazolin-10-yl)oxy)phenyl)propane-1-sulfonamide (11 g, 65% yield) as a white solid.

Step 4: Synthesis of N-(2-Chloro-3-((3,4-dihydro-2H-pyrimido[1,2-c]quinazolin-10-yl)oxy)phenyl)propane-1-sulfonamide To a solution of N-(4-amino-2-chloro-3-((3,4-dihydro-2H-pyrimido[1,2-c]quinazolin-10-yl)oxy)phenyl)propane-1-sulfonamide (11.0 g, 24.6 mmol) in THF (200 mL) was added amyl nitrate (32.8 g, 246 mmol). The reaction mixture was degassed with $N_2$ and stirred at reflux overnight. The resulting mixture was evaporated and purified by column chromatography on silica gel (DCM/MeOH from 100:1 to 50:1, v/v) to afford N-(2-chloro-3-((3,4-dihydro-2H-pyrimido[1,2-c]quinazolin-10-yl)oxy)phenyl)propane-1-sulfonamide (4.0 g, 38% yield) as an off-white solid. $^1$H NMR (400 MHz, DMSO-$d_6$): δ 9.55 (br, 1H), 7.63 (s, 1H), 7.42 (d, J=8.4 Hz, 1H), 7.36-7.28 (m, 4H), 6.96-6.94 (m, 1H), 3.86 (t, J=5.2 Hz, 2H), 3.43 (t, J=5.2 Hz, 2H), 3.09 (t, J=7.6 Hz, 2H), 1.86-1.83 (m, 2H), 1.77-1.71 (m, 2H), 0.97 (t, J=7.6 Hz, 3H). LC-MS: 433.1 [M+1]+.

Example 22: Preparation of N-(2-((3,4-Dihydro-2H-pyrimido[1,2-c]quinazolin-10-yl)oxy)-3-nitropyridin-4-yl)propane-1-sulfonamide (Compound 22)

Step 2: Synthesis of N-(2-((3,4-Dihydro-2H-pyrimido[1,2-c]quinazolin-10-yl)oxy)-3-nitropyridin-4-yl)propane-1-sulfonamide To a solution of N-(2-chloro-3-nitropyridin-4-yl)propane-1-sulfonamide (138 mg, 0.50 mmol) and 3,4-dihydro-2H-pyrimido[1,2-c]quinazolin-10-ol (100 mg, 0.50 mmol) in DMF (10 mL) was added $Cs_2CO_3$ (326 mg, 1.02 mmol). The reaction mixture was degassed with $N_2$ and stirred at 140° C. overnight. The resulting mixture was evaporated and the residue was purified by column chromatography on silica gel (DCM/MeOH from 100:1 to 10:1, v/v) to afford N-(2-((3,4-dihydro-2H-pyrimido[1,2-c]quinazolin-10-yl)oxy)-3-nitropyridin-4-yl)propane-1-sulfonamide (50 mg, 22% yield) as a white solid. $^1$H NMR (400 MHz, DMSO-$d_6$): δ 10.94 (br, 1H), 8.41 (s, 1H), 8.24 (s, 1H), 7.84 (d, J=8.8 Hz, 1H), 7.75 (d, J=8.8 Hz, 1H), 7.55 (d, J=6.0 Hz, 1H), 7.11 (d, J=6.0 Hz, 1H), 4.30-4.25 (m, 2H), 3.60-3.58 (m, 2H), 2.77-2.73 (m, 2H), 2.20-2.16 (m, 2H), 1.68-1.62 (m, 2H), 0.93 (t, J=7.2 Hz, 3H); LC-MS: 445.2 [M+1]+.

Example 23: Preparation of N-(4-((3,4-Dihydro-2H-pyrimido[1,2-c]quinazolin-10-yl)oxy)-3-nitropyridin-2-yl)propane-1-sulfonamide (Compound 23)

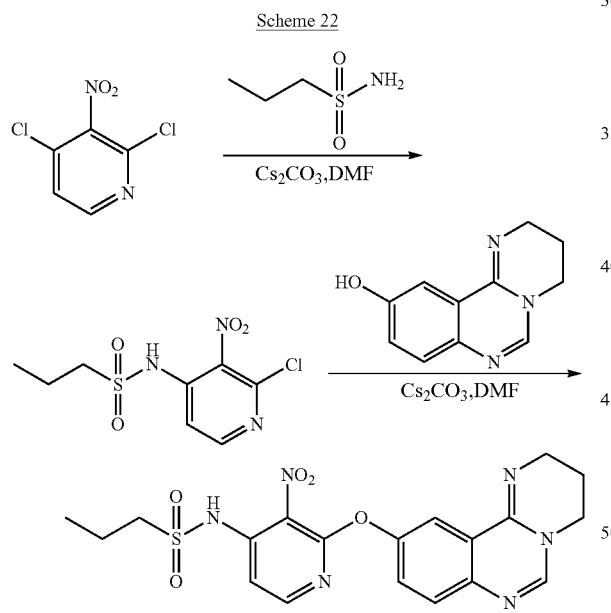

Scheme 22

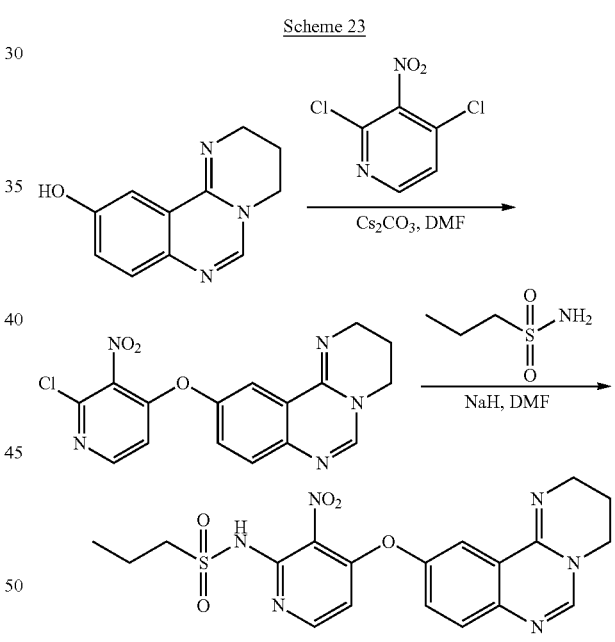

Scheme 23

Step 1: Synthesis of N-(2-Chloro-3-nitropyridin-4-yl)propane-1-sulfonamide

To a solution of 2,4-dichloro-3-nitropyridine (1.0 g, 5.21 mmol) and propane-1-sulfonamide (320 mg, 2.61 mmol) in DMF (10.0 mL) was added $Cs_2CO_3$ (1.28 g, 3.92 mmol). The reaction mixture was degassed with $N_2$ and stirred at 60° C. for 3 hours. The resulting mixture was evaporated and the residue was purified by column chromatography on silica gel (DCM/MeOH from 100:1 to 30:1, v/v) to afford N-(2-chloro-3-nitropyridin-4-yl)propane-1-sulfonamide (0.6 g, 82% yield) as a yellow solid.

Step 1: Synthesis of 10-((2-Chloro-3-nitropyridin-4-yl)oxy)-3,4-dihydro-2H-pyrimido[1,2-c]quinazoline To a solution of 2,4-dichloro-3-nitropyridine (710 mg, 3.72 mmol) and 3,4-dihydro-2H-pyrimido[1,2-c]quinazolin-10-ol (500 mg, 2.48 mmol) in DMF (10 mL) was added $Cs_2CO_3$ (1.6 g, 4.96 mmol). The reaction mixture was degassed with $N_2$ and stirred at 60° C. for 2 hours. The resulting mixture was evaporated and the residue was purified by column chromatography on silica gel (DCM/MeOH from 100:1 to 20:1, v/v) to afford 10-((2-chloro-3-nitropyridin-4-yl)oxy)-3,4-dihydro-2H-pyrimido[1,2-c]quinazoline (600 mg, 68% yield) as a yellow solid.

Step 2: Synthesis of N-(4-((3,4-Dihydro-2H-pyrimido[1,2-c]quinazolin-10-yl)oxy)-3-nitropyridin-2-yl)propane-1-sulfonamide NaH (60% in mineral oil, 42 mg, 1.06 mmol) was slowly added to a solution of propane-1-sulfonamide (100 mg, 0.81 mmol) in DMF (10.0 mL) at 0° C. The reaction mixture was degassed with $N_2$ and stirred at room temperature for 60 minutes. Then 10-((2-chloro-3-nitropyridin-4-yl)oxy)-3,4-dihydro-2H-pyrimido[1,2-c]quinazoline (180 mg, 0.50 mmol) was added and the mixture was stirred at 100° C. overnight under $N_2$. The resulting mixture was evaporated and the residue was purified by column chromatography on silica gel (DCM/MeOH from 100:1 to 10:1, v/v) to afford N-(4-((3,4-dihydro-2H-pyrimido[1,2-c]quinazolin-10-yl)oxy)-3-nitropyridin-2-yl)propane-1-sulfonamide (35 mg, 16% yield) as an off-white solid. 1H NMR (400 MHz, DMSO-$d_6$): δ 10.67 (br, 1H), 8.46 (s, 1H), 8.17 (d, J=2.4 Hz, 1H), 7.90 (d, J=9.2 Hz, 1H), 7.82 (dd, J=9.2, 2.4 Hz, 1H), 7.55 (d, J=6.0 Hz, 1H), 7.12 (d, J=6.0 Hz, 1H), 4.28 (t, J=5.2 Hz, 2H), 3.60 (t, J=5.2 Hz, 2H), 2.78-2.73 (m, 2H), 2.20-2.16 (m, 2H), 1.68-1.63 (m, 2H), 0.93 (t, J=7.6 Hz, 3H); LC-MS: 445.2 [M+I]+.

Example 24: Preparation of N-(3-Cyano-4-((3,4-dihydro-2H-pyrimido[1,2-c]quinazolin-10-yl)oxy)pyridin-2-yl)propane-1-sulfonamide (Compound 24)

2H-pyrimido[1,2-c]quinazolin-10-yl)oxy)nicotinonitrile (400 mg, 48% yield) as an off-white solid.

Step 2: Synthesis of N-(3-Cyano-4-((3,4-dihydro-2H-pyrimido[1,2-c]quinazolin-10-yl)oxy)pyridin-2-yl)propane-1-sulfonamide NaH (60% in mineral oil, 23 mg, 0.58 mmol) was slowly added to a solution of propane-1-sulfonamide (55 mg, 0.45 mmol) in DMF (6.0 mL) at 0° C. The reaction mixture was degassed with $N_2$ and stirred at room temperature for 60 minutes. Then 2-chloro-4-((3,4-dihydro-2H-pyrimido[1,2-c]quinazolin-10-yl)oxy)nicotinonitrile (100 mg, 0.30 mmol) was added and the mixture was stirred at 100° C. overnight under $N_2$. The resulting mixture was evaporated and the residue was purified by column chromatography on silica gel (DCM/MeOH from 100:1 to 20:1, v/v) to afford N-(3-cyano-4-((3,4-dihydro-2H-pyrimido[1,2-c]quinazolin-10-yl)oxy)pyridin-2-yl)propane-1-sulfonamide (40 mg, 31% yield) as an off-white solid. 1H NMR (400 MHz, DMSO-$d_6$): δ 10.67 (br, 1H), 8.35 (s, 1H), 8.12 (s, 1H), 7.85-7.80 (m, 2H), 7.54 (d, J=6.4 Hz, 1H), 6.98 (d, J=6.4 Hz, 1H), 4.29-4.22 (m, 2H), 3.61-3.58 (m, 2H), 2.81-2.77 (m, 2H), 2.20-2.16 (m, 2H), 1.73-1.68 (m, 2H), 0.96 (t, J=7.2 Hz, 3H); LC-MS: 425.3 [M+1]+.

Example 25: Synthesis of N-(3-Cyano-2-((3,4-dihydro-2H-pyrimido[1,2-c]quinazolin-10-yl)oxy)pyridin-4-yl)propane-1-sulfonamide (Compound 25)

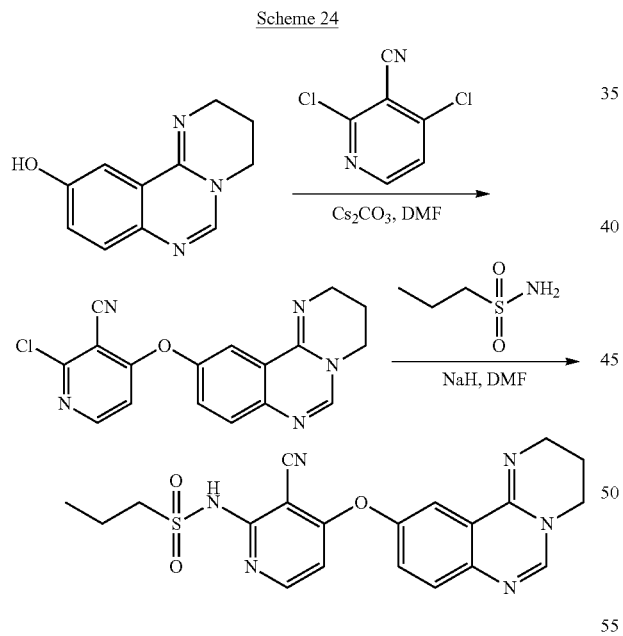

Scheme 24

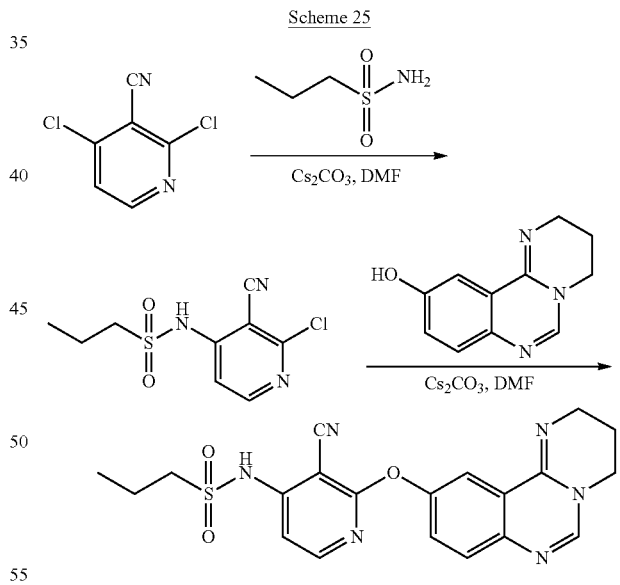

Scheme 25

Step 1: Synthesis of 2-Chloro-4-((3,4-dihydro-2H-pyrimido[1,2-c]quinazolin-10-yl)oxy)nicotinonitrile To a solution of 3,4-dihydro-2H-pyrimido[1,2-c]quinazolin-10-ol (500 mg, 2.49 mmol) and 2,4-dichloronicotinonitrile (646 mg, 3.73 mmol) in DMF (10.0 mL) was added $Cs_2CO_3$ (1.6 g, 4.96 mmol). The reaction mixture was degassed with $N_2$ and stirred at 60° C. for 2 hours. The resulting mixture was evaporated and the residue was purified by column chromatography on silica gel (DCM/MeOH from 100:1 to 20:1, v/v) to afford 2-chloro-4-((3,4-dihydro-

Step 1: Synthesis of N-(2-Chloro-3-cyanopyridin-4-yl)propane-1-sulfonamide

To a solution of 2,4-dichloronicotinonitrile (630 mg, 3.66 mmol) and propane-1-sulfonamide (300 mg, 2.44 mmol) in DMF (20 mL) was added $Cs_2CO_3$ (1.20 g, 3.66 mmol). The reaction mixture was degassed with $N_2$ and stirred at 60° C. for 3 hours. The resulting mixture was evaporated and the residue was purified by column chromatography on silica gel (DCM/MeOH from 100:1 to 20:1, v/v) to afford N-(2- chloro-3-cyanopyridin-4-yl)propane-1-sulfonamide (200 mg, 31% yield) as a yellow solid.

Step 2: Synthesis of N-(3-Cyano-2-((3,4-dihydro-2H-pyrimido[1,2-c]quinazolin-10-yl)oxy)pyridin-4-yl)propane-1-sulfonamide To a solution of N-(2-chloro-3-cyanopyridin-4-yl)propane-1-sulfonamide (155 mg, 0.60 mmol) and 3,4-dihydro-2H-pyrimido[1,2-c]quinazolin-10-ol (100 mg, 0.50 mmol) in DMF (10.0 mL) was added $Cs_2CO_3$ (326 mg, 1.02 mmol). The reaction mixture was degassed with $N_2$ and stirred at 130° C. overnight. The resulting mixture was evaporated and the residue was purified by column chromatography on silica gel (DCM/MeOH from 100:1 to 10:1, v/v) to afford N-(3-cyano-2-((3,4-dihydro-2H-pyrimido[1,2-c]quinazolin-10-yl)oxy)pyridin-4-yl)propane-1-sulfonamide (50 mg, 24% yield) as an off-white solid. 1H NMR (400 MHz, DMSO-$d_6$): δ 10.60 (br, 1H), 8.47 (s, 1H), 8.19 (s, 1H), 7.92-7.86 (m, 2H), 7.54 (d, J=6.0 Hz, 1H), 6.99 (d, J=6.0 Hz, 1H), 4.29 (t, J=5.2 Hz, 2H), 3.61 (t, J=5.2 Hz, 2H), 2.80 (t, J=7.6 Hz, 2H), 2.20-2.16 (m, 2H), 1.74-1.68 (m, 2H), 0.96 (t, J=7.6 Hz, 3H); LC-MS: 425.3 [M+1]+.

Example 26: Preparation of N-(3-Chloro-4-((3,4-dihydro-2H-pyrimido[1,2-c]quinazolin-10-yl)oxy)pyridin-2-yl)propane-1-sulfonamide (Compound 26)

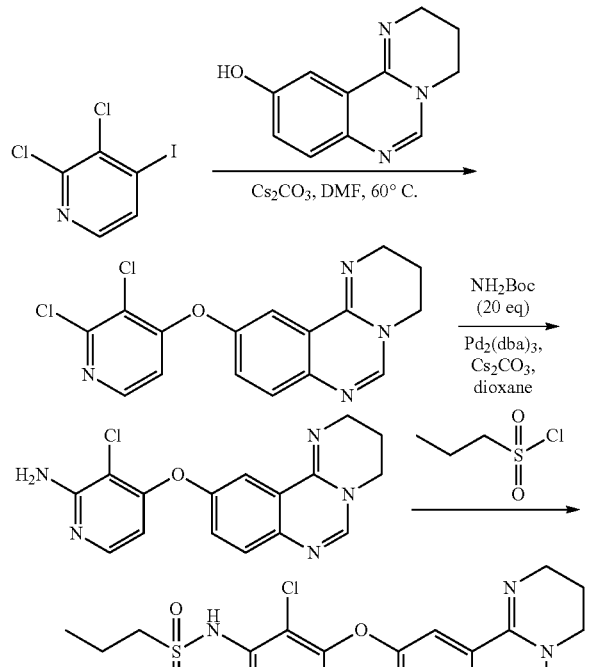

Scheme 26

Step 1: Synthesis of 10-((2,3-Dichloropyridin-4-yl)oxy)-3,4-dihydro-2H-pyrimido[1,2-c]quinazoline To a solution of 2,3-dichloro-4-iodopyridine (1.2 g, 4.4 mmol) and 3,4-dihydro-2H-pyrimido[1,2-c]quinazolin-10-ol (0.8 g, 4.0 mmol) in DMF (30 mL) was added $Cs_2CO_3$ (14.7 g, 5.0 mmol). The reaction mixture was degassed with $N_2$ and stirred at 60° C. for 3 hours. The resulting mixture was evaporated and the residue was purified by column chromatography on silica gel (DCM/MeOH from 100:1 to 30:1, v/v) to afford 10-((2,3-dichloropyridin-4-yl)oxy)-3,4-dihydro-2H-pyrimido[1,2-c]quinazoline (0.6 g, 44% yield) as a white solid.

Step 2: Synthesis of 3-Chloro-4-((3,4-dihydro-2H-pyrimido[1,2-c]quinazolin-10-yl)oxy)pyridin-2-amine A solution of 10-((2,3-dichloropyridin-4-yl)oxy)-3,4-dihydro-2H-pyrimido[1,2-c]quinazoline (1.0 g, 2.89 mmol) and tert-butyl carbamate (3.4 g, 28.9 mmol) in dioxane (30 mL) was added $Pd_2(dba)_3$ (0.53 g, 0.58 mmol), Xantphos (0.67 g, 1.16 mmol), $Cs_2CO_3$ (2.0 g, 4.3 mmol). The reaction mixture was degassed with $N_2$ and stirred at 100° C. overnight. The resulting mixture was evaporated and the residue was purified by column chromatography on silica gel (DCM/MeOH from 100:1 to 20:1, v/v) to afford 3-chloro-4-((3,4-dihydro-2H-pyrimido[1,2-c]quinazolin-10-yl)oxy)pyridin-2-amine (0.5 g, 53% yield) as an off-white solid.

Step 3: Synthesis of N-(3-Chloro-4-((3,4-dihydro-2H-pyrimido[1,2-c]quinazolin-10-yl)oxy)pyridin-2-yl)propane-1-sulfonamide NaH (60% in mineral oil, 8 mg, 0.20 mmol) was slowly added to a solution of 3-chloro-4-((3,4-dihydro-2H-pyrimido[1,2-c]quinazolin-10-yl)oxy)pyridin-2-amine (50 mg, 0.15 mmol) in DMF (20 mL) at 0° C. The reaction mixture was degassed with $N_2$ and stirred at room temperature for 30 minutes. Then propane-1-sulfonyl chloride (26 mg, 0.20 mmol) was added and the mixture was stirred at 130° C. overnight under $N_2$. The resulting mixture was evaporated and the residue was purified by flash column (ACN/$H_2O$) to afford N-(3-chloro-4-((3,4-dihydro-2H-pyrimido[1,2-c]quinazolin-10-yl)oxy)pyridin-2-yl)propane-1-sulfonamide (20 mg, 31% yield) as a white solid. $^1$H NMR (400 MHz, $CDCl_3$): δ 8.03 (d, J=5.6 Hz, 1H), 7.94 (s, 1H), 7.55 (d, J=8.8 Hz, 1H), 7.48 (s, 1H), 7.30 (dd, J=8.8, 2.8 Hz, 1H), 6.43 (d, J=5.6 Hz, 1H), 3.93 (t, J=5.6 Hz, 2H), 3.69-3.63 (m, 4H), 2.10-2.04 (m, 2H), 1.98-1.92 (m, 2H), 1.10 (t, J=7.2 Hz, 3H). LC-MS: 434.2 [M+1]+.

Example 27: Preparation of N-(2-Cyano-3-((3,4-dihydro-2H-pyrido[4,3-e]pyrimido[1,2-c]pyrimidin-10-yl)oxy)phenyl)propane-1-sulfonamide (Compound 27)

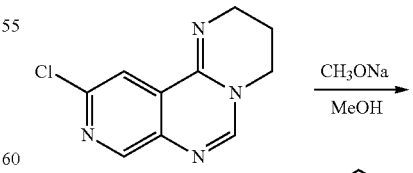

Scheme 27

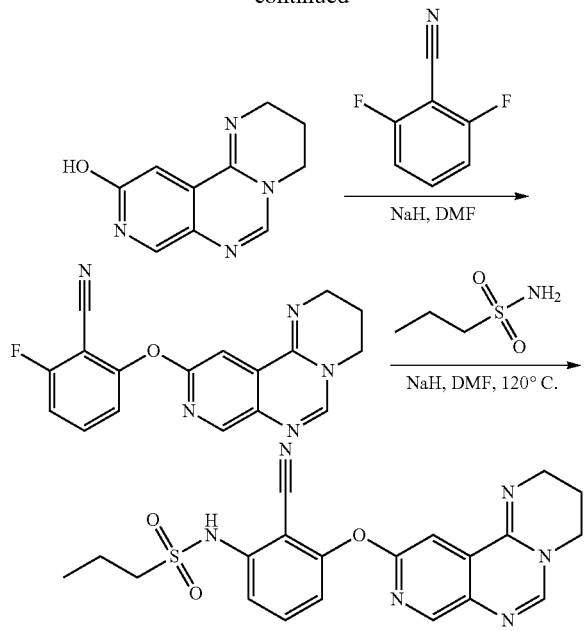

Step 1: Synthesis of 10-Methoxy-3,4-dihydro-2H-pyrido[4,3-e]pyrimido[1,2-c]pyrimidine To a solution of 10-chloro-3,4-dihydro-2H-pyrido[4,3-e]pyrimido[1,2-c]pyrimidine (1.0 g, 4.54 mmol) in MeOH (5.0 mL) was added CH₃ONa (aq) (25 mL). The reaction mixture was degassed with N₂ and stirred at 80° C. overnight. The resulting mixture was evaporated and the residue was purified by column chromatography on silica gel (DCM/MeOH from 100:1 to 20:1, v/v) to afford 10-methoxy-3,4-dihydro-2H-pyrido[4,3-e]pyrimido[1,2-c]pyrimidine (0.8 g, 82% yield) as a white solid.

Step 2: Synthesis of 3,4-Dihydro-2H-pyrido[4,3-e]pyrimido[1,2-c]pyrimidin-10-ol

To a solution of 10-methoxy-3,4-dihydro-2H-pyrido[4,3-e]pyrimido[1,2-c]pyrimidine (0.8 g, 3.7 mmol) in DMF (15.0 mL) was added NaSEt (940 mg, 11.2 mmol). The reaction mixture was degassed with N₂ and stirred at 130° C. overnight. After the reaction mixture was cooled down to room temperature, the resulting mixture was evaporated and the residue was purified by column chromatography on silica gel (DCM/MeOH from 50:1 to 20:1, v/v) to afford 3,4-dihydro-2H-pyrido[4,3-e]pyrimido[1,2-c]pyrimidin-10-ol (400 mg, 54% yield) as a yellow solid.

Step 3: Synthesis of 2-((3,4-Dihydro-2H-pyrido[4,3-e]pyrimido[1,2-c]pyrimidin-10-yl)oxy)-6-fluorobenzonitrile NaH (60% in mineral oil, 40 mg, 1.0 mmol) was slowly added to a solution of 3,4-dihydro-2H-pyrido[4,3-e]pyrimido[1,2-c]pyrimidin-10-ol (100 mg, 0.50 mmol) in DMF (15 mL) at 0° C. The reaction mixture was degassed with N₂ and stirred at room temperature for 15 minutes. Then 2,6-difluorobenzonitrile (137 mg, 1.0 mmol) was added and the mixture was stirred at 60° C. overnight. The resulting mixture was evaporated and the residue was purified by column chromatography on silica gel (DCM/MeOH from 100:1 to 30:1, v/v) to afford 2-((3,4-dihydro-2H-pyrido[4,3-e]pyrimido[1,2-c]pyrimidin-10-yl)oxy)-6-fluorobenzonitrile (60 mg, 38% yield).

Step 4: Synthesis of N-(2-Cyano-3-((3,4-dihydro-2H-pyrido[4,3-e]pyrimido[1,2-c]pyrimidin-10-yl)oxy)phenyl)propane-1-sulfonamide NaH (60% in mineral oil, 65 mg, 1.60 mmol) was slowly added to a solution of propane-1-sulfonamide (100 mg, 0.56 mmol) in DMF (10.0 mL) at 0° C. The reaction mixture was degassed with N₂ and stirred at room temperature for 30 minutes. Then 2-((3,4-dihydro-2H-pyrido[4,3-e]pyrimido[1,2-c]pyrimidin-10-yl)oxy)-6-fluorobenzonitrile (60 mg, 0.18 mmol) was added and the mixture was stirred at 120° C. overnight under N₂. The resulting mixture was evaporated and the residue was purified by flash column (ACN/H₂O) to afford N-(2-cyano-3-((3,4-dihydro-2H-pyrido[4,3-e]pyrimido[1,2-c]pyrimidin-10-yl)oxy)phenyl)propane-1-sulfonamide (15 mg, 20% yield) as a white solid. 1H NMR (400 MHz, CD₃OD): δ 8.38 (s, 1H), 7.68 (s, 1H), 7.54 (s, 1H), 7.44-7.39 (m, 2H), 6.68 (dd, J=7.6, 1.2 Hz, 1H), 4.00 (t, J=5.6 Hz, 2H), 3.65 (t, J=5.6 Hz, 2H), 2.07-2.04 (m, 2H), 1.92-1.81 (m, 2H), 1.38-1.29 (m, 2H), 1.08 (t, J=7.2 Hz, 3H). LC-MS: 425.3 [M+1]+.

Example 28: Preparation of N-(2-Cyano-3-((2,3,4,5-tetrahydro-[1,3]diazepino[1,2-c]quinazolin-1-yl)oxy)phenyl)propane-1-sulfonamide (Compound 28)

Scheme 28

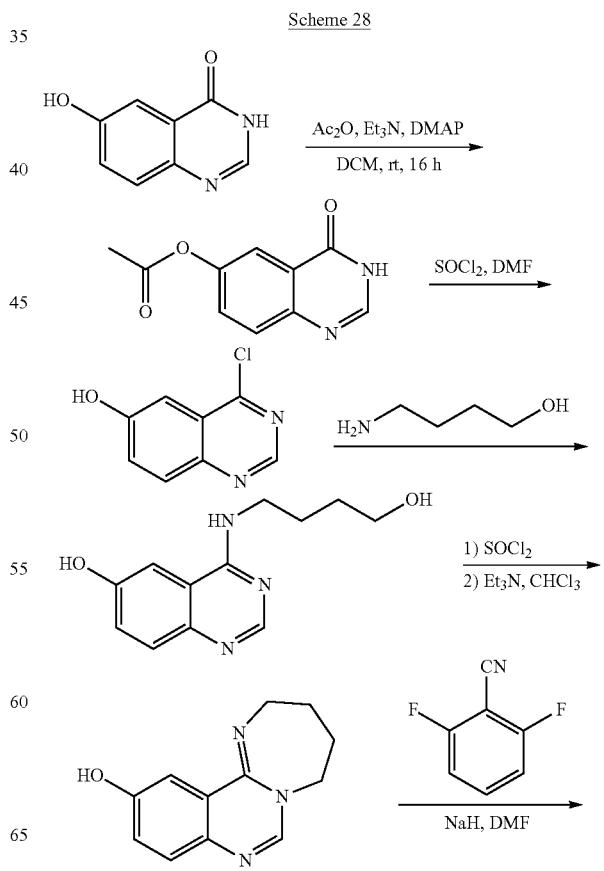

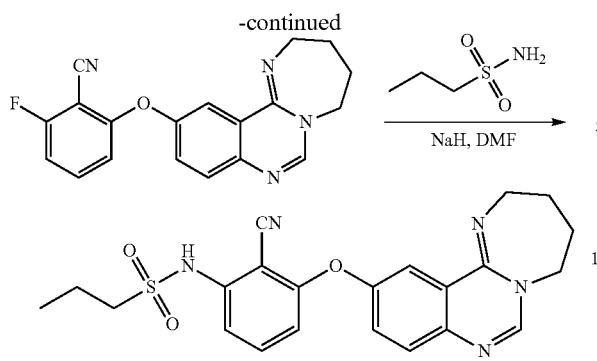

Step 1: Synthesis of 4-Oxo-3,4-dihydroquinazolin-6-yl acetate

To a solution of 6-hydroxyquinazolin-4(3H)-one (5.0 g, 30.8 mmol) in DCM (50.0 mL) was added DMAP (0.75 g, 6.20 mmol) and Ac$_2$O (6.30 g, 6.20 mmol), Et$_3$N (6.20 g, 61.6 mmol). The reaction mixture was stirred at room temperature overnight. The resulting mixture was evaporated and to the residue was added H$_2$O (50 mL) and stirred at room temperature for 20 minutes. The solid was filtered and dried in vacuo to afford 4-oxo-3,4-dihydroquinazolin-6-yl acetate (5.3 g, 85% yield) as a tan solid.

Step 2: Synthesis of 4-Chloroquinazolin-6-ol

To a solution of 4-oxo-3,4-dihydroquinazolin-6-yl acetate (5.0 g, 24.4 mmol) in SOCl$_2$ (50 mL) was added DMF (1 mL). The reaction mixture was stirred at reflux overnight. The resulting mixture was evaporated and to the residue was added toluene (30 mL) and stirred at room temperature for 20 minutes. The solid was filtered and dried in vacuo to afford 4-chloroquinazolin-6-ol (3.0 g, 68% yield) as a tan solid.

Step 3: Synthesis of 4-((4-Hydroxybutyl)amino)quinazolin-6-ol

To a solution of 4-chloroquinazolin-6-ol (1.0 g, 5.56 mmol) and 4-aminobutan-1-ol (1.0 g, 11.1 mmol) in isopropanol (20 mL) was added Et$_3$N (1.7 g, 16.8 mmol) at ice-water. The reaction mixture was stirred at reflux for 1 hour. The resulting mixture was evaporated and the residue was purified by column chromatography on silica gel (DCM/MeOH from 100:1 to 20:1, v/v) to afford 4-((4-hydroxybutyl)amino)quinazolin-6-ol (0.8 g, 62% yield) as a white solid.

Step 4: Synthesis of 2,3,4,5-Tetrahydro-[1,3]diazepino[1,2-c]quinazolin-11-ol A solution of 4-((4-hydroxybutyl)amino)quinazolin-6-ol (800 mg, 3.43 mmol) in SOCl$_2$ (10 mL) was stirred at reflux for 2 hours. The mixture was concentrated and to the residue was added Et$_3$N (6 mL) and CHCl$_3$ (30 mL). The reaction mixture was stirred at reflux for 3 days. The resulting mixture was evaporated and the residue was purified by column chromatography on silica gel (DCM/MeOH from 100:1 to 30:1, v/v) to afford 2,3,4,5-tetrahydro-[1,3]diazepino[1,2-c]quinazolin-11-ol (300 mg, 41% yield) as a white solid.

Step 5: Synthesis of 2-Fluoro-6-((2,3,4,5-tetrahydro-[1,3]diazepino[1,2-c]quinazolin-11-yl)oxy)benzonitrile 60% NaH (40% in mineral oil, 45 mg, 1.12 mmol) was slowly added to a solution of 2,3,4,5-tetrahydro-[1,3]diazepino[1,2-c]quinazolin-11-ol (200 mg, 0.93 mmol) in DMF (20 mL) at 0° C. The reaction mixture was degassed with N$_2$ and stirred at room temperature for 30 minutes. Then 2,6-difluorobenzonitrile (130 mg, 0.93 mmol) was added and the mixture was stirred at room temperature for 2 hours under N$_2$. The resulting mixture was evaporated and the residue was purified by column chromatography on silica gel (DCM/MeOH from 100:1 to 20:1, v/v) to afford 2-fluoro-6-((2,3,4,5-tetrahydro-[1,3]diazepino[1,2-c]quinazolin-11-yl)oxy)benzonitrile (100 mg, 32% yield) as a white solid.

Step 6: Synthesis of N-(2-Cyano-3-((2,3,4,5-tetrahydro-[1,3]diazepino[1,2-c]quinazolin-11-yl)oxy)phenyl)propane-1-sulfonamide 60% NaH (40% in mineral oil, 16 mg, 0.40 mmol) was slowly added to a solution of propane-1-sulfonamide (44 mg, 0.36 mmol) in DMF (10 mL) at 0° C. The reaction mixture was degassed with N$_2$ and stirred at room temperature for 30 minutes. Then 2-fluoro-6-((2,3,4,5-tetrahydro-[1,3]diazepino[1,2-c]quinazolin-11-yl)oxy)benzonitrile (60 mg, 0.18 mmol) was added and the mixture was stirred at 100° C. overnight under N$_2$. The resulting mixture was evaporated and the residue was purified by flash column (ACN/H$_2$O) to afford N-(2-cyano-3-((2,3,4,5-tetrahydro-[1,3]diazepino[1,2-c]quinazolin-11-yl)oxy)phenyl)propane-1-sulfonamide (18 mg, 23% yield) as a white solid. 1H NMR (400 MHz, DMSO-d$_6$): δ 10.35 (br, 1H), 8.45 (s, 1H), 7.90 (s, 1H), 7.79 (d, J=8.8 Hz, 1H), 7.61 (dd, J=9.2, 2.0 Hz, 1H), 7.45-7.41 (m, 1H), 7.18 (d, J=8.0 Hz, 1H), 6.55-6.52 (m, 1H), 3.81-3.79 (m, 4H), 3.07 (t, J=7.2 Hz, 2H), 1.94-1.92 (m, 4H), 1.80-1.74 (m, 2H), 0.99 (t, J=7.2 Hz, 3H). LC-MS: 438.2 [M+1]$^+$

Example 29: Preparation of N-(2-Chloro-3-((3,4-dihydro-2H-pyrimido[1,2-c]quinazolin-10-yl)oxy)phenyl)ethanesulfonamide (Compound 37)

Scheme 29

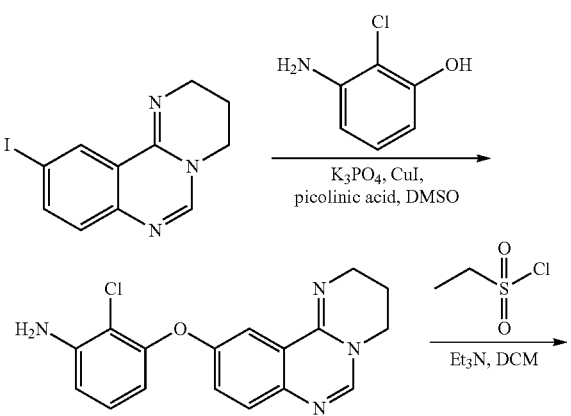

-continued

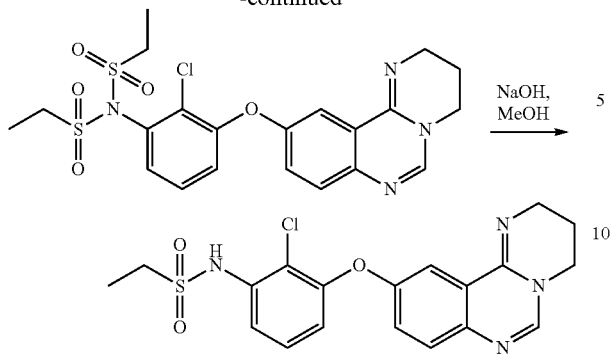

Step 1: Synthesis of 2-Chloro-3-((3,4-dihydro-2H-pyrimido[1,2-c]quinazolin-10 yl)oxy)aniline A solution of 10-iodo-3,4-dihydro-2H-pyrimido[1,2-c]quinazoline (2.0 g, 6.43 mmol), 3-amino-2-chlorophenol (1.85 g, 12.86 mmol), $K_3PO_4$ (4.1 g, 19.3 mmol), CuI (366 mg, 1.93 mmol) and picolinic acid (79 mg, 0.64 mmol) in DMSO (20 mL) was stirred at 90° C. for 16 hours under $N_2$. After the reaction was completed, EtOAc was added, the mixture was filtered, the cake was washed with EtOAc, the filtrate was added to water (50 mL) and extracted with EtOAc (100 mL×3), the combined organic layers were washed with brine, dried and concentrated to afford 2-chloro-3-((3,4-dihydro-2H-pyrimido[1,2-c]quinazolin-10-yl)oxy)aniline (800 mg, 38% yield) as a green solid.

Step 2: Synthesis of N-(2-Chloro-3-((3,4-dihydro-2H-pyrimido[1,2-c]quinazolin-10-yl)oxy)phenyl)-N-(ethylsulfonyl)ethanesulfonamide To a solution of 2-chloro-3-((3,4-dihydro-2H-pyrimido[1,2-c]quinazolin-10-yl)oxy)aniline (1.0 g, 3.1 mmol) and $Et_3N$ (3.7 g, 36.6 mmol) in DCM (50 mL) was added ethanesulfonyl chloride (3.9 g, 30.4 mmol) at 0° C., then the reaction was stirred at room temperature for 16 hours, LCMS showed 76% of N-(2-chloro-3-((3,4-dihydro-2H-pyrimido[1,2-c]quinazolin-10-yl)oxy)phenyl)-N-(ethylsulfonyl)ethanesulfonamide and 8% of 2-chloro-3-((3,4-dihydro-2H-pyrimido[1,2-c]quinazolin-10-yl)oxy)aniline, the solvent was removed, the residue was used to the next step without purification.

Step 3: Synthesis of N-(2-Chloro-3-((3,4-dihydro-2H-pyrimido[1,2-c]quinazolin-10-yl)oxy)phenyl)ethanesulfonamide To a solution of N-(2-chloro-3-((3,4-dihydro-2H-pyrimido[1,2-c]quinazolin-10-yl)oxy)phenyl)-N-(ethylsulfonyl)ethanesulfonamide (1.56 g, 3.07 mmol) in MeOH (20 mL) was added NaOH (245 mg, 6.13 mmol). The mixture was stirred at room temperature for 1 hour, LCMS showed the reaction was not completed, NaOH (1.0 g, 25 mmol) was added, after 2 hours, LCMS showed the reaction was completed. Conc. HCl was added until pH=6-7, the mixture was extracted with DCM (200 mL×3), the combined organic layers were dried and concentrated, the residue was purified by column chromatography on silica gel (DCM/MeOH=150/1+0.5% $NH_3 \cdot H_2O$) to afford N-(2-chloro-3-((3,4-dihydro-2H-pyrimido[1,2-c]quinazolin-10-yl)oxy)phenyl)ethanesulfonamide (660 mg, 52% yield) as a yellow solid. 1H NMR (400 MHz, DMSO-$d_6$): δ 9.81 (br s, 1H), 7.76 (s, 1H), 7.50 (d, J=8.8 Hz, 1H), 7.45 (d, J=2.0 Hz, 1H), 7.38-7.35 (m, 3H), 7.03 (t, J=4.8 Hz, 1H), 3.93 (t, J=5.6 Hz, 2H), 3.45 (t, J=5.6 Hz, 2H), 3.17 (q, J=7.2 Hz, 2H), 1.92-1.87 (m, 2H), 1.27 (t, J=7.2 Hz, 3H). LCMS (M+H$^+$) m/z: 419.2.

Example 30: Preparation of N-(2-Chloro-3-((3,4-dihydro-2H-pyrimido[1,2-c]quinazolin-10-yl)oxy)phenyl)-3-fluoropropane-1-sulfonamide (Compound 38)

Scheme 30

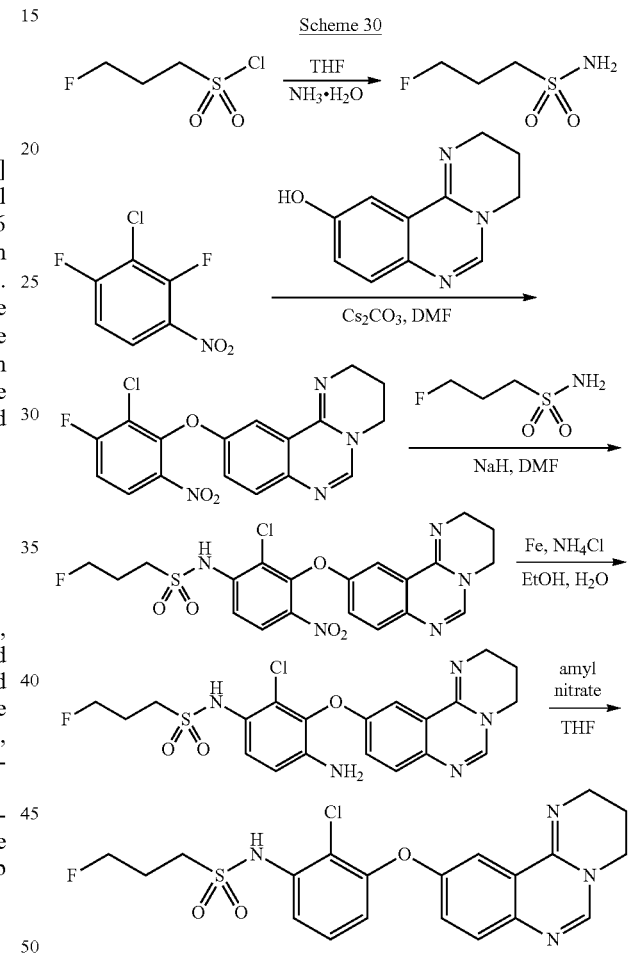

Step 1: Synthesis of 3-Fluoropropane-1-sulfonamide

A solution of 3-fluoropropane-1-sulfonyl chloride (700 mg, 4.36 mmol) in THF (3 mL) was added slowly at 0° C. to $NH_3 \cdot H_2O$ (20 mL). The reaction mixture was stirred at room temperature for 2 hours. The reaction mixture was filtered, the filtrate was concentrated to afford 3-fluoropropane-1-sulfonamide (560 mg, 91% yield) as a white solid.

Step 2: Synthesis of 10-(2-Chloro-3-fluoro-6-nitrophenoxy)-3,4-dihydro-2H-pyrimido[1,2-c]quinazoline A mixture of 2-chloro-1,3-difluoro-4-nitrobenzene (3.84 g, 20 mmol), 3,4-dihydro-2H-pyrimido[1,2-c]quinazolin- 10-ol (2.0 g, 10 mmol) and Cs$_2$CO$_3$ (6.48 g, 20 mmol) in DMF (40 mL) was stirred at room temperature for 2 hours. The reaction mixture was evaporated, the residue was purified by column chromatography on silica gel (DCM/MeOH from 100:1 to 30:1, v/v) to afford 10-(2-chloro-3-fluoro-6-nitrophenoxy)-3,4-dihydro-2H-pyrimido[1,2-c]quinazoline (2.49 g, 66% yield) as a yellow solid.

Step 3: Synthesis of N-(2-Chloro-3-((3,4-dihydro-2H-pyrimido[1,2-c]quinazolin-10-yl)oxy)-4-nitrophenyl)-3-fluoropropane-1-sulfonamide To a solution of 3-fluoropropane-1-sulfonamide (300 mg, 2.12 mmol) in DMF (10 mL) was added NaH (94 mg, 2.34 mmol, 60% in mineral oil) at 0° C. The reaction mixture was stirred at room temperature for 30 minutes, then 10-(2-chloro-3-fluoro-6-nitrophenoxy)-3,4-dihydro-2H-pyrimido[1,2-c]quinazoline (717 mg, 1.91 mmol) was added. The reaction mixture was stirred at room temperature overnight and quenched by MeOH (2 mL). The reaction mixture was concentrated, the residue was purified by column chromatography on silica gel (DCM/MeOH from 50:1 to 10:1, v/v) to afford N-(2-chloro-3-((3,4-dihydro-2H-pyrimido[1,2-c]quinazolin-10-yl)oxy)-4-nitrophenyl)-3-fluoropropane-1-sulfonamide (570 mg, 54% yield) as a brown solid.

Step 4: Synthesis of N-(4-Amino-2-chloro-3-((3,4-dihydro-2H-pyrimido[1,2-c]quinazolin-10-yl)oxy)phenyl)-3-fluoropropane-1-sulfonamide A mixture of N-(2-chloro-3-((3,4-dihydro-2H-pyrimido[1,2-c]quinazolin-10-yl)oxy)-4-nitrophenyl)-3-fluoropropane-1-sulfonamide (570 mg, 1.15 mmol), Fe (330 mg, 5.75 mmol) and NH$_4$Cl (432 mg, 8.06 mmol) in EtOH (15 mL) and H$_2$O (5 mL) was stirred at 80° C. overnight. The reaction mixture was evaporated, the residue was purified by column chromatography on silica gel (DCM/MeOH from 50:1 to 10:1, v/v) to afford N-(4-amino-2-chloro-3-((3,4-dihydro-2H-pyrimido[1,2-c]quinazolin-10-yl)oxy)phenyl)-3-fluoropropane-1-sulfonamide (480 mg, 89% yield) as a brown solid.

Step 5: Synthesis of N-(2-Chloro-3-((3,4-dihydro-2H-pyrimido[1,2-c]quinazolin-10-yl)oxy)phenyl)-3-fluoropropane-1-sulfonamide A mixture of N-(4-amino-2-chloro-3-((3,4-dihydro-2H-pyrimido[1,2-c]quinazolin-10-yl)oxy)phenyl)-3-fluoropropane-1-sulfonamide (480 mg, 1.03 mmol) and amyl nitrate (1.21 g, 10.3 mmol) in THF (15 mL) was stirred at 70° C. under N$_2$ overnight. After removal most of the volatile, the residue was purified by Prep-HPLC to afford N-(2-chloro-3-((3,4-dihydro-2H-pyrimido[1,2-c]quinazolin-10-yl)oxy)phenyl)-3-fluoropropane-1-sulfonamide (17 mg, 3.6% yield) as a white solid. 1H NMR (400 MHz, DMSO-d$_6$): δ 7.72 (s, 1H), 7.48 (d, J=8.4 Hz, 1H), 7.40 (d, J=2.8 Hz, 1H), 7.36-7.30 (m, 3H), 6.93 (dd, J=7.6, 2.4 Hz, 1H), 4.57 (dt, J=47.2, 6.0 Hz, 2H), 3.91 (t, J=5.6 Hz, 2H), 3.44 (t, J=5.6 Hz, 2H), 3.22-3.17 (m, 2H), 2.17-2.07 (m, 2H), 1.89-1.87 (m, 2H). LCMS (M+H$^+$) m/z: 451.3.

Example 31: Preparation of N-(2-Chloro-3-((3,4-dihydro-2H-pyrimido[1,2-c]quinazolin-10-yl)oxy)phenyl)-3-hydroxypropane-1-sulfonamide (Compound 39)

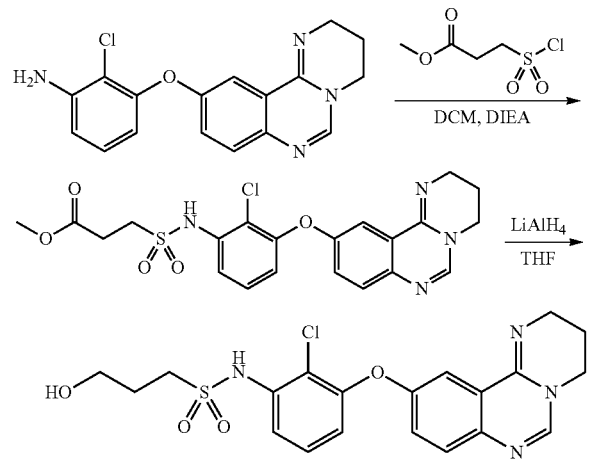

Scheme 31

Step 1: Synthesis of Methyl 3-(N-(2-chloro-3-((3,4-dihydro-2H-pyrimido[1,2-c]quinazolin-10-yl)oxy)phenyl)sulfamoyl)propanoate A mixture of 2-chloro-3-((3,4-dihydro-2H-pyrimido[1,2-c]quinazolin-10-yl)oxy)aniline (100 mg, 0.31 mmol), methyl 3-(chlorosulfonyl)propanoate (86 mg, 0.46 mmol), and DIEA (80 mg, 0.61 mmol) in DCM (10 mL) was stirred at room temperature for 4 hours. The mixture was concentrated, the residue was purified by column chromatography on silica gel (DCM/MeOH from 50:1 to 30:1, v/v) to afford methyl 3-(N-(2-chloro-3-((3,4-dihydro-2H-pyrimido[1,2-c]quinazolin-10-yl)oxy)phenyl)sulfamoyl)propanoate (100 mg, 68% yield) as brown oil.

Step 2: Synthesis of N-(2-Chloro-3-((3,4-dihydro-2H-pyrimido[1,2-c]quinazolin-10-yl)oxy)phenyl)-3-hydroxypropane-1-sulfonamide To a mixture of methyl 3-(N-(2-chloro-3-((3,4-dihydro-2H-pyrimido[1,2-c]quinazolin-10-yl)oxy)phenyl)sulfamoyl)propanoate (100 mg, 0.21 mmol) in THF (10 mL) was added LiAlH$_4$ (40 mg, 1.1 mmol) at 0° C., the reaction mixture was stirred at room temperature for 2 hours. MeOH and EtOAc were added, the reaction mixture was stirred at room temperature for 30 minutes, the mixture was filtered, the filtrate was evaporated, the residue was purified by Prep-HPLC to afford N-(2-chloro-3-((3,4-dihydro-2H-pyrimido[1,2-c]quinazolin-10-yl)oxy)phenyl)-3-hydroxypropane-1-sulfonamide (TFA salt, 17 mg, 14% yield) as a white solid. 1H NMR (400 MHz, DMSO-d$_6$): δ 10.73 (br s, 1H), 9.69 (s, 1H), 8.47 (s, 1H), 7.95-7.92 (m, 2H), 7.76-7.73 (m, 1H), 7.46-7.44 (m, 2H), 7.15-7.13 (m, 1H), 4.29 (t, J=5.6 Hz, 2H), 3.64-3.56 (m, 4H), 3.24-3.20 (m, 2H), 2.19-2.16 (m, 2H), 1.90-1.86 (m, 2H). LCMS (M+H$^+$) m/z: 449.3.

Example 32: Preparation of (R)—N-(2-Chloro-3-((3,4-dihydro-2H-pyrimido[1,2-c]quinazolin-10-yl)oxy)phenyl)-3-fluoropyrrolidine-1-sulfonamide (Compound 40)

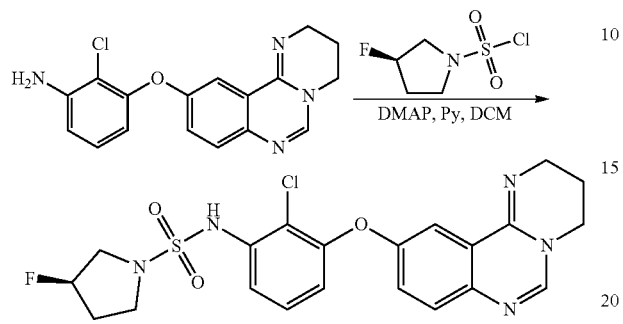

Scheme 32

To a solution of 2-chloro-3-((3,4-dihydro-2H-pyrimido[1,2-c]quinazolin-10-yl)oxy)aniline (120 mg, 0.37 mmol) and DMAP (2.2 mg) and pyridine (2 mL) in DCM (5 mL) wad added (R)-3-fluoropyrrolidine-1-sulfonyl chloride (630 mg, 3.3 mmol) at 0° C. The reaction was stirred at 0° C. for 2 hours. The mixture was quenched with MeOH (2 mL) and concentrated. The residue was purified by Prep-HPLC to afford (R)—N-(2-chloro-3-((3,4-dihydro-2H-pyrimido[1,2-c]quinazolin-10-yl)oxy)phenyl)-3-fluoropyrrolidine-1-sulfonamide (8.0 mg, 4.5% yield) as a yellow solid. $^1$H NMR (400 MHz, CD$_3$OD): δ 8.25 (s, 1H), 7.88 (d, J=9.2 Hz, 1H), 7.71 (d, J=2.4 Hz, 1H), 7.64-7.61 (m, 2H), 7.38 (t, J=8.4 Hz, 1H), 7.04 (dd, J=8.4, 1.2 Hz, 1H), 5.24 (dt, J=52.8, 3.6 Hz, 1H), 4.33 (t, J=5.6 Hz, 2H), 3.67 (t, J=5.6 Hz, 2H), 3.61-3.30 (m, 4H), 2.29-1.97 (m, 4H). LCMS (M+H$^+$) m/z: 478.1.

Example 33: Preparation of N-(2-Chloro-3-((3,4-dihydro-2H-pyrimido[1,2-c]quinazolin-10-yl)oxy)phenyl)-N-ethyl-N-methylamino-1-sulfonamide (Compound 41)

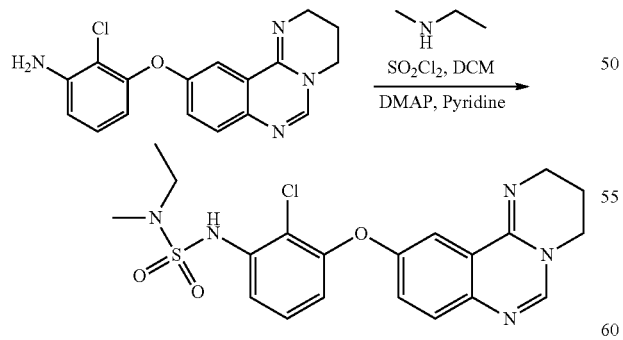

Scheme 33

To a mixture of SO$_2$Cl$_2$ (1.14 g, 8.47 mmol) in DCM (10 mL) was added N-methylethanamine (500 mg, 8.47 mmol) slowly at 0° C., the mixture was stirred at 0° C. under N$_2$ for 30 minutes. The mixture was added to the solution of 2-chloro-3-((3,4-dihydro-2H-pyrimido[1,2-c]quinazolin-10-yl)oxy)aniline (100 mg, 0.31 mmol) and DMAP (2 mg, 0.01 mmol) in pyridine (5 mL) dropwise, the mixture was stirred at room temperature for 30 minutes. After the reaction was completed, the mixture was evaporated, the residue was purified by prep-HPLC to afford N-(2-chloro-3-((3,4-dihydro-2H-pyrimido[1,2-c]quinazolin-10-yl)oxy)phenyl)-N-ethyl-N-methylamino-1-sulfonamide (TFA salt, 2.7 mg, 1.5% yield) as a brown solid. 1H NMR (400 MHz, CD$_3$OD): δ 8.26 (s, 1H), 7.90 (d, J=9.2 Hz, 1H), 7.72 (d, J=2.8 Hz, 1H), 7.65 (dd, J=9.2, 2.8 Hz, 1H), 7.56 (dd, J=8.4, 1.6 Hz, 1H), 7.38 (t, J=8.4 Hz, 1H), 7.03 (dd, J=8.4, 1.2 Hz, 1H), 4.34 (t, J=5.6 Hz, 2H), 3.68 (t, J=5.6 Hz, 2H), 3.25 (q, J=7.2 Hz, 2H), 2.85 (s, 3H), 2.31-2.25 (m, 2H), 1.11 (t, J=7.2 Hz, 3H). LCMS (M+H$^+$) m/z: 448.1.

Example 34: Preparation of N-(2-Cyano-3-((3,4-dihydro-2H-pyrido[4,3-e]pyrimido[1,2-c]pyrimidin-10-yl)(methyl)amino)phenyl)propane-1-sulfonamide (Compound 42)

Scheme 34

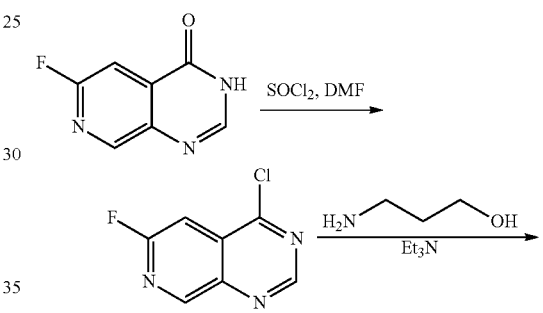

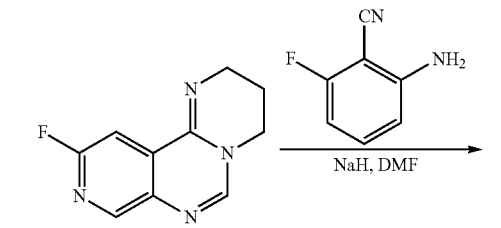

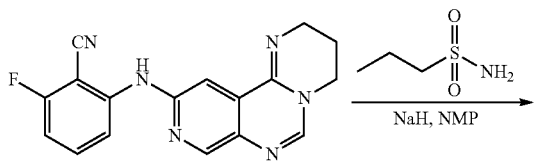

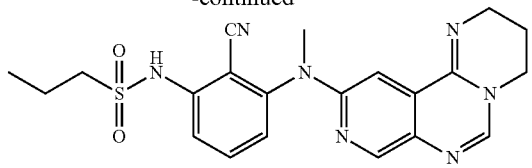

Step 1: Synthesis of 4-Chloro-6-fluoropyrido[3,4-d]pyrimidine

To a solution of 6-fluoropyrido[3,4-d]pyrimidin-4(3H)-one (1.0 g, 6.1 mmol) in SOCl₂ (20 mL) was added DMF (3 drops) under N₂. The resulting mixture was stirred at 90° C. for 48 hours. The mixture was evaporated to afford 4-chloro-6-fluoropyrido[3,4-d]pyrimidine (1.1 g, 100% yield).

Step 2: Synthesis of 3-((6-Fluoropyrido[3,4-d]pyrimidin-4-yl)amino)propan-1-ol To a solution of 4-chloro-6-fluoropyrido[3,4-d]pyrimidine (1.1 g, 6.01 mmol) in 3-aminopropan-1-ol (20 mL) was added Et₃N (1.8 g, 18.03 mmol). The resulting mixture was stirred at room temperature for 20 minutes. The mixture was evaporated and the residue was purified by column flash chromatography on silica gel (PE/EtOAc from 5:1 to DCM/MeOH 20:1, v/v) to afford 3-((6-fluoropyrido[3,4-d]pyrimidin-4-yl)amino)propan-1-ol (1.33 g, 100% yield).

Step 3: Synthesis of 10-Fluoro-3,4-dihydro-2H-pyrido[4,3-e]pyrimido[1,2-c]pyrimidine To a solution of 3-((6-fluoropyrido[3,4-d]pyrimidin-4-yl)amino)propan-1-ol (1.33 g, 6.1 mmol) in CHCl₃ (15 mL) was added SOCl₂ (3 mL) under N₂. The resulting mixture was stirred at 80° C. overnight. The mixture was evaporated under vacuum to dryness. The residue was added CHCl₃ (15 mL), Et₃N (2.46 g, 24.4 mmol). The mixture was stirred at room temperature overnight. The mixture was evaporated and the residue was purified by column flash chromatography on silica gel (PE/EtOAc from 5:1 to DCM/MeOH 20:1, v/v) to afford 10-fluoro-3,4-dihydro-2H-pyrido[4,3-e]pyrimido[1,2-c]pyrimidine (2.0 g, crude).

Step 4: Synthesis of 2-((3,4-Dihydro-2H-pyrido[4,3-e]pyrimido[1,2-c]pyrimidin-10-yl)amino)-6-fluorobenzonitrile To a solution of 10-fluoro-3,4-dihydro-2H-pyrido[4,3-e]pyrimido[1,2-c]pyrimidine (400 mg, 2.0 mmol) in DMF (10 mL) was added NaH (360 mg, 9.0 mmol, 60% in mineral oil) under N₂. The mixture was stirred at room temperature for 15 minutes under N₂. Then 2-amino-6-fluorobenzonitrile (272 mg, 2.0 mmol) was added into the reaction mixture. The resulting mixture was stirred at 60° C. for 48 hours under N₂. The mixture was evaporated and the residue was purified by flash chromatography on silica gel (PE/EtOAc from 2:1 to DCM/MeOH 20:1, v/v) to afford 2-((3,4-dihydro-2H-pyrido[4,3-e]pyrimido[1,2-c]pyrimidin-10-yl)amino)-6-fluorobenzonitrile (140 mg, 22% yield).

Step 5: Synthesis of 2-((3,4-Dihydro-2H-pyrido[4,3-e]pyrimido[1,2-c]pyrimidin-10-yl)(methyl)amino)-6-fluorobenzonitrile To a solution of 2-((3,4-dihydro-2H-pyrido[4,3-e]pyrimido[1,2-c]pyrimidin-10-yl)amino)-6-fluorobenzonitrile (200 mg, 0.64 mmol) in dry THF (12 mL) was added NaH (33 mg, 0.83 mmol, 60% in mineral oil) under N₂. The mixture was stirred at 0° C. for 30 minutes under N₂. Then CH₃I (90 mg, 0.64 mmol) was added into the reaction mixture. The resulting mixture was stirred at room temperature for 2 hours under N₂. The mixture was evaporated and the residue was purified by column chromatography on silica gel (PE/EtOAc from 2:1 to DCM/MeOH 20:1, v/v) to afford 2-((3,4-dihydro-2H-pyrido[4,3-e]pyrimido[1,2-c]pyrimidin-10-yl)(methyl)amino)-6-fluorobenzonitrile (100 mg, 48% yield).

Step 6: Synthesis of N-(2-Cyano-3-((3,4-dihydro-2H-pyrido[4,3-e]pyrimido[1,2-c]pyrimidin-10-yl)(methyl)amino)phenyl)propane-1-sulfonamide To a solution of 2-((3,4-dihydro-2H-pyrido[4,3-e]pyrimido[1,2-c]pyrimidin-10-yl)(methyl)amino)-6-fluorobenzonitrile (100 mg, 0.3 mmol) in NMP (6 mL) was added NaH (120 mg, 3.0 mmol, 60% in mineral oil) under N₂. The mixture was stirred at 0° C. for 15 min under N₂. Then propane-1-sulfonamide (369 mg, 3.0 mmol) was added into the reaction mixture. The resulting was stirred at 100° C. overnight under N₂. The mixture was evaporated and the residue was purified by Prep-HPLC to afford N-(2-cyano-3-((3,4-dihydro-2H-pyrido[4,3-e]pyrimido[1,2-c]pyrimidin-10-yl)(methyl)amino)phenyl)propane-1-sulfonamide (10.0 mg, 5% yield) as a white solid. 1H NMR (400 MHz, CD₃OD): δ 8.52 (s, 1H), 7.71 (s, 1H), 7.62 (t, J=8.4 Hz, 1H), 7.52 (dd, J=8.4, 0.8 Hz, 1H), 7.14 (dd, J=8.0, 0.8 Hz, 1H), 7.09 (s, 1H), 4.06 (t, J=5.6 Hz, 2H), 3.60 (t, J=5.6 Hz, 2H), 3.52 (s, 3H), 3.17-3.13 (m, 2H), 2.11-2.08 (m, 2H), 1.92-1.87 (m, 2H), 1.05 (t, J=7.2 Hz, 3H). LCMS (M+H⁺) m/z: 438.1.

Example 35: Preparation of N-(2-Cyano-3-((3,4-dihydro-2H-pyrido[4,3-e]pyrimido[1,2-c]pyrimidin-10-yl)amino)phenyl)propane-1-sulfonamide (Compound 43)

Scheme 35

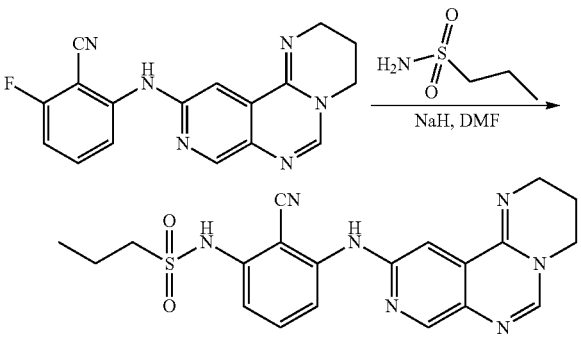

To a solution of 2-((3,4-dihydro-2H-pyrido[4,3-e]pyrimido[1,2-c]pyrimidin-10-yl)amino)-6-fluorobenzonitrile (120 mg, 0.37 mmol) and propane-1-sulfonamide (54 mg, 0.44 mol) in DMF (5.0 mL) was added NaH (22 mg, 0.55 mmol, 60% in mineral oil). The reaction mixture was stirred at 120° C. overnight. The residue was purified by Prep-HPLC to afford N-(2-cyano-3-((3,4-dihydro-2H-pyrido[4,3-e]pyrimido[1,2-c]pyrimidin-10-yl)amino)phenyl)propane-1-sulfonamide (7.0 mg, 5% yield) as a yellow solid. 1H NMR (400 MHz, DMSO-d$_6$): δ 10.19 (br s, 1H), 9.38 (s, 1H), 8.41 (s, 1H), 7.69 (s, 1H), 7.54-7.53 (m, 2H), 7.49 (s, 1H), 7.12 (dd, J=6.8, 2.4 Hz, 1H), 3.94 (t, J=5.6 Hz, 2H), 3.55 (t, J=5.6 Hz, 2H), 3.15-3.12 (m, 2H), 1.96-1.93 (m, 2H), 1.82-1.76 (m, 2H), 0.99 (t, J=7.6 Hz, 3H). LCMS (M+H$^+$) m/z: 424.2.

Example 36: Preparation of N-(2-Chloro-3-((2,3-dihydroimidazo[1,2-c]quinazolin-9-yl)oxy)phenyl)propane-2-sulfonamide (Compound 44)

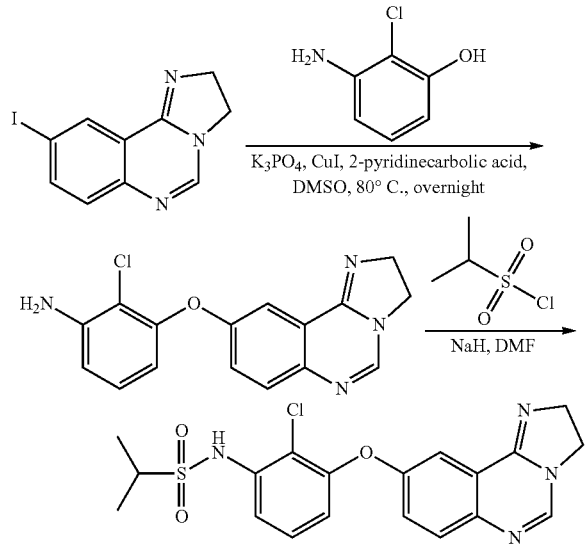

Step 1: Synthesis of 2-Chloro-3-((2,3-dihydroimidazo[1,2-c]quinazolin-9-yl)oxy)aniline To a solution of 9-iodo-2,3-dihydroimidazo[1,2-c]quinazoline (1.0 g, 3.36 mmol) and 3-amino-2-chlorophenol (0.96 g, 6.73 mmol) in DMSO (20.0 mL) was added CuI (64 mg, 0.34 mmol), K$_3$PO$_4$ (1.40 g, 6.60 mmol), 2-pyridinecarbolic acid (41 mg, 0.34 mmol). The mixture was stirred at 80° C. under N$_2$ overnight. The reaction mixture was cooled to room temperature and extracted with DCM (100 mL×3) from water (30.0 mL), the organic layers were washed brine (50 mL×2), dried over Na$_2$SO$_4$, filtered, concentrated in vacuo. The resulting mixture was evaporated and purified by column chromatography on silica gel (DCM/MeOH from 100:1 to 50:1, v/v) to afford 2-chloro-3-((2,3-dihydroimidazo[1,2-c]quinazolin-9-yl)oxy)aniline (0.6 g, 60% yield) as a tan solid.

Step 2: Synthesis of N-(2-Chloro-3-((2,3-dihydroimidazo[1,2-c]quinazolin-9-yl)oxy)phenyl)propane-2-sulfonamide To a solution of 2-chloro-3-((2,3-dihydroimidazo[1,2-c]quinazolin-9-yl)oxy)aniline (200 mg, 0.64 mmol) in DMF (5 mL) was added NaH (256 mg, 6.4 mmol, 60% in mineral oil) at 0° C. under N$_2$, the mixture was stirred at 0° C. for 0.5 hour. Propane-2-sulfonyl chloride (454 mg, 3.2 mmol) was added to the mixture. The reaction mixture was stirred at 60° C. overnight. The mixture was quenched with MeOH (1.0 mL) and concentrated to remove the solvent. The residue was purified by Prep-HPLC to afford N-(2-chloro-3-((2,3-dihydroimidazo[1,2-c]quinazolin-9-yl)oxy)phenyl)propane-2-sulfonamide (TFA salt, 4.5 mg, 1.3% yield) as a yellow solid. 1H NMR (400 MHz, DMSO-d$_6$): δ 9.72 (br, 1H), 8.09 (s, 1H), 7.58 (d, J=8.8 Hz, 1H), 7.45-7.37 (m, 3H), 7.27 (s, 1H), 7.08 (d, J=7.6 Hz, 1H), 4.22 (t, J=10.0 Hz, 2H), 3.94 (t, J=10.0 Hz, 2H), 3.38-3.31 (m, 1H), 1.30 (d, J=6.8 Hz, 6H). LCMS (M+H$^+$) m/z: 419.2.

Example 37: Preparation of N-(2-Chloro-3-((2,3-dihydroimidazo[1,2-c]quinazolin-9-yl)oxy)phenyl)-N-ethyl-N-methylamino-1-sulfonamide (Compound 45)

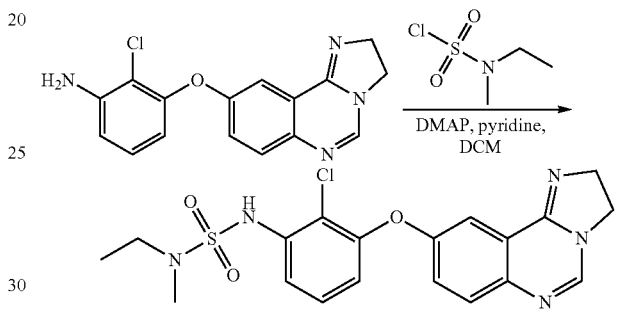

To a solution of 2-chloro-3-((2,3-dihydroimidazo[1,2-c]quinazolin-9-yl)oxy)aniline (150 mg, 0.48 mmol) in DCM (20 mL) wad added DMAP (3.0 mg, 0.05 mmol) ethyl (methyl)sulfamoyl chloride (136 mg, 1.44 mmol) and pyridine (75 mg, 0.96 mmol) at room temperature. The reaction was stirred at 60° C. for 4 days. The mixture was concentrated to remove the solvent. The residue was purified by Prep-HPLC to afford N-(2-chloro-3-((2,3-dihydroimidazo[1,2-c]quinazolin-9-yl)oxy)phenyl)-N-ethyl-N-methylamino-1-sulfonamide (TFA salt, 18.0 mg, 7% yield) as a yellow solid. $^1$H NMR (400 MHz, DMSO-d$_6$): δ 11.45 (br, 1H), 9.55 (s, 1H), 8.66 (s, 1H), 7.98 (d, J=8.8 Hz, 1H), 7.81 (d, J=8.4 Hz, 1H), 7.68 (s 1H), 7.48-7.46 (m, 2H), 7.15 (d, J=6.4 Hz, 1H), 4.66 (t, J=10.0 Hz, 2H), 4.12 (t, J=10.0 Hz, 2H), 3.17-3.12 (m, 2H), 2.76 (s, 3H), 1.03 (t, J=7.2 Hz, 3H). LCMS (M+H$^+$)m/z: 434.3.

Example 38: Preparation of (R)—N-(2-Chloro-3-((2,3-dihydroimidazo[1,2-c]quinazolin-9-yl)oxy)phenyl)-3-fluoropyrrolidine-1-sulfonamide (Compound 46)

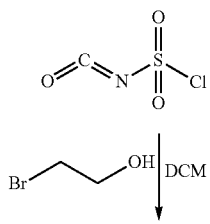

95

-continued

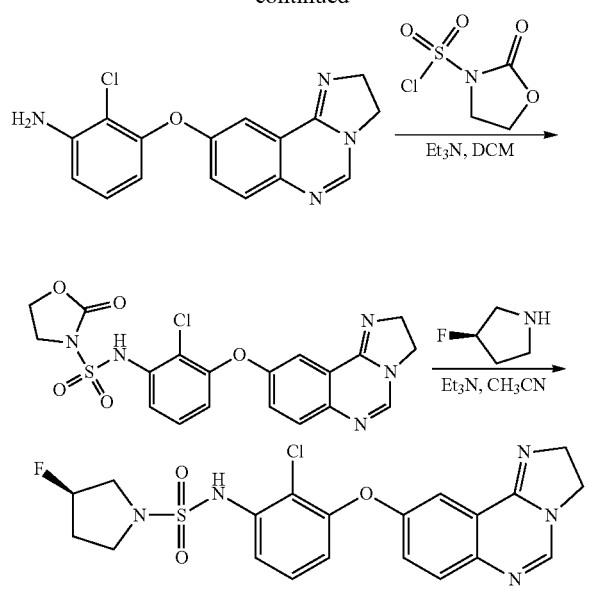

Step 1: Synthesis of N-(2-Chloro-3-((2,3-dihydroimidazo[1,2-c]quinazolin-9-yl)oxy)phenyl)-2-oxooxazolidine-3-sulfonamide To a solution of chlorosulfonyl isocyanate (9.07 g, 64 mmol) in DCM (50 mL) was added 2-bromoethan-1-ol (7.93 g, 64 mmol) at −5° C. under $N_2$. The mixture was stirred at −5-0° C. for 2 hours. A solution of 2-chloro-3-((2,3-dihydroimidazo[1,2-c]quinazolin-9-yl)oxy)aniline (1.0 g, 3.2 mmol) and $Et_3N$ (8.74 mL, 64 mmol) in DCM (100 mL) was added to above solution at 0° C. under $N_2$. The mixture was stirred at 10° C. for 4 hours. The mixture was concentrated and the residue was purified by column chromatography on silica gel (DCM/MeOH=10/1, v/v) to give N-(2-chloro-3-((2,3-dihydroimidazo[1,2-c]quinazolin-9-yl)oxy)phenyl)-2-oxooxazolidine-3-sulfonamide (800 mg, 54% yield) as a white solid.

Step 2: Synthesis of (R)—N-(2-Chloro-3-((2,3-dihydroimidazo[1,2-c]quinazolin-9-yl)oxy)phenyl)-3-fluoropyrrolidine-1-sulfonamide To a solution of N-(2-chloro-3-((2,3-dihydroimidazo[1,2-c]quinazolin-9-yl)oxy)phenyl)-2-oxooxazolidine-3-sulfonamide (120 mg, 0.26 mmol) and (R)-3-fluoropyrrolidine (231 mg, 2.6 mmol) in acetonitrile (5 mL) was added $Et_3N$ (78 mg, 0.78 mmol). The mixture was stirred at 120° C. under microwave for 40 minutes. The mixture was concentrated and the residue was purified by Prep-HPLC to afford (R)—N-(2-chloro-3-((2,3-dihydroimidazo[1,2-c]quinazolin-9-yl)oxy)phenyl)-3-fluoropyrrolidine-1-sulfonamide (TFA salt, 43.5 mg, 29% yield) as a white solid. $^1$H NMR (400 MHz, DMSO-$d_6$): δ 11.39 (s, 1H), 9.71 (s, 1H), 8.67 (s, 1H), 7.98 (d, J=8.8 Hz, 1H), 7.81 (t, J=9.2, 2.8 Hz, 1H), 7.67 (d, J=2.4 Hz, 1H), 7.54-7.44 (m, 2H), 7.17 (d, J=8.4 Hz, 1H), 5.31 (d, J=54 Hz, 1H), 4.67 (t, J=10.0 Hz, 2H), 4.12 (t, J=10.0 Hz, 2H), 3.34-3.30 (m, 4H), 2.14-1.97 (m, 2H). LCMS (M+H$^+$) m/z: 464.2.

96

Example 39: Preparation of N-(2-Chloro-3-((2,3-dihydroimidazo[1,2-c]quinazolin-9-yl)oxy)phenyl)-(2-fluoroethyl)(methyl)amino-1-sulfonamide (Compound 47)

Scheme 39

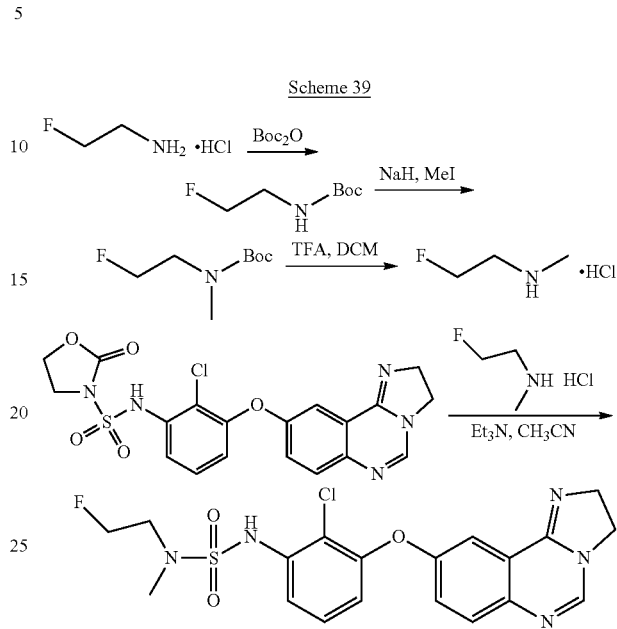

Step 1: Synthesis of tert-Butyl (2-fluoroethyl)carbamate

To a solution of 2-fluoroethan-1-amine hydrochloride (5.0 g, 0.05 mol) in THF/$H_2O$ (80 mL/80 mL) was added $NaHCO_3$ (16.8 g, 0.2 mol) at 0° C. After 5 minutes, $Boc_2O$ (12.4 mL, 0.05 mol) was added. The reaction mixture was stirred at room temperature overnight. The solution was concentrated, diluted with $H_2O$ (100 mL), and extracted with DCM (100 mL×3), the combined organic layers were washed with $H_2O$ (100 mL) and dried over $Na_2SO_4$. Concentration gave tert-butyl (2-fluoroethyl)carbamate (7.8 g, 96%) as colourless oil.

Step 2: Synthesis of tert-Butyl (2-fluoroethyl)(methyl)carbamate

To a solution of tert-butyl (2-fluoroethyl)carbamate (7.8 g, 47.8 mmol) in dried THF (100 mL) was added NaH (2.25 g, 71.7 mmol, 60% in mineral oil) at 0° C. under $N_2$. The mixture was stirred at 0° C. for 0.5 hour. MeI (10.1 g, 71.7 mmol) was added into the reaction. The reaction mixture was stirred at rt overnight. The mixture was quenched with $H_2O$ (2 mL) and concentrated. The residue was partitioned between DCM and water. The organic layer was dried over $Na_2SO_4$ and concentrated to give tert-butyl (2-fluoroethyl)(methyl)carbamate (crude, 9.2 g, 100%) as an oil.

Step 3: Synthesis of 2-fluoro-N-methylethan-1-amine hydrochloride

To a solution of tert-butyl (2-fluoroethyl)(methyl)carbamate (8.8 g, 49.7 mmol) in DCM (20 mL) was added TFA (20 mL) at 0° C. The mixture was stirred at room temperature overnight. The reaction mixture was concentrated, and the residue was dissolved in HCl/MeOH (2M, 20 mL). The mixture was concentrated and the residue was washed with $Et_2O$ (50 mL×2). The solid was dried under vacuum to give 2-fluoro-N-methylethan-1-amine hydrochloride (5.0 g, 89%) as a white solid.

Step 4: Synthesis of N-(2-Chloro-3-((2,3-dihydro-imidazo[1,2-c]quinazolin-9-yl)oxy)phenyl)-(2-fluoroethyl)(methyl)amino-1-sulfonamide To a mixture of N-(2-chloro-3-((2,3-dihydroimidazo[1,2-c]quinazolin-9-yl)oxy)phenyl)-2-oxooxazolidine-3-sulfonamide (100 mg, 0.22 mmol) and 2-fluoro-N-methylethan-1-amine hydrochloride (237 mg, 2.1 mmol) in CH$_3$CN (4 mL) was added Et$_3$N (212 mg, 2.1 mmol) at room temperature. The mixture was stirred at 120° C. under microwave for 40 minutes. After removal of the solvent, the residue was purified by Prep-HPLC to give N-(2-chloro-3-((2,3-dihydroimidazo[1,2-c]quinazolin-9-yl)oxy)phenyl)-(2-fluoroethyl)(methyl)amino-1-sulfonamide (TFA salt, 6.7 mg, 5% yield) as a white solid. $^1$H NMR (400 MHz, DMSO-d$_6$): δ 11.61 (br s, 1H), 9.68 (s, 1H), 8.67 (s, 1H), 7.97 (d, J=8.8 Hz, 1H), 7.79 (dd, J=8.8, 2.8 Hz, 1H), 7.75 (d, J=2.8 Hz, 1H), 7.49-7.43 (m, 2H), 7.17 (dd, J=7.2, 2.4 Hz, 1H), 4.70-4.65 (m, 2H), 4.51 (dt, J=47.2, 4.8 Hz, 1H), 4.15-4.10 (m, 2H), 3.41 (dt, J=26.8, 4.8 Hz, 1H), 3.38 (t, J=4.8 Hz, 1H), 2.84 (s, 3H). LCMS (M+H$^+$) m/z: 452.2.

Example 40: Preparation of N-(2-Chloro-3-((2,3-dihydroimidazo[1,2-c]quinazolin-9-yl)oxy)phenyl)pyrrolidine-1-sulfonamide (Compound 48)

Scheme 40

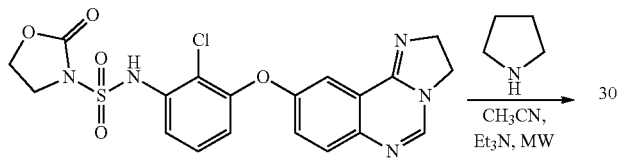

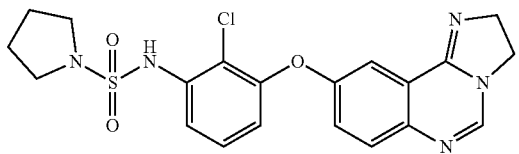

A mixture of N-(2-chloro-3-((2,3-dihydroimidazo[1,2-c]quinazolin-9-yl)oxy)phenyl)-2-oxooxazolidine-3-sulfonamide (50 mg, 0.11 mmol), pyrrolidine (16 mg, 0.22 mmol) and Et$_3$N (34 mg, 0.33 mmol) in CH$_3$CN (5 mL) was heated at 120° C. under microwave for 1 hour. The mixture was evaporated, and the residue was purified by Prep-HPLC to afford N-(2-chloro-3-((2,3-dihydroimidazo[1,2-c]quinazolin-9-yl)oxy)phenyl)pyrrolidine-1-sulfonamide (10 mg, 20% yield) as a brown solid. 1H NMR (400 MHz, CD$_3$OD): δ 8.03 (s, 1H), 7.60-7.56 (m, 2H), 7.42-7.39 (m, 2H), 7.33 (t, J=8.0 Hz, 1H), 6.98 (d, J=8.0 Hz, 1H), 4.30 (t, J=10.0 Hz, 2H), 4.04 (t, J=10.0 Hz, 2H), 3.31-3.28 (m, 4H), 1.86-1.83 (m, 4H). LCMS (M+H$^+$) m/z: 446.1.

Example 41: Preparation of N-(5-((2,3-Dihydroimidazo[1,2-c]quinazolin-9-yl)oxy)-2-fluorophenyl)pyrrolidine-1-sulfonamide (Compound 49)

Scheme 41

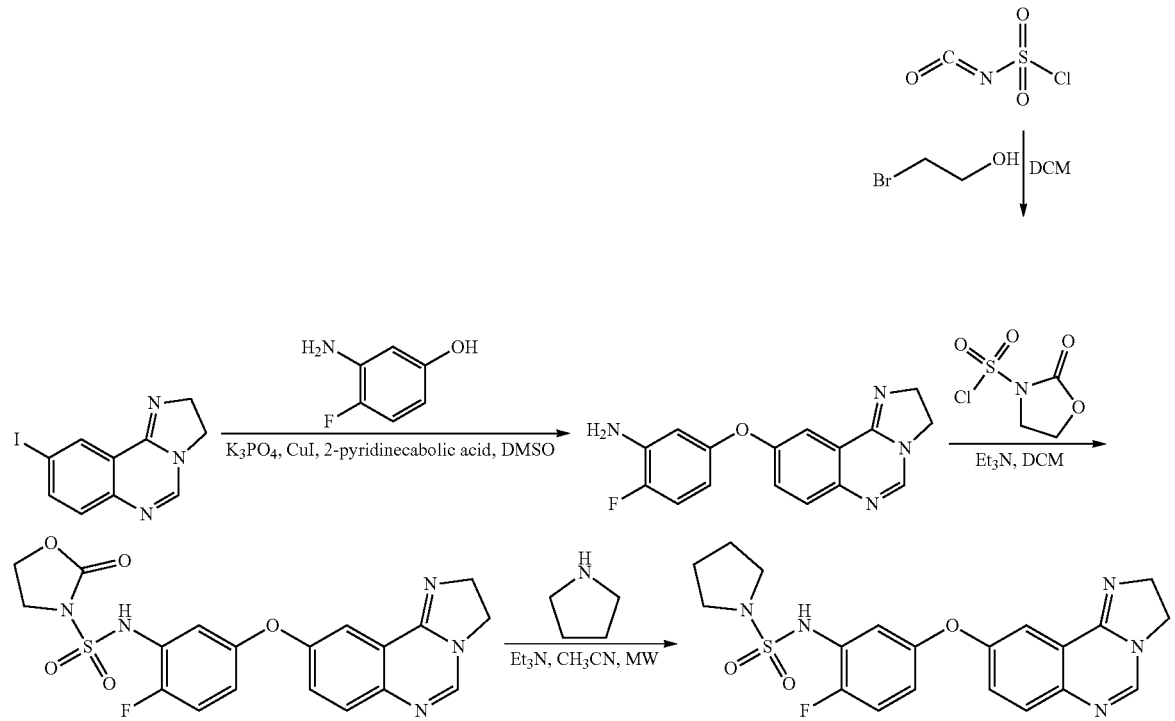

Step 1: Synthesis of 5-((2,3-Dihydroimidazo[1,2-c]quinazolin-9-yl)oxy)-2-fluoroaniline To a solution of 9-iodo-2,3-dihydroimidazo[1,2-c]quinazoline (1.0 g, 3.37 mmol) and 3-amino-4-fluorophenol (0.85 g, 6.73 mmol) in DMSO was added CuI (64 mg, 0.34 mmol), K₃PO₄ (2.14 g, 10.11 mmol), 2-pyridinecarbolic acid (41 mg, 0.34 mmol). The mixture was stirred at 80° C. under N₂ overnight. The reaction mixture was cooled to room temperature and partitioned between DCM and water. The organic layers were washed brine (50 mL×2), dried over Na₂SO₄. The resulting mixture was concentrated and the residue was purified by column chromatography on silica gel (DCM/MeOH from 100:1 to 50:1, v/v) to afford 5-((2,3-dihydroimidazo[1,2-c]quinazolin-9-yl)oxy)-2-fluoroaniline (0.6 g, 60% yield) as a tan solid.

Step 2: Synthesis of N-(5-((2,3-Dihydroimidazo[1,2-c]quinazolin-9-yl)oxy)-2-fluorophenyl)-2-oxooxazolidine-3-sulfonamide To a solution of chlorosulfonyl isocyanate (104 mg, 0.74 mmol) in DCM (20 mL) was added 2-bromoethan-1-ol (92 mg, 0.74 mmol) at −5° C. The mixture was stirred at −5-0° C. for 2 hours. A solution of 5-((2,3-dihydroimidazo[1,2-c]quinazolin-9-yl)oxy)-2-fluoroaniline (200 mg, 0.67 mmol) and Et₃N (135 mg, 1.34 mmol) in DCM (10 mL) was added to above solution at 0° C. under N₂. The mixture was stirred at 10° C. for 4 hours. The mixture was concentrated and the residue was purified by column chromatography on silica gel (DCM/MeOH=30/1, v/v) to give N-(5-((2,3-dihydroimidazo[1,2-c]quinazolin-9-yl)oxy)-2-fluorophenyl)-2-oxooxazolidine-3-sulfonamide (50 mg, 17% yield) as a white solid.

Step 3: Synthesis of N-(5-((2,3-Dihydroimidazo[1,2-c]quinazolin-9-yl)oxy)-2-fluorophenyl)pyrrolidine-1-sulfonamide To a solution of N-(5-((2,3-dihydroimidazo[1,2-c]quinazolin-9-yl)oxy)-2-fluorophenyl)-2-oxooxazolidine-3-sulfonamide (50 mg, 0.11 mmol) and pyrrolidine (80 mg, 1.12 mmol) in acetonitrile (5 mL) was added Et₃N (33 mg, 0.33 mmol). The mixture was stirred at 150° C. for 1 hour under microwave. The mixture was concentrated to remove the solvent. The residue was purified by Prep-HPLC to afford N-(5-((2,3-dihydroimidazo[1,2-c]quinazolin-9-yl)oxy)-2-fluorophenyl)pyrrolidine-1-sulfonamide (TFA salt, 10 mg, 16% yield) as a white solid. 1H NMR (400 MHz, DMSO-d₆): δ 11.43 (br, 1H), 9.93 (s, 1H), 8.67 (s, 1H), 7.98 (d, J=9.2 Hz, 1H), 7.82 (dd, J=8.8, 2.8 Hz, 1H), 7.77 (d, J=2.4 Hz, 1H), 7.39 (t, J=9.2 Hz, 1H), 7.20 (dd, J=6.8, 2.8 Hz, 1H), 7.01-6.98 (m, 1H), 4.69 (t, J=10.0 Hz, 2H), 4.14 (t, J=10.0 Hz, 2H), 3.17-3.13 (m, 4H), 1.77-1.73 (m, 4H). LCMS (M+H⁺) m/z: 430.3.

Example 42: Preparation of N-(5-((2,3-Dihydroimidazo[1,2-c]quinazolin-9-yl)oxy)-2-fluorophenyl)-N,N-dimethylamino-1-sulfonamide (Compound 50)

Scheme 42

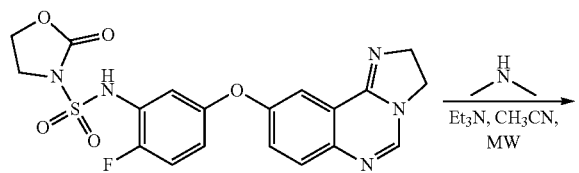

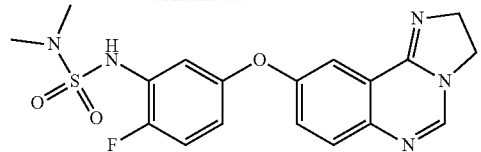

To a solution of N-(5-((2,3-dihydroimidazo[1,2-c]quinazolin-9-yl)oxy)-2-fluorophenyl)-2-oxooxazolidine-3-sulfonamide (50 mg, 0.11 mmol) and dimethylamine/THF (0.5 mL) in acetonitrile (5 mL) was added Et₃N (34 mg, 0.33 mmol). The mixture was stirred at 150° C. for 60 minutes under microwave. The mixture was concentrated to remove the solvent. The residue was purified by Prep-HPLC to afford N-(5-((2,3-dihydroimidazo[1,2-c]quinazolin-9-yl)oxy)-2-fluorophenyl)-N,N-dimethylamino-1-sulfonamide (TFA salt, 12 mg, 21% yield) as a white solid. 1H NMR (400 MHz, DMSO-d₆): δ 11.41 (br, 1H), 9.97 (s, 1H), 8.67 (s, 1H), 7.98 (d, J=9.2 Hz, 1H), 7.82 (dd, J=9.2, 2.8 Hz, 1H), 7.76 (d, J=2.8 Hz, 1H), 7.39 (t, J=9.6 Hz, 1H), 7.21-7.18 (m, 1H), 7.02-6.98 (m, 1H), 4.68 (t, J=10.0 Hz, 2H), 4.14 (t, J=10.0 Hz, 2H), 2.70 (s, 6H). LCMS (M+H⁺) m/z: 404.2.

Example 43: Preparation of N-(5-((2,3-Dihydroimidazo[1,2-c]quinazolin-9-yl)oxy)-2-fluorophenyl)propane-1-sulfonamide (Compound 51)

Scheme 43

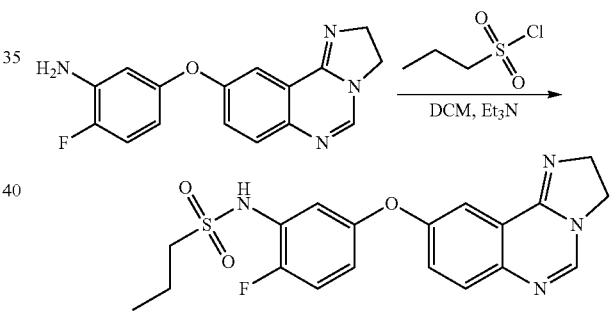

A mixture of 5-((2,3-dihydroimidazo[1,2-c]quinazolin-9-yl)oxy)-2-fluoroaniline (100 mg, 0.33 mmol), propane-1-sulfonyl chloride (433.6 mg, 3.04 mmol) and Et₃N (411 mg, 4.05 mmol) in DCM (10 mL) was stirred at 30° C. overnight. The mixture was concentrated, MeOH (10 mL) and aq. NaOH (10 mL, 2N) was added to the residue. The reaction mixture was stirred at room temperature for 4 hours. After the reaction was completed, conc. HCl was added to the mixture until pH=6-7. After removal of the volatile, the residue was extracted by DCM/MeOH (10/1), dried over Na₂SO₄. Concentration gave crude product, which was purified by Prep-HPLC to afford N-(5-((2,3-dihydroimidazo[1,2-c]quinazolin-9-yl)oxy)-2-fluorophenyl)propane-1-sulfonamide (TFA salt, 62.8 mg, 37% yield) as a white solid. 1H NMR (400 MHz, DMSO-d₆): δ 11.49 (br, 1H), 9.96 (s, 1H), 8.68 (s, 1H), 7.98 (d, J=9.2 Hz, 1H), 7.84 (dd, J=9.2, 2.8 Hz, 1H), 7.76 (d, J=2.4 Hz, 1H), 7.42 (t, J=9.2 Hz, 1H), 7.23-7.21 (m, 1H), 7.06-7.03 (m, 1H), 4.69 (t, J=10.0 Hz, 2H), 4.14 (t, J=10.0 Hz, 2H), 3.14 (t, J=7.2 Hz, 2H), 1.75-1.70 (m, 2H), 0.96 (t, J=7.2 Hz, 3H). LCMS (M+H⁺) m/z: 403.2.

Example 44: Preparation of N-(5-((2,3-Dihydroimidazo[1,2-c]quinazolin-9-yl)oxy)-2-fluorophenyl)propane-2-sulfonamide (Compound 52)

Scheme 44

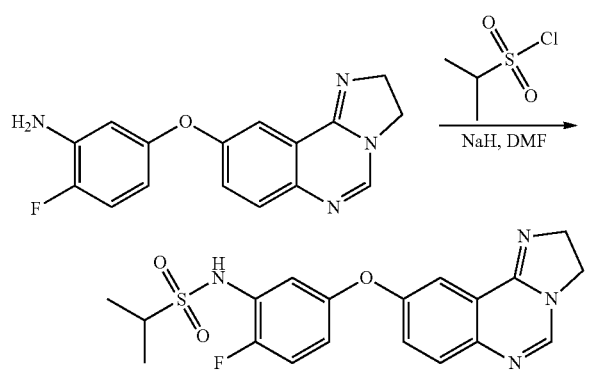

To a solution of 5-((2,3-dihydroimidazo[1,2-c]quinazolin-9-yl)oxy)-2-fluoroaniline (100 mg, 0.33 mmol) in DMF (5 mL) was added NaH (60% in mineral oil, 270 mg, 6.7 mmol, 60% in mineral oil) at 0° C. under $N_2$. the mixture was stirred at 0° C. for 0.5 hour. Propane-2-sulfonyl chloride (430 mg, 3.0 mmol) was added to the mixture. The reaction mixture was stirred at 80° C. overnight. The mixture was quenched with MeOH (1.0 mL) and concentrated to remove the solvent. The residue was partitioned between DCM and water. The organic layer was concentrated and purified by Prep-HPLC to afford N-(5-((2,3-dihydroimidazo[1,2-c]quinazolin-9-yl)oxy)-2-fluorophenyl)propane-2-sulfonamide (TFA salt, 4.6 mg, 3% yield) as a yellow solid. 1H NMR (400 MHz, DMSO-$d_6$): δ 9.83 (br, 1H), 7.95 (s, 1H), 7.47 (d, J=8.8 Hz, 1H), 7.35-7.30 (m, 2H), 7.25 (d, J=2.4 Hz, 1H), 7.16-7.14 (m, 1H), 6.94-6.92 (m, 1H), 4.11 (t, J=9.6 Hz, 2H), 3.90 (t, J=10.0 Hz, 2H), 3.32-3.30 (m, 1H), 1.25 (d, J=6.8 Hz, 6H). LCMS (M+H$^+$) m/z: 403.2.

Example 45: Preparation of (R)—N-(2-Chloro-3-((2,2-dimethyl-2,3-dihydroimidazo[1,2-c]quinazolin-9-yl)oxy)phenyl)-3-fluoropyrrolidine-1-sulfonamide (Compound 53)

Scheme 45

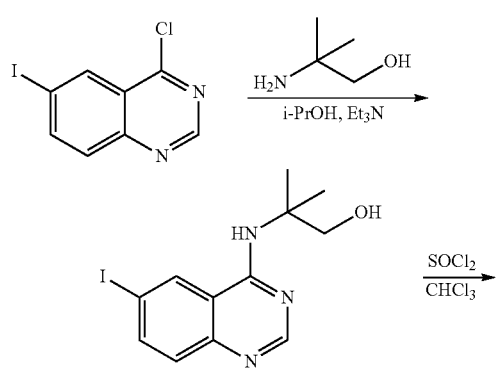

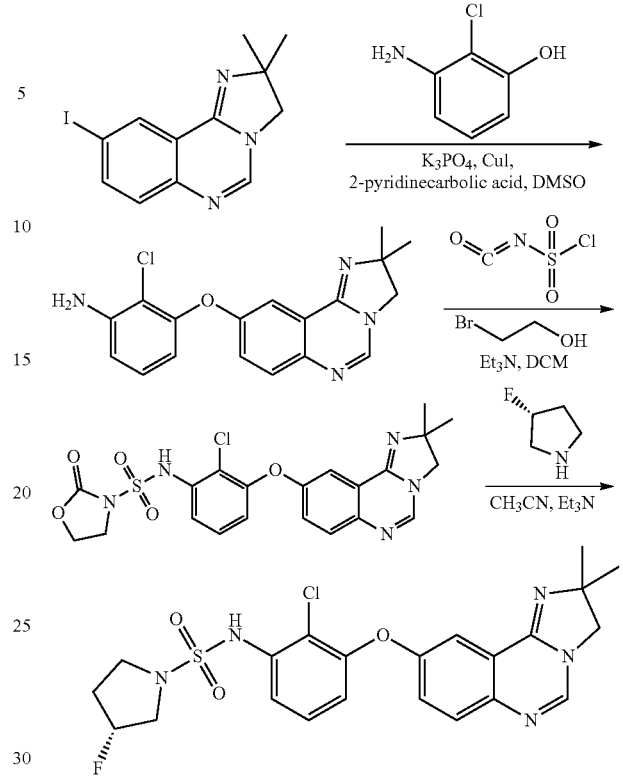

Step 1: Synthesis of 2-((6-Iodoquinazolin-4-yl)amino)-2-methylpropan-1-ol

To a solution of 4-chloro-6-iodoquinazoline (3.0 g, 10.3 mmol) and 2-amino-2-methylpropan-1-ol (1.8 g, 20.6 mmol) in i-PrOH (30.0 mL) was added $Et_3N$ (2.1 g, 20.6 mmol). The reaction mixture was stirred at 80° C. for 16 hours. The resulting mixture was cooled to room temperature and the solid was filtered to afford 2-((6-iodoquinazolin-4-yl)amino)-2-methylpropan-1-ol (3.5 g, 100% yield) as a white solid.

Step 2: Synthesis of 9-Iodo-2,2-dimethyl-2,3-dihydroimidazo[1,2-c]quinazoline To a solution of 2-((6-iodoquinazolin-4-yl)amino)-2-methylpropan-1-ol (3.5 g, 10.2 mmol) in CHCl$_3$ (10.0 mL) was added SOCl$_2$ (20.0 mL). The reaction mixture was stirred at reflux overnight. The resulting mixture was concentrated, to the residue was added MeOH and DCM. The reaction mixture was stirred at room temperature for 10 minutes. The solid was filtered to afford 9-iodo-2,2-dimethyl-2,3-dihydroimidazo[1,2-c]quinazoline (3.3 g, 100% yield) as an off-white solid.

Step 3: Synthesis of 2-Chloro-3-((2,2-dimethyl-2,3-dihydroimidazo[1,2-c]quinazolin-9-yl)oxy)aniline To a solution of 9-iodo-2,2-dimethyl-2,3-dihydroimidazo[1,2-c]quinazoline (1.0 g, 3.07 mmol) and 3-amino-2-chlorophenol (0.88 g, 6.15 mmol) in DMSO (20.0 mL) was added CuI (176 mg, 0.92 mmol), $K_3PO_4$ (2.94 g, 13.8 mmol), 2-pyridinecarbolic acid (114 mg, 0.92 mmol). The mixture was stirred at 80° C. under $N_2$ overnight. The reaction mixture was cooled to room temperature and extracted with DCM (100 mL×3) from water (40.0 mL), the organic layers were washed brine (60 mL×2), dried over Na₂SO₄, filtered, concentrated in vacuo. The resulting mixture was evaporated and purified by column chromatography on silica gel (DCM/MeOH from 100:1 to 20:1, v/v) to afford 2-chloro-3-((2,2-dimethyl-2,3-dihydroimidazo[1,2-c]quinazolin-9-yl)oxy)aniline (0.43 g, 41% yield) as a tan solid.

Step 4: Synthesis of N-(2-Chloro-3-((2,2-dimethyl-2,3-dihydroimidazo[1,2-c]quinazolin-9-yl)oxy)phenyl)-2-oxooxazolidine-3-sulfonamide To a solution of chlorosulfonyl isocyanate (333 mg, 2.35 mmol) in DCM (20 mL) was added a solution of 2-bromoethan-1-ol (295 mg, 2.35 mmol) in DCM (5 mL) slowly at 0° C. The mixture was stirred at 0° C. for 1 hour, and then the mixture was added dropwise to the stirred solution of 2-chloro-3-((2,2-dimethyl-2,3-dihydroimidazo[1,2-c]quinazolin-9-yl)oxy)aniline (200 mg, 0.59 mmol) and Et₃N (238 mg, 2.35 mmol) in DCM (15 mL), the mixture was stirred at room temperature overnight. Concentration gave crude product, which was purified by column chromatography on silica gel (DCM/MeOH from 50:1 to 10:1, v/v) to afford N-(2-chloro-3-((2,2-dimethyl-2,3-dihydroimidazo[1,2-c]quinazolin-9-yl)oxy)phenyl)-2-oxooxazolidine-3-sulfonamide (100 mg, 35% yield) as a brown solid.

Step 5: Synthesis of (R)—N-(2-Chloro-3-((2,2-dimethyl-2,3-dihydroimidazo[1,2-c]quinazolin-9-yl)oxy)phenyl)-3-fluoropyrrolidine-1-sulfonamide A mixture of N-(2-chloro-3-((2,2-dimethyl-2,3-dihydroimidazo[1,2-c]quinazolin-9-yl)oxy)phenyl)-2-oxooxazolidine-3-sulfonamide (30 mg, 0.06 mmol), (R)-3-fluoropyrrolidine (7 mg, 0.07 mmol) and Et₃N (8 mg, 0.07 mmol) in CH₃CN (2 mL) was stirred at 120° C. under microwave for 1 hour. The mixture was concentrated, the residue was purified by Prep-HPLC to afford (R)—N-(2-chloro-3-((2,2-dimethyl-2,3-dihydroimidazo[1,2-c]quinazolin-9-yl)oxy)phenyl)-3-fluoropyrrolidine-1-sulfonamide (TFA salt, 4 mg, 11% yield) as a white solid. 1H NMR (400 MHz, CD₃OD): δ 8.47 (s, 1H), 8.00 (d, J=8.8 Hz, 1H), 7.81 (dd, J=8.8, 2.8 Hz, 1H), 7.66 (dd, J=8.4, 1.2 Hz, 1H), 7.45-7.39 (m, 2H), 7.13-7.09 (m, 1H), 5.25 (dt, J=50.4, 3.6 Hz, 1H), 4.52 (s, 2H), 3.61-3.41 (m, 4H), 2.20-2.00 (m, 2H), 1.58 (s, 6H). LCMS (M+H⁺) m/z: 492.2.

Example 46: Preparation of N-(2-Chloro-3-((2,2-dimethyl-2,3-dihydroimidazo[1,2-c]quinazolin-9-yl)oxy)phenyl)pyrrolidine-1-sulfonamide (Compound 54)

Scheme 46

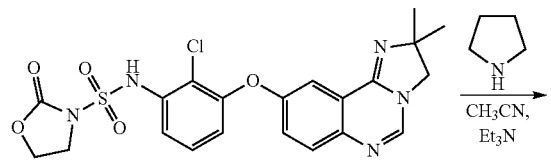

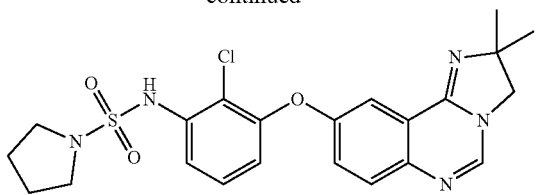

A mixture of N-(2-chloro-3-((2,2-dimethyl-2,3-dihydroimidazo[1,2-c]quinazolin-9-yl)oxy)phenyl)-2-oxooxazolidine-3-sulfonamide (70 mg, 0.14 mmol), pyrrolidine (13 mg, 0.17 mmol) and Et₃N (18 mg, 0.17 mmol) in CH₃CN (2 mL) was stirred at 120° C. under microwave for 1 hour. The mixture was concentrated, the residue was purified by Prep-HPLC to afford N-(2-chloro-3-((2,2-dimethyl-2,3-dihydroimidazo[1,2-c]quinazolin-9-yl)oxy)phenyl)pyrrolidine-1-sulfonamide (TFA salt, 6 mg, 7% yield) as a white solid. ¹H NMR (400 MHz, CD₃OD): δ 7.95 (s, 1H), 7.60-7.54 (m, 2H), 7.39-7.32 (m, 3H), 6.99 (dd, J=8.0, 1.2 Hz, 1H), 3.98 (s, 2H), 3.34-3.28 (m, 4H), 1.86-1.83 (m, 4H), 1.36 (s, 6H). LCMS (M+H⁺) m/z: 474.4.

Example 47: Preparation of N-(2-Chloro-3-((2,2-dimethyl-2,3-dihydroimidazo[1,2-c]quinazolin-9-yl)oxy)phenyl)propane-1-sulfonamide (Compound 55)

Scheme 47

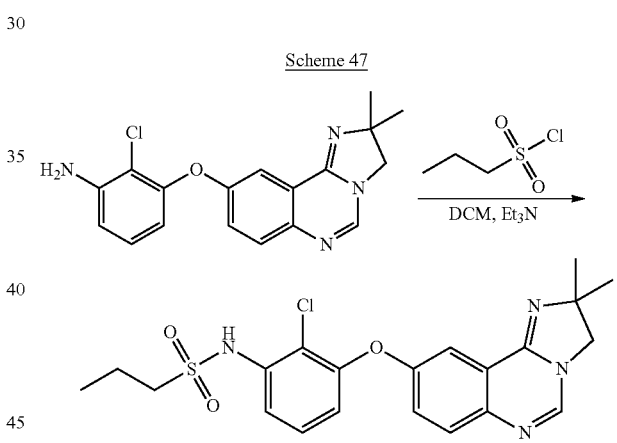

A mixture of 2-chloro-3-((2,2-dimethyl-2,3-dihydroimidazo[1,2-c]quinazolin-9-yl)oxy)aniline (100 mg, 0.29 mmol), propane-1-sulfonyl chloride (378 mg, 2.64 mmol) and Et₃N (357 mg, 3.53 mmol) in DCM (10 mL) was stirred at 30° C. overnight. The mixture was concentrated, MeOH (10 mL) and aq NaOH (10 mL, 2N) was added to the residue, the reaction mixture was stirred at room temperature for 4 hours. Concentrated HCl was added to the until pH=6-7. The mixture was evaporated, the residue was extracted with DCM/MeOH (10/1), dried over Na₂SO₄. Concentration gave crude product, which was purified by Prep-HPLC to afford N-(2-chloro-3-((2,2-dimethyl-2,3-dihydroimidazo[1,2-c]quinazolin-9-yl)oxy)phenyl)propane-1-sulfonamide (TFA salt, 37 mg, 22% yield) as a brown solid. ¹H NMR (400 MHz, DMSO-d₆): δ 11.57 (br s, 1H), 9.70 (s, 1H), 8.64 (s, 1H), 8.00 (d, J=8.8 Hz, 1H), 7.86 (dd, J=9.2, 2.8 Hz, 1H), 7.59 (d, J=2.8 Hz, 1H), 7.50-7.48 (m, 2H), 7.23 (t, J=4.8 Hz, 1H), 4.44 (s, 2H), 3.19-3.15 (m, 2H), 1.80-1.72 (m, 2H), 1.52 (s, 6H), 0.97 (t, J=7.2 Hz, 3H). LCMS (M+H⁺) m/z: 447.2.

Example 48: Preparation of N-(2-Chloro-3-((3-((dimethylamino)methyl)-2,3-dihydroimidazo[1,2-c]quinazolin-9-yl)oxy)phenyl)propane-1-sulfonamide (Compound 56)

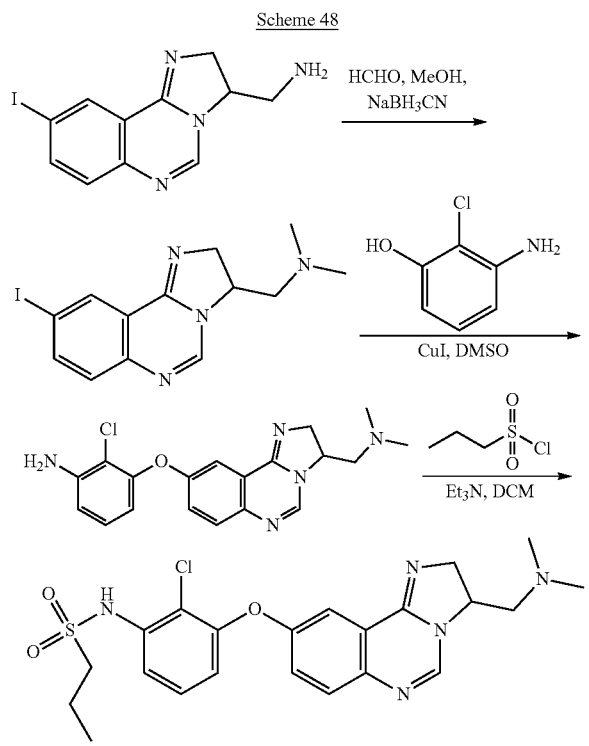

Scheme 48

Step 1: Synthesis of 1-(9-Iodo-2,3-dihydroimidazo[1,2-c]quinazolin-3-yl)-N,N-dimethylmethanamine A solution of (9-iodo-2,3-dihydroimidazo[1,2-c]quinazolin-3-yl)methanamine (100 mg, 0.31 mmol), formaldehyde (5 drops), NaBH$_3$CN (40 mg, 0.62 mmol) in MeOH (5 mL) was stirred at room temperature overnight. Water was added, the resulting mixture was extracted with EtOAc (20 mL×3). The combined organic layers were washed with brine (20 mL×2), dried over Na$_2$SO$_4$. Concentration gave crude product, which was purified by column chromatography on silica gel (DCM/MeOH from 100:1 to 20:1, v/v) to afford 1-(9-iodo-2,3-dihydroimidazo[1,2-c]quinazolin-3-yl)-N,N-dimethylmethanamine (43 mg, 40% yield) as a white solid.

Step 2: Synthesis of 2-Chloro-3-((3-((dimethylamino)methyl)-2,3-dihydroimidazo[1,2-c]quinazolin-9-yl)oxy)aniline A solution of 1-(9-iodo-2,3-dihydroimidazo[1,2-c]quinazolin-3-yl)-N,N-dimethylmethanamine (43 mg, 0.12 mmol), 3-amino-2-chlorophenol (34 mg, 0.24 mmol), CuI (3 mg, 0.012 mmol) in DMSO (5 mL) was stirred at 90° C. overnight. The residue was purified by Prep-HPLC to afford 2-chloro-3-((3-((dimethylamino)methyl)-2,3-dihydroimidazo[1,2-c]quinazolin-9-yl)oxy)aniline (15 mg, 33% yield) as a white solid.

Step 3: Synthesis of N-(2-Chloro-3-((3-((dimethylamino)methyl)-2,3-dihydroimidazo[1,2-c]quinazolin-9-yl)oxy)phenyl)propane-1-sulfonamide To a solution of 2-chloro-3-((3-((dimethylamino)methyl)-2,3-dihydroimidazo[1,2-c]quinazolin-9-yl)oxy)aniline (15 mg, 0.04 mmol) and Et$_3$N (10 mg, 0.08 mmol) in DCM (1 mL), was added propane-1-sulfonyl chloride (5 mg, 0.04 mmol). The mixture was stirred at room temperature for 2 hours. Aq. NaOH (1 mL, 1 mmol/mL) was added, the mixture was stirred at room temperature for further 2 hours. Concentration gave crude product, which was purified by Prep-HPLC to afford N-(2-chloro-3-((3-((dimethylamino)methyl)-2,3-dihydroimidazo[1,2-c]quinazolin-9-yl)oxy)phenyl)propane-1-sulfonamide (10.0 mg, 50% yield) as a white solid. 1H NMR (400 MHz, CD$_3$OD): δ 7.97 (s, 1H), 7.55 (d, J=8.8 Hz, 1H), 7.50 (d, J=8.0 Hz, 1H), 7.42-7.36 (m, 2H), 7.33 (t, J=8.0 Hz, 1H), 7.00 (d, J=8.0 Hz, 1H), 4.50-4.46 (m, 1H), 4.37-4.33 (m, 1H), 4.04-3.99 (m, 1H), 3.15 (t, J=7.6 Hz, 2H), 2.71-2.68 (m, 2H), 2.45 (s, 6H), 1.88-1.83 (m, 2H), 1.03 (t, J=7.6 Hz, 3H). LCMS (M+H$^+$) m/z: 476.2.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The in vitro and in vivo activities of the compounds of Formula (I) were determined using the following procedures.

Biological Example B1

Antiproliferation Assays

In vitro anti-proliferation study of test compounds in A375 cell line by CellTiter Glo. The cells were routinely maintained as a monolayer culture in corresponding culture medium, at 37° C. with 5% CO$_2$ in air.

Harvest the exponential growth cells by trypsin-EDTA digestion. Re-suspend the cell pellet in fresh culture medium, and adjust the concentration to needed (the cell density per well was listed in following form). The cell viability is over 98% by Trypan blue staining. Inoculate cells into 96 wells plates according to the plate map (90 µL/well). Incubate the plates at 37° C. and 5% CO$_2$ overnight. The next day, prepare the 10×compound containing medium according to the plate map. Transfer 10 µL of 10×compound containing medium into each well of the assay plates (the final DMSO concentration is 0.5%). Gently mix the medium and incubate at 37° C. and 5% CO$_2$ for another 72 hours or 144 hours.

Prepare the reagent according to the manufacture's instruction. Add 50 µL CellTiter-Glo Reagent in each well. Mix contents for 2 minutes on an orbital shaker to induce cell lysis. Allow the plate to incubate at room temperature for 10 minutes to stabilize luminescent signal. Transfer 100

µL of reaction contents of each well from the clear plates into white walled/white opaque 96-well plates. Record the luminescence on Envision.

Using the luminescence measurements [time zero (T0), control growth (C), and test growth in the presence of drug at the six concentration levels (Ti)], the percentage growth is calculated at each of the drug concentrations levels.

Percentage growth inhibition (GI) is calculated as: GI (%)=[(Ti-T0)/(C-T0)]×100 for concentrations for which Ti>=T0, and GI (%)=[(Ti-T0)/T0]×100 for concentrations for which Ti<T0. Data were analyzed using the XLFit (Excel) tool, fitting to a 4-parameter equation to generate concentration response curves. Concentration of compound that inhibits 50% of control cell growth (GI50) was back-interpolated when y=50% of net growth of DMSO treated control wells using nonlinear regression with the equation: f(x) 205 [fit=(A+((B−A)/(1+((C/x)^))))], where A is the minimum response (Ymin), B is the maximum response (Ymax), C is the inflection point of the curve (Re GI50) and D is the Hill coefficient. Growth inhibition of 50% (GI50) was calculated at the 50% Growth inhibition on the curve. Index values were the sum of Inhibition rate (IR) at each tested compound concentration. Table A shows the antiproliferation of synthesized compounds at A375 melanoma cells and HT-29 colon cancer cells.

TABLE A

| Cmpd No. | Compound | MS (MH+) | 1H NMR | A375 | Ht-29 |
|---|---|---|---|---|---|
| 1 | N-(2-cyano-3-((2,3-dihydroimidazo[1,2-c]quinazolin-9-yl)oxy)phenyl)propane-1-sulfonamide | 410.70 | 1H NMR (400 MHz, DMSO-d6): δ 8.73 (s, 1H), 8.06-7.96 (m, 3H), 7.75 (t, J = 8.0 Hz, 1H), 7.40 (d, J = 8.0 Hz, 1H), 7.08 (d, J = 8.4 Hz, 1H), 4.74-4.69 (m, 2H), 4.19-4.15 (m, 2H), 3.25 (t, J = 7.2 Hz, 2H), 1.85-1.79 (m, 2H), 1.02 (t, J = 7.2 Hz, 3H). | +++ | +++ |
| 2 | N-(2-cyano-3-((2,3-dihydroimidazo[1,2-c]quinazolin-9-yl)oxy)phenyl)-N-methylpropane-1-sulfonamide | 424.2 | 1H NMR (400 MHz, DMSO-d6): δ 7.98 (s, 1H), 7.72 (t, J = 8.4 Hz, 1H), 7.54-7.44 (m, 4H), 7.07 (d, J = 8.4 Hz, 1H), 4.12 (t, J = 9.6 Hz, 2H), 3.92 (t, J = 9.6 Hz, 2H), 3.34-3.30 (m, 2H), 3.29 (s, 3H), 1.81-1.75 (m, 2H), 1.02 (t, J = 7.2 Hz, 3H). | + | ND |
| 3 | N-(2-cyano-3-((2,3-dihydroimidazo[1,2-c]quinazolin-9-yl)oxy)-4-fluorophenyl)propane-1-sulfonamide | 428.70 | 1H NMR (400 MHz, CD3OD): δ 7.91 (s, 1H), 7.50 (d, J = 8.8 Hz, 1H), 7.43-7.34 (m, 3H), 7.25 (t, J = 9.6 Hz, 1H), 4.19 (t, J = 9.6 Hz, 2H), 4.00 (t, J = 9.6 Hz, 2H), 2.98-2.94 (m, 2H), 1.88-1.83 (m, 2H), 1.02 (t, J = 7.2 Hz, 3H). | +++ | ND |
| 4 | N-(2-cyano-3-((2,3-dihydroimidazo[1,2-c]quinazolin-9-yl)oxy)-4,6-difluorophenyl)propane-1-sulfonamide | 446.2 | 1H NMR (400 MHz, CD3OD): δ 8.11 (s, 1H), 7.71-7.66 (m, 2H), 7.56 (dd, J = 8.8, 2.8 Hz, 1H), 7.48 (d, J = 2.4 Hz, 1H), 4.37 (t, J = 10.0 Hz, 2H), 4.08 (t, J = 10.0 Hz, 2H), 3.19 (t, J = 7.6 Hz, 2H), 1.97-1.91 (m, 2H), 1.07 (t, J = 7.6 Hz, 3H). | ++ | ND |
| 5 | N-(2-cyano-3-((2,3-dihydroimidazo[1,2-c]quinazolin-9-yl)oxy)-6-fluorophenyl)propane-1-sulfonamide | 428.2 | 1H NMR (400 MHz, DMSO-d6): δ 10.48 (br, 1H), 8.13 (s, 1H), 7.63-7.52 (m, 3H), 7.45 (d, J = 2.4 Hz, 1H), 6.99-6.96 (m, 1H), 4.24 (t, J = 10.0 Hz, 2H), 3.96 (t, J = 10.0 Hz, 2H), 3.12 (t, J = 7.6 Hz, 2H), 1.85-1.79 (m, 2H), 1.00 (t, J = 7.2 Hz, 3H). | ++ | ND |
| 6 | N-(2-chloro-3-((2,3-dihydroimidazo[1,2-c]quinazolin-9-yl)oxy)phenyl)propane-1-sulfonamide | 419.1 | 1H NMR (400 MHz, CD3OD): δ 8.03 (s, 1H), 7.58 (d, J = 8.4 Hz, 1H), 7.51 (d, J = 7.6 Hz, 1H), 7.43-7.33 (m, 3H), 7.02 (d, J = 7.2 Hz, 1H), 4.29 (t, J = 10.0 Hz, 2H), 4.04 (t, J = 10.0 Hz, 2H), 3.15 (t, J = 7.6 Hz, 2H), 1.88-1.82 (m, 2H), 1.03 (t, J = 7.6 Hz, 3H). | +++ | ++ |
| 7 | N-(3-((2,3-dihydroimidazo[1,2-c]quinazolin-9-yl)oxy)-2-fluoro-4-nitrophenyl)propane-1-sulfonamide | 448.1 | 1H NMR (400 MHz, DMSO-d6): δ 11.19 (br s, 1H), 8.46 (s, 1H), 7.93 (d, J = 9.6 Hz, 1H), 7.85 (d, J = 9.2 Hz, 1H), 7.78 (dd, J = 9.2, 2.0 Hz, 1H), 7.50 (s, 1H), 7.38 (t, J = 8.8 Hz, 1H), 4.51 (t, J = 10.0 | + | ND |

TABLE A-continued

| Cmpd No. | Compound | MS (MH+) | 1H NMR | A375 | Ht-29 |
|---|---|---|---|---|---|
| | | | Hz, 2H), 4.05 (t, J = 10.0 Hz, 2H), 2.93 (t, J = 7.6 Hz, 2H), 1.73-1.68 (m, 2H), 0.95 (t, J = 7.6 Hz, 3H). | | |
| 8 | N-(4-amino-3-((2,3-dihydroimidazo[1,2-c]quinazolin-9-yl)oxy)-2-fluorophenyl)propane-1-sulfonamide | 418.2 | 1H NMR (400 MHz, DMSO-d6): δ 11.46 (br, 1H), 9.15 (s, 1H), 8.65 (s, 1H), 7.97 (d, J = 9.2 Hz, 1H), 7.79 (dd, J = 9.2, 2.4 Hz, 1H), 7.64 (s, 1H), 7.05 (t, J = 8.8 Hz, 1H), 6.66 (d, J = 8.4 Hz, 1H), 4.68 (t, J = 10.0 Hz, 2H), 4.12 (t, J = 10.0 Hz, 2H), 2.97 (t, J = 7.6 Hz, 2H), 1.73-1.67 (m, 2H), 0.92 (t, J = 7.6 Hz, 3H). | + | ND |
| 9 | N-(3-((2,3-dihydroimidazo[1,2-c]quinazolin-9-yl)oxy)-2-fluorophenyl)propane-1-sulfonamide | 403.2 | 1H NMR (400 MHz, DMSO-d6): δ 11.62 (br, 1H), 9.92 (s, 1H), 8.67 (s, 1H), 7.98 (d, J = 9.2 Hz, 1H), 7.86 (dd, J = 9.2, 2.4 Hz, 1H), 7.78 (s, 1H), 7.40-7.38 (m, 1H), 7.30 (t, J = 8.8 Hz, 1H), 7.22-7.19 (m, 1H), 4.68 (t, J = 10.0 Hz, 2H), 4.13 (t, J = 10.0 Hz, 2H), 3.15 (t, J = 8.0 Hz, 2H), 1.76-1.71 (m, 2H), 0.96 (t, J = 7.6 Hz, 3H). | ++ | ND |
| 10 | N-(3-((2,3-dihydroimidazo[1,2-c]quinazolin-9-yl)oxy)-2,4-difluorophenyl)propane-1-sulfonamide | 421.1 | 1H NMR (400 MHz, DMSO-d6): δ 9.61 (br, 1H), 7.99 (s, 1H), 7.52-7.45 (m, 2H), 7.38-7.35 (m, 2H), 7.18 (s, 1H), 4.14 (t, J = 9.6 Hz, 2H), 3.91 (t, J = 9.6 Hz, 2H), 3.07 (t, J = 7.6 Hz, 2H), 1.73-1.67 (m, 2H), 0.89 (t, J = 7.6 Hz, 3H). | + | ND |
| 11 | N-(3-((2,3-dihydroimidazo[1,2-c]quinazolin-9-yl)oxy)-2-(trifluoromethyl)phenyl)propane-1-sulfonamide | 453.1 | 1H NMR (400 MHz, DMSO-d6): δ 11.54 (br, 1H), 9.70 (s, 1H), 8.69 (s, 1H), 8.00 (d, J = 8.8 Hz, 1H), 7.87-7.84 (m, 2H), 7.73 (t, J = 8.0 Hz, 1H), 7.40 (d, J = 8.0 Hz, 1H), 7.19 (d, J = 8.0 Hz, 1H), 4.70 (t, J = 10.0 Hz, 2H), 4.15 (t, J = 10.0 Hz, 2H), 3.18 (t, J = 7.6 Hz, 2H), 1.82-1.76 (m, 2H), 1.02 (t, J = 7.6 Hz, 3H). | ++ | ND |
| 12 | N-(3-((2,3-dihydroimidazo[1,2-c]quinazolin-9-yl)oxy)-2-nitrophenyl)propane-1-sulfonamide | 430.1 | 1H NMR (400 MHz, DMSO-d6): δ 8.24 (s, 1H), 7.67 (d, J = 8.8 Hz, 1H), 7.57-7.51 (m, 2H), 7.39-7.32 (m, 2H), 6.68 (d, J = 7.2 Hz, 1H), 4.34 (t, J = 10.0 Hz, 2H), 4.00 (t, J = 10.0 Hz, 2H), 2.96 (t, J = 7.6 Hz, 2H), 1.72-1.66 (m, 2H), 0.96 (t, J = 7.6 Hz, 3H). | +++ | ND |
| 13 | N-(2-amino-3-((2,3-dihydroimidazo[1,2-c]quinazolin-9-yl)oxy)phenyl)propane-1-sulfonamide | 400.1 | 1H NMR (400 MHz, DMSO-d6): δ 8.94 (br s, 1H), 7.89 (s, 1H), 7.43 (d, J = 8.8 Hz, 1H), 7.29 (dd, J = 8.8, 2.8 Hz, 1H), 7.09 (d, J = 2.8 Hz, 1H), 7.05 (d, J = 7.6 Hz, 1H), 6.83 (d, J = 7.6 Hz, 1H), 6.62 (t, J = 7.6 Hz, 1H), 5.00 (br s, 2H), 4.07 (t, J = 10.0 Hz, 2H), 3.86 (t, J = 10.0 Hz, 2H), 3.02 (t, J = 7.6 Hz, 2H), 1.77-1.68 (m, 2H), 0.95 (t, J = 7.6 Hz, 3H). | + | ND |
| 14 | N-(2-cyano-3-((2,3-dihydroimidazo[1,2-c]quinazolin-9-yl)oxy)phenyl)-2-fluorobenzenesulfonamide | 462.2 | 1H NMR (400 MHz, DMSO-d6): δ 7.92 (s, 1H), 7.82-7.76 (m, 1H), 7.69-7.64 (m, 1H), 7.45-7.30 (m, 3H), 7.25-7.17 (m, 3H), 7.07 (t, J = 8.4 Hz, 1H), 6.95 (d, J = 8.8 Hz, 1H), 6.08 (d, J = 7.6 Hz, 1H), 4.09 (t, J = 9.6 Hz, 2H), 3.90 (t, J = 9.6 Hz, 2H). | +++ | ND |

TABLE A-continued

| Cmpd No. | Compound | MS (MH+) | 1H NMR | A375 | Ht-29 |
|---|---|---|---|---|---|
| 15 | N-(2-cyano-3-((2,3-dihydroimidazo[1,2-c]quinazolin-9-yl)oxy)phenyl)thiophene-2-sulfonamide | 450.1 | 1H NMR (400 MHz, DMSO-d6): δ 7.92 (s, 1H), 7.54 (d, J = 3.6 Hz, 1H), 7.44 (d, J = 8.8 Hz, 1H), 7.33-7.30 (m, 2H), 7.24 (d, J = 2.8 Hz, 1H), 7.14-7.06 (m, 2H), 6.96 (dd, J = 4.8, 3.6 Hz, 1H), 6.10 (d, J = 7.6 Hz, 1H), 4.09 (t, J = 9.6 Hz, 2H), 3.90 (t, J = 9.6 Hz, 2H). | ++ | ND |
| 16 | N-(2-cyano-3-((3,4-dihydro-2H-pyrimido[1,2-c]quinazolin-10-yl)oxy)phenyl)propane-1-sulfonamide | 424.2 | 1H NMR (400 MHz, DMSO-d6): δ 8.21 (s, 1H), 7.88 (d, J = 2.4 Hz, 1H), 7.78 (d, J = 8.8 Hz, 1H), 7.65 (dd, J = 8.8, 2.4 Hz, 1H), 7.28 (t, J = 8.4 Hz, 1H), 7.18 (d, J = 8.4 Hz, 1H), 6.26 (d, J = 8.0 Hz, 1H), 4.17 (t, J = 5.2 Hz, 2H), 3.56 (t, J = 5.2 Hz, 2H), 2.86 (t, J = 7.6 Hz, 2H), 2.10-2.06 (m, 2H), 1.75-1.69 (m, 2H), 0.96 (t, J = 7.6 Hz, 3H). | +++ | +++ |
| 17 | N-(2-cyano-3-((3,4-dihydro-2H-pyrimido[1,2-c]quinazolin-10-yl)oxy)-4-fluorophenyl)propane-1-sulfonamide | 442.4 | 1H NMR (400 MHz, DMSO-d6): δ 10.65 (br s, 1H), 8.27 (s, 1H), 7.83-7.78 (m, 2H), 7.71 (d, J = 8.8 Hz, 1H), 7.38 (t, J = 9.6 Hz, 1H), 7.28 (dd, J = 9.6, 4.4 Hz, 1H), 4.18 (t, J = 5.6 Hz, 2H), 3.56 (t, J = 5.6 Hz, 2H), 2.82 (t, J = 7.6 Hz, 2H), 2.12-2.08 (m, 2H), 1.73-1.67 (m, 2H), 0.95 (t, J = 7.6 Hz, 3H). | +++ | ND |
| 18 | N-(3-((3,4-dihydro-2H-pyrimido[1,2-c]quinazolin-10-yl)oxy)-2-fluorophenyl)propane-1-sulfonamide | 417.3 | 1H NMR (400 MHz, CD3OD): δ 8.30 (s, 1H), 7.93 (d, J = 8.8 Hz, 1H), 7.79 (s, 1H), 7.74 (d, J = 8.8 Hz, 1H), 7.46 (t, J = 7.6 Hz, 1H), 7.25 (t, J = 8.0 Hz, 1H), 7.09 (t, J = 7.6 Hz, 1H), 4.37 (m, 2H), 3.69 (t, J = 4.8 Hz, 2H), 3.15 (t, J = 7.2 Hz, 2H), 2.30 (m, 2H), 1.88-1.82 (m, 2H), 1.04 (t, J = 7.2 Hz, 3H). | +++ | ++ |
| 19 | N-(3-((3,4-dihydro-2H-pyrimido[1,2-c]quinazolin-10-yl)oxy)-2-fluoro-6-nitrophenyl)propane-1-sulfonamide | 462.1 | 1H NMR (400 MHz, DMSO-d6): δ 10.36 (br, 1H), 8.05 (s, 1H), 7.78 (d, J = 2.0 Hz, 1H), 7.71-7.61 (m, 3H), 6.88 (t, J = 8.0 Hz, 1H), 4.08 (t, J = 4.8 Hz, 2H), 3.53 (t, J = 5.2 Hz, 2H), 2.92 (t, J = 7.6 Hz, 2H), 2.03-2.00 (m, 2H), 1.75-1.65 (m, 2H), 0.93 (t, J = 7.6 Hz, 3H). | + | ND |
| 20 | N-(6-amino-3-((3,4-dihydro-2H-pyrimido[1,2-c]quinazolin-10-yl)oxy)-2-fluorophenyl)propane-1-sulfonamide | 432.1 | 1H NMR (400 MHz, DMSO-d6): δ 9.00 (br s, 1H), 7.56 (s, 1H), 7.35 (d, J = 8.8 Hz, 1H), 7.28 (d, J = 2.4 Hz, 1H), 7.23 (dd, J = 8.8, 2.8 Hz, 1H), 7.00 (t, J = 8.8 Hz, 1H), 6.60 (d, J = 8.8 Hz, 1H), 5.33 (br s, 2H), 3.84 (t, J = 5.2 Hz, 2H), 3.42 (t, J = 5.2 Hz, 2H), 3.06 (t, J = 7.6 Hz, 2H), 1.84-1.79 (m, 2H), 1.77-1.69 (m, 2H), 0.93 (t, J = 7.2 Hz, 3H). | + | ND |
| 21 | N-(2-chloro-3-((3,4-dihydro-2H-pyrimido[1,2-c]quinazolin-10-yl)oxy)phenyl)propane-1-sulfonamide | 433.1 | 1H NMR (400 MHz, DMSO-d6): δ 9.55 (br, 1H), 7.63 (s, 1H), 7.42 (d, J = 8.4 Hz, 1H), 7.36-7.28 (m, 4H), 6.96-6.94 (m, 1H), 3.86 (t, J = 5.2 Hz, 2H), 3.43 (t, J = 5.2 Hz, 2H), 3.09 (t, J = 7.6 Hz, 2H), 1.86-1.83 (m, 2H), 1.77-1.71 (m, 2H), 0.97 (t, J = 7.6 Hz, 3H). | +++ | +++ |
| 22 | N-(2-((3,4-dihydro-2H-pyrimido[1,2- | 445.2 | 1H NMR (400 MHz, DMSO-d6): δ 10.94 (br, 1H), 8.41 (s, | + | ND |

TABLE A-continued

| Cmpd No. | Compound | MS (MH+) | 1H NMR | A375 | Ht-29 |
|---|---|---|---|---|---|
| | c]quinazolin-10-yl)oxy)-3-nitropyridin-4-yl)propane-1-sulfonamide | | 1H), 8.24 (s, 1H), 7.84 (d, J = 8.8 Hz, 1H), 7.75 (d, J = 8.8 Hz, 1H), 7.55 (d, J = 6.0 Hz, 1H), 7.11 (d, J = 6.0 Hz, 1H), 4.30-4.25 (m, 2H), 3.60-3.58 (m, 2H), 2.77-2.73 (m, 2H), 2.20-2.16 (m, 2H), 1.68-1.62 (m, 2H), 0.93 (t, J = 7.2 Hz, 3H). | | |
| 23 | N-(4-((3,4-dihydro-2H-pyrimido[1,2-c]quinazolin-10-yl)oxy)-3-nitropyridin-2-yl)propane-1-sulfonamide | 445.2 | 1H NMR (400 MHz, DMSO-d6): δ 10.67 (br, 1H), 8.46 (s, 1H), 8.17 (d, J = 2.4 Hz, 1H), 7.90 (d, J = 9.2 Hz, 1H), 7.82 (dd, J = 9.2, 2.4 Hz, 1H), 7.55 (d, J = 6.0 Hz, 1H), 7.12 (d, J = 6.0 Hz, 1H), 4.28 (t, J = 5.2 Hz, 2H), 3.60 (t, J = 5.2 Hz, 2H), 2.78-2.73 (m, 2H), 2.20-2.16 (m, 2H), 1.68-1.63 (m, 2H), 0.93 (t, J = 7.6 Hz, 3H). | + | + |
| 24 | N-(3-cyano-4-((3,4-dihydro-2H-pyrimido[1,2-c]quinazolin-10-yl)oxy)pyridin-2-yl)propane-1-sulfonamide | 425.3 | 1H NMR (400 MHz, DMSO-d6): δ 10.67 (br, 1H), 8.35 (s, 1H), 8.12 (s, 1H), 7.85-7.80 (m, 2H), 7.54 (d, J = 6.4 Hz, 1H), 6.98 (d, J = 6.4 Hz, 1H), 4.29-4.22 (m, 2H), 3.61-3.58 (m, 2H), 2.81-2.77 (m, 2H), 2.20-2.16 (m, 2H), 1.73-1.68 (m, 2H), 0.96 (t, J = 7.2 Hz, 3H). | + | ND |
| 25 | N-(3-cyano-2-((3,4-dihydro-2H-pyrimido[1,2-c]quinazolin-10-yl)oxy)pyridin-4-yl)propane-1-sulfonamide | 425.3 | 1H NMR (400 MHz, DMSO-d6): δ 10.60 (br, 1H), 8.47 (s, 1H), 8.19 (s, 1H), 7.92-7.86 (m, 2H), 7.54 (d, J = 6.0 Hz, 1H), 6.99 (d, J = 6.0 Hz, 1H), 4.29 (t, J = 5.2 Hz, 2H), 3.61 (t, J = 5.2 Hz, 2H), 2.80 (t, J = 7.6 Hz, 2H), 2.20-2.16 (m, 2H), 1.74-1.68 (m, 2H), 0.96 (t, J = 7.6 Hz, 3H). | + | ND |
| 26 | N-(3-chloro-4-((3,4-dihydro-2H-pyrimido[1,2-c]quinazolin-10-yl)oxy)pyridin-2-yl)propane-1-sulfonamide | 434.2 | 1H NMR (400 MHz, CDCl3): δ 0.83 (d, J = 5.6 Hz, 1H), 7.94 (s, 1H), 7.55 (d, J = 8.8 Hz, 1H), 7.48 (s, 1H), 7.30 (dd, J = 8.8, 2.8 Hz, 1H), 6.43 (d, J = 5.6 Hz, 1H), 3.93 (t, J = 5.6 Hz, 2H), 3.69-3.63 (m, 4H), 2.10-2.04 (m, 2H), 1.98-1.92 (m, 2H), 1.10 (t, J = 7.2 Hz, 3H). | +++ | +++ |
| 27 | N-(2-cyano-3-((3,4-dihydro-2H-pyrido[4,3-e]pyrimido[1,2-c]pyrimidin-10-yl)oxy)phenyl)propane-1-sulfonamide | 425.3 | 1H NMR (400 MHz, CD3OD): δ 8.38 (s, 1H), 7.68 (s, 1H), 7.54 (s, 1H), 7.44-7.39 (m, 2H), 6.68 (dd, J = 7.6, 1.2 Hz, 1H), 4.00 (t, J = 5.6 Hz, 2H), 3.65 (t, J = 5.6 Hz, 2H), 2.07-2.04 (m, 2H), 1.92-1.81 (m, 2H), 1.38-1.29 (m, 2H), 1.08 (t, J = 7.2 Hz, 3H). | ++ | ND |
| 28 | N-(2-cyano-3-((2,3,4,5-tetrahydro-[1,3]diazepino[1,2-c]quinazolin-11-yl)oxy)phenyl)propane-1-sulfonamide | 438.2 | 1H NMR (400 MHz, DMSO-d6): δ 10.35 (br, 1H), 8.45 (s, 1H), 7.90 (s, 1H), 7.79 (d, J = 8.8 Hz, 1H), 7.61 (dd, J = 9.2, 2.0 Hz, 1H), 7.45-7.41 (m, 1H), 7.18 (d, J = 8.0 Hz, 1H), 6.55-6.52 (m, 1H), 3.81-3.79 (m, 4H), 3.07 (t, J = 7.2 Hz, 2H), 1.94-1.92 (m, 4H), 1.80-1.74 (m, 2H), 0.99 (t, J = 7.2 Hz, 3H). | + | ND |
| 37 | N-(2-chloro-3-((3,4-dihydro-2H-pyrimido[1,2-c]quinazolin-10-yl)oxy)phenyl)ethane sulfonamide | 419.2 | 1H NMR (400 MHz, DMSO-d6): δ 9.81 (br s, 1H), 7.76 (s, 1H), 7.50 (d, J = 8.8 Hz, 1H), 7.45 (d, J = 2.0 Hz, 1H), 7.38-7.35 (m, 3H), 7.03 (t, J = 4.8 Hz, 1H), 3.93 (t, J = 5.6 Hz, | ND | ND |

TABLE A-continued

| Cmpd No. | Compound | MS (MH+) | 1H NMR | A375 | Ht-29 |
|---|---|---|---|---|---|
| | | | 2H), 3.45 (t, J = 5.6 Hz, 2H), 3.17 (q, J = 7.2 Hz, 2H), 1.92-1.87 (m, 2H), 1.27 (t, J = 7.2 Hz, 3H). | | |
| 38 | N-(2-chloro-3-((3,4-dihydro-2H-pyrimido[1,2-c]quinazolin-10-yl)oxy)phenyl)-3-fluoropropane-1-sulfonamide | 451.3 | 1H NMR (400 MHz, DMSO-d6): δ 7.72 (s, 1H), 7.48 (d, J = 8.4 Hz, 1H), 7.40 (d, J = 2.8 Hz, 1H), 7.36-7.30 (m, 3H), 6.93 (dd, J = 7.6, 2.4 Hz, 1H), 4.57 (dt, J = 47.2, 6.0 Hz, 2H), 3.91 (t, J = 5.6 Hz, 2H), 3.44 (t, J = 5.6 Hz, 2H), 3.22-3.17 (m, 2H), 2.17-2.07 (m, 2H), 1.89-1.87 (m, 2H). | +++ | ND |
| 39 | N-(2-chloro-3-((3,4-dihydro-2H-pyrimido[1,2-c]quinazolin-10-yl)oxy)phenyl)-3-hydroxypropane-1-sulfonamide | 449.3 | 1H NMR (400 MHz, DMSO-d6): δ 10.73 (br s, 1H), 9.69 (s, 1H), 8.47 (s, 1H), 7.95-7.92 (m, 2H), 7.76-7.73 (m, 1H), 7.46-7.44 (m, 2H), 7.15-7.13 (m, 1H), 4.29 (t, J = 5.6 Hz, 2H), 3.64-3.56 (m, 4H), 3.24-3.20 (m, 2H), 2.19-2.16 (m, 2H), 1.90-1.86 (m, 2H). | ++ | ND |
| 40 | (R)-N-(2-chloro-3-((3,4-dihydro-2H-pyrimido[1,2-c]quinazolin-10-yl)oxy)phenyl)-3-fluoropyrrolidine-1-sulfonamide | 478.1 | 1H NMR (400 MHz, CD3OD): δ 8.25 (s, 1H), 7.88 (d, J = 9.2 Hz, 1H), 7.71 (d, J = 2.4 Hz, 1H), 7.64-7.61 (m, 2H), 7.38 (t, J = 8.4 Hz, 1H), 7.04 (dd, J = 8.4, 1.2 Hz, 1H), 5.24 (dt, J = 52.8, 3.6 Hz, 1H), 4.33 (t, J = 5.6 Hz, 2H), 3.67 (t, J = 5.6 Hz, 2H), 3.61-3.30 (m, 4H), 2.29-1.97 (m, 4H). | +++ | ND |
| 41 | N-(2-chloro-3-((3,4-dihydro-2H-pyrimido[1,2-c]quinazolin-10-yl)oxy)phenyl)-N-ethyl-N-methylamino-1-sulfonamide | 448.1 | 1H NMR (400 MHz, CD3OD): δ 8.26 (s, 1H), 7.90 (d, J = 9.2 Hz, 1H), 7.72 (d, J = 2.8 Hz, 1H), 7.65 (dd, J = 9.2, 2.8 Hz, 1H), 7.56 (dd, J = 8.4, 1.6 Hz, 1H), 7.38 (t, J = 8.4 Hz, 1H), 7.03 (dd, J = 8.4, 1.2 Hz, 1H), 4.34 (t, J = 5.6 Hz, 2H), 3.68 (t, J = 5.6 Hz, 2H), 3.25 (q, J = 7.2 Hz, 2H), 2.85 (s, 3H), 2.31-2.25 (m, 2H), 1.11 (t, J = 7.2 Hz, 3H). | +++ | ND |
| 42 | N-(2-cyano-3-((3,4-dihydro-2H-pyrido[4,3-e]pyrimido[1,2-c]pyrimidin-10-yl)(methyl)amino)phenyl)propane-1-sulfonamide | 438.1 | 1H NMR (400 MHz, CD3OD): δ 8.52 (s, 1H), 7.71 (s, 1H), 7.62 (t, J = 8.4 Hz, 1H), 7.52 (dd, J = 8.4, 0.8 Hz, 1H), 7.14 (dd, J = 8.0, 0.8 Hz, 1H), 7.09 (s, 1H), 4.06 (t, J = 5.6 Hz, 2H), 3.60 (t, J = 5.6 Hz, 2H), 3.52 (s, 3H), 3.17-3.13 (m, 2H), 2.11-2.08 (m, 2H), 1.92-1.87 (m, 2H), 1.05 (t, J = 7.2 Hz, 3H). | + | ND |
| 43 | N-(2-cyano-3-((3,4-dihydro-2H-pyrido[4,3-e]pyrimido[1,2-c]pyrimidin-10-yl)amino)phenyl)propane-1-sulfonamide | 424.2 | 1H NMR (400 MHz, DMSO-d6): δ 10.19 (br s, 1H), 9.38 (s, 1H), 8.41 (s, 1H), 7.69 (s, 1H), 7.54-7.53 (m, 2H), 7.49 (s, 1H), 7.12 (dd, J = 6.8, 2.4 Hz, 1H), 3.94 (t, J = 5.6 Hz, 2H), 3.55 (t, J = 5.6 Hz, 2H), 3.15-3.12 (m, 2H), 1.96-1.93 (m, 2H), 1.82-1.76 (m, 2H), 0.99 (t, J = 7.6 Hz, 3H). | ++ | ND |
| 44 | N-(2-chloro-3-((2,3-dihydroimidazo[1,2-c]quinazolin-9-yl)oxy)phenyl)propane-2-sulfonamide | 419.2 | 1H NMR (400 MHz, DMSO-d6): δ 9.72 (br, 1H), 8.09 (s, 1H), 7.58 (d, J = 8.8 Hz, 1H), 7.45-7.37 (m, 3H), 7.27 (s, 1H), 7.08 (d, J = 7.6 Hz, 1H), 4.22 (t, J = 10.0 Hz, 2H), 3.94 (t, J = 10.0 Hz, 2H), 3.38-3.31 (m, 1H), 1.30 (d, J = 6.8 Hz, 6H). | +++ | ND |
| 45 | N-(2-chloro-3-((2,3-dihydroimidazo[1,2- | 434.3 | 1H NMR (400 MHz, DMSO-d6): δ 11.45 (br, 1H), 9.55 (s, | + | ND |

TABLE A-continued

| Cmpd No. | Compound | MS (MH+) | 1H NMR | A375 | Ht-29 |
|---|---|---|---|---|---|
| | c]quinazolin-9-yl)oxy)phenyl)-N-ethyl-N-methylamino-1-sulfonamide | | 1H), 8.66 (s, 1H), 7.98 (d, J = 8.8 Hz, 1H), 7.81 (d, J = 8.4 Hz, 1H), 7.68 (s 1H), 7.48-7.46 (m, 2H), 7.15 (d, J = 6.4 Hz, 1H), 4.66 (t, J = 10.0 Hz, 2H), 4.12 (t, J = 10.0 Hz, 2H), 3.17-3.12 (m, 2H), 2.76 (s, 3H), 1.03 (t, J = 7.2 Hz, 3H). | | |
| 46 | (R)-N-(2-chloro-3-((2,3-dihydroimidazo[1,2-c]quinazolin-9-yl)oxy)phenyl)-3-fluoropyrrolidine-1-sulfonamide | 464.2 | 1H NMR (400 MHz, DMSO-d6): δ 11.39 (s, 1H), 9.71 (s, 1H), 8.67 (s, 1H), 7.98 (d, J = 8.8 Hz, 1H), 7.81 (t, J = 9.2, 2.8 Hz, 1H), 7.67 (d, J = 2.4 Hz, 1H), 7.54-7.44 (m, 2H), 7.17 (d, J = 8.4 Hz, 1H), 5.31 (d, J = 54 Hz, 1H), 4.67 (t, J = 10.0 Hz, 2H), 4.12 (t, J = 10.0 Hz, 2H), 3.34-3.30 (m, 4H), 2.14-1.97 (m, 2H). | +++ | ND |
| 47 | N-(2-chloro-3-((2,3-dihydroimidazo[1,2-c]quinazolin-9-yl)oxy)phenyl)-(2-fluoroethyl)(methyl)amino-1-sulfonamide | 452.2 | 1H NMR (400 MHz, DMSO-d6): δ 11.61 (br s, 1H), 9.68 (s, 1H), 8.67 (s, 1H), 7.97 (d, J = 8.8 Hz, 1H), 7.79 (dd, J = 8.8, 2.8 Hz, 1H), 7.75 (d, J = 2.8 Hz, 1H), 7.49-7.43 (m, 2H), 7.17 (dd, J = 7.2, 2.4 Hz, 1H), 4.70-4.65 (m, 2H), 4.51 (dt, J = 47.2, 4.8 Hz, 1H), 4.15-4.10 (m, 2H), 3.41 (dt, J = 26.8, 4.8 Hz, 1H), 3.38 (t, J = 4.8 Hz, 1H), 2.84 (s, 3H). | +++ | ND |
| 48 | N-(2-chloro-3-((2,3-dihydroimidazo[1,2-c]quinazolin-9-yl)oxy)phenyl)pyrrolidine-1-sulfonamide | 446.1 | 1H NMR (400 MHz, CD3OD): δ 8.03 (s, 1H), 7.60-7.56 (m, 2H), 7.42-7.39 (m, 2H), 7.33 (t, J = 8.0 Hz, 1H), 6.98 (d, J = 8.0 Hz, 1H), 4.30 (t, J = 10.0 Hz, 2H), 4.04 (t, J = 10.0 Hz, 2H), 3.31-3.28 (m, 4H), 1.86-1.83 (m, 4H). | +++ | ND |
| 49 | N-(5-((2,3-dihydroimidazo[1,2-c]quinazolin-9-yl)oxy)-2-fluorophenyl)pyrrolidine-1-sulfonamide | 430.3 | 1H NMR (400 MHz, DMSO-d6): δ 11.43 (br, 1H), 9.93 (s, 1H), 8.67 (s, 1H), 7.98 (d, J = 9.2 Hz, 1H), 7.82 (dd, J = 8.8, 2.8 Hz, 1H), 7.77 (d, J = 2.4 Hz, 1H), 7.39 (t, J = 9.2 Hz, 1H), 7.20 (dd, J = 6.8, 2.8 Hz, 1H), 7.01-6.98 (m, 1H), 4.69 (t, J = 10.0 Hz, 2H), 4.14 (t, J = 10.0 Hz, 2H), 3.17-3.13 (m, 4H), 1.77-1.73 (m, 4H). | + | ND |
| 50 | N-(5-((2,3-dihydroimidazo[1,2-c]quinazolin-9-yl)oxy)-2-fluorophenyl)-N,N-dimethylamino-1-sulfonamide | 404.2 | 1H NMR (400 MHz, DMSO-d6): δ 11.41 (br, 1H), 9.97 (s, 1H), 8.67 (s, 1H), 7.98 (d, J = 9.2 Hz, 1H), 7.82 (dd, J = 9.2, 2.8 Hz, 1H), 7.76 (d, J = 2.8 Hz, 1H), 7.39 (t, J = 9.6 Hz, 1H), 7.21-7.18 (m, 1H), 7.02-6.98 (m, 1H), 4.68 (t, J = 10.0 Hz, 2H), 4.14 (t, J = 10.0 Hz, 2H), 2.70 (s, 6H). | ND | ND |
| 51 | N-(5-((2,3-dihydroimidazo[1,2-c]quinazolin-9-yl)oxy)-2-fluorophenyl)propane-1-sulfonamide | 403.2 | 1H NMR (400 MHz, DMSO-d6): δ 11.49 (br, 1H), 9.96 (s, 1H), 8.68 (s, 1H), 7.98 (d, J = 9.2 Hz, 1H), 7.84 (dd, J = 9.2, 2.8 Hz, 1H), 7.76 (d, J = 2.4 Hz, 1H), 7.42 (t, J = 9.2 Hz, 1H), 7.23-7.21 (m, 1H), 7.06-7.03 (m, 1H), 4.69 (t, J = 10.0 Hz, 2H), 4.14 (t, J = 10.0 Hz, 2H), 3.14 (t, J = 7.2 Hz, 2H), 1.75-1.70 (m, 2H), 0.96 (t, J = 7.2 Hz, 3H). | + | ND |
| 52 | N-(5-((2,3-dihydroimidazo[1,2-c]quinazolin-9-yl)oxy)-2-fluorophenyl)propane- | 403.2 | 1H NMR (400 MHz, DMSO-d6): δ 9.83 (br, 1H), 7.95 (s, 1H), 7.47 (d, J = 8.8 Hz, 1H), 7.35-7.30 (m, 2H), 7.25 (d, J = 2.4 Hz, 1H), 7.16-7.14 (m, | ND | ND |

TABLE A-continued

| Cmpd No. | Compound | MS (MH+) | 1H NMR | A375 | Ht-29 |
|---|---|---|---|---|---|
| | 2-sulfonamide | | 1H), 6.94-6.92 (m, 1H), 4.11 (t, J = 9.6 Hz, 2H), 3.90 (t, J = 10.0 Hz, 2H), 3.32-3.30 (m, 1H), 1.25 (d, J = 6.8 Hz, 6H). | | |
| 53 | (R)-N-(2-chloro-3-((2,2-dimethyl-2,3-dihydroimidazo[1,2-c]quinazolin-9-yl)oxy)phenyl)-3-fluoropyrrolidine-1-sulfonamide | 492.2 | 1H NMR (400 MHz, CD3OD): δ 8.47 (s, 1H), 8.00 (d, J = 8.8 Hz, 1H), 7.81 (dd, J = 8.8, 2.8 Hz, 1H), 7.66 (dd, J = 8.4, 1.2 Hz, 1H), 7.45-7.39 (m, 2H), 7.13-7.09 (m, 1H), 5.25 (dt, J = 50.4, 3.6 Hz, 1H), 4.52 (s, 2H), 3.61-3.41 (m, 4H), 2.20-2.00 (m, 2H), 1.58 (s, 6H). | +++ | ND |
| 54 | N-(2-chloro-3-((2,2-dimethyl-2,3-dihydroimidazo[1,2-c]quinazolin-9-yl)oxy)phenyl)pyrrolidine-1-sulfonamide | 474.4 | 1H NMR (400 MHz, CD3OD): δ 7.95 (s, 1H), 7.60-7.54 (m, 2H), 7.39-7.32 (m, 3H), 6.99 (dd, J = 8.0, 1.2 Hz, 1H), 3.98 (s, 2H), 3.34-3.28 (m, 4H), 1.86-1.83 (m, 4H), 1.36 (s, 6H). | +++ | ND |
| 55 | N-(2-chloro-3-((2,2-dimethyl-2,3-dihydroimidazo[1,2-c]quinazolin-9-yl)oxy)phenyl)propane-1-sulfonamide | 447.2 | 1H NMR (400 MHz, DMSO-d6): δ 11.57 (br s, 1H), 9.70 (s, 1H), 8.64 (s, 1H), 8.00 (d, J = 8.8 Hz, 1H), 7.86 (dd, J = 9.2, 2.8 Hz, 1H), 7.59 (d, J = 2.8 Hz, 1H), 7.50-7.48 (m, 2H), 7.23 (t, J = 4.8 Hz, 1H), 4.44 (s,2H), 3.19-3.15 (m, 2H), 1.80-1.72 (m, 2H), 1.52 (s, 6H), 0.97 (t, J = 7.2 Hz, 3H). | +++ | ND |
| 56 | N-(2-chloro-3-((3-((dimethylamino)methyl)-2,3-dihydroimidazo[1,2-c]quinazolin-9-yl)oxy)phenyl)propane-1-sulfonamide | 476.2 | 1H NMR (400 MHz, CD3OD): δ 7.97 (s, 1H), 7.55 (d, J = 8.8 Hz, 1H), 7.50 (d, J = 8.0 Hz, 1H), 7.42-7.36 (m, 2H), 7.33 (t, J = 8.0 Hz, 1H), 7.00 (d, J = 8.0 Hz, 1H), 4.50-4.46 (m, 1H), 4.37-4.33 (m, 1H), 4.04-3.99 (m, 1H), 3.15 (t, J = 7.6 Hz, 2H), 2.71-2.68 (m, 2H), 2.45 (s, 6H), 1.88-1.83 (m, 2H), 1.03 (t, J = 7.6 Hz, 3H). | ND | ND |

+++: <100 nM;
++: 100-1000 nM;
+: >1000 nM;
ND: Not Determined

Biological Example B2

MDCK-MDR1 Permeability Assay

MDCK-MDR1 cells originate from transfection of Madin Darby canine kidney (MDCK) cells with the MDR1 gene, the gene encoding for the efflux protein, P-glycoprotein. This cell line is ideal for identifying substrates of P-gp, with or without an inhibitor. The cells are seeded on a Multiscreen™ plate to form a confluent monolayer over 4 days prior to the experiment. On day 4, the test compound (1-30 µM concentration) is added to the apical side of the membrane and the transport of the compound across the monolayer is monitored over a 120 minutes time period. To study drug efflux, it is also necessary to investigate transport of the compound from the basolateral compartment to the apical compartment and calculate an efflux ratio.

The permeability coefficient ($P_{app}$) is calculated from the following equation:

$$P_{app} = [(dQ/dt)/C_0 \times A]$$

where dQ/dt is the rate of permeation of the drug across the cells, $C_0$ is the donor compartment concentration at time zero and A is the area of the cell monolayer.

An efflux ratio is calculated from the mean apical to basolateral (A-B) $P_{app}$ data and basolateral to apical (B-A) $P_{app}$ data.

$$\text{Efflux Ratio} = P_{app}(B-A)/P_{app}(A-B)$$

Table B summarizes the permeability of selected compounds in a MDCK-MDR1 Assay.

TABLE B

| Cmpd No. | Papp (a to b) | Papp (b to a) | Efflux Ratio |
|---|---|---|---|
| 1 | 3.65 | 23.83 | 6.53 |
| 2 | 19.01 | 50.01 | 2.63 |
| 3 | 2.15 | 21.18 | 9.85 |
| 5 | 1.21 | 2.19 | 1.82 |
| 6 | 26.30 | 37.25 | 1.42 |
| 9 | 17.59 | 43.36 | 2.47 |
| 11 | 34.64 | 42.34 | 1.22 |
| 12 | 6.60 | 28.37 | 4.30 |
| 14 | 3.03 | 8.29 | 2.73 |
| 15 | 3.10 | 5.36 | 1.73 |
| 16 | 1.01 | 8.89 | 8.79 |

TABLE B-continued

| Cmpd No. | Papp (a to b) | Papp (b to a) | Efflux Ratio |
|---|---|---|---|
| 17 | 0.70 | 9.28 | 13.21 |
| 21 | 24.10 | 40.54 | 1.68 |
| 26 | 3.95 | 19.63 | 4.98 |
| 46 | 20.79 | 57.91 | 2.79 |

Biological Example B3

Caco-2 Permeability Assay

Caco-2 cells are widely used as an in vitro assay to measure the permeability of a drug compound. The Caco-2 cell line is derived from a human colorectal carcinoma, and when cultured, the cells spontaneously differentiate into monolayers of polarized enterocytes. Caco-2 cells express P-glycoprotein and breast cancer resistance protein, two of the most relevant cell membrane active transporters that affect drug compound's permeability into cells and blood brain barrier.

The cells are seeded on Millipore Millicell plates and form a confluent monolayer over 20 days prior to the experiment. On day 20, the test compound (1-30 μM concentration) is added to the apical side of the membrane and the transport of the compound across the monolayer is monitored over a 120 minutes time period. To study drug efflux, it is also necessary to investigate transport of the compound from the basolateral compartment to the apical compartment.

The permeability coefficient ($P_{app}$) is calculated from the following equation:

$$P_{app} = [(dQ/dt)/C_0 \times A]$$

where dQ/dt is the rate of permeation of the drug across the cells, $C_0$ is the donor compartment concentration at time zero and A is the area of the cell monolayer. $C_0$ is obtained from analysis of the dosing solution at the start experiment.

The permeability of selected compounds in the Caco-2 Assay is summarized in Table C.

TABLE C

| Cmpd No. | Papp (a to b) | Papp (b to a) | Efflux Ratio |
|---|---|---|---|
| 1 | 6.42 | 18.71 | 2.92 |
| 3 | 9.24 | 13.71 | 1.48 |
| 6 | 43.49 | 13.51 | 0.31 |
| 14 | 6.37 | 17.66 | 2.77 |
| 15 | 5.08 | 14.93 | 2.94 |
| 18 | 11.32 | 24.85 | 2.20 |
| 21 | 52.89 | 19.24 | 0.36 |

Biological Example B4

Mouse Pharmacokinetics Study

The pharmacokinetic properties of selected compounds were studied CD-1 mice via intravenous and oral administration by using a standard protocol. The test articles were formulated in 20% Hydroxypropyl-beta-cyclodextrin, either as a clear solution or fine suspension. Table D shows the pharmacokinetic characterization by intravenous injection of selected compounds in mice.

TABLE D

| Cmpd No. | IV Dose (mg/kg) | $t_{1/2}$ (h) | $Cl_p$ (ml/min · kg) | $V_d$ (L/kg) |
|---|---|---|---|---|
| 1 | 2.5 | 1.47 ± 0.19 | 2.77 ± 0.52 | 0.348 ± 0.037 |
| 6 | 2.5 | 0.467 ± 0.012 | 30.3 ± 4.64 | 1.22 ± 0.16 |
| 21 | 2.5 | 1.21 ± 0.10 | 9.03 ± 1.31 | 0.948 ± 0.166 |

Table E shows the plasma exposure by oral administration of selected compounds in mice.

TABLE E

| Cmpd No. | PO Dose (mg/kg) | $C_{max}$ (ng/mL) | $T_{max}$ (h) | AUC (ng/mL · h) | F (%) |
|---|---|---|---|---|---|
| 1 | 30 | 37267 ± 6243 | 1.00 ± 0.00 | 206509 ± 25861 | 112 ± 14 |
| 6 | 25 | 4217 ± 1351 | 0.250 ± 0.00 | 8221 ± 3003 | 58.9 ± 21.5 |
| 21 | 25 | 11720 ± 2378 | 0.500 ± 0.000 | 53845 ± 5207 | 113 ± 11.1 |

Biological Example B5

In Vivo Pharmacodynamic Study

The activity of the compounds of formula (I), in vivo, can be determined by the amount of inhibition of tumor growth by a test compound relative to a control. The tumor growth inhibitory effects of various compounds are measured according to the method of Corbett T. H., et al., "Tumor Induction Relationships in Development of Transplantable Cancers of the Colon in Mice for Chemotherapy Assays, with a Note on Carcinogen Structure", Cancer Res., 35, 2434-2439 (1975) and Corbett T. H., et al., "A Mouse Colon-tumor Model for Experimental Therapy", Cancer Chemother. Rep. (Part 2)", 5, 169-186 (1975), with slight modifications. Tumors are induced in the left flank by subcutaneous injection of 1-5 million log phase cultured tumor cells (human A375 melanoma or HT-29 colorectal cancer cells) suspended in 0.1 ml RPMI 1640 medium. After sufficient time has elapsed for the tumors to become palpable (100-150 mm$^3$ in size/5-6 mm in diameter) the test animals (BALB/c nude female mice) are treated with test compound (formulated at a concentration of 10 to 15 mg/ml in 20% hydroxypropyl-beta-cyclodextrine) by oral route of administration once or twice daily. In order to determine an anti-tumor effect, the tumor is measured in millimeters with a Vernier caliper across two diameters and the tumor size (mm3) is calculated using the formula: Tumor size (mm$^3$)= (length×width$^2$)/2, according to the methods of Geran, R. I., et al. "Protocols for Screening Chemical Agents and Natural Products Against Animal Tumors and Other Biological Systems", Third Edition, Cancer Chemother. Rep., 3, 1-104 (1972). Results are expressed as percent inhibition, according to the formula: Inhibition (%)=(TuW$_{control}$−TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXEMPLARY EMBODIMENTS

1. A cyclic iminopyrimidine derivative of the Formula Ia

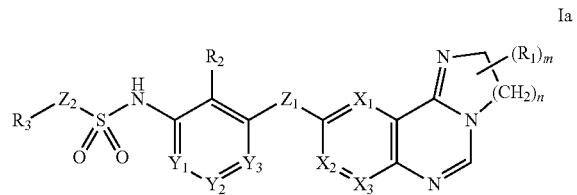

and their isotopic derivatives to pharmaceutically acceptable salts and solvates thereof, wherein:

$X_1$, $X_2$, and $X_3$ are each independently N or CR$^a$;

$Y_1$, $Y_2$, and $Y_3$ are each independently N or CR$^b$;

$Z_1$ is O, S, NR$^c$ or CR$^d$R$^e$;

$Z_2$ is a bond, or NR$^f$;

m=0, 1, 2 or 3;

n=1, 2 or 3;

$R_1$ is hydrogen, $C_1$-$C_6$ alkyl, which is optionally substituted with halogen, OH, $C_1$-$C_6$ alkoxy, or $C_1$-$C_6$ dialkylamino;

$R_2$ is hydrogen, cyano, nitro, halogen, CF$_3$, MeSO$_2$, $C_1$-$C_6$ alkyl, $C_1$-$C_6$ alkoxy, or $C_1$-$C_6$ dialkylamino;

$R_3$ is $C_1$-$C_6$ alkyl, or aryl or heteroaryl, each optionally substituted with 1-3 halogen or $C_1$-$C_6$ alkyl R$^a$ and R$^b$ are independently selected from the group consisting of hydrogen, halogen, cyano, nitro, $C_1$-$C_6$ alkyl, $C_1$-$C_6$ alkoxyl, and $C_1$-$C_6$ dialkylamino; R$^c$ is hydrogen, or $C_1$-$C_6$ alkyl;

each R$^d$, R$^e$ and R$^f$ is independently selected from hydrogen and $C_1$-$C_6$ alkyl.

2. A cyclic iminopyrimidine derivative of the formula Ia as described in embodiment 1, selected from a structure below

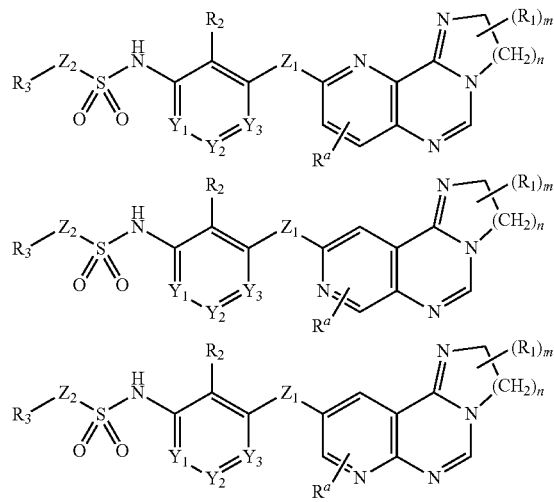

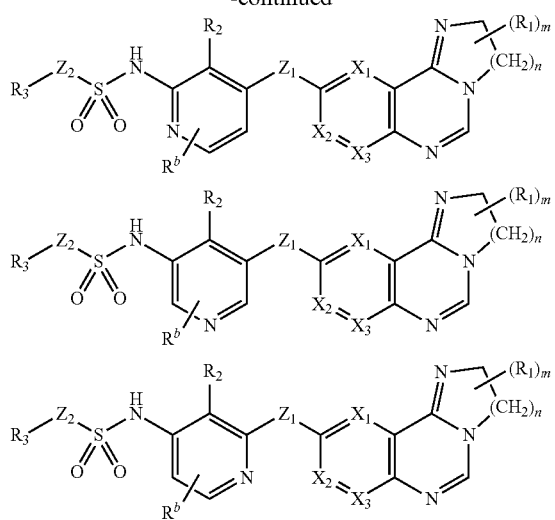

3. A cyclic iminopyrimidine derivative of the formula Ia as described in embodiment 1, selected from a structure below

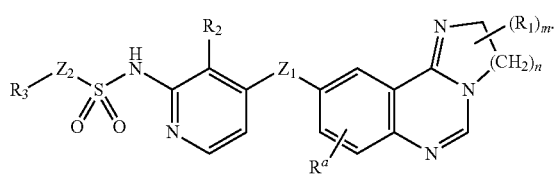

4. A cyclic iminopyrimidine derivative of the formula Ia as described in embodiment 1, selected from a structure below

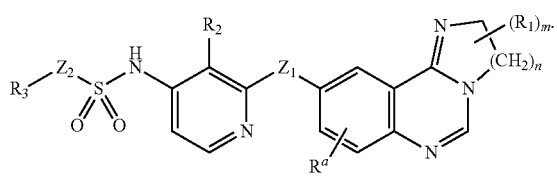

5. A cyclic iminopyrimidine derivative of the formula Ia as described in embodiment 1, selected from a structure below

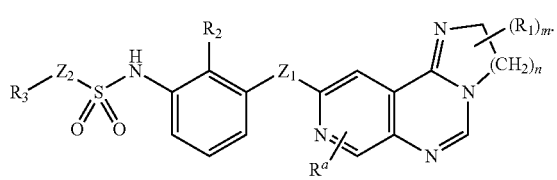

6. A cyclic iminopyrimidine derivative of the formula Ia as described in embodiment 1, selected from a structure below

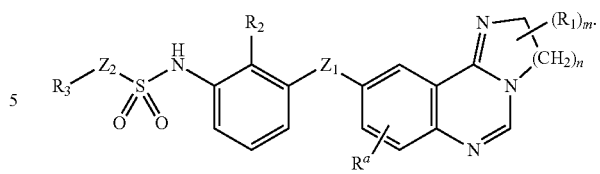

7. Other specific embodiments of the compounds of formula Ia include those wherein $Z_1$ is O.

8. Other specific embodiments of the compounds of formula Ia include those wherein $Z_2$ is a bond.

9. Other specific embodiments of the compounds of formula Ia include those wherein m=0.

10. Other specific embodiments of the compounds of formula Ia include those wherein n=1.

11. Other specific embodiments of the compounds of formula Ia include those wherein n=2.

12. Other specific embodiments of the compounds of formula Ia include those wherein $R_1$=H.

13. Other specific embodiments of the compounds of formula Ia include those wherein $R_2$ is CN.

14. Other specific embodiments of the compounds of formula Ia include those wherein $R_2$ is Cl.

15. Other specific embodiments of the compounds of formula Ia include those wherein $R_3$ is 2-FPh.

16. Other specific embodiments of the compounds of formula Ia include those wherein $R_3$ is propyl.

17. Other specific embodiments of the compounds of formula Ia include those wherein $R_3$ is thiophenyl.

18. Other specific embodiments of the compounds of formula Ia include those wherein $R^a$ is H. Other specific embodiments of the compounds of formula Ia include those wherein $R^b$ is H.

19. Other specific embodiments of the compounds of formula Ia include those wherein $R^a$ is F. Other specific embodiments of the compounds of formula Ia include those wherein $R^b$ is F.

20. A method for producing in mammals an inhibitory effect against the B-Raf V600E kinase enzymes which comprises administering to said animal an effective amount of a cyclic iminopyrimidine derivative of the formula Ia, or a pharmaceutically acceptable salt thereof, as described in any one of embodiments 1 to 19.

21. A pharmaceutical composition which comprises a cyclic iminopyrimidine derivative of the formula Ia, or a pharmaceutically-acceptable salt thereof, as described in any one of embodiments 1 to 19 in association with a pharmaceutically-acceptable diluent or carrier.

22. A method for producing an anti-cancer effect mammals in need of such treatment which comprises administering to said mammal an effective amount of a cyclic iminopyrimidine derivative of the formula Ia, or a pharmaceutically-acceptable salt thereof, as described in any one of embodiments 1 to 19.

23. A method for producing an anti-neurodegenerative effect mammals in need of such treatment which comprises administering to said mammal an effective amount of a cyclic iminopyrimidine derivative of the formula Ia, or a pharmaceutically-acceptable salt thereof, as described in any one of embodiments 1 to 19.

24. A method for producing an anti-proliferative effect in mammals having a cancer which is sensitive to inhibition of the B-Raf V600E kinase enzymes which comprises administering to said animal an effective amount of a cyclic

The invention claimed is:

1. A compound of Formula (I):

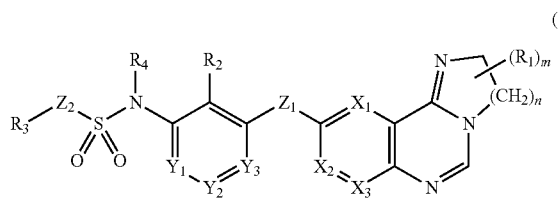

(I)

or a pharmaceutically acceptable salt or isotopic derivative thereof, wherein:
$X_1$, $X_2$, and $X_3$ are each independently N or $CR^a$;
$Y_1$, $Y_2$, and $Y_3$ are each independently N or $CR^b$;
$Z_1$ is O, S, $NR^c$ or $CR^dR^e$;
$Z_2$ is a bond or $NR^f$;
m is 0, 1, 2 or 3;
n is 1, 2 or 3;
$R_1$, $R_2$, $R_3$, $R^a$, $R^b$, $R^d$, and $R^e$ are each independently selected from the group consisting of hydrogen, halogen, —CN, —NO$_2$, substituted or unsubstituted $C_1$-$C_6$ alkyl, substituted or unsubstituted $C_2$-$C_6$ alkenyl, substituted or unsubstituted $C_2$-$C_6$ alkynyl, —OR$^g$, —SR$^g$, —S(O)$_2$R$^g$, —NR$^h$R$^i$, —C(O)R$^g$, —OC(O)R$^g$, —C(O)OR$^g$, —C(O)NR$^h$R$^i$, —OC(O)NR$^h$R$^i$, —NR$^g$C(O)R$^h$, —NR$^g$C(O)OR$^h$, substituted or unsubstituted cycloalkyl, substituted or unsubstituted cycloalkenyl, substituted or unsubstituted aryl, substituted or unsubstituted heteroaryl, and substituted or unsubstituted heterocycloalkyl;
$R_4$ is hydrogen or $C_1$-$C_6$ alkyl; and
$R^e$, $R^f$, $R^g$, $R^h$, and $R^i$ are each independently H, $C_1$-$C_6$ alkyl, or $C_1$-$C_6$ haloalkyl.

2. The compound of claim 1, wherein the compound is of Formula (I-2a), (I-2b), or (I-2c):

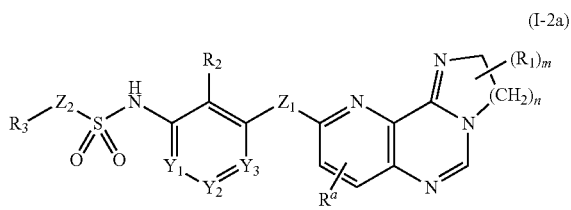

(I-2a)

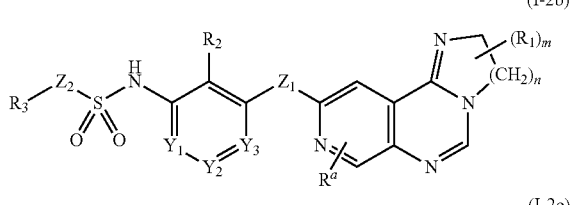

(I-2b)

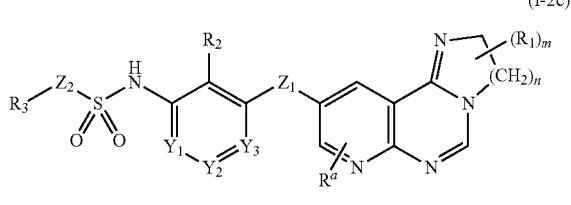

(I-2c)

or a pharmaceutically acceptable salt or isotopic derivative thereof, wherein $Y_1$, $Y_2$, $Y_3$, $Z_1$, $Z_2$, $R_1$, $R_2$, $R_3$, m, n, and $R^a$ are as defined for Formula (I).

3. The compound of claim 1, wherein the compound is of Formula (I-2d), (I-2e), or (I-2f):

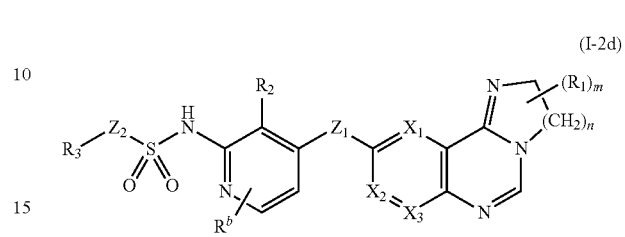

(I-2d)

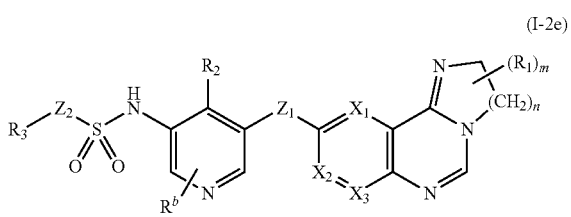

(I-2e)

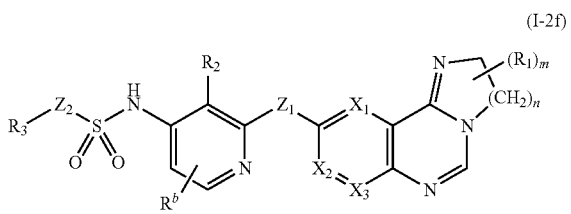

(I-2f)

or a pharmaceutically acceptable salt, solvate or isotopic derivative thereof, wherein $X_1$, $X_2$, $X_3$, $Z_1$, $Z_2$, $R_1$, $R_2$, $R_3$, m, n, and $R^b$ are as defined for Formula (I).

4. The compound of claim 1, wherein the compound is of Formula (I-3a) or (I-3b):

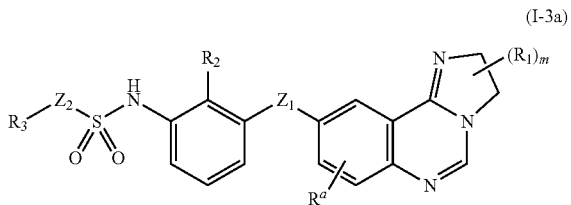

(I-3a)

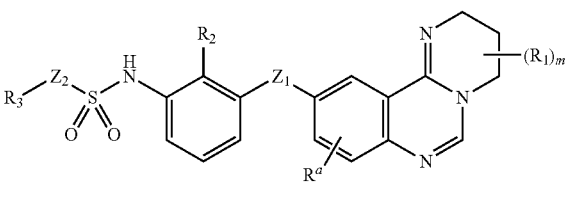

(I-3b)

or a pharmaceutically acceptable salt or isotopic derivative thereof, wherein $Z_1$, $Z_2$, $R_1$, $R_2$, $R_3$, m, and $R^a$ are as defined for Formula (I).

5. The compound of claim 1, wherein the compound is of Formula (I-4a), (I-4b), or (I-4c):

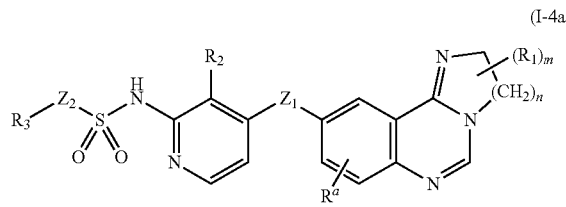
(I-4a)

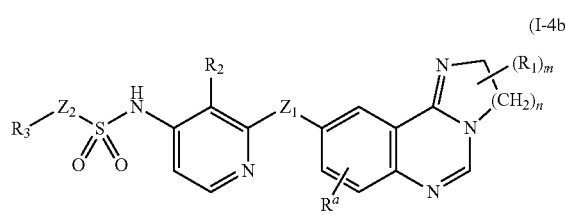
(I-4b)

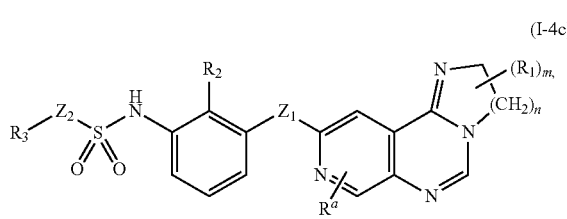
(I-4c)

or a pharmaceutically acceptable salt or isotopic derivative thereof, wherein $Z_1$, $Z_2$, $R_1$, $R_2$, $R_3$, m, n, and $R^a$ are as defined for Formula (I).

6. The compound of claim 1, wherein the compound is of Formula (I-5a) or (I-5b):

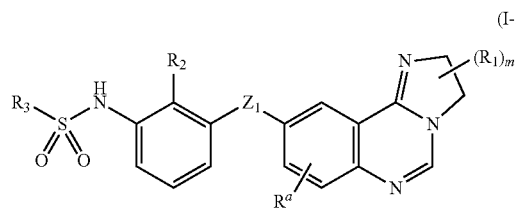
(I-5a)

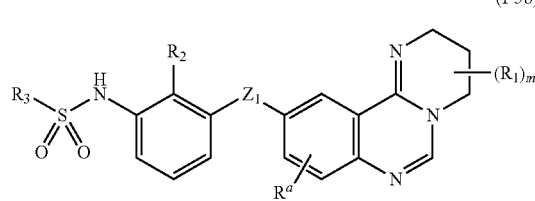
(I-5b)

or a pharmaceutically acceptable salt or isotopic derivative thereof, wherein $Z_1$, $R_1$, $R_2$, $R_3$, m, and $R^a$ are as defined for Formula (I).

7. The compound of claim 1, or a pharmaceutically acceptable salt or isotopic derivative thereof, wherein $Z_1$ is O.

8. The compound of claim 1, or a pharmaceutically acceptable salt or isotopic derivative thereof, wherein $Z_2$ is a bond.

9. The compound of claim 1, or a pharmaceutically acceptable salt or isotopic derivative thereof, wherein n is 1 or 2.

10. The compound of claim 1, or a pharmaceutically acceptable salt or isotopic derivative thereof, wherein m is 0, 1, or 2.

11. The compound of claim 1, or a pharmaceutically acceptable salt or isotopic derivative thereof, wherein each $R_1$ is independently hydrogen, —OH, —$C_1$-$C_6$ alkyl, $C_1$-$C_6$ alkoxy, or $C_1$-$C_6$ dialkylamino, wherein the $C_1$-$C_6$ alkyl is optionally substituted with halogen.

12. The compound of claim 1, or a pharmaceutically acceptable salt or isotopic derivative thereof, wherein each $R_1$ is independently $C_1$-$C_6$ alkyl substituted with halogen, —CN, —$NO_2$, —OH, oxo, and —$NR^{1a}R^{1b}$, wherein $R^{1a}$ and $R^{1b}$ are each independently H or $C_1$-$C_6$ alkyl.

13. The compound of claim 1, or a pharmaceutically acceptable salt or isotopic derivative thereof, wherein $R_2$ is hydrogen, cyano, nitro, halogen, $MeSO_2$, $C_1$-$C_6$ alkyl, $C_1$-$C_6$ alkoxy, or —$NR^hR^i$, wherein the $C_1$-$C_6$ alkyl is optionally substituted with one or more halogen, and $R^h$ and $R^i$ are each independently $C_1$-$C_6$ alkyl.

14. The compound of claim 13, or a pharmaceutically acceptable salt or isotopic derivative thereof, wherein $R_2$ is —CN, Cl, or —$CF_3$.

15. The compound of claim 1, or a pharmaceutically acceptable salt or isotopic derivative thereof, wherein $R_3$ is $C_1$-$C_6$ alkyl, aryl, or heteroaryl, wherein the aryl or heteroaryl is optionally substituted with one or more groups selected from halogen and $C_1$-$C_6$ alkyl.

16. The compound of claim 15, or a pharmaceutically acceptable salt or isotopic derivative thereof, wherein $R_3$ is 2-fluorophenyl, pyrrolidinyl, 3-fluoropyrrolidinyl, propyl, or thiophenyl.

17. The compound of claim 1, or a pharmaceutically acceptable salt or isotopic derivative thereof, wherein $R_3$ is $C_1$-$C_6$ alkyl substituted with one or more groups selected from halogen, —CN, —$NO_2$, —OH, oxo, and —$NR^{3a}R^{3b}$, wherein $R^{3a}$ and $R^{3b}$ are each independently H or $C_1$-$C_6$ alkyl.

18. The compound of claim 17, or a pharmaceutically acceptable salt or isotopic derivative thereof, wherein $R_3$ is 3-fluoropropyl or 3-hydroxypropyl.

19. The compound of claim 1, or a pharmaceutically acceptable salt or isotopic derivative thereof, wherein $R_3$ is —$NR^hR^i$, and $R^h$ and $R^i$ are each independently H or $C_1$-$C_6$ alkyl, or $C_1$-$C_6$ haloalkyl.

20. The compound of claim 19, or a pharmaceutically acceptable salt or isotopic derivative thereof, wherein $R_3$ is —$N(CH_3)CH_2CH_3$, —$N(CH_3)CH_2CH_2F$, or —$N(CH_3)CH_3$.

21. The compound of claim 1, or a pharmaceutically acceptable salt or isotopic derivative thereof, wherein each $R^a$ and each $R^b$ are independently H or F.

22. A compound selected from a compound of Table 1:

| Compound No. | Structure | Chemical Name |
|---|---|---|
| 1 | 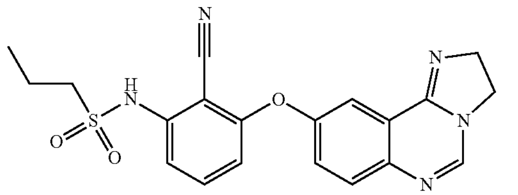 [SMILES: CCCS(=O)(=O)Nc1cccc(Oc2ccc3c(c2)C2=NCCN2C=N3)c1C#N] | N-(2-Cyano-3-((2,3-dihydroimidazo[1,2-c]quinazolin-9-yl)oxy)phenyl)propane-1-sulfonamide |
| 2 | 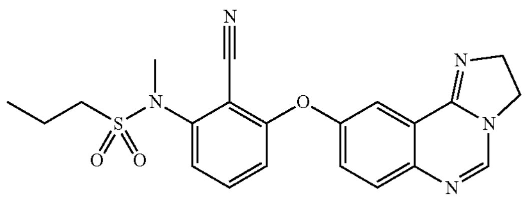 [SMILES: CCCS(=O)(=O)N(C)c1cccc(Oc2ccc3c(c2)C2=NCCN2C=N3)c1C#N] | N-(2-Cyano-3-((2,3-dihydroimidazo[1,2-c]quinazolin-9-yl)oxy)phenyl)-N-methylpropane-1-sulfonamide |
| 3 | 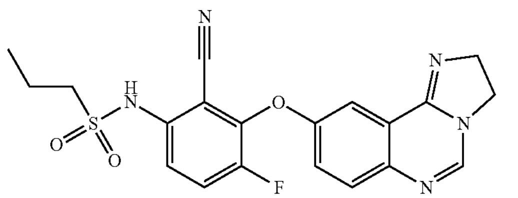 [SMILES: CCCS(=O)(=O)Nc1ccc(F)c(Oc2ccc3c(c2)C2=NCCN2C=N3)c1C#N] | N-(2-Cyano-3-((2,3-dihydroimidazo[1,2-c]quinazolin-9-yl)oxy)-4-fluorophenyl)propane-1-sulfonamide |
| 4 | 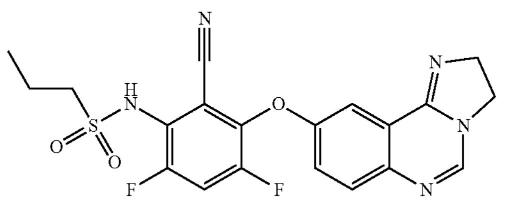 [SMILES: CCCS(=O)(=O)Nc1c(F)cc(F)c(Oc2ccc3c(c2)C2=NCCN2C=N3)c1C#N] | N-(2-Cyano-3-((2,3-dihydroimidazo[1,2-c]quinazolin-9-yl)oxy)-4,6-difluorophenyl)propane-1-sulfonamide |
| 5 | 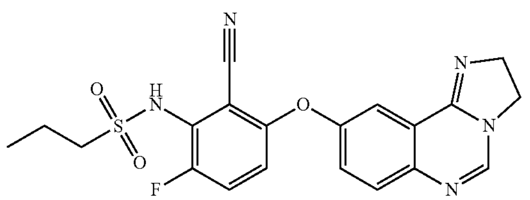 [SMILES: CCCS(=O)(=O)Nc1c(F)ccc(Oc2ccc3c(c2)C2=NCCN2C=N3)c1C#N] | N-(2-Cyano-3-((2,3-dihydroimidazo[1,2-c]quinazolin-9-yl)oxy)-6-fluorophenyl)propane-1-sulfonamide |
| 6 | 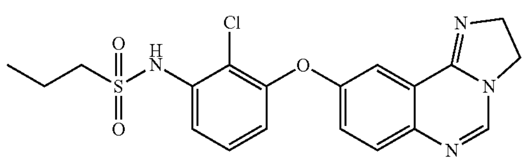 | N-(2-Chloro-3-((2,3-dihydroimidazo[1,2-c]quinazolin-9-yl)oxy)phenyl)propane-1-sulfonamide |
| 7 | 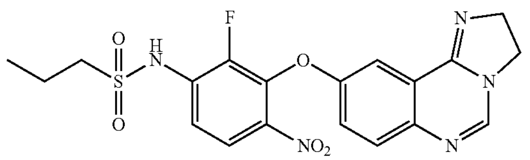 [SMILES: CCCS(=O)(=O)Nc1ccc([N+](=O)[O-])c(Oc2ccc3c(c2)C2=NCCN2C=N3)c1F] | N-(3-((2,3-Dihydroimidazo[1,2-c]quinazolin-9-yl)oxy)-2-fluoro-4-nitrophenyl)propane-1-sulfonamide |
| 8 | 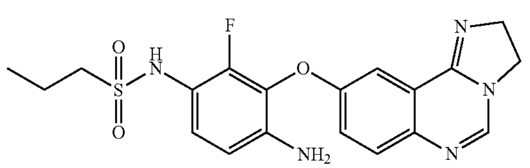 | N-(4-Amino-3-((2,3-dihydroimidazo[1,2-c]quinazolin-9-yl)oxy)-2-fluorophenyl)propane-1-sulfonamide |

-continued

| Compound No. | Structure | Chemical Name |
|---|---|---|
| 9 | 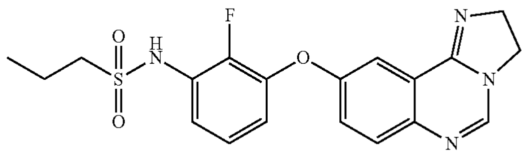 [SMILES: CCCS(=O)(=O)Nc1cccc(Oc2ccc3c(c2)C2=NCCN2C=N3)c1F] | N-(3-((2,3-Dihydroimidazo[1,2-c]quinazolin-9-yl)oxy)-2-fluorophenyl)propane-1-sulfonamide |
| 10 | 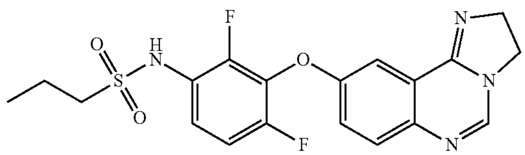 [SMILES: CCCS(=O)(=O)Nc1ccc(F)c(Oc2ccc3c(c2)C2=NCCN2C=N3)c1F] | N-(3-((2,3-Dihydroimidazo[1,2-c]quinazolin-9-yl)oxy)-2,4-difluorophenyl)propane-1-sulfonamide |
| 11 | 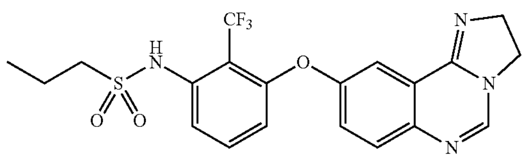 [SMILES: CCCS(=O)(=O)Nc1cccc(Oc2ccc3c(c2)C2=NCCN2C=N3)c1C(F)(F)F] | N-(3-((2,3-Dihydroimidazo[1,2-c]quinazolin-9-yl)oxy)-2-(trifluoromethyl)phenyl)propane-1-sulfonamide |
| 12 | 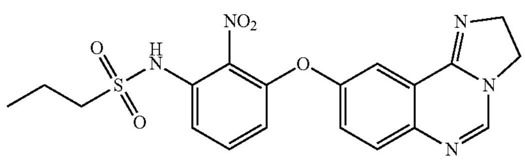 [SMILES: CCCS(=O)(=O)Nc1cccc(Oc2ccc3c(c2)C2=NCCN2C=N3)c1[N+](=O)[O-]] | N-(3-((2,3-Dihydroimidazo[1,2-c]quinazolin-9-yl)oxy)-2-nitrophenyl)propane-1-sulfonamide |
| 13 | 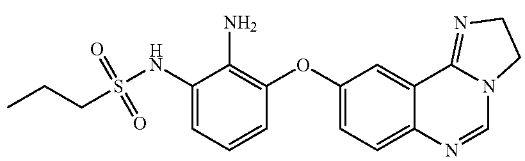 | N-(2-Amino-3-((2,3-dihydroimidazo[1,2-c]quinazolin-9-yl)oxy)phenyl)propane-1-sulfonamide |
| 14 | 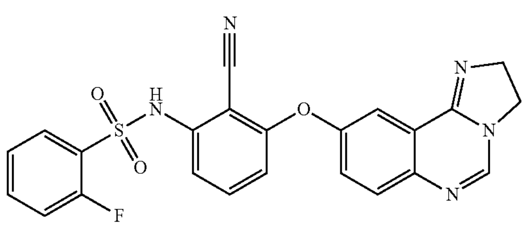 [SMILES: N#Cc1c(NS(=O)(=O)c2ccccc2F)cccc1Oc1ccc2c(c1)C1=NCCN1C=N2] | N-(2-Cyano-3-((2,3-dihydroimidazo[1,2-c]quinazolin-9-yl)oxy)phenyl)-2-fluorobenzenesulfonamide |
| 15 | 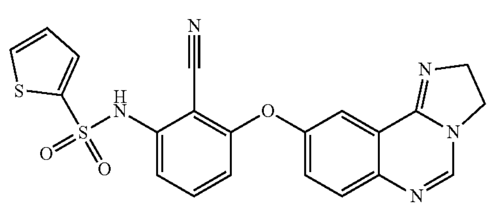 [SMILES: N#Cc1c(NS(=O)(=O)c2cccs2)cccc1Oc1ccc2c(c1)C1=NCCN1C=N2] | N-(2-Cyano-3-((2,3-dihydroimidazo[1,2-c]quinazolin-9-yl)oxy)phenyl)thiophene-2-sulfonamide |
| 16 | 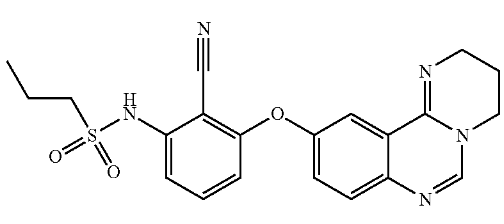 [SMILES: CCCS(=O)(=O)Nc1cccc(Oc2ccc3c(c2)C2=NCCCN2C=N3)c1C#N] | N-(2-cyano-3-((3,4-dihydro-2H-pyrimido[1,2-c]quinazolin-10-yl)oxy)phenyl)propane-1-sulfonamide |

-continued

| Compound No. | Structure | Chemical Name |
|---|---|---|
| 17 | 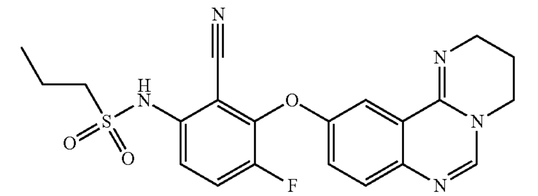 [SMILES: CCCS(=O)(=O)Nc1ccc(F)c(Oc2ccc3c(c2)C2=NCCCN2C=N3)c1C#N] | N-(2-cyano-3-((3,4-dihydro-2H-pyrimido[1,2-c]quinazolin-10-yl)oxy)-4-fluorophenyl)propane-1-sulfonamide |
| 18 | 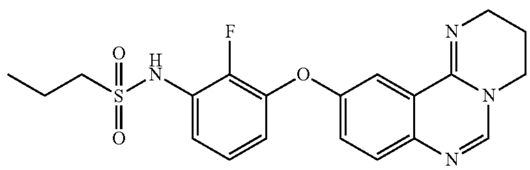 [SMILES: CCCS(=O)(=O)Nc1cccc(Oc2ccc3c(c2)C2=NCCCN2C=N3)c1F] | N-(3-((3,4-Dihydro-2H-pyrimido[1,2-c]quinazolin-10-yl)oxy)-2-fluorophenyl)propane-1-sulfonamide |
| 19 | 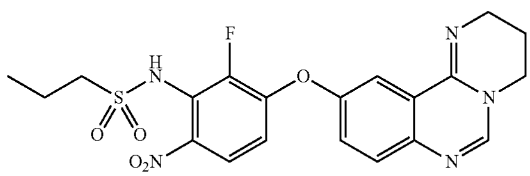 | N-(3-((3,4-Dihydro-2H-pyrimido[1,2-c]quinazolin-10-yl)oxy)-2-fluoro-6-nitrophenyl)propane-1-sulfonamide |
| 20 | 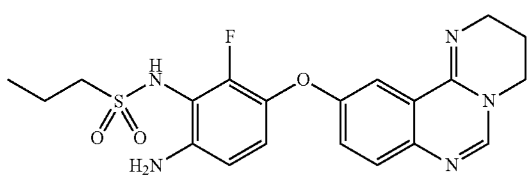 [SMILES: CCCS(=O)(=O)Nc1c([N+](=O)[O-])ccc(Oc2ccc3c(c2)C2=NCCCN2C=N3)c1F] | N-(6-Amino-3-((3,4-dihydro-2H-pyrimido[1,2-c]quinazolin-10-yl)oxy)-2-fluorophenyl)propane-1-sulfonamide |
| 21 | 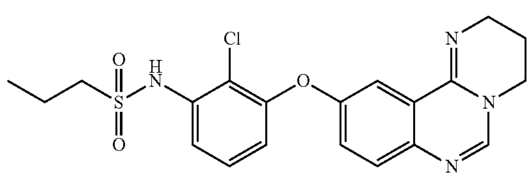 [SMILES: CCCS(=O)(=O)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)propane-1-sulfonamide |
| 22 | 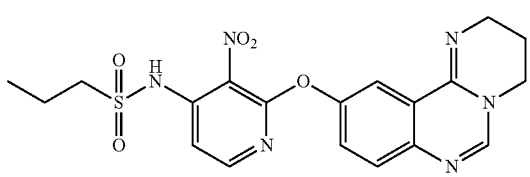 [SMILES: CCCS(=O)(=O)Nc1ccnc(Oc2ccc3c(c2)C2=NCCCN2C=N3)c1[N+](=O)[O-]] | N-(2-((3,4-Dihydro-2H-pyrimido[1,2-c]quinazolin-10-yl)oxy)-3-nitropyridin-4-yl)propane-1-sulfonamide |
| 23 | 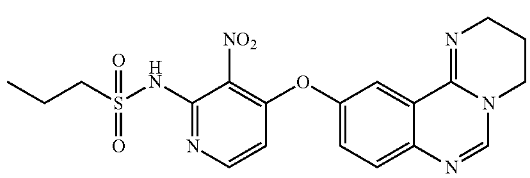 [SMILES: CCCS(=O)(=O)Nc1nccc(Oc2ccc3c(c2)C2=NCCCN2C=N3)c1[N+](=O)[O-]] | N-(4-((3,4-Dihydro-2H-pyrimido[1,2-c]quinazolin-10-yl)oxy)-3-nitropyridin-2-yl)propane-1-sulfonamide |
| 24 | 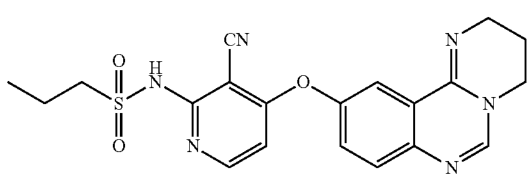 [SMILES: CCCS(=O)(=O)Nc1nccc(Oc2ccc3c(c2)C2=NCCCN2C=N3)c1C#N] | N-(3-Cyano-4-((3,4-dihydro-2H-pyrimido[1,2-c]quinazolin-10-yl)oxy)pyridin-2-yl)propane-1-sulfonamide |

| Compound No. | Structure | Chemical Name |
|---|---|---|
| 25 | 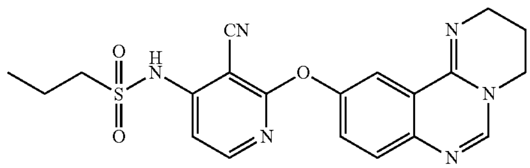 [SMILES: CCCS(=O)(=O)Nc1ccnc(Oc2ccc3c(c2)C2=NCCCN2C=N3)c1C#N] | N-(3-Cyano-2-((3,4-dihydro-2H-pyrimido[1,2-c]quinazolin-10-yl)oxy)pyridin-4-yl)propane-1-sulfonamide |
| 26 | 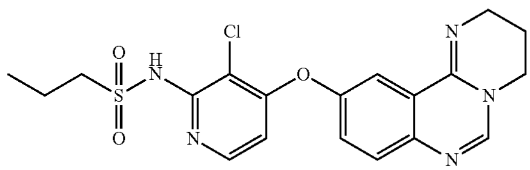 [SMILES: CCCS(=O)(=O)Nc1nccc(Oc2ccc3c(c2)C2=NCCCN2C=N3)c1Cl] | N-(3-Chloro-4-((3,4-dihydro-2H-pyrimido[1,2-c]quinazolin-10-yl)oxy)pyridin-2-yl)propane-1-sulfonamide |
| 27 | 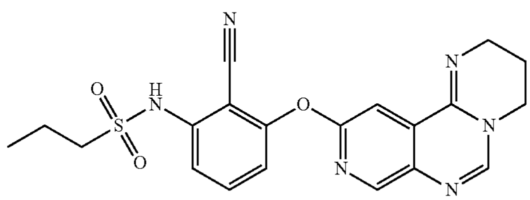 [SMILES: CCCS(=O)(=O)Nc1cccc(Oc2cc3c(cn2)N=CN2CCCN=C32)c1C#N] | N-(2-Cyano-3-((3,4-dihydro-2H-pyrido[4,3-e]pyrimido[1,2-c]pyrimidin-10-yl)oxy)phenyl)propane-1-sulfonamide |
| 28 | 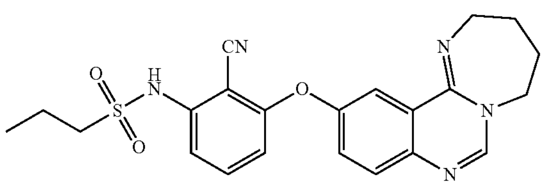 [SMILES: CCCS(=O)(=O)Nc1cccc(Oc2ccc3c(c2)C2=NCCCCN2C=N3)c1C#N] | N-(2-Cyano-3-((2,3,4,5-tetrahydro-[1,3]diazepino[1,2-c]quinazolin-11-yl)oxy)phenyl)propane-1-sulfonamide |
| 37 | 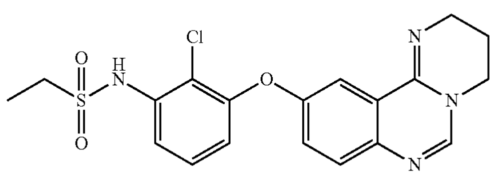 [SMILES: CCS(=O)(=O)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)ethanesulfonamide |
| 38 | 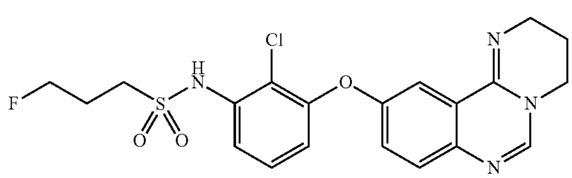 [SMILES: O=S(=O)(CCCF)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)-3-fluoropropane-1-sulfonamide |
| 39 | 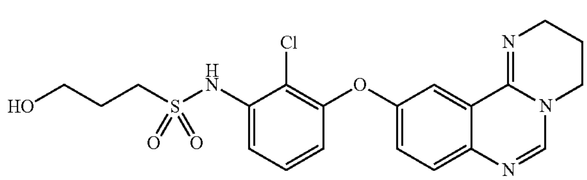 [SMILES: O=S(=O)(CCCO)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)-3-hydroxypropane-1-sulfonamide |
| 40 | 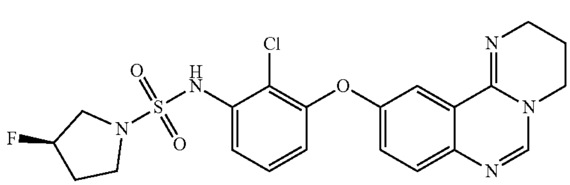 [SMILES: O=S(=O)(Nc1cccc(Oc2ccc3c(c2)C2=NCCCN2C=N3)c1Cl)N1CC[C@@H](F)C1] | (R)-N-(2-Chloro-3-((3,4-dihydro-2H-pyrimido[1,2-c]quinazolin-10-yl)oxy)phenyl)-3-fluoropyrrolidine-1-sulfonamide |

-continued

| Compound No. | Structure | Chemical Name |
|---|---|---|
| 41 | 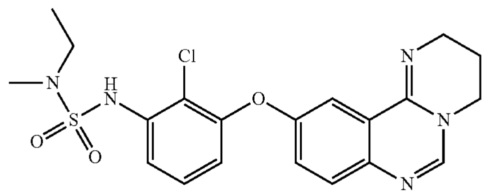 [SMILES: CCN(C)S(=O)(=O)Nc1cccc(Oc2ccc3c(c2)C2=NCCCN2C=N3)c1Cl] | N-(2-Chloro-3-((3,4-dihydro-2H-pyrimido[1,2-c]quinazolin-10-yl)oxy)phenyl)-N-ethyl-N-methylamino-1-sulfonamide |
| 42 | 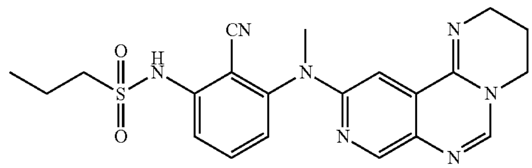 [SMILES: CCCS(=O)(=O)Nc1cccc(N(C)c2cc3c(cn2)N=CN2CCCN=C32)c1C#N] | N-(2-Cyano-3-((3,4-dihydro-2H-pyrido[4,3-c]pyrimido[1,2-c]pyrimidin-10-yl)(methyl)amino)phenyl)propane-1-sulfonamide |
| 43 | 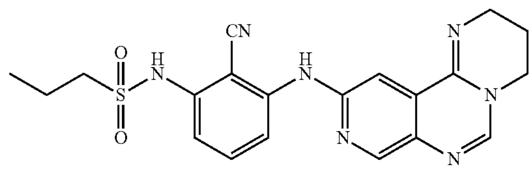 [SMILES: CCCS(=O)(=O)Nc1cccc(Nc2cc3c(cn2)N=CN2CCCN=C32)c1C#N] | N-(2-Cyano-3-((3,4-dihydro-2H-pyrido[4,3-c]pyrimido[1,2-c]pyrimidin-10-yl)amino)phenyl)propane-1-sulfonamide |
| 44 | 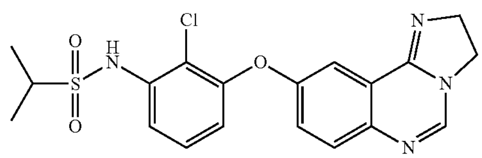 [SMILES: CC(C)S(=O)(=O)Nc1cccc(Oc2ccc3c(c2)C2=NCCN2C=N3)c1Cl] | N-(2-Chloro-3-((2,3-dihydroimidazo[1,2-c]quinazolin-9-yl)oxy)phenyl)propane-2-sulfonamide |
| 45 | 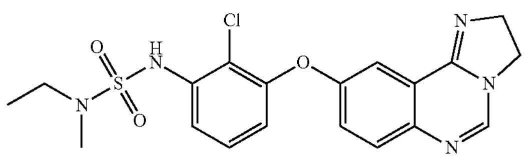 [SMILES: CCN(C)S(=O)(=O)Nc1cccc(Oc2ccc3c(c2)C2=NCCN2C=N3)c1Cl] | N-(2-Chloro-3-((2,3-dihydroimidazo[1,2-c]quinazolin-9-yl)oxy)phenyl)-N-ethyl-N-methylamino-1-sulfonamide |
| 46 | 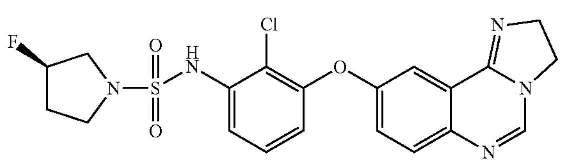 [SMILES: O=S(=O)(Nc1cccc(Oc2ccc3c(c2)C2=NCCN2C=N3)c1Cl)N1CC[C@@H](F)C1] | (R)-N-(2-Chloro-3-((2,3-dihydroimidazo[1,2-c]quinazolin-9-yl)oxy)phenyl)-3-fluoropyrrolidine-1-sulfonamide |
| 47 | 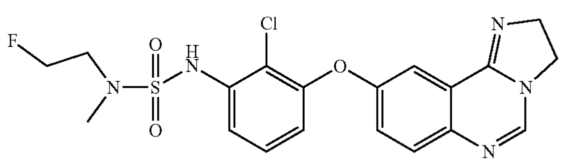 [SMILES: CN(CCF)S(=O)(=O)Nc1cccc(Oc2ccc3c(c2)C2=NCCN2C=N3)c1Cl] | N-(2-Chloro-3-((2,3-dihydroimidazo[1,2-c]quinazolin-9-yl)oxy)phenyl)-(2-fluoroethyl)(methyl)amino-1-sulfonamide |
| 48 | 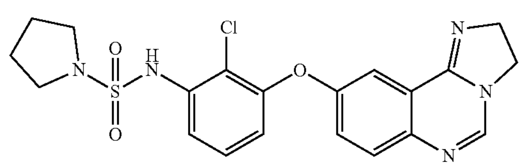 [SMILES: O=S(=O)(Nc1cccc(Oc2ccc3c(c2)C2=NCCN2C=N3)c1Cl)N1CCCC1] | N-(2-Chloro-3-((2,3-dihydroimidazo[1,2-c]quinazolin-9-yl)oxy)phenyl)pyrrolidine-1-sulfonamide |
| 49 | 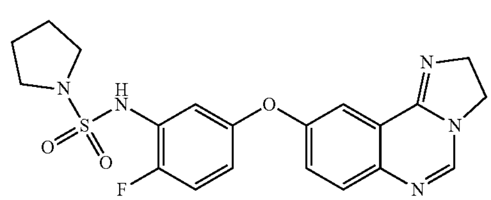 [SMILES: O=S(=O)(Nc1cc(Oc2ccc3c(c2)C2=NCCN2C=N3)ccc1F)N1CCCC1] | N-(5-((2,3-Dihydroimidazo[1,2-c]quinazolin-9-yl)oxy)-2-fluorophenyl)pyrrolidine-1-sulfonamide |

| Compound No. | Structure | Chemical Name |
|---|---|---|
| 50 | 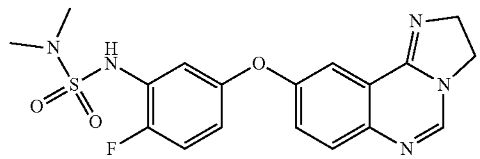 [SMILES: CN(C)S(=O)(=O)Nc1cc(Oc2ccc3c(c2)C2=NCCN2C=N3)ccc1F] | N-(5-((2,3-Dihydroimidazo[1,2-c]quinazolin-9-yl)oxy)-2-fluorophenyl)-N,N-dimethylamino-1-sulfonamide |
| 51 | 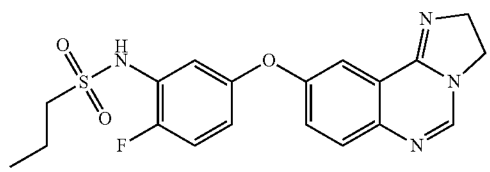 [SMILES: CCCS(=O)(=O)Nc1cc(Oc2ccc3c(c2)C2=NCCN2C=N3)ccc1F] | N-(5-((2,3-Dihydroimidazo[1,2-c]quinazolin-9-yl)oxy)-2-fluorophenyl)propane-1-sulfonamide |
| 52 | 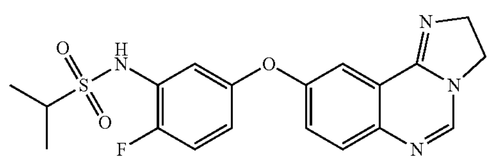 [SMILES: CC(C)S(=O)(=O)Nc1cc(Oc2ccc3c(c2)C2=NCCN2C=N3)ccc1F] | N-(5-((2,3-Dihydroimidazo[1,2-c]quinazolin-9-yl)oxy)-2-fluorophenyl)propane-2-sulfonamide |
| 53 | 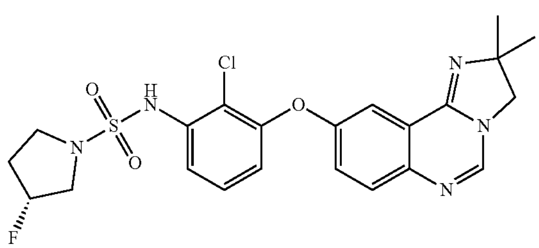 [SMILES: CC1(C)CN2C=Nc3ccc(Oc4cccc(NS(=O)(=O)N5CC[C@@H](F)C5)c4Cl)cc3C2=N1] | (R)-N-(2-Chloro-3-((2,2-dimethyl-2,3-dihydroimidazo[1,2-c]quinazolin-9-yl)oxy)phenyl)-3-fluoropyrrolidine-1-sulfonamide |
| 54 | 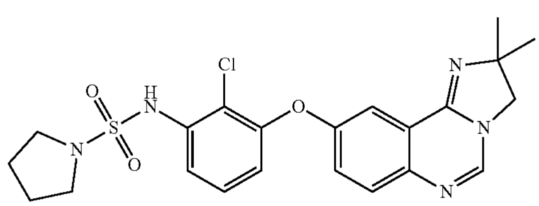 [SMILES: CC1(C)CN2C=Nc3ccc(Oc4cccc(NS(=O)(=O)N5CCCC5)c4Cl)cc3C2=N1] | N-(2-Chloro-3-((2,2-dimethyl-2,3-dihydroimidazo[1,2-c]quinazolin-9-yl)oxy)phenyl)pyrrolidine-1-sulfonamide |
| 55 | 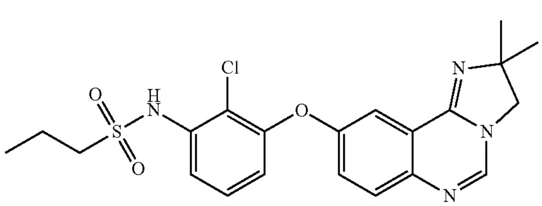 [SMILES: CCCS(=O)(=O)Nc1cccc(Oc2ccc3c(c2)C2=NC(C)(C)CN2C=N3)c1Cl] | N-(2-Chloro-3-((2,2-dimethyl-2,3-dihydroimidazo[1,2-c]quinazolin-9-yl)oxy)phenyl)propane-1-sulfonamide |

-continued

| Compound No. | Structure | Chemical Name |
|---|---|---|
| 56 | | N-(2-Chloro-3-((3-((dimethylamino)methyl)-2,3-dihydroimidazo[1,2-c]quinazolin-9-yl)oxy)phenyl)propane-1-sulfonamide | or a pharmaceutically acceptable salt or isotopic derivative thereof.

23. A compound selected from a compound of Table 2:

| Compound No. | Structure | Chemical Name |
|---|---|---|
| 1 | 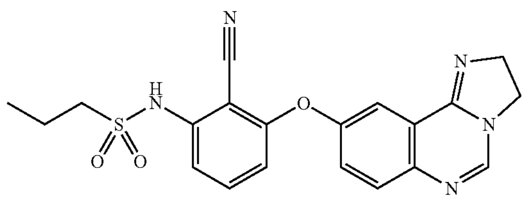 [SMILES: CCCS(=O)(=O)Nc1cccc(Oc2ccc3c(c2)C2=NCCN2C=N3)c1C#N] | N-(2-Cyano-3-((2,3-dihydroimidazo[1,2-c]quinazolin-9-yl)oxy)phenyl)propane-1-sulfonamide |
| 16 | 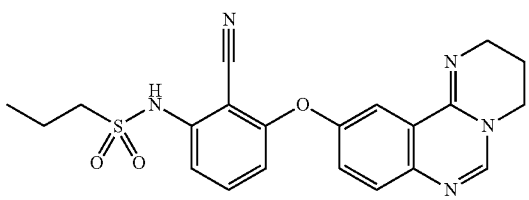 [SMILES: CCCS(=O)(=O)Nc1cccc(Oc2ccc3c(c2)C2=NCCCN2C=N3)c1C#N] | N-(2-cyano-3-((3,4-dihydro-2H-pyrimido[1,2-c]quinazolin-10-yl)oxy)phenyl)propane-1-sulfonamide |
| 12 | 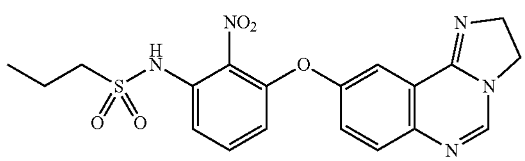 [SMILES: CCCS(=O)(=O)Nc1cccc(Oc2ccc3c(c2)C2=NCCN2C=N3)c1[N+](=O)[O-]] | N-(3-((2,3-Dihydroimidazo[1,2-c]quinazolin-9-yl)oxy)-2-nitrophenyl)propane-1-sulfonamide |
| 29 | 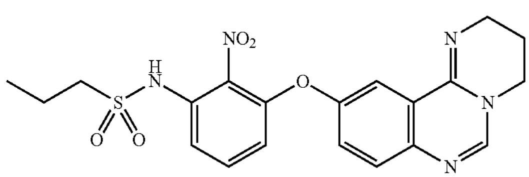 [SMILES: CCCS(=O)(=O)Nc1cccc(Oc2ccc3c(c2)C2=NCCCN2C=N3)c1[N+](=O)[O-]] | N-(3-((3,4-dihydro-2H-pyrimido[1,2-c]quinazolin-10-yl)oxy)-2-nitrophenyl)propane-1-sulfonamide |
| 9 | 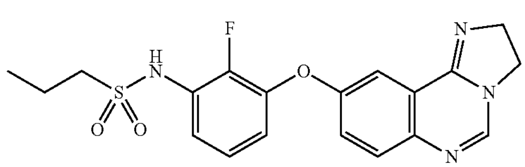 [SMILES: CCCS(=O)(=O)Nc1cccc(Oc2ccc3c(c2)C2=NCCN2C=N3)c1F] | N-(3-((2,3-Dihydroimidazo[1,2-c]quinazolin-9-yl)oxy)-2-fluorophenyl)propane-1-sulfonamide |
| 18 | 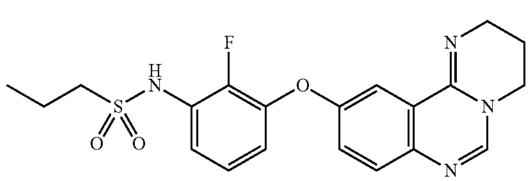 [SMILES: CCCS(=O)(=O)Nc1cccc(Oc2ccc3c(c2)C2=NCCCN2C=N3)c1F] | N-(3-((3,4-Dihydro-2H-pyrimido[1,2-c]quinazolin-10-yl)oxy)-2-fluorophenyl)propane-1-sulfonamide |

-continued

| Compound No. | Structure | Chemical Name |
|---|---|---|
| 6 | 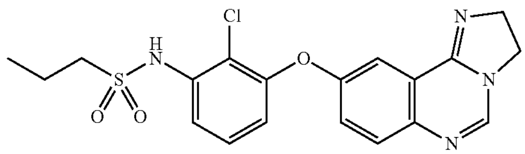 | N-(2-Chloro-3-((2,3-dihydroimidazo[1,2-c]quinazolin-9-yl)oxy)phenyl)propane-1-sulfonamide |
| 21 | 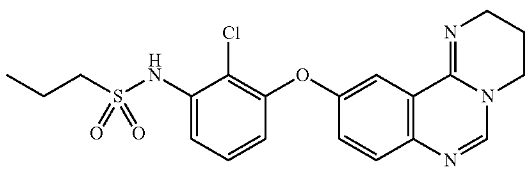 | N-(2-Chloro-3-((3,4-dihydro-2H-pyrimido[1,2-c]quinazolin-10-yl)oxy)phenyl)propane-1-sulfonamide |
| 11 | 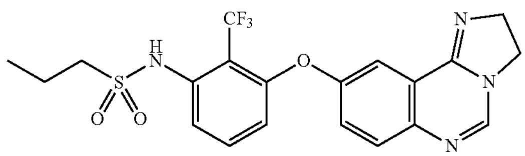 | N-(3-((2,3-Dihydroimidazo[1,2-c]quinazolin-9-yl)oxy)-2-(trifluoromethyl)phenyl)propane-1-sulfonamide |
| 30 | 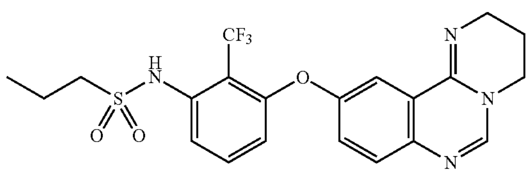 [SMILES: CCCS(=O)(=O)Nc1cccc(Oc2ccc3c(c2)C2=NCCCN2C=N3)c1Cl] | N-(3-((3,4-dihydro-2H-pyrimido[1,2-c]quinazolin-10-yl)oxy)-2-(trifluoromethyl)phenyl)propane-1-sulfonamide |
| 31 | 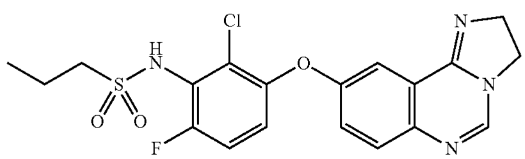 | N-(2-chloro-3-((2,3-dihydroimidazo[1,2-c]quinazolin-9-yl)oxy)-6-fluorophenyl)propane-1-sulfonamide |
| 32 | 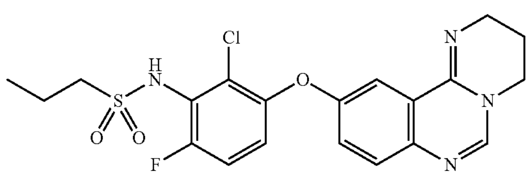 [SMILES: CCCS(=O)(=O)Nc1c(F)ccc(Oc2ccc3c(c2)C2=NCCCN2C=N3)c1Cl] | N-(2-chloro-3-((3,4-dihydro-2H-pyrimido[1,2-c]quinazolin-10-yl)oxy)-6-fluorophenyl)propane-1-sulfonamide |
| 33 | 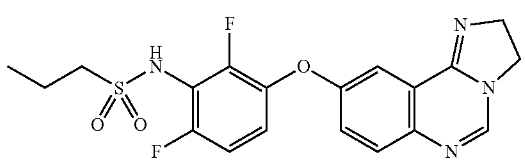 [SMILES: CCCS(=O)(=O)Nc1c(F)ccc(Oc2ccc3c(c2)C2=NCCN2C=N3)c1F] | N-(3-((2,3-dihydroimidazo[1,2-c]quinazolin-9-yl)oxy)-2,6-difluorophenyl)propane-1-sulfonamide |
| 34 | 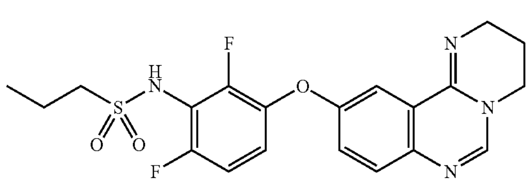 [SMILES: CCCS(=O)(=O)Nc1c(F)ccc(Oc2ccc3c(c2)C2=NCCCN2C=N3)c1F] | N-(3-((3,4-dihydro-2H-pyrimido[1,2-c]quinazolin-10-yl)oxy)-2,6-difluorophenyl)propane-1-sulfonamide |
| 10 | 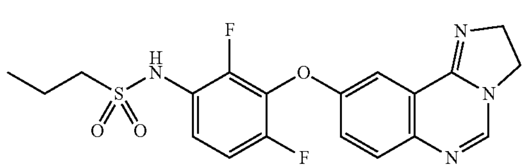 [SMILES: CCCS(=O)(=O)Nc1ccc(F)c(Oc2ccc3c(c2)C2=NCCN2C=N3)c1F] | N-(3-((2,3-Dihydroimidazo[1,2-c]quinazolin-9-yl)oxy)-2,4-difluorophenyl)propane-1-sulfonamide |

-continued

| Compound No. | Structure | Chemical Name |
|---|---|---|
| 35 | 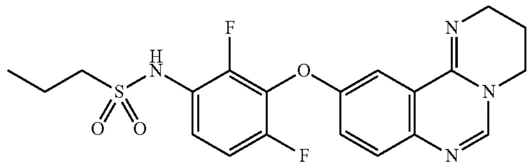 [SMILES: CCCS(=O)(=O)Nc1ccc(F)c(Oc2ccc3c(c2)C2=NCCCN2C=N3)c1F] | N-(3-((3,4-dihydro-2H-pyrimido[1,2-c]quinazolin-10-yl)oxy)-2,4-difluorophenyl)propane-1-sulfonamide |
| 36 | 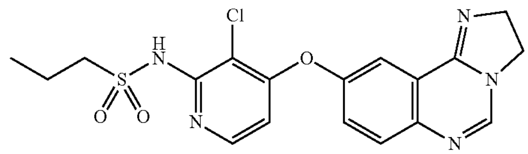 [SMILES: CCCS(=O)(=O)Nc1nccc(Oc2ccc3c(c2)C2=NCCN2C=N3)c1Cl] | N-(3-chloro-4-((2,3-dihydroimidazo[1,2-c]quinazolin-9-yl)oxy)pyridin-2-yl)propane-1-sulfonamide |
| 26 | 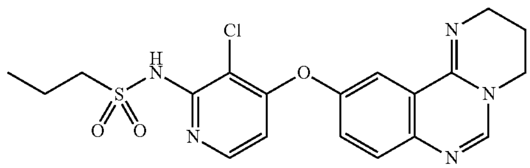 [SMILES: CCCS(=O)(=O)Nc1nccc(Oc2ccc3c(c2)C2=NCCCN2C=N3)c1Cl] | N-(3-Chloro-4-((3,4-dihydro-2H-pyrimido[1,2-c]quinazolin-10-yl)oxy)pyridin-2-yl)propane-1-sulfonamide |
| 40 | 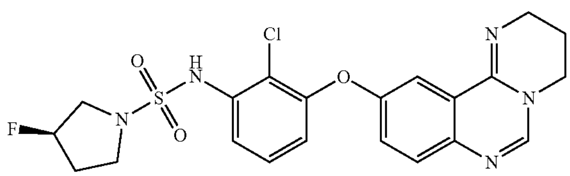 [SMILES: O=S(=O)(Nc1cccc(Oc2ccc3c(c2)C2=NCCCN2C=N3)c1Cl)N1CC[C@@H](F)C1] | (R)-N-(2-Chloro-3-((3,4-dihydro-2H-pyrimido[1,2-c]quinazolin-10-yl)oxy)phenyl)-3-fluoropyrrolidine-1-sulfonamide |
| 46 | 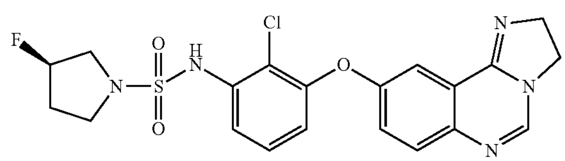 [SMILES: O=S(=O)(Nc1cccc(Oc2ccc3c(c2)C2=NCCN2C=N3)c1Cl)N1CC[C@@H](F)C1] | (R)-N-(2-Chloro-3-((2,3-dihydroimidazo[1,2-c]quinazolin-9-yl)oxy)phenyl)-3-fluoropyrrolidine-1-sulfonamide |
| 48 | | N-(2-Chloro-3-((2,3-dihydroimidazo[1,2-c]quinazolin yl)oxy)phenyl)pyrrolidine-1-sulfonamide | or a pharmaceutically acceptable salt or isotopic derivative thereof.

24. A pharmaceutical composition comprising a compound of claim 1, or a pharmaceutically acceptable salt or isotopic derivative thereof, and a pharmaceutically acceptable diluent or carrier.

25. A combination comprising a compound of claim 1, or a pharmaceutically acceptable salt or isotopic derivative thereof, and a second prophylactic or therapeutic agent.

26. A method for treating a proliferation disorder, a cancer, or a tumor which is sensitive to inhibition of B-Raf V600E kinase in a subject, wherein the method comprises administering to the subject an effective amount of a compound of claim 1, or a pharmaceutically acceptable salt or isotopic derivative thereof.

27. The method of claim 26, wherein the proliferation disorder or cancer is selected from the group consisting of malignant or benign tumors of the liver, kidney, bladder, breast, gastric, ovarian, colorectal, prostate, pancreatic, lung, vulval, thyroid, hepatic carcinomas, sarcomas, glioblastomas, head and neck, melanoma, and other hyperplastic conditions such as benign hyperplasia of the skin, benign hyperplasia of the prostate, and brain metastates originating from these disorders.

28. A method for producing an anti-proliferative effect in a subject having a proliferation disorder, a cancer, or a tumor which is sensitive to inhibition of B-Raf V600E kinase, comprising administering to the subject an effective amount of a compound of claim 1, or a pharmaceutically acceptable salt or isotopic derivative thereof.

29. A method for treating a neurodegenerative disease sensitive to inhibition of B-Raf V600E kinase in a subject, wherein the method comprises administering to the subject an effective amount of a compound of claim 1, or a pharmaceutically acceptable salt or isotopic derivative thereof.

30. The method of claim 29, wherein the neurodegenerative disease is selected from the group consist of Amyotrophic lateral sclerosis, Parkinson's disease, Alzheimer's disease, and Huntington's disease.

31. A method for inhibiting an activity of a B-Raf V600E kinase in a cell, comprising contacting the cell with an effective amount of a compound of claim 1, or a pharmaceutically acceptable salt or isotopic derivative thereof, wherein the contacting is in vitro, ex vivo, or in vivo.

* * * * *